US012697366B2

(12) United States Patent
Ziouzenkova et al.

(10) Patent No.: US 12,697,366 B2
(45) Date of Patent: Aug. 4, 2026

(54) THERMOGENIC COMPOSITIONS AND METHODS

(71) Applicant: Ohio State Innovation Foundation, Columbus, OH (US)

(72) Inventors: Ouliana Ziouzenkova, Columbus, OH (US); Jonathan R. Parquette, Hilliard, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 1338 days.

(21) Appl. No.: 17/380,536

(22) Filed: Jul. 20, 2021

(65) Prior Publication Data

US 2022/0175872 A1 Jun. 9, 2022

Related U.S. Application Data

(63) Continuation-in-part of application No. 16/088,267, filed as application No. PCT/US2017/024701 on Mar. 29, 2017, now abandoned.

(60) Provisional application No. 62/314,796, filed on Mar. 29, 2016.

(51) Int. Cl.
| | |
|---|---|
| *A61K 38/00* | (2006.01) |
| *A61K 38/05* | (2006.01) |
| *A61K 38/07* | (2006.01) |
| *A61K 47/54* | (2017.01) |
| *A61P 3/04* | (2006.01) |
| *A61P 3/10* | (2006.01) |

(52) U.S. Cl.
CPC .............. *A61K 38/07* (2013.01); *A61K 38/05* (2013.01); *A61K 47/54* (2017.08); *A61K 47/545* (2017.08); *A61P 3/04* (2018.01); *A61P 3/10* (2018.01)

(58) Field of Classification Search
CPC ........ A61K 38/05; A61K 38/07; A61K 47/54; A61K 47/545; A61K 47/64; A61K 2300/00; A61K 38/1808; A61K 38/185; A61K 38/1883; A61K 38/19; A61K 38/30; A61K 38/43; A61K 45/06; A61K 47/6919; A61K 47/6929; A61K 47/6949; A61K 9/0019; A61P 3/04; A61P 3/10
See application file for complete search history.

(56) References Cited

U.S. PATENT DOCUMENTS

2014/0155577 A1* 6/2014 Parquette ............. A61K 47/542
530/331

FOREIGN PATENT DOCUMENTS

WO WO-2015017529 A2 * 2/2015 ................ A61P 3/00

OTHER PUBLICATIONS

Brust, et al., "Gαi/o-Coupled Receptor-mediated Sensitization of Adenylyl Cyclase: 40 Years Later", European Journal of Pharmacology, vol. 763, 2015, pp. 223-232.
Bulló, et al., "Circulating Nerve Growth Factor Levels in Relation to Obesity and the Metabolic Syndrome in Women", European Journal of Endocrinology, vol. 157, 2007, pp. 303-310.
Collard, et al., "Identification of 3-deoxyglucosone Dehydrogenase as Aldehyde Dehydrogenase 1A1 (Retinaldehyde Dehydrogenase 1)", Biochimie, vol. 89, 2007, pp. 369-373.
Cortez, et al., "Chapter 9—Glucose Intolerance, Metabolic Syndrome, and Neuropathy", Handbook of Clinical Neurology, vol. 126, 2014, pp. 109-122.
Fan, et al., "Targeted Disruption of Aldh1a1 (Raldh1) Provides Evidence for a Complex Mechanism of Retinoic Acid Synthesis in the Developing Retina", Molecular and Cellular Biology, vol. 23, No. 13, Jul. 2003, pp. 4637-4648.
Hernández-Miranda, et al., "Robo1 Regulates Semaphorin Signaling to Guide the Migration of Cortical Interneurons through the Ventral Forebrain", The Journal of Neuroscience, vol. 31, No. 16, Apr. 20, 2011, pp. 6174-6187.
Hornberger, et al., "Modulation of EphA Receptor Function by Coexpressed EphrinA Ligands on Retinal Ganglion Cell Axons", Neuron, vol. 22, Apr. 1999, pp. 731-742.
Huq, et al., "Regulation of Retinal Dehydrogenases and Retinoic Acid Synthesis by Cholesterol Metabolites", The EMBO Journal, vol. 25, No. 13, 2006, pp. 3203-3213.
Janes, et al., "Adam Meets Eph: An ADAM Substrate Recognition Module Acts as a Molecular Switch for Ephrin Cleavage in trans", Cell, vol. 123, Oct. 21, 2005, pp. 291-304.
Kang, et al., "Autologous Adipose Tissue-derived Stromal Cells for Treatment of Spinal Cord Injury", Stem Cells and Development, vol. 15, 2006, pp. 583-594.
Kir, et al., "Tumour-derived PTHrP Triggers Adipose Tissue Browning and Cancer Cachexia", Nature, vol. 513, 2014, pp. 100-104.
Ladewig, et al., "Small Molecules Enable Highly Efficient Neuronal Conversion of Human Fibroblasts", Nature Methods, vol. 9, No. 6, Jun. 2012, pp. 575-576.
Lee, et al., "Amino Acid-based Compound Activates Atypical PKC and Leptin Receptor Pathways to Improve Glycemia and Anxiety Like Behavior in Diabetic Mice", Biomaterials, vol. 239, 2020, pp. 1-16.

(Continued)

*Primary Examiner* — Lianko G Garyu
*Assistant Examiner* — Mercy H Sabila
(74) *Attorney, Agent, or Firm* — PABST PATENT GROUP LLP

(57) ABSTRACT

Thermogenic molecules and methods of using these molecules for treating or preventing a condition in a subject selected from the group consisting of visceral fat accumulation (e.g., Crohn's disease associated with visceral fat accumulation), obesity, diabetes, pre-diabetes, hypothermia, and chronic inflammation are disclosed. Also disclosed is a method for promoting glucose uptake in peripheral tissues (e.g., adipocytes and muscles) of a subject, enhancing nerve innervation in a subject, activating PI3 kinase in cell, and inducing leptin secretion by an adipocyte. Also disclosed are inhibitors of thermogenic molecules and methods of using these inhibitors to decrease thermogenesis of adipocytes in a subject. Also disclosed are self-assembled, biocompatible nanostructure non-covalently associated with a therapeutic or diagnostic peptide or peptidomimetic.

9 Claims, 127 Drawing Sheets

Specification includes a Sequence Listing.

(56) References Cited

OTHER PUBLICATIONS

Liesi, et al., "Nerve Growth Factor Induces Adrenergic Neuronal Differentiation in F9 Teratocarcinoma Cells", Nature, vol. 306, Nov. 17, 1983, pp. 265-267.

Molotkov, et al., "Genetic Evidence That Retinaldehyde Dehydrogenase Raldh1 (Aldh1a1) Functions Downstream of Alcohol Dehydrogenase Adh1 in Metabolism of Retinol to Retinoic Acid", The Journal of Biological Chemistry, vol. 278, No. 38, Sep. 19, 2003, pp. 36085-36090.

Moreno-Bravo, et al., "Developmental Guidance of the Retroflex Tract at Its Bending Point Involves Robo1-Slit2-mediated Floor Plate Repulsion", Brain Structure and Function, vol. 221, 2016, pp. 665-678.

Murphy, et al., "Leptin-sensitive Sensory Nerves Innervate White Fat", American Journal of Physiology-Endocrinology and Metabolism, vol. 304, 2013, pp. E1338-E1347.

Overman, et al., "A Role for Ephrin-A5 in Axonal Sprouting, Recovery, and Activity-dependent Plasticity After Stroke", Proceedings of the National Academy of Sciences of the USA, vol. 109, 2012, pp. E2230-E2239.

Rao, et al., "Meteorin-like Is a Hormone that Regulates Immune-Adipose Interactions to Increase Beige Fat Thermogenesis", Cell, vol. 157, Jun. 5, 2014, pp. 1279-1291.

Shen, et al., "Egg Yolks Inhibit Activation of NF-κB and Expression of Its Target Genes in Adipocytes after Partial Delipidation", Journal of Agricultural and Food Chemistry, vol. 63, 2015, pp. 2013-2025.

Shi, et al., "Retinoic Acid Receptor γ (Rarg) and Nuclear Receptor Subfamily 5, Group A, Member 2 (Nr5a2) Promote Conversion of Fibroblasts to Functional Neurons", The Journal of Biological Chemistry, vol. 289, No. 10, Mar. 7, 2014, pp. 6415-6428.

Shimizu, et al., "Semaphorin3E-Induced Inflammation Contributes to Insulin Resistance in Dietary Obesity", Cell Metabolism, vol. 18, Oct. 1, 2013, pp. 491-504.

Vozza, et al., "UCP2 Transports C4 Metabolites Out of Mitochondria, Regulating Glucose and Glutamine Oxidation", Proceedings of the National Academy of Sciences of the USA, vol. 111, No. 3, Jan. 21, 2014, pp. 960-965.

Wilson, et al., "Sonic Hedgehog Regulates Its Own Receptor on Postcrossing Commissural Axons in a Glypican1-Dependent Manner", Neuron, vol. 79, Aug. 7, 2013, pp. 478-491.

Wion, et al., "Retinoic Acid Increases the Expression of NGF Gene in Mouse L Cells", Biochemical and Biophysical Research Communications, vol. 149, No. 2, Dec. 16, 1987, pp. 510-514.

Wu, et al., "Beige Adipocytes Are a Distinct Type of Thermogenic Fat Cell in Mouse and Human", Cell, vol. 150, Jul. 20, 2012, pp. 366-376.

Xu, et al., "Ephrin Reverse Signaling in Axon Guidance and Synaptogenesis", Seminars in Cell & Developmental Biology, vol. 23, 2012, pp. 58-64.

Yasmeen, et al., "Autocrine Function of Aldehyde Dehydrogenase 1 as a Determinant of Diet- and Sex-Specific Differences in Visceral Adiposity", Diabetes, vol. 62, Jan. 2013, pp. 124-136.

Yu, et al., "Retinoic Acid Induces Neurogenesis by Activating Both Retinoic Acid Receptors (RARs) and Peroxisome Proliferator-activated Receptor β/δ (PPARβ/δ)", The Journal of Biological Chemistry, vol. 287, No. 50, Dec. 7, 2012, pp. 42195-42205.

* cited by examiner

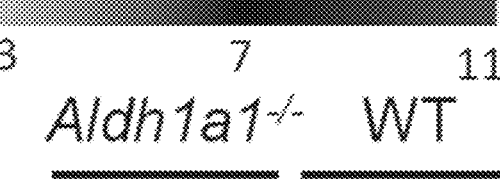
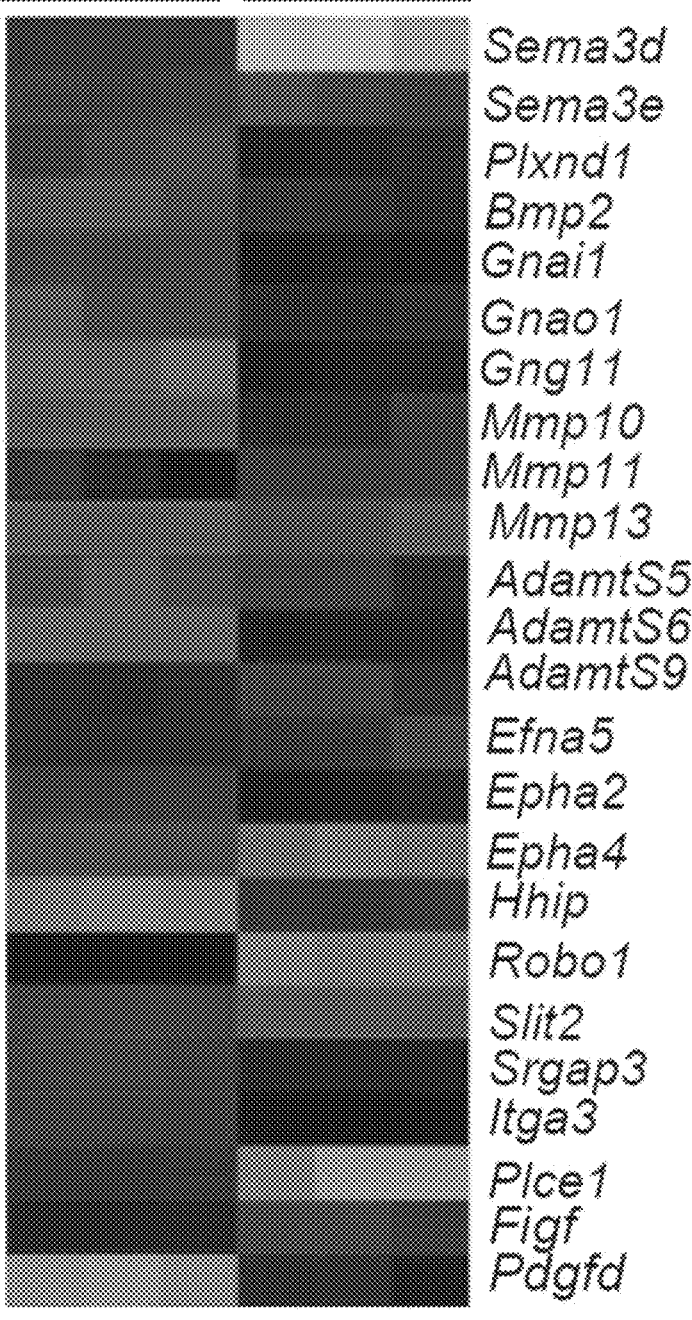
FIG. 1G

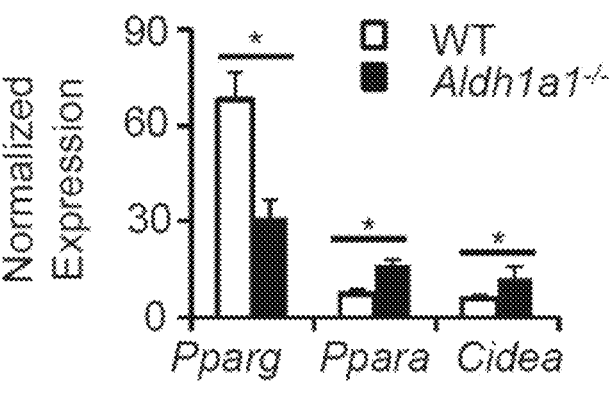
FIG. 2A
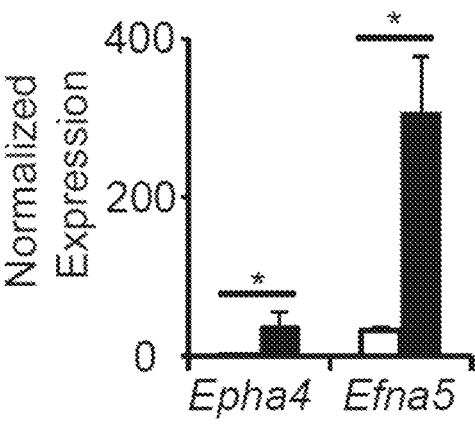
FIG. 2B
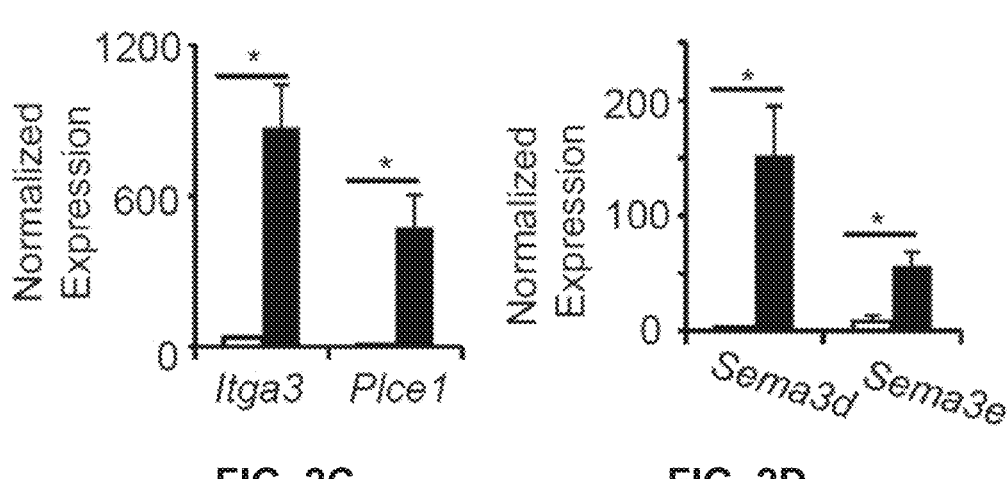
FIG. 2C                              FIG. 2D

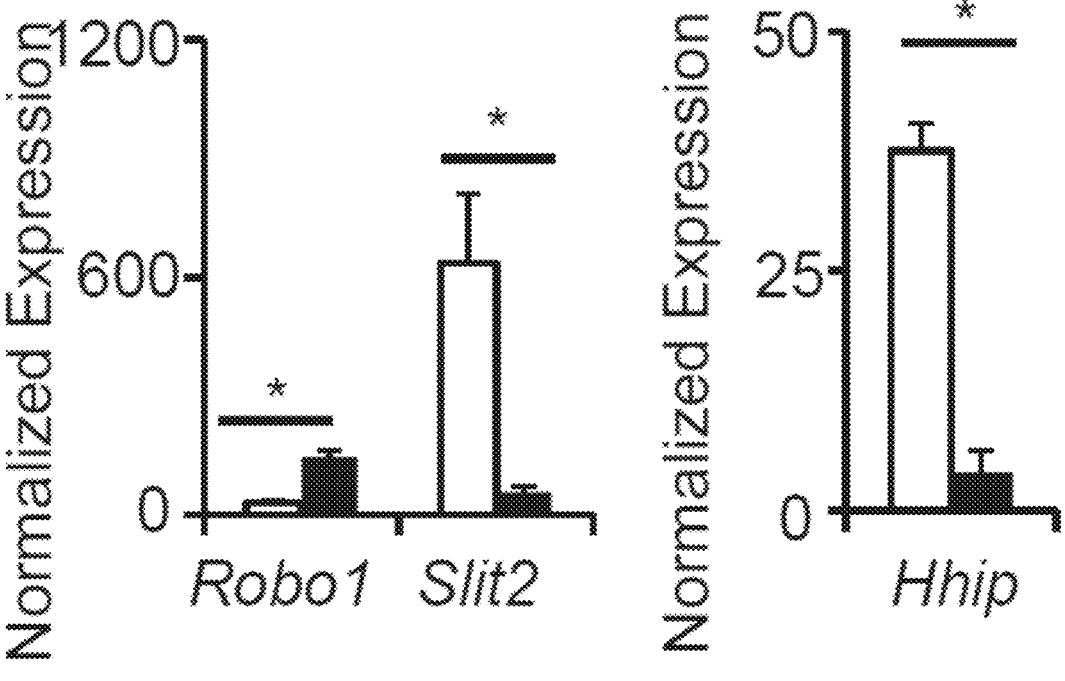
FIG. 2E
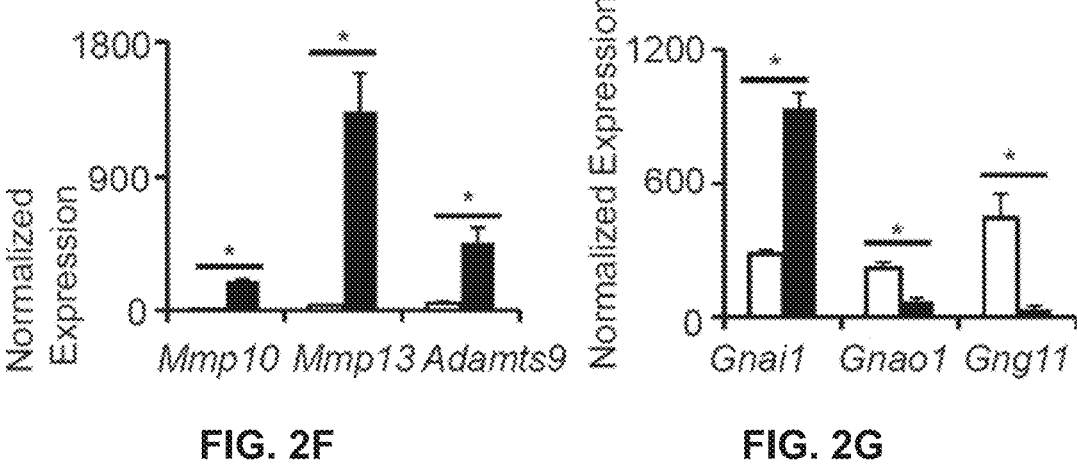
FIG. 2F                    FIG. 2G

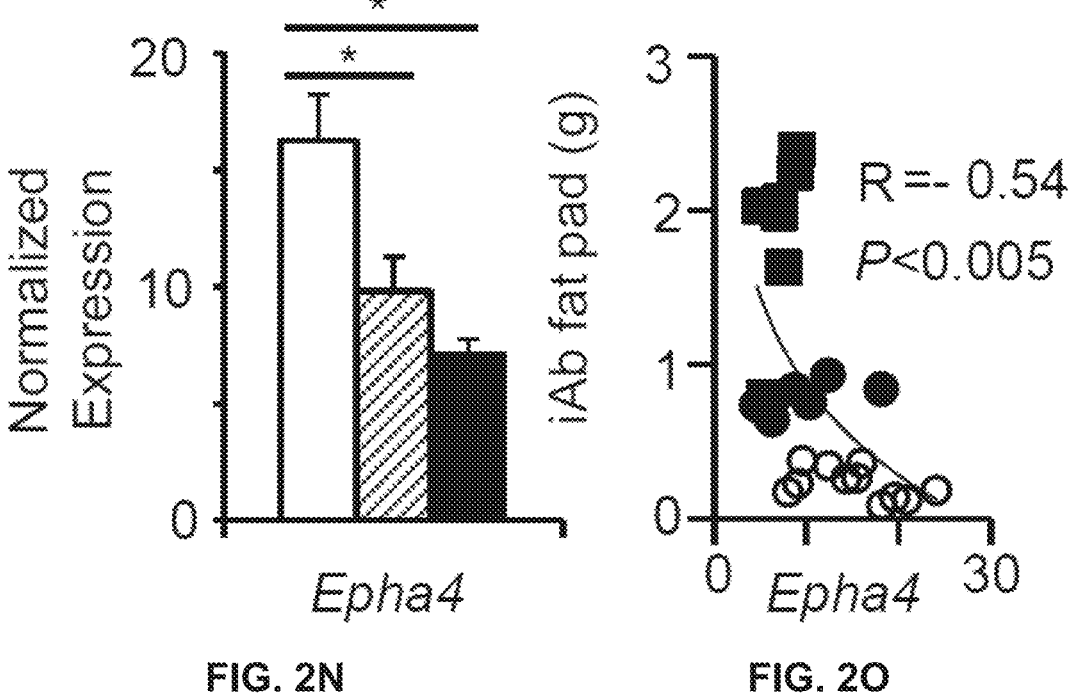
FIG. 2N　　　　　FIG. 2O

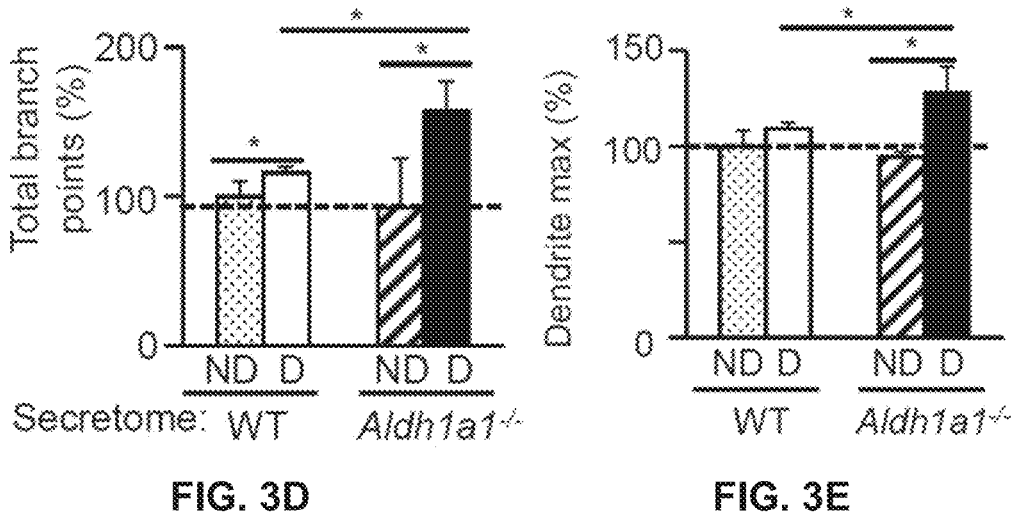
FIG. 3D            FIG. 3E
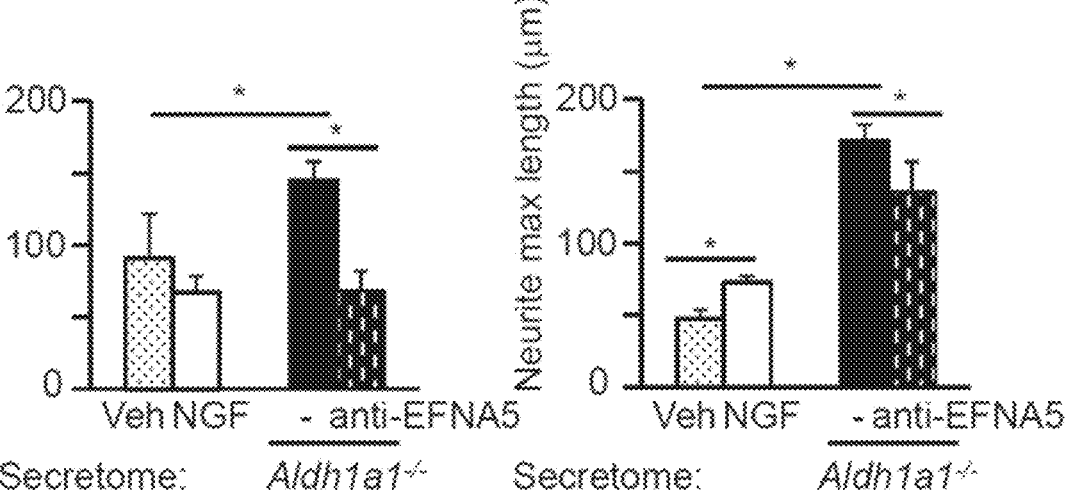
FIG. 3F

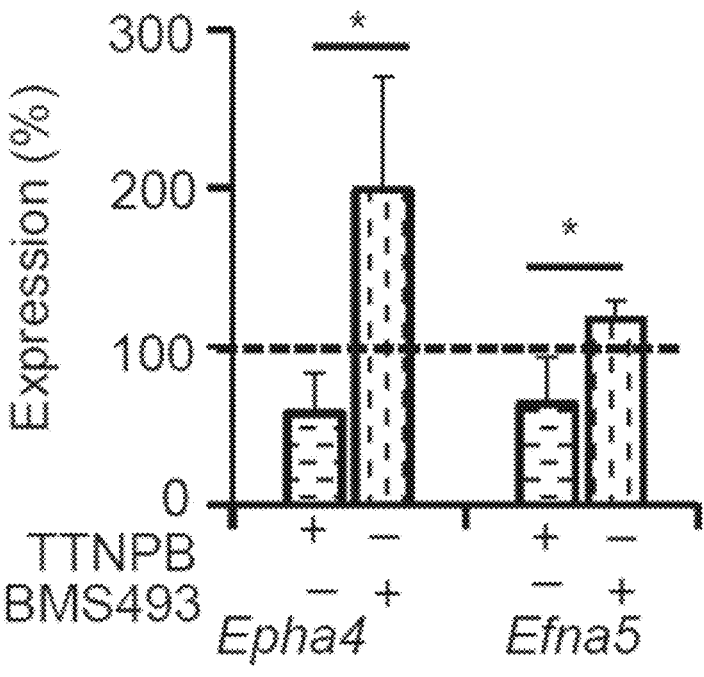
FIG. 5D
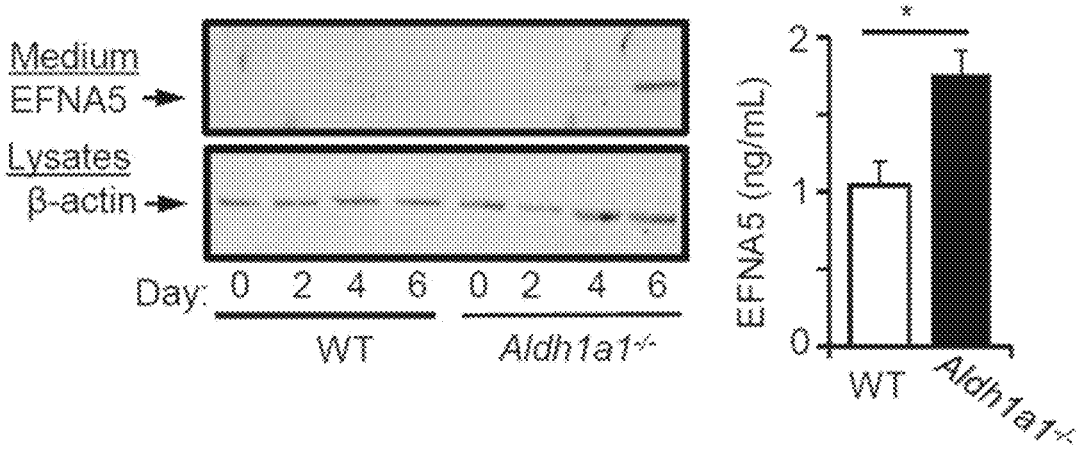
FIG. 5E                              FIG. 5F

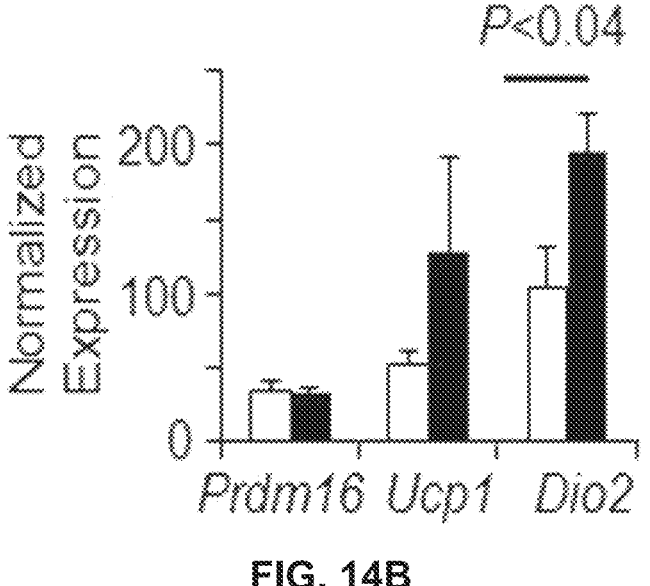
FIG. 14B
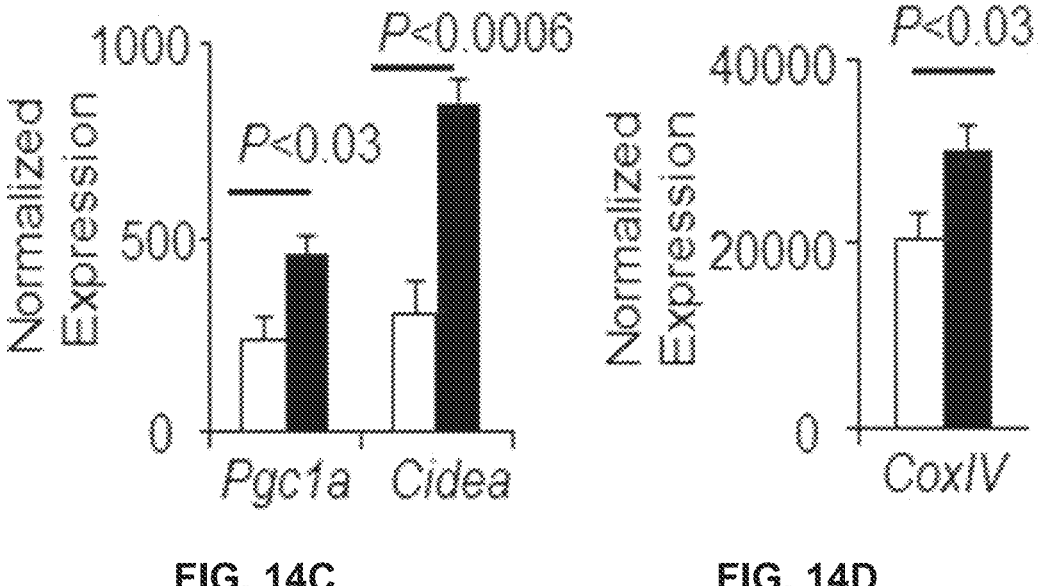
FIG. 14C                    FIG. 14D

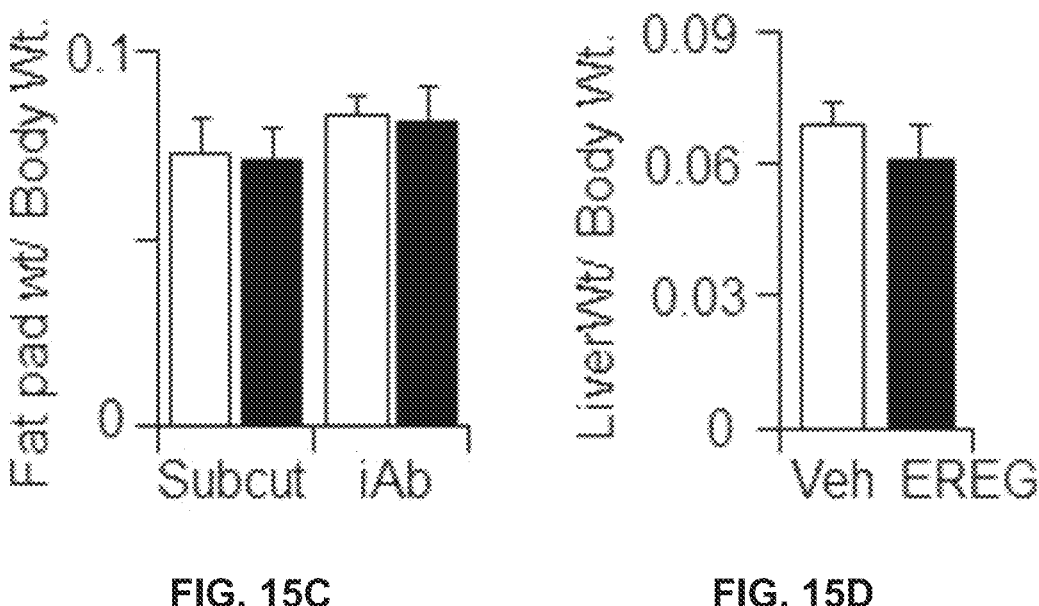
FIG. 15C                    FIG. 15D
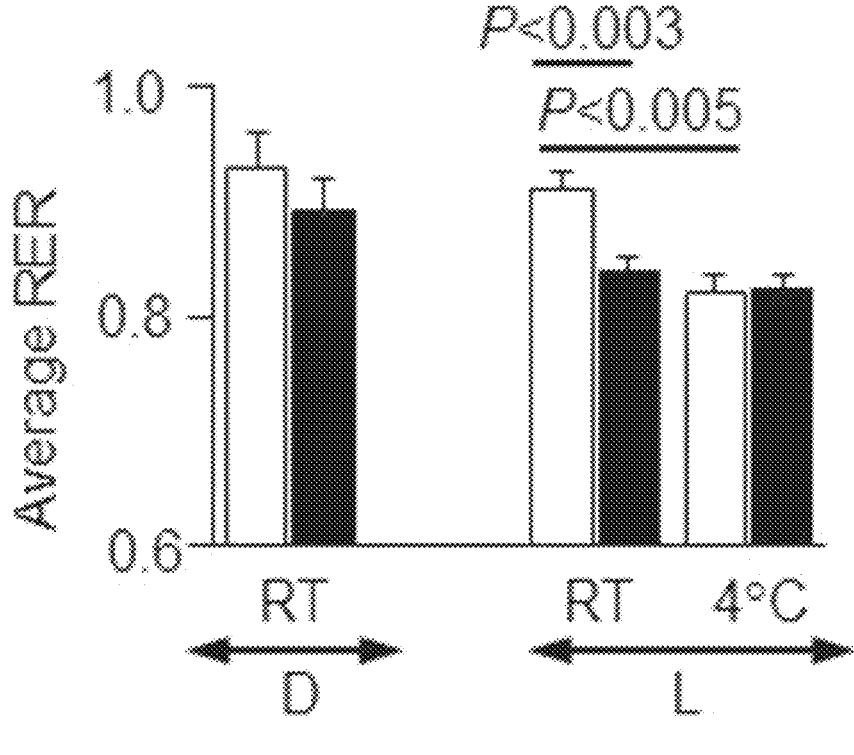
FIG. 15E

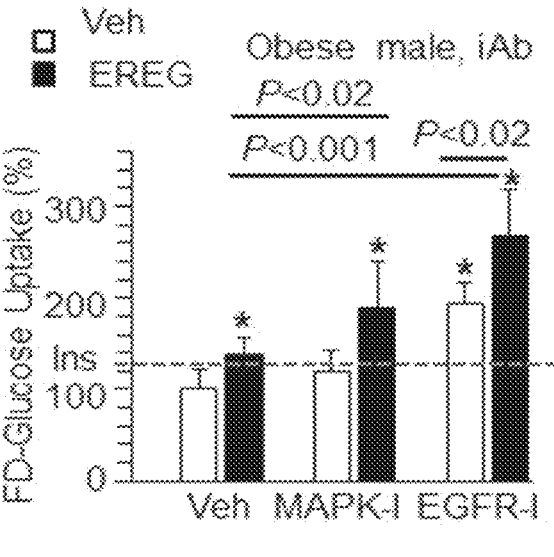
FIG. 16G
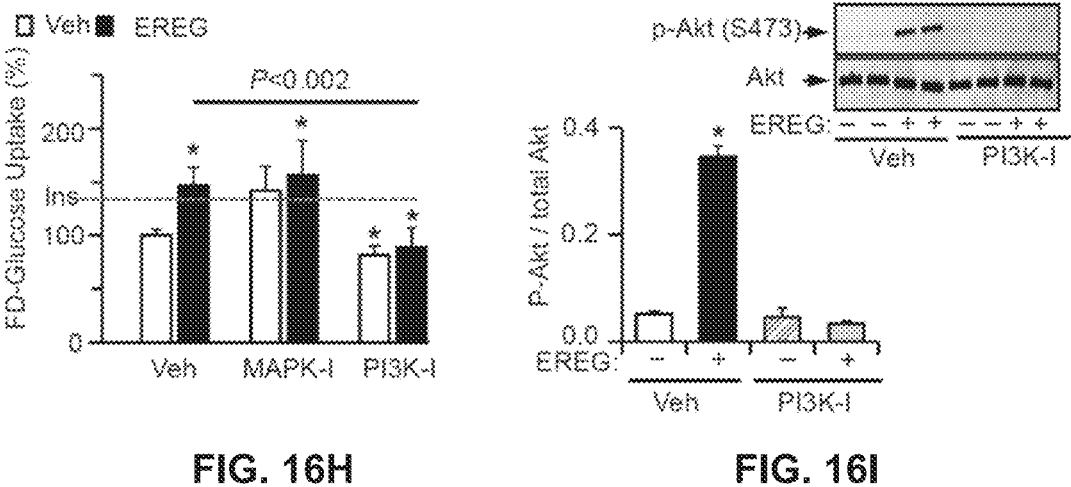
FIG. 16H                                    FIG. 16I

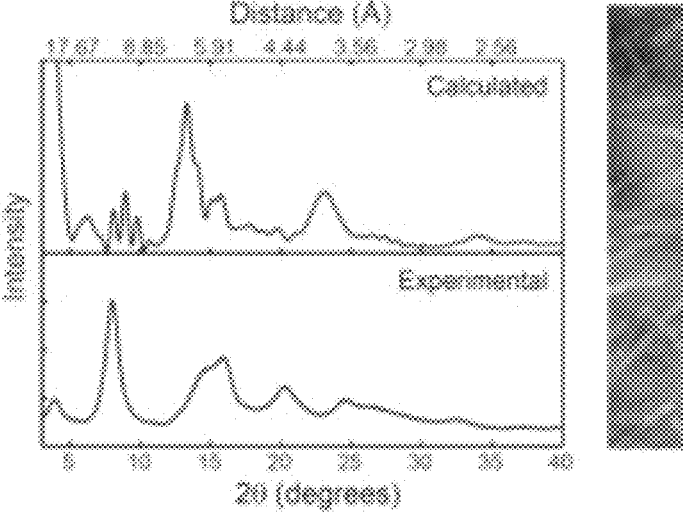
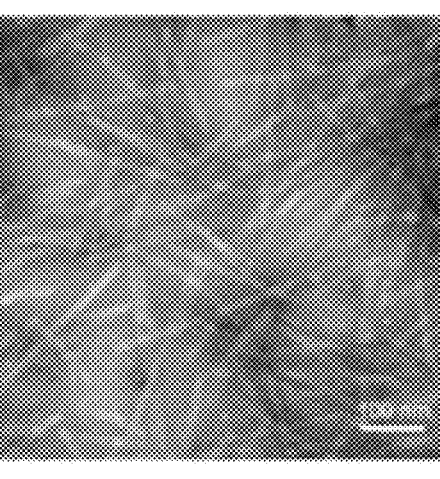
FIG. 18F                    FIG. 18G
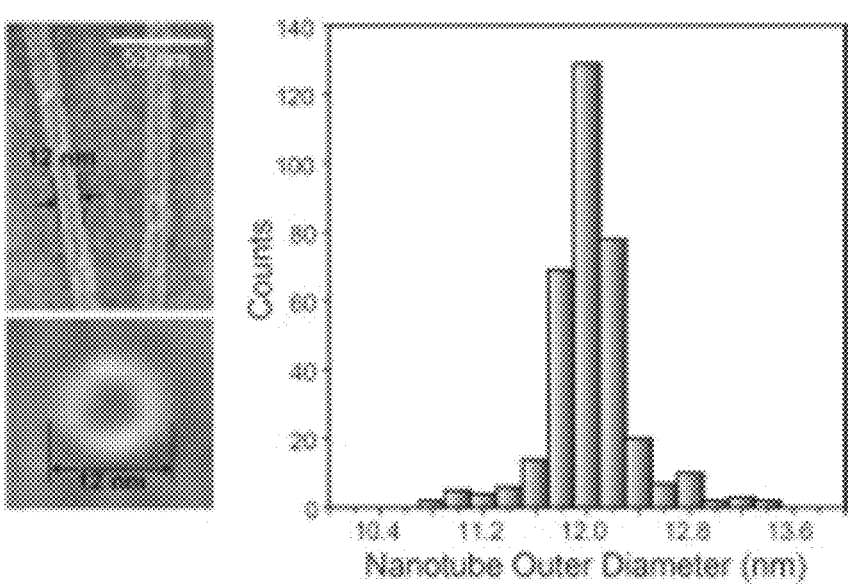
FIG. 18H                    FIG. 18I

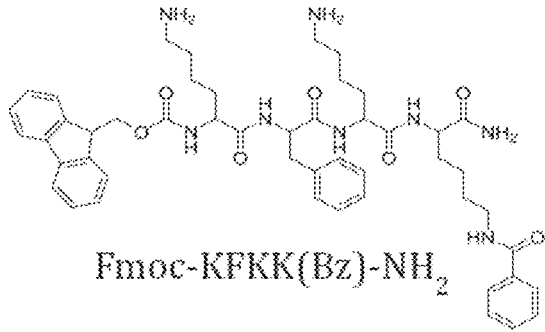
Fmoc-KFKK(Bz)-NH₂
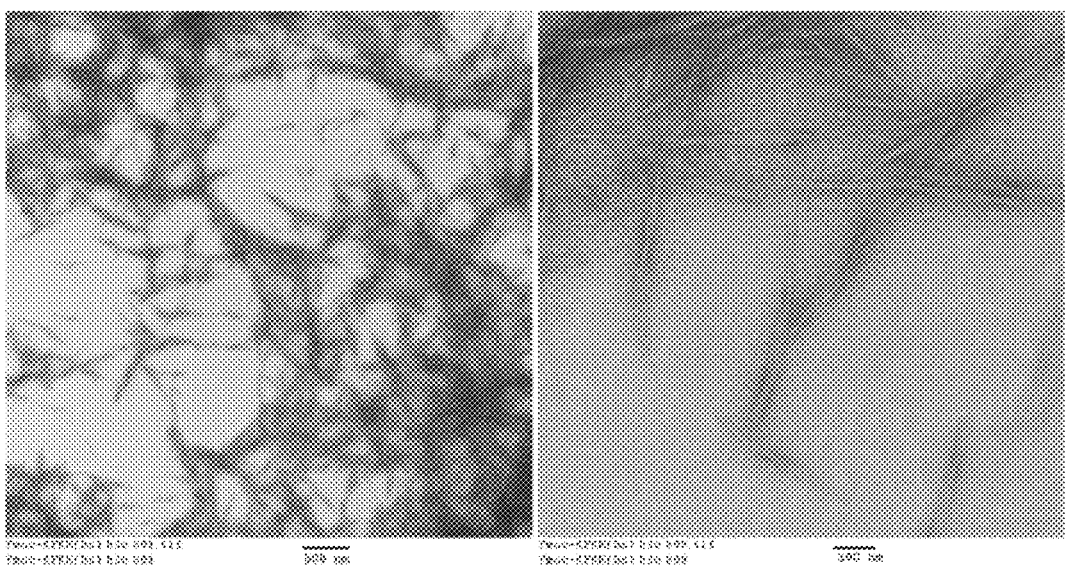
FIG. 19

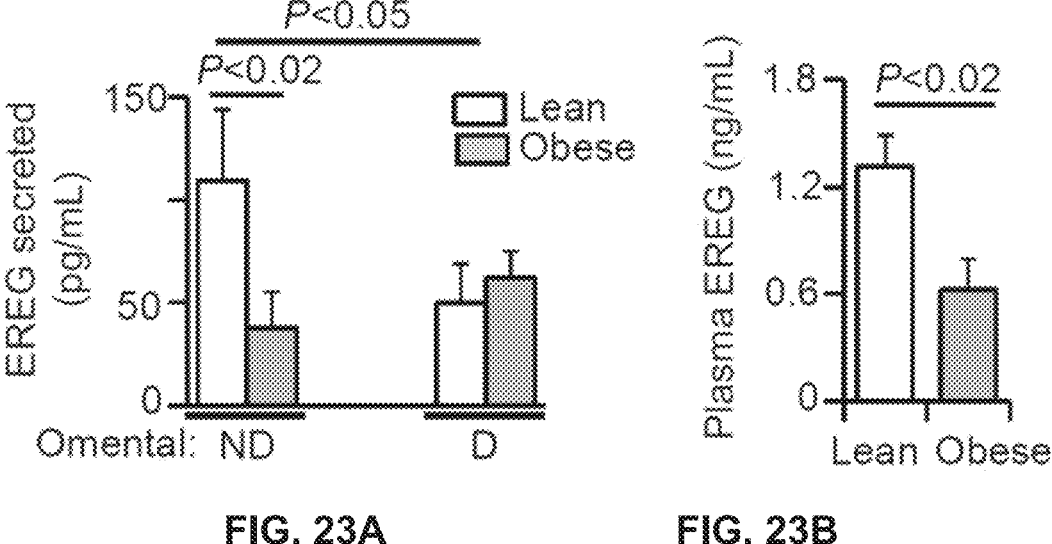
FIG. 23A          FIG. 23B
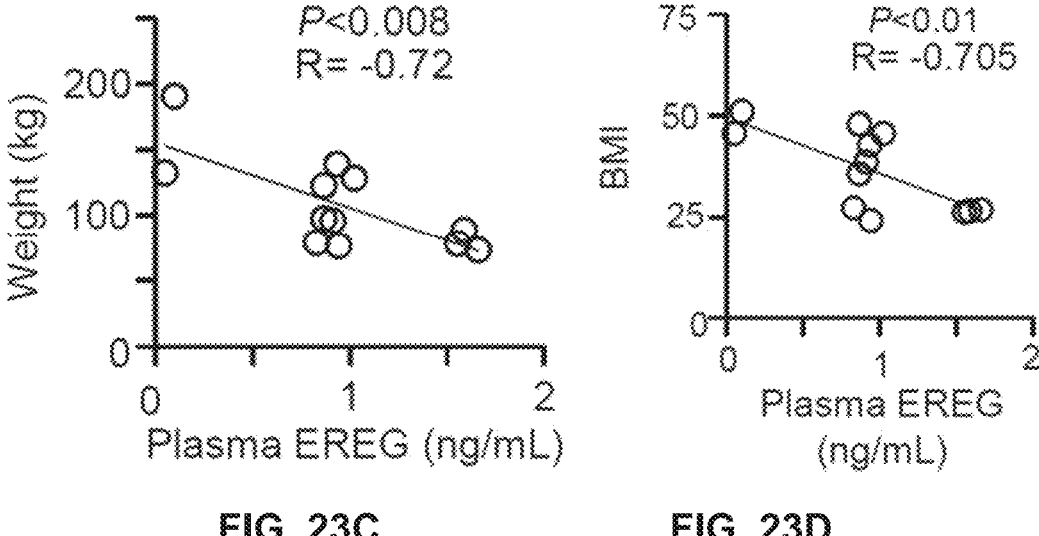
FIG. 23C          FIG. 23D

Cells

Cells only

Insulin-FITC (10 mg/mL, free)

Without nanoscaffold

Veh (PBS)     Insulin-FITC (10 mg/mL, bound)

With nanoscaffold (1 mM)

Veh (PBS)

Insulin (10 μg/mL, bound)

With nanoscaffold (10 μM)

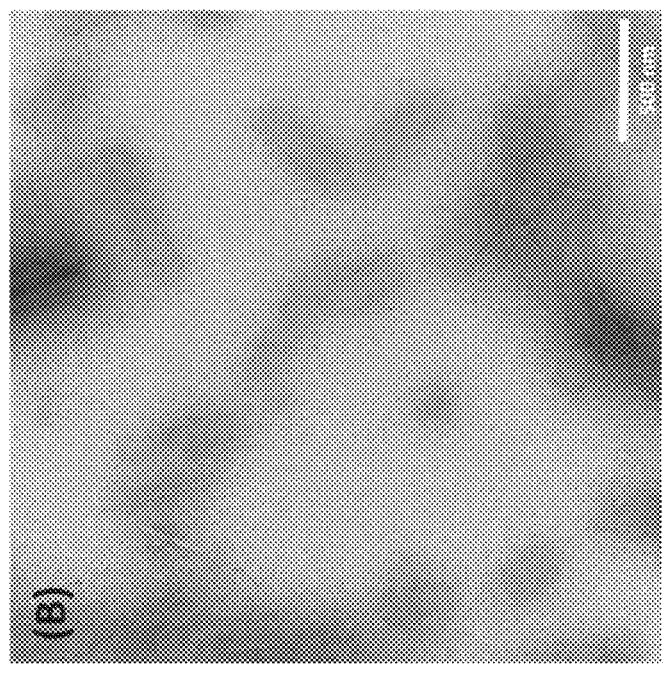
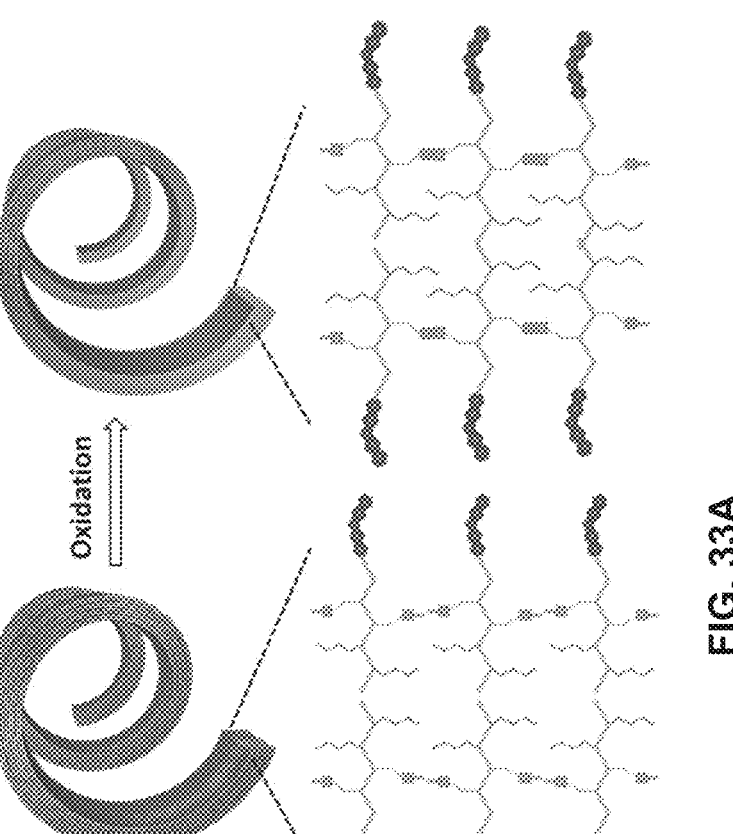
FIG. 33B
FIG. 33A

AAC2
Fmoc-KK-DAC

☐ DAC (7-(Diethylamino)
coumarin-3-carboxylic acid)

AAC1
Fmoc-KK-Suc

☐ Suc (benzyl succinate)
☐ Lysine

AAC4
Fmoc-EK-DAC

AAC3
Fmoc-KFKK-BA     □ BA (benzamide)

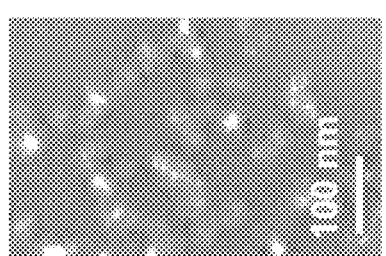
AAC6
Fmoc-KK-NH2
FIG. 40F
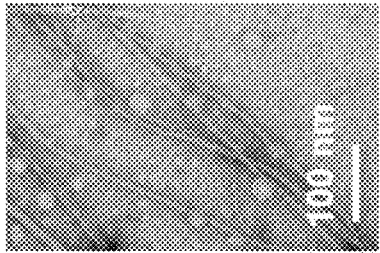
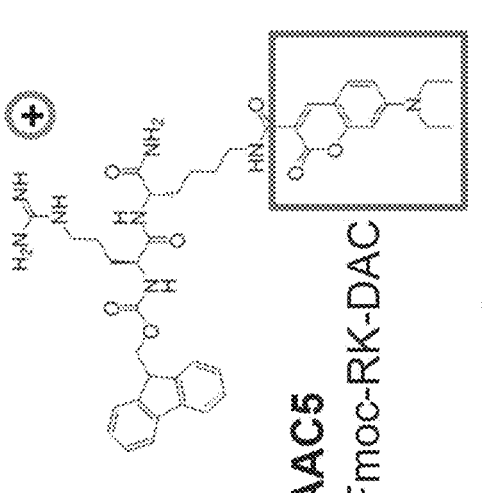
AAC5
Fmoc-RK-DAC
FIG. 40E

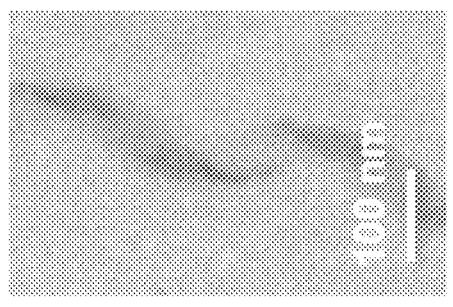
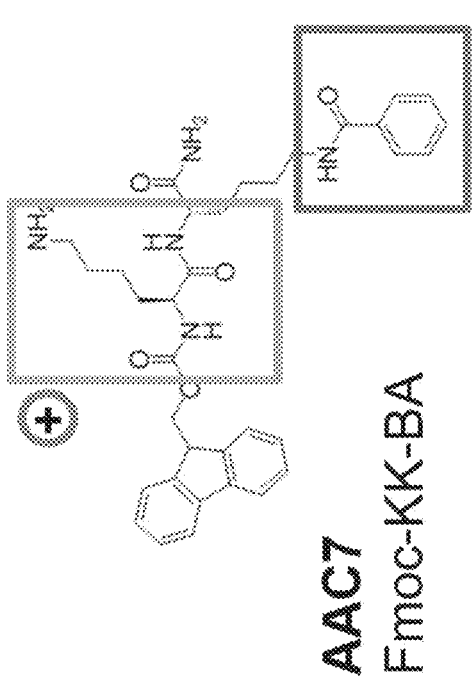
AAC7
Fmoc-KK-BA
FIG. 40G

Cell toxicity in response to different AAC in mouse 3T3-L1 cells

Efficacy of different AAC to withstand reactive oxygen species (ROS)–induced stress in mouse 3T3-L1 cells

Human brain endothelial cells

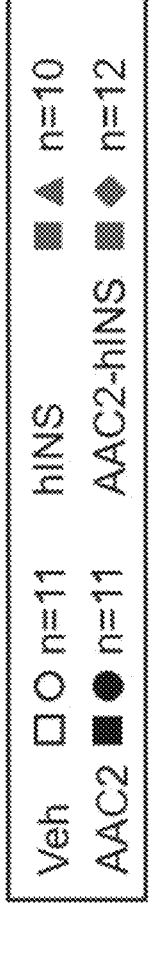
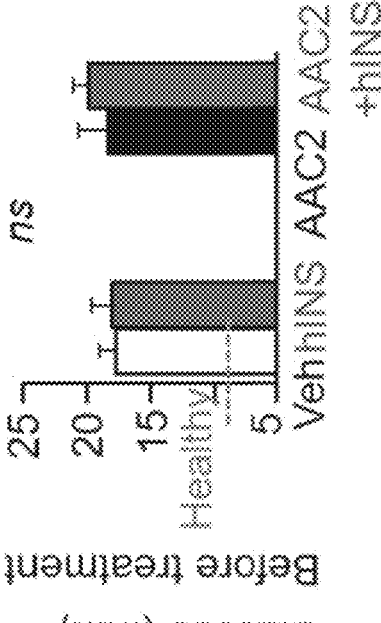
FIG. 57B

THERMOGENIC COMPOSITIONS AND METHODS

CROSS-REFERENCE TO RELATED APPLICATIONS

This application is a continuation-in-part of copending application Ser. No. 16/088,267, filed Sep. 25, 2018, which is a National Stage of International Application No. PCT/US2017/024701, filed Mar. 29, 2017, which claims benefit of U.S. Provisional Application No. 62/314,796, filed Mar. 29, 2016, which is hereby incorporated herein by reference in its entirety.

STATEMENT REGARDING FEDERALLY SPONSORED RESEARCH OR DEVELOPMENT

This invention was made with Government Support under Grant Nos. OD017244, NS047175, DK050456, RR025755, and CA016058 awarded by the National Institutes of Health. The Government has certain rights in the invention.

BACKGROUND

Obesity remains a major worldwide public health problem increasing risks for insulin resistance, type 2 diabetes, and cardiovascular disease. In obesity, white adipose tissue (WAT) in subcutaneous location and visceral or intra-abdominal (iAb) adipose tissue surrounding visceral organs as well as brown adipose tissue (BAT) become hypertrophic and exert reduced ability for energy dissipation as heat (thermogenesis) and energy utilization via mitochondrial oxidation. Hypertrophic adipocytes from WAT acquire pro-inflammatory and insulin-resistant characteristics due to enhanced secretion of adipokines, including resistin, visfatin, and TNFα. iAb and subcutaneous WAT have different developmental origin determining deleterious insulin resistant and inflammatory characteristics of iAb fat and its reduced propensity for thermogenesis. Accumulation of iAb WAT in both lean and obese patients increases their risks for all-cause mortality. The increase in iAb fat leads to progressive development of insulin resistance and type 2 diabetes in all BMI groups ranging from lean to obese patients. The prevalence of iAb obesity is increased in aging populations and increase their risks for dementia, including vascular dementia and Alzheimer's disease. The increasing efforts to treat iAb obesity have had only marginal success.

SUMMARY

Epiregulin, insulin-like growth factor-binding protein 4 (IGFBP4), insulin-like growth factor-binding protein 7 (IGFBP7), glia maturation factor beta (GMFB), amphiregulin, ephrin A5, ADAMT S9, and semaphorin 3E are shown herein to be molecules inducing thermogenesis. Therefore, a thermogenic composition is disclosed that contains two or more molecules selected from the group consisting of epiregulin, IGFBP4, IGFBP7, GMFB, ephrin A5, ADAMT S9, and semaphorin 3E, in a pharmaceutically acceptable carrier. In some cases, the composition comprises at least 1, 2, 3, or more adipose-based molecule selected from the group consisting of epiregulin, amphiregulin, IGFBP4, and IGFBP7, and at least 1, 2, 3, or more innervation-stimulating molecules selected from the group consisting of GMFB, ephrin A5, ADAMT S9, semaphorin 3E, IGFBP4, and IGFBP7.

In some embodiments, the thermogenic composition is formulated for delayed release. In some embodiments, the thermogenic composition is formulated for release into adipose tissue.

Also disclosed is a thermogenic composition disclosed herein in combination with a biocompatible nanostructure.

Also disclosed is a method for treating or preventing a condition in a subject selected from the group consisting of visceral fat accumulation (e.g., Crohn's disease associated with visceral fat accumulation), obesity, diabetes, pre-diabetes, insulin resistance, hyperinsulinemia, hypothermia, diabetes- and aged-related dementia, and chronic inflammation, comprising administering to the subject an effective amount of a composition comprising 1, 2, 3, 4, 5, 6, or 7 molecules selected from the group consisting of epiregulin, IGFBP4, IGFBP7, GMFB, ephrin A5, ADAMT S9, and semaphorin 3E.

Also disclosed is a method for promoting glucose uptake in peripheral tissues (e.g., adipocytes and muscles) of a subject, comprising administering to the subject an effective amount of a composition comprising 1, 2, 3, 4, 5, 6, or 7 molecules selected from the group consisting of epiregulin, IGFBP4, IGFBP7, GMFB, ephrin A5, ADAMT S9, and semaphorin 3E. In some embodiments, the method further involves administering to the subject a therapeutically effective amount of an epidermal growth factor receptor (EGFR) inhibitor, an ErbB receptor inhibitor, a MAPK inhibitor, or a combination thereof.

In some embodiments, the subject is resistant to insulin. In some embodiments, the subject has diminished insulin production. In some embodiments, the subject is obese. In some embodiments, the subject has developed side effects or tolerance to insulin therapy.

Also disclosed is a method for enhancing innervation in a subject, comprising administering to the subject an effective amount of a composition comprising 1, 2, 3, 4, 5, 6, or 7 molecules selected from the group consisting of epiregulin, IGFBP4, IGFBP7, GMFB, ephrin A5, ADAMT S9, and semaphorin 3E. In some cases the method involves administering to the subject a composition comprising Complement C3 factor.

The disclosed molecules, such as epiregulin, are also shown herein to be effective activators of PI3 and Akt kinases. Therefore, also disclosed is a method for activating PI3 kinase in cell, comprising contacting the cell with a composition comprising epiregulin.

The disclosed molecules, such as epiregulin, are also shown herein to be effective at inducing leptin secretion. Therefore, also disclosed is a method for inducing leptin secretion by an adipocyte, comprising contacting the adipocyte with a composition comprising epiregulin.

In some cases, it is advantageous to decrease thermogenesis of adipocytes in a subject. For example, cachexia or wasting syndrome is loss of weight, muscle atrophy, fatigue, weakness, and significant loss of appetite in someone who is not actively trying to lose weight. Therefore, a method is disclosed that involves administering to the subject an effective amount of a composition that inhibits 1, 2, 3, 4, 5, 6, or 7 molecules selected from the group consisting of epiregulin, IGFBP4, IGFBP7, GMFB, ephrin A5, ADAMT S9, and semaphorin 3E. For example, the inhibitor can be an antibody that binds and inactivates the molecule. In some cases, the inhibitor is a decoy molecule, soluble receptor, or the like. In some cases, the inhibitor is a gene silencing functional nucleic acid, such as an antisense DNA, RNAi, siRNA, shRNA, or miRNA. In some case, the inhibitor is a small molecule shown to inhibit one or more activities of the molecule.

Also provided herein are pharmaceutical compositions that comprise a self-assembled, biocompatible nanostructure non-covalently associated with a therapeutic or diagnostic peptide or peptidomimetic. The biocompatible nanostructure can enhance the stability of the non-covalently associated therapeutic or diagnostic peptide or peptidomimetic, thereby improving the efficacy of the therapeutic or diagnostic peptide or peptidomimetic upon administration to a subject in need thereof.

Also provided herein are methods of treating cancer in a subject, comprising administering to the subject a composition comprising a self-assembled, biocompatible nanostructure disclosed herein.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A to 1G show Aldh1a1 deficiency induces innervation in iAb WAT in vivo without increase in neural precursors or fibroblast neurogenesis. FIGS. 1A to 1D: WT and Aldh1a1$^{-/-}$ male (triangle, n=5) and female (circle, n=5) mice (n=10 per group) on a HF diet for 180 days (Table 1, Study 1). Fat depots were dissected. Peripherin was analyzed by immunohistochemistry and Western blot in paraffin-embedded iAb from the same groups of WT and Aldh1a1$^{-/-}$ mice (n=5). Arrows in the 20× image show peripherin-positive nerves in the WAT of Aldh1a1$^{-/-}$ and WT mice; the enlarged (40×) insert shows peripherin-positive neurons and nerves. Bars represent peripherin levels from the same tissues normalized for β-actin levels (n=4). The insert shows representative Western blots. An asterisk indicates a significant difference between WT and Aldh1a1$^{-/-}$ groups (P<0.05; Mann-Whitney test). The Mann-Whitney test was used throughout these studies for group comparison. FIGS. 1B and 1C: Relative expression of markers for neuronal and their precursor measured by TaqMan: Rbfox3 (FIG. 1B) and Nestin (FIG. 1C) in iAb from WT and Aldh1a1$^{-/-}$ males (triangle) and females (circle) in the same groups of mice. The expression was normalized to Tata box protein (TBP). An asterisk indicates a significant difference between WT and Aldh1a1$^{-/-}$ groups (P<0.05). n.s. not significant, Mann-Whitney test. FIG. 1D: nerve growth factor (NGF) plasma levels examined by ELISA in same WT and Aldh1a1$^{-/-}$ mice fed regular chow or HF diet. FIG. 1E: NGF levels in media collected from differentiated WT, and Aldh1a1$^{-/-}$ fibroblasts (n=4 per group) were analyzed by ELISA. FIG. 1F: Morphological changes in 3T3-L1, WT, and Aldh1a1$^{-/-}$ fibroblasts (n=3 per group) with and without induction of neurogenesis in the presence and absence of forskolin (10 μM). 2 days later, the medium was switched to neuronal differentiation medium with and without forskolin. Images of cultured cells were taken at 20× magnification. FIG. 1G: Expression heat map reveals differences in expression of the LTA axon guidance cluster of genes between WT and Aldh1a$^{-/-}$ preadipocytes (n=3 per group). Microarray gene analysis was performed using Affymetrix microarray. Axon guidance cluster was identified by Ingenuity Pathway Analysis.

FIGS. 2A to 2O show axon guidance signaling is the principal pathway characterizing genome differences between WT adipocytes and Aldh1a1$^{-/-}$ thermocytes. FIGS. 2A to 2G: WT (white bars) and Aldh1a1$^{-/-}$ (black bars) preadipocytes (n=3) were differentiated for 4 days. Gene expression was measured in purified mRNA samples using a customized NanoString mouse panel including markers for adipogenesis, thermogenesis, and axon guidance genes. Data represent mean±SD. An asterisk indicates P<0.05; Mann Whitney U test. FIGS. 2H, 2J to 2O: Lipolysis thermogenesis associated (LTA) axon guiding gene expression was analyzed in iAb fat pads of WT lean mice (white bars, white circles), WT mice with HF diet-induced obesity (upward diagonal bars, black circles), and ob/ob mice (black bars, black squares) using NanoString mouse innervation panel (Table 1, Study 2). An asterisk indicates P<0.05; Mann-Whitney U test (n=5/group, mean±SD). The Pearson test was used to examine significance by correlation analysis.

FIGS. 3A to 3F show secretome from Aldh1a1$^{-/-}$ thermocytes promotes axon growth in dorsal root ganglion (DRG) neurons in vitro. DRG neurons (500 neurons per well) were cultured in DRG culture medium only, or DRG culture medium with NT-3 (1 ng/mL), with NGF (10 ng/mL), with WT secretome (1/1, v/v), or with Aldh1a1$^{-/-}$ secretome (1/1, v/v) for 24 hours. WT and Aldh1a1$^{-/-}$ adipocytes differentiated for 5 days. Secretome is the media collected from these cells for 24 h. Neurite outgrowth parameters were assayed using the Thermo Scientific™ ArrayScan™ XTI Live High Content microscope and analyzed with the Neuronal Profiling Algorithm (ThermoFisher). Nine independent experiments were performed using DRG from three mice. Each DRG batch was analyzed in triplicate. Data are shown as mean±SD obtained with one DRG batch. Asterisks indicate P<0.05 between different groups; Mann-Whitney U test. FIGS. 3A and 3B: Representative images and quantification of neurite length in neurons 24 hours after stimulation. The larger area is shown in (FIG. 3A). FIGS. 3C to 3E: Axon guidance effects of secretomes from non-differentiated WT (dotted bars) and Aldh1a1$^{-/-}$ (upward hatched bars) preadipocytes and differentiated (5 days) WT (white bars) and Aldh1a1$^{-/-}$ (black bars) adipocytes on DRG neurons. Total and average length (FIG. 3C), total branch points (FIG. 3D) as well as ramification index, critical value, and dendrite max (FIG. 3E) were measured in DRG neurons and analyzed by Neuronal Profiling Algorithm. Data show mean±SD obtained with one DRG batch. Asterisks indicate P<0.05 between different groups; Mann-Whitney U test. FIG. 3F: The neurite outgrowth and max length of neurons treated for 24 h I with and without NGF in DRG culture medium or in presence of Aldh1a1$^{-/-}$ secretome (1/1 DRG culture medium, v/v) with and without blocking EFNA5 antibody (1 μg/mL). Asterisks indicate P<0.05 between different groups; Mann-Whitney U test.

FIGS. 4A and 4B show immunohistochemical analysis of peripherin protein levels in axons of animal groups in Study 3. FIG. 4A: Representative images of peripherin immunoreactive areas in nerves found in paraffin-embedded iAb fat from mice injected with vehicle and encapsulated WT and Aldh1a1$^{-/-}$ cells at 20× magnification. Arrows indicate examples of peripherin-positive axons in nerves at 40× magnification. 'C' indicates empty core of microcapsules because encapsulated cells are attached at the inner surface of capsules. The 'A' letters show examples of adipocytes. FIG. 4B: Peripherin was analyzed by Western blot in whole homogenized iAb fat pad from mice in Study 2. Bars show peripherin levels from same tissues normalized to β-actin levels (n=4). An asterisk indicates significant difference between empty and Aldh1a1$^{-/-}$ groups (P<0.05; Mann-Whitney U test). FIG. 4C: Immunohistochemical analysis of tyrosine hydroxylase (brown) protein levels in sympathetic axons of animal groups in Study 4. Note that tyrosine hydroxylase-positive areas are found within nerves (40×) or in areas containing numerous small multilocular adipocytes.

FIG. 5A to 5I show retinoids regulate the LTA axon guiding secretome via ephrin A5. FIG. 5A: DRG neurons were cultured in DRG culture medium with secretome from Aldh1a1$^{-/-}$ adipocytes (1/1, v/v) that were treated with or without RA (100 nM). RA was added to Aldh1a1$^{-/-}$ differentiation medium (Day 0, 2, 5). To prepare this secretome, medium was collected for last 24 hours. Representative images were selected from three independent experiments. Average neurite growth indices were measured by XTI microscopy in DRG neurons in DRG culture medium containing veh (white bar), NGF (vertical lined bar), or Aldh1a1$^{-/-}$ secretome treated without (black bar) or with RA (hatched bar). An asterisk indicates P<0.05; Mann-Whitney U test. FIG. 5B: 3T3-L1 adipocytes (n=3) were cultured in differentiation medium for 4 days. At day 5, medium was replaced by UV-treated 1% FBS-contained DMEM with and without Rald (30 nM). 24 hrs post stimulation, cells were harvested for mRNA. The gene expression was measured by the customized NanoString mouse innervation panel. An asterisk indicates P<0.05; Mann-Whitney U test. FIGS. 5C and 5D: 3T3-L1 adipocytes were cultured in differentiation medium for 4 days. At day 5, medium was replaced by UV-treated 1% FBS-containing DMEM with and without TTNPB (50 nM) or BMS493 (100 nM). 24 hrs post stimulation, cells were harvested for mRNA. Gene expression was measured by the NanoString mouse innervation panel. Data (mean±SD, n=3) were normalized to levels found in the non-treated control (100%, dashed line). An asterisk indicates P<0.05; Mann-Whitney U test. FIG. 5E: WT and Aldh1a1$^{-/-}$ preadipocytes were differentiated for 6 days. Protein levels of ephrin-A5 ligand (EFNA5) in medium EFNA5 and β-actin in cell lysates were analyzed by Western blot at Day 0, 2, 4, and 6. FIG. 5F: Plasma from WT and Aldh1a1$^{-/-}$ mice (Table 1, Study 4) was measured by EFNA5 ELISA (n=5 per group) Table 1, Study 4. FIG. 5G: Representative images and neuron growth indexes were obtained by XTI microscopy in DRGs neurons cultured in DRG culture medium with (dashed bars) and without (white bars) recombinant EFNA5 (30 ng/mL) for 24 hours. An asterisk indicates P<0.05; Mann Whitney, U test (n=3). FIG. 5H: Tyrosine hydroxylase (TH) protein levels was analyzed in whole subcutaneous (Western blot insert) and iAb fat pads from mice injected with PBS (n=3) or EFNA5 (n=4, Table 1, Study 5) by Western blot. Data are normalized to β-actin levels. An asterisk indicates P<0.05 difference between groups (mean±SD), Mann-Whitney U test. FIG. 5I: Heat (metabolic rate) was measured in PBS- and EFNA5-injected mice from Study 4 after 4° C. exposure by an open circuit indirect calorimetry treadmill (basal metabolic rate for 42 h is shown in FIG. 9C). The asterisk indicates P<0.04 significance between groups (n=4/group, mean±SEM); Mann-Whitney U test.

FIG. 6A: ALDHA1 is an intracrine regulator of axon guidance capacity in WAT. The expression of ALDH1A1 in unilocular iAb adipocytes generate RA, which blocks expression of Efna5 and Epha4 by RAR dependent pathway. In the absence of Aldh1a1, white adipocyte undergo thermogenic differentiation autonomously, which results in expression of Efna5 and Epha4 and LTA molecules and their secretion. These LTA secretome stimulate growth of TH-positive axons that induce lipolysis in monolocular adipocytes in tissue. Lipolysis by ATGL induces thermogenic modification in these adipocytes via PPARa-dependent mechanism. This newly-formed multilocular thermocytes produce LTA secretome. FIG. 6B: Schematic for bidirectional communication between adipocytes and CNS. Previous work showed the secretion of SEMA3A from WAT. SEMA3A secretion was decreased during fasting inducing physiological lipolysis. Aldh1a1$^{-/-}$ thermocytes secrete LTA-axon growth factors including ENFA5 with stimulate outgrowth of axons in the remodeled WAT. Activated sympathetic axons release neurotransmitters activating lipolysis and thermogenesis via β-adrenergic pathway. NGF is secreted at similar levels by WAT WT adipocytes and Aldh1a1$^{-/-}$ thermocytes.

FIG. 9A: Representative images show ~25% of area used for the automatic quantification of neuronal parameters in FIG. 3 per one condition. An image in FIG. 3A shows enlarged single square image that was randomly selected as a representative image from (n=9). FIG. 9B: Secreted EFNA5 levels in the medium from 3T3-L1 preadipocytes and adipocytes differentiated for 4d were analyzed by ELISA. FIG. 9C: Basal metabolic rate (heat) was measured in PBS- and EFNA5-injected mice from Table 1, Study 4 by an open circuit indirect calorimetry treadmill. FIG. 9D: Ucp1 expression levels in 3T3-L1 cells differentiated with or without recombinant EFNA5 (10 ng/mL) for 4 days. Expression was measured by RT-PCR and normalized by 18S.

FIG. 11A: Expression heat map reveals differences in Ereg expression between WT and Aldh1a1$^{-/-}$ preadipocytes (n=3 per group). Microarray gene analysis was performed using Affymetrix microarray. FIG. 11B: Ereg expression was measured in non-differentiated and differentiated (day 5) 3T3-L1 adipocytes (Mann-Whitney test) using a customized NanoString mouse panel. FIG. 11C: Ereg expression was measured in differentiated (day 5) 3T3-L1 and Aldh1a1$^{-/-}$ adipocytes by Taqman and normalized to TATA box protein (TBP). FIG. 11D: Plasma EREG concentrations were measured in mice from Study 1 by western blot. Representative Western blot shows image of four animals per group containing precursor and cleaved form of EREG. FIG. 11E: Plasma EREG concentrations were measured and quantified in iAb of WT and ob/ob mice from Study 2 by western blot (n=5 per each group). Representative western blot shows image of four animals per group containing precursor (43 kD) and active cleaved form (27 kd) of EREG. FIG. 11F: EREG was measured in iAb, subcutaneous and brown fat by western blot. Fat pads were dissected from WT mice on regular chow (Study 1). FIG. 11G: Ucp2 and Ucp1 expression was measured in differentiated 3T3-L1 adipocytes (day 5) stimulated with vehicle (PBS) or recombinant EREG (50 ng/mL) added in the differentiation medium I and II. Expression level were measured by Taqman and normalized by TBP. FIGS. 11H and 11I: HEK293 cells were transiently transfected with PPARα-LBD, UASTK-luciferase, and renilla. Cells were stimulated with indicated concentrations of recombinant EREG with or without HSL inhibitor (HSL-1, CAY10499, 10 μM) for 12 hrs #, indicates statistical difference between control and EREG-stimulated PPARα-LBD activation; *, shows statistical difference between samples non-treated and treated with HSL-I. FIG. 11I: PPARα-LBD activation in HEK293 cells stimulated with and without EREG (50 ng/mL) and inhibitors for EGFR (EGFR-I, AG1478, 10 μM), MAPK (MAPK-I, UO126, 10 μM), HSL-I, SRC (SRC-I, AZM475271, 1 μM), and PI3K (PI3K-I, wortmannin, 100 nM) inhibitors. Data represents % PPARα-LBD activation. Asterisks indicate significant difference (p<0.05) compared to vehicle control, #, indicates statistical difference between PPARα-LBD activation by EREG alone and in the presence of inhibitors. Data represent mean±SD. The Mann-Whitney test was used throughout these studies for group comparison.

FIG. 12A: DIO WT males (n=7/group, Study 3) were injected with 100 μL PBS (Veh) without or with EREG (20 ng) into both epididymal iAb fat pads every other day for 2 weeks. Body temperature (thermomap) was scanned using infrared camera (79R5437 FLK-TIS 9HZ Thermal Imaging Scanner: Fluke, WA) in four mice per group. Arrow indicates the injected areas and an increased temperature in the injected iAb areas in mice treated with EREG, but not with PBS. Right panel shows subtracted images from control and EREG treated groups. Arrow indicates the injected areas and an increased temperature. Thermomap obtained after cold exposure was subtracted from the thermomap obtained at ambient temperature using ImageJ Software. FIG. 12B: Mice from Study 3 (n=4/group) were placed in individual metabolic cages equipped with CLAMS. Metabolic rate in PBS-injected (open circles) and EREG-injected (closed red circles) mice were analyzed at room temperature (RT) and during cold exposure. Data represent mean±SEM. Asterisks showed statistical difference between control and EREG-treated group. FIG. 12C: Metabolic rate (MR) kinetics during cold exposure was used to measure time until control (white bar) and EREG-treated mice (black bar) reached MR maximum in PBS-treated. FIG. 12D: Locomotor activity in X, Y, Z, directions at RT and during cold exposure was measured by CLAMS in control (white bar) and EREG-treated mice (black bar). D and L represent 'dark' and 'light' cycles. FIG. 12E: Respiratory exchange ratio (RER) during cold exposure in PBS-injected (open circles) and EREG-injected (closed circles) mice.

FIG. 13A: Initial and final body weight comparison in Veh- and EREG treated DIO mice from Study 3. HF-fed. The changes in initial and final body weights within groups (n=7/group) was examined by paired Student's t-test. Triangles, weight of individual mice in control group. Circles, weight of individual mice in EREG-treated group. Bars showed mean±SD of weight gain and average food intake in Veh- (white) and EREG-treated (black) groups. FIG. 13 to 13D: Organ weight normalized to body weight for liver (FIG. 13B, mean±SD), BAT and subcutaneous WAT (FIG. 13C, individual values), and iAb epididymal WAT (FIG. 13D, individual values). Line shows an average iAb to body weight ratio in Veh- and EREG-treated mice. FIG. 13E: Free, non-esterified fatty acids (NEFA) release using commercially available kit (mean±SD). FIG. 13F: Plasma TG, using commercially available kit (mean±SD).

FIGS. 14A to 14H and 14L: Markers for thermogenesis, adipogenesis, and inflammatory genes were analyzed using homogenates from whole iAb fat pads isolated from Veh- (white bars) and EREG-treated (black bars) DIO mice (Study 3). Gene expression was quantified using a customized NanoString panel. Data represent mean±SD, n.s.,—non-significant. FIG. 14I: LEP was measured in plasma in the same mice by ELISA. Data (mean±SD) are shown as percent to control (Veh, 100%) and is indicated as a dashed line. FIG. 14N: LEP release following stimulation of iAb fat explants (2 h) from WT mice with inhibitors of EGFR (10 µM) and MAPK (10 µM) in the presence or absence of EREG (50 ng/ml). Data (mean±SD) are shown as percent to control (Veh, 100%).

FIGS. 15A to 15I show leptin deficiency abolishes thermogenic effects of EREG in vivo. FIG. 15A: Weight kinetics in ob/ob mice (n=5/group) injected with PBS (Veh) (open circles) and without EREG (closed circles) Study 4. The difference in weight gain before and after treatment is shown as mean±SD for Veh- (white bar) and EREG-treated ob/ob mice (black bar). Mice were pair-fed a high-fat diet throughout this study and consumed similar amount of food (insert). FIGS. 15B to 15D: Organ weight normalized to body weight for BAT (FIG. 15B), subcutaneous and iAb fat (FIG. 15C), liver (FIG. 15D). FIGS. 15E to 15H: Metabolic parameters were analyzed in Veh and EREG-injected mice (N=4/group) at RT and after cold exposure in metabolic cages equipped with CLAMS. RER (mean±SD) (FIG. 15E), locomotor activity (FIG. 15F) (mean±SD), and metabolic rate kinetics (FIG. 15G, 15H) were measured in Veh-treated (white bars, or open circles) and EREG-treated (black bars, or closed circles) ob/ob mice. D and L represent 'dark' and 'light' cycles. FIG. 15I: Expression of thermogenic and PPARa target genes in iAb fat from ob/ob mice (same Study 4) was performed using NanoString mouse metabolic panel. Data show mean±SD. The difference was not significant.

FIGS. 16A to 16M show EREG improves glucose uptake in ob/ob mice and in mouse and human preadipocytes. FIG. 16A: GTT was performed on fasting Veh (open circles) and EREG-treated (closed circles) ob/ob (N=5/group, Study 4) mice (12 hrs) using a single 25% dextrose injection (0.004 mL/g body weight). Asterisks indicate significant differences between Veh- and EREG-treated groups. FIG. 16B: ITT was performed in the same mice groups. FIGS. 16C to 16C: Fluorescently-labelled (FD) glucose uptake was measured in mouse 3T3-L3 preadipocytes. FIG. 16C: Preadipocytes were treated with vehicle, insulin (ins), EREG and forskolin for 30 mins. Data show mean±SD. Asterisks represent significant differences compared to vehicle (P<0.05). FIG. 16D: Dose dependent increase in FD-glucose uptake by 3T3-L1 preadipocytes stimulated with different EREG concentrations. Data are shown as a percent of Veh-treated control. FIGS. 16E to 16G: FD-glucose uptake was measured in omental iAb preadipocytes isolated from lean (FIG. 16E) and obese insulin-resistant (FIG. 16F, 16G) patients in the presence of insulin, EREG, and forskolin. Data show mean±SD (FIG. 16G, 16K). Omental preadipocytes from obese insulin resistant man (FIG. 16G) and woman (FIG. 16K) were also stimulated with and without EREG in presence and absence of EGFR and MAPK inhibitors for 30 mins. Data were calculated as a percent to non-stimulated control (Veh, 100%, dash line) and shown as a mean±SD. Asterisks represent significant differences compared to vehicle (P<0.05), Mann-Whitney U test. FIG. 16H: FD-glucose uptake was measured in mouse 3T3-L1 preadipocytes with or without EREG (50 ng/mL) and inhibitors of MAPK and PI3K (MAPK-I, 10 uM, and PI3K-I, 200 nM). Data (mean±SD) are shown as percent to control (Veh 100%). Dashed line shows FD glucose uptake mediated by insulin (Ins, 10 µg/mL). P<0.05 indicate significant differences between EREG-treated and PI3K-I/EREG treated groups. Asterisks indicate significant differences between vehicle control and treatments with inhibitors. FIG. 16I: Phosphorylated (p-Akt) and non-phosphorylated (total) Akt protein levels were measured in mouse 3T3-L1 preadipocytes stimulated with or without EREG (50 ng/ml), PI3K-I (200 nM) for 20 mins by western blot and quantified by ImageJ Software. Data show mean±SD, n=4. Asterisks represent significant differences compared to vehicle (P<0.05). FIG. 16J: Plasma insulin levels in fasting Veh and EREG-treated ob/ob mice measured by ELISA. FIG. 16L: Phosphorylated Akt protein levels were measured by western blot in human preadipocytes from an obese woman stimulated with or without EREG (50 ng/ml) and PI3K-I (200 nM) for 20 mins. Data show mean±SD, n=4. Asterisks represent significant differences compared to vehicle (P<0.05). Mann-Whitney U test. FIG. 16M: Schematic depicting two different pathways involved in EREG-mediated induction of thermogenesis and glucose uptake. EREG acts via MAPK to induce leptin secretion and also stimulates hormone sensitive lipase (HSL). HSL hydrolyzes free fatty acids activating PPARα activation. EGF, EGFR inhibition, or MAPK inhibition streamlines EREG-dependent PI3K/Akt activation that increase glucose uptake.

FIG. 18F: Calculated and experimental powder diffraction spectra. FIGS. 18G to 18I: TEM imaging of nanotube assemblies.

FIG. 19 shows TEM images of Fmoc-KFKK(Bz)-NH2, assembled in PBS (2.5 mM) showing twisted nanoribbons and nanofiber morphology.

FIG. 23A: EREG secretion from non-differentiated and differentiated human adipocytes from lean (n=3) and obese donors (n=5) were quantified using ELISA. P<0.05 indicates significant difference. Data represent mean±SD. The Mann-Whitney test was used for group comparison. FIG. 23B: Plasma EREG levels from lean (n=5) and obese donors (n=6) were measured by ELISA. FIGS. 23C and 23D: Correlation (Pearson test) between plasma EREG and weight (FIG. 23C) or BMI (FIG. 23D) in human donors (n=12).

FIG. 28A: Non-stimulated cells are shown in panel A. FIG. 28B: The cells we stimulated with solution of insulin tagged with fluorescent FITC (Insulin-FITC, 10 mg/m). FIG. 28C: The cells we stimulated with nanoscaffold 2 (1 mM). FIG. 28D: Cells were stimulated with same amount of insulin-FITC (10 mg/mL) that was bound to nanoscaffold 2 (1 mM). Insulin-FITC bound to nanoscaffold 2 refracted light and insulin-FITC/nanoscaffold complex appear yellow-brown solution on the image. All images were taken at 20× magnification.

FIG. 30A: GLUT4 (white vesicles) in cells (arrow) treated with vehicle are mainly in the cytosol. FIG. 30B: GLUT4s are translocated from cytosol to membrane with solution of insulin (10 μg/mL). FIG. 30C: Cells treated with nanoscaffold only (10 μM) did not show GLUT4 translocation. FIG. 39D: Cells were stimulated with same amount of insulin (10 μg/mL) that was bound to nanoscaffold 2 (10 μM) showed translocation of GLUT4. All images were taken at 60× magnification.

FIG. 33A is an illustration of oxidative crosslinking in self-assembled nanotubes. FIG. 33B shows a TEM of nanotubes after oxidative crosslinking in PBS (pH=7.4).

FIG. 37A shows mean±SEM of six independent experiments. Asterisks represent significant differences compared to vehicle (P<0.05, one-way ANOVA). Dose dependent increase in FD-glucose uptake by 3T3-L1 preadipocytes stimulated with different EREG concentrations. FIG. 37B shows a percent of Veh-treated control (100%, n=6 per concentration).

FIGS. 40A to 40G show chemical structures and charge of AAC1-7 molecules and their electron microscopy nanostructure after self-assembly.

FIGS. 54E and 54F show fluorescent image of FITC insulin bound with AAC2 fibers at excitation (402 nm) and emission (487 nm) using confocal microscopy.

FIG. 57B shows onset of hyperglycemia characteristic for type 1 diabetes in STZ mice prior to treatment with free AAC2, free INS, or AAC2-INS combination.

FIG. 60F shows that significantly increased expression of Glutathone peroxidase (GPX6) in STZ mice treated with free INS is abolished in AAC2-INS-treated animals. GPX6 a key antioxidant enzyme induced in the liver in response to oxidative stress.

DETAILED DESCRIPTION

Definitions

Figure 1A:
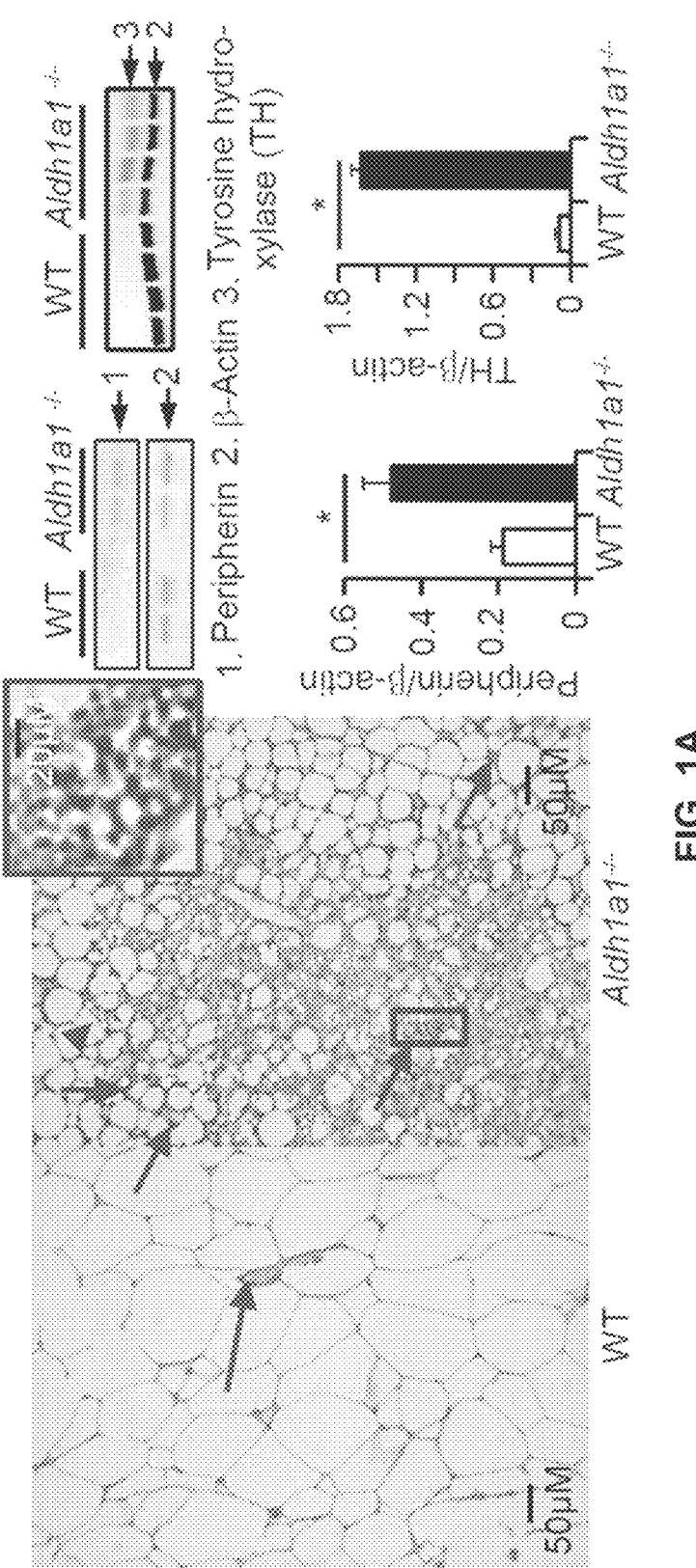
Figures 1B, 1C:
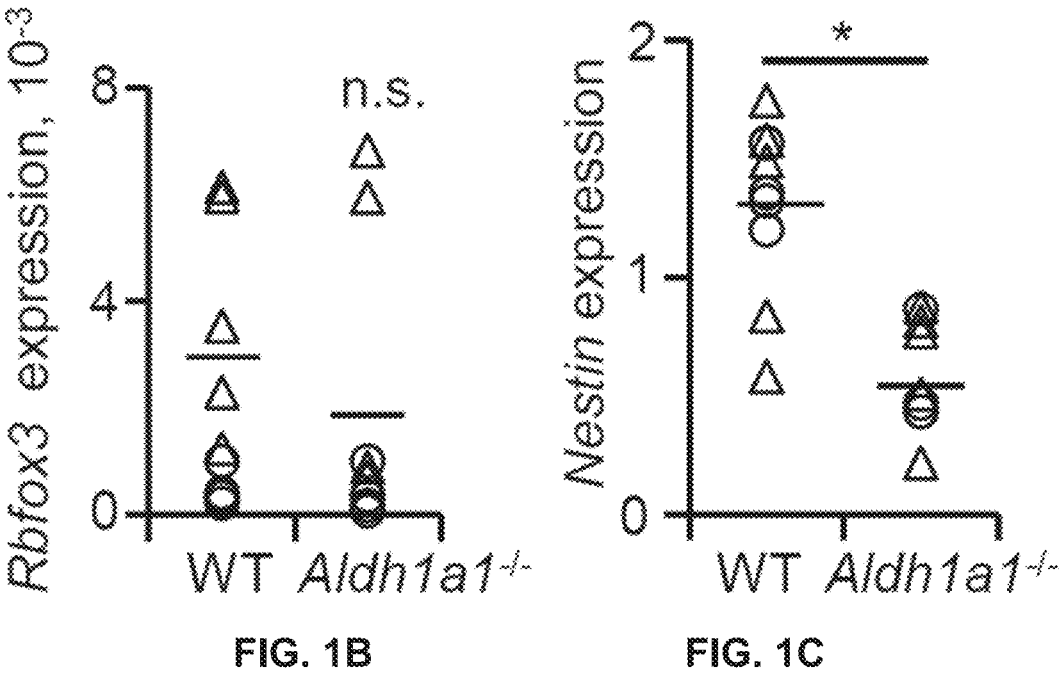
Figures 1D, 1E:
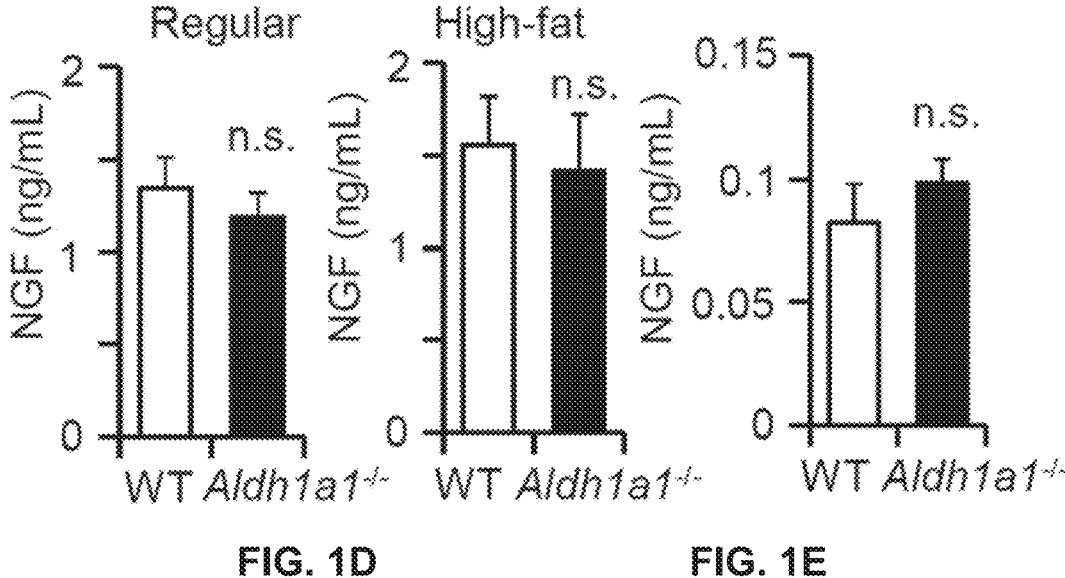
Figure 1F:
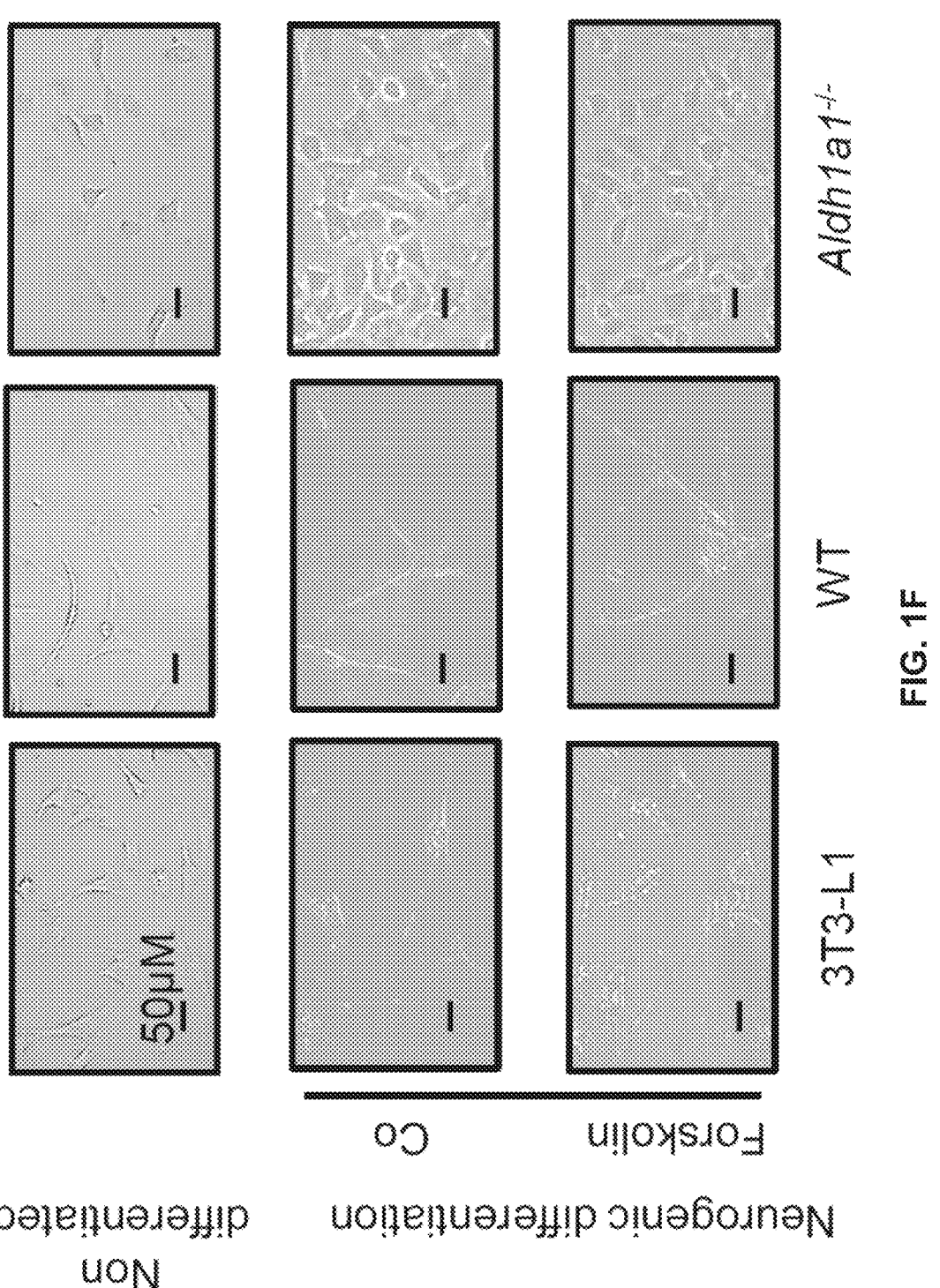

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

As used herein, the term "amphiphilic" means the ability to dissolve in both water and lipids/apolar environments. Typically, an amphiphilic compound comprises a hydrophilic portion and a hydrophobic portion. "Hydrophobic" designates a preference for apolar environments (e.g., a hydrophobic substance or moiety is more readily dissolved in or wetted by non-polar solvents, such as hydrocarbons, than by water). As used herein, the term "hydrophilic" means the ability to dissolve in water.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

When substituted, the substituents of a substituted group can include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen or deuterium, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents can be joined together to form a fused five-, six-, or seven-membered carbocyclic or heterocyclic ring consisting of zero to three heteroatoms, for example forming methylenedioxy or ethylenedioxy. An optionally substituted group can be unsubstituted (e.g., $-CH_2CH_3$), fully substituted (e.g., $-CF_2CF_3$), monosubstituted (e.g., $-CH_2CH_2F$) or substituted at a level anywhere in-between fully substituted and monosubstituted (e.g., $-CH_2CF_3$). Where substituents are recited without qualification as to substitution, both substituted and unsubstituted forms are encompassed. Where a substituent is qualified as "substituted," the substituted form is specifically intended.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as $-OZ^1$ where $Z^1$ is alkyl as defined above.

The term "alkenyl" as used herein is a hydrocarbon group of from 2 to 24 carbon atoms with a structural formula containing at least one carbon-carbon double bond. Asymmetric structures such as $(Z^1Z^2)C=C(Z^3Z^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "nonheteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms.

Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C=O, which is also referred to herein as a "carbonyl."

The terms "amine" or "amino" as used herein are represented by the formula —$NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —C(O)$NZ^1Z^2$.

The term "carboxylic acid" as used herein is represented by the formula —C(O)OH. A "carboxylate" or "carboxyl" group as used herein is represented by the formula —C(O)O—.

The term "ester" as used herein is represented by the formula —OC(O)$Z^1$ or —C(O)O$Z^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1$O$Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1$C(O)$Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "lower," as used herein, alone or in a combination, where not otherwise specifically defined, means containing from 1 to and including 6 carbon atoms.

The term "lower alkyl," as used herein, alone or in a combination, means C1-$C_6$ straight or branched chain alkyl. The term "lower alkenyl" means $C_2$-$C_6$ straight or branched chain alkenyl. The term "lower alkynyl" means $C_2$-$C_6$ straight or branched chain alkynyl.

The term "lower aryl," as used herein, alone or in combination, means phenyl or naphthyl, either of which can be optionally substituted as provided.

The term "lower heteroaryl," as used herein, alone or in combination, means either 1) monocyclic heteroaryl comprising five or six ring members, of which between one and four said members can be heteroatoms chosen from O, S, and N, or 2) bicyclic heteroaryl, wherein each of the fused rings comprises five or six ring members, comprising between them one to four heteroatoms chosen from O, S, and N.

The term "lower cycloalkyl," as used herein, alone or in combination, means a monocyclic cycloalkyl having between three and six ring members. Lower cycloalkyls can be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four can be heteroatoms chosen from O, S, and N. Examples of lower heterocycloalkyls include pyrrolidinyl, imidazolidinyl, pyrazolidinyl, piperidinyl, piperazinyl, and morpholinyl. Lower heterocycloalkyls can be unsaturated.

The term "lower carboxyl," as used herein, alone or in combination, means —C(O)R, wherein R is chosen from hydrogen, lower alkyl, cycloalkyl, cycloheterolkyl, and lower heteroalkyl, any of which can be optionally substituted with hydroxyl, (O), and halogen.

The term "lower amino," as used herein, alone or in combination, refers to —NRR', wherein R and R' are independently chosen from hydrogen, lower alkyl, and lower heteroalkyl, any of which can be optionally substituted. Additionally, the R and R' of a lower amino group can combine to form a five- or six-membered heterocycloalkyl, either of which can be optionally substituted.

The term "nitro" as used herein is represented by the formula —$NO_2$.

The term "nanotube" is used herein in a general sense to refer to an elongated nanostructure. This term is meant to include nanobars, nanowhiskers, helixes, nanospheres, nanoparticles, and the like. In some examples, the nanotube is not a β-sheet.

The term "silyl" as used herein is represented by the formula —Si$Z^1Z^2Z^3$, where $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2Z^1$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)₂NH—.

The term "thiol" as used herein is represented by the formula —SH.

The term "thio" as used herein is represented by the formula —S—.

"R¹," "R²," "R³," "R″," etc., where n is some integer, as used herein can, independently, possess one or more of the groups listed above. For example, if R¹ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Thermogenic Molecules

The thermogenesis inducing molecules epiregulin, insulin-like growth factor-binding protein 4 (IGFBP4), insulin-like growth factor-binding protein 7 (IRBP7), glia maturation factor beta (GMFB), ephrin A5, ADAMT S9, and semaphorin 3E, as well as agents that promote or inhibit these molecules are disclosed. In some cases, the thermogenic molecule is a purified, synthetic, or recombinant protein. Therefore, amino acid and nucleic acid sequences are disclosed that can be used to produce these thermogenesis inducing molecules. These molecules can be inhibited using binding agents, such as antibodies, decoy receptors, and the like. Other agonists and antagonists are known or can be identified using routine methods.

Epiregulin

Epiregulin is a protein that in humans is encoded by the EREG gene. Epiregulin consists of 46 amino acid residues. Epiregulin is a member of the epidermal growth factor family. Epiregulin can function as a ligand of epidermal growth factor receptor (EGFR), as well as a ligand of most members of the ERBB (v-erb-b2 oncogene homolog) family of tyrosine-kinase receptors. Epiregulin recruits MAPK via EGFR1. Epiregulin also uses an alternative pathway. In a similar fashion to insulin, epiregulin mobilizes glucose uptake via PI3K/Akt.

Human proepiregulin preprotein, which is cleaved to form epiregulin, can have the amino acid sequence set forth in Accession No. NP_001423. Human proepiregulin preprotein can be encoded by the nucleic acid sequence set forth in Accession No. NM_001432. Recombinant Human Epiregulin Protein is also commercially available from R&D Systems (#1195-EP; Minneapolis, MN), from PeproTech (#100-04; Rocky Hill, NJ), and from BioLegend (#550206; San Diego, CA). Recombinant Mouse Epiregulin Protein is commercially available from R&D Systems (#1068-EP; Minneapolis, MN), Sigma (#E8780; St. Louise, MO), Sino Biological Inc. (#50599-M01H; Beijing, China).

Antibodies that bind and in some cases inactivate epiregulin can be produced and are commercially available from R&D Systems (Human: #AF1195, MAB1425; Mouse:

AF1068; MAB1068; Minneapolis, MN), Santa Cruz (Mouse: #376284; Dallas, TX).

Insulin-Like Growth Factor-Binding Protein 4 (IGFBP4)

Insulin-like growth factor-binding protein 4 (IGFBP4) is a protein that in humans is encoded by the IGFBP4 gene. This gene is a member of the insulin-like growth factor binding protein (IGFBP) family and encodes a protein with an IGFBP domain and a thyroglobulin type-I domain. The protein binds both insulin-like growth factors (IGFs) I and II and circulates in the plasma in both glycosylated and non-glycosylated forms.

Human IGFBP4 can have the amino acid sequence set forth in Accession No. NP_001543. Human IGFBP4 can be encoded by the nucleic acid sequence set forth in Accession No. NM_001552. Recombinant Human IGFBP4 is also commercially available from PeproTech (#350-05B, Rocky Hill, NJ), Advanced ImmunoChemical Inc. (#8-IGBP-rh; Long Beach, CA). Recombinant Mouse IGFBP4 is commercially available from R&D Systems (#8066 GB, Minneapolis, MN), Thermo Fisher Scientific (#50250-M08H, Waltham, MA), Sino Biological Inc. (#5LMO-8HL; Beijing, China).

Antibodies against human IGFBP4 are commercially available from R&D Systems (#AF804; MAB8041, Minneapolis, MN), Thermo Fisher Scientific (#PA5-25925, Waltham, MA) and mouse IGFBP4 from Abcam (#4253; Cambridge, MA), Santa Cruz (#13092; Dallas, TX).

Insulin-Like Growth Factor-Binding Protein 7 (IGFBP7)

Insulin-like growth factor-binding protein 7 (IGFBP7) is a protein that in humans is encoded by the IGFBP7 gene. The major function of the protein is the regulation of availability of insulin-like growth factors (IGFs) in tissue as well as in modulating IGF binding to its receptors. IGFBP7 binds to IGF with high affinity. It also stimulates cell adhesion. IGFBP7 has also been shown to interact with Insulin-like growth factor 1 and VPS24.

Human IGFBP7 can have the amino acid sequence set forth in Accession No. NP_001240764. Human IGFBP7 can be encoded by the nucleic acid sequence set forth in Accession No. NM_001253835. Recombinant IGFBP7 and antibodies are commercially available from R&D Systems [(Rec. Protein Human: #1334-B7; Mouse: #MAB2120-B7); (Antibodies Human: AF1334; Mouse: MAB2120); Minneapolis, MN).

Glia Maturation Factor Beta (GMFB)

Glia maturation factor beta (GMFB) is a nerve growth factor implicated in nervous system development, angiogenesis and immune function. GMFB is a protein that in humans is encoded by the GMFB gene.

Human GMFB can have the amino acid sequence set forth in Accession No. NP_004115. Human GMFB can be encoded by the nucleic acid sequence set forth in Accession No. NM_004124. Recombinant Human GMFB is also commercially available from Novoprotein (#CH77; Summit, NJ), PeproTech (#450-37; Rocky Hill, NJ), Abcam (#54243; Cambridge, MA). Human GMF-beta Antibodies can be purchased from R&D Systems (#MAB1276; Minneapolis, MN), AssayPro (#30101-05171; St. Charles, MO) and mouse GMF-beta antibodies from ProteinTech (#10690-1-AP; Rosemont, IL), Abcam (#55063; Cambridge, MA).

Ephrin A5

Ephrin-A5 is a protein that in humans is encoded by the EFNA5 gene. Ephrin-A5 is a glycosylphosphatidylinositol (GPI)-anchored protein of the ephrin-A subclass of ephrin ligands that binds to the EphA subclass of Eph receptors. Ephrin-A5 has also been shown to bind to the EphB2 receptor.

Human Ephrin-A5 can have the amino acid sequence set forth in Accession No. NP_001953. Human Ephrin-A5 can be encoded by the nucleic acid sequence set forth in Accession No. NM_001962. Recombinant Ephrin-A5 is also commercially available from R&D Systems (Human #374-EA; Mouse #7396, Minneapolis, MN), Novoprotein (Human #CJ76; Mouse #CD23; Summit, NJ), Thermo Fisher Scientific (Human #10192-H02H; Mouse #50597-M08H; Waltham, MA) and Ephin-A5 antibodies from R&D Systems (#AF3743; BAF3743; Minneapolis, MA), Abcam (#70114; Cambridge, MA), Santa Cruz (#6075; Dallas, TX).

ADAMTS9

A disintegrin and metalloproteinase with thrombospondin motifs 9 (ADAMTS9) is an enzyme that in humans is encoded by the ADAMTS9 gene.

Human ADAMTS9 can have the amino acid sequence set forth in Accession No. NP_891550. Human ADAMTS9 can be encoded by the nucleic acid sequence set forth in Accession No. NM_182920. Recombinant Human ADAMTS9 protein is commercially available from Novus Biologicals (#NBP1-82915PEP; Littleton, CO), MyBioSource (#MBS1384928; San Diego, CA).

Antibodies that bind and in some cases inactivate ADAMTS9 can be produced and are commercially available from Sigma-Aldrich (#HPA028567; St. Louis, MO), Thermo Fisher Scientific (#PA1-1760; Waltham, MA), Abcam (#32565, Cambridge, CA), Santa Cruz (#21502; Dallas, TX).

Semaphorin 3E Semaphorin-3A is a protein that in humans is encoded by the SEMA3A gene.

Human semaphorin-3A can have the amino acid sequence set forth in Accession No. NP_006071. Human Semaphorin-3A can be encoded by the nucleic acid sequence set forth in Accession No. NM_006080. Recombinant human semaphorin-3A is also commercially available from R&D Systems (#3239-S3B; Minneapolis, MN)), EMD Millipore (#GF240; Billerica, MA), MyBioSource (#MBS692128; San Diego, CA), Abnova (#H00010371-Q01; Taipei City, Taiwan).

Antibodies that bind and in some cases inactivate semaphorin-3A can be produced and are commercially available from R&D Systems (#3239-S3; Minneapolis, MN), Abcam (#23393; Cambridge, CA), Santa Cruz (#1146; #1148; Dallas, TX), Thermo Fisher Scientific (#PA5-14857; Waltham, MA).

Complement C3

Recombinant C3 protein and its cleavage fragments are commercially available from Novus Biologicals (Littleton, CO, Cat No P3343)

Pharmaceutical Compositions

Disclosed are pharmaceutical compositions containing therapeutically effective amounts of one or more of the disclosed thermogenic molecules or inhibitors thereof and a pharmaceutically acceptable carrier. Pharmaceutical carriers suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. For example, the compounds may be formulated or combined with known NSAIDs, anti-inflammatory compounds, steroids, and/or antibiotics, inhibitors of ERB receptors.

The compositions contain one or more thermogenic molecules or inhibitors thereof, provided herein. The thermogenic inducers or inhibitors thereof, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the thermogenic inducers or inhibitors thereof are formulated into pharmaceutical compositions using techniques and procedures well known in the art (See, e.g., Ansel, Introduction to Pharmaceutical Dosage Forms, 4th Edition, 1985, 126).

In one embodiment, the compositions are formulated for single dosage administration. To formulate a composition, the weight fraction of compound is dissolved, suspended, dispersed or otherwise mixed in a selected carrier at an effective concentration such that the treated condition is relieved or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro, ex vivo and in vivo systems, and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art.

Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

In one embodiment, active compound is administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 2 µg to about 100 µg per kg of body weight. Alternatively, the amount of active compound administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

The pharmaceutical compositions described herein can be formulated for action without release or controlled release including immediate release, delayed release, extended release, pulsatile release, and combinations thereof.

For parenteral administration, the compounds, and optionally one or more additional active agents, can be incorporated into microparticles, nanoparticles, or combinations thereof that provide controlled release. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the compounds and/or one or more additional active agents can be incorporated into polymeric microparticles which provide controlled release of the drug (s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including, but not limited to, fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material which is normally solid at room temperature and has a melting point of from about 30 to 300° C.

In some cases, it may be desirable to alter the rate of water penetration into the microparticles. To this end, rate-controlling agents may be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropylcellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins which are water insoluble, such as zein, can also be used as materials for the formation of drug containing microparticles. Additionally, proteins, polysaccharides and combinations thereof which are water soluble can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug containing microparticles can be achieved through known pharmaceutical formulation techniques. In the case of formulation in alginate poly-L-lysines, fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads.

For some carrier materials it may be desirable to use a solvent evaporation technique to produce drug containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin (Cortesi, R., et al., *Biomaterials* 19 (1998) 1641-1649). Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water soluble protein can be spray coated onto the microparticles and subsequently cross-linked by the one of the methods described above. Alternatively, drug containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

Self-Assembled Nanostructures

Also provided herein are pharmaceutical compositions that comprise a self-assembled, biocompatible nanostructure non-covalently associated with a therapeutic or diagnostic peptide or peptidomimetic. The biocompatible nanostructure can enhance the stability of the non-covalently associated therapeutic or diagnostic peptide or peptidomimetic, thereby improving the efficacy of the therapeutic or diagnostic peptide or peptidomimetic upon administration to a subject in need thereof.

The biocompatible nanostructure can be any suitable nanostructure formed from the self-assembly of an organic small molecule. The organic small molecule can be, for example, a small molecule that includes one or more moieties (e.g., amino acid residues) that facilitates self-assembly of the small molecules in aqueous solution. For example, the organic small molecule can include one or more amino acid residues that drives β-sheet aggregation in aqueous solution. The organic small molecule can further include one or more hydrophobic moieties in combination with the one or more amino acid residues so as to drive the amphiphilic association of the small molecules in aqueous solution. The biocompatible nanostructure can be, for example, a self-assembled, biocompatible nanotube, a self-assembled, biocompatible nanofiber, a self-assembled, biocompatible nanosheet, a self-assembled, biocompatible nanoribbon, a self-assembled, biocompatible nanobelt, a self-assembled biocompatible matrix, or a self-assembled, biocompatible nanoring.

In some embodiments, the biocompatible nanostructure can be formed from the self-assembly of a peptide conjugate. Peptide conjugates capable of self-assembling in aqueous solution to form nanostructures are known in the art. Suitable peptide conjugates can include a hydrophobic moiety linked to an amino acid or peptide. For example, the peptide conjugate can be a compound represented by Formula I.

$$\text{D-L-AA} \qquad\qquad (I)$$

where D represents a hydrophobic moiety, L represents an optional linker moiety, and AA represents an amino acid moiety (e.g., a single amino acid or a peptide).

Hydrophobic Moieties

The hydrophobic moiety can be any suitable hydrophobic moiety. In combination with the one or more amino acid residues in the conjugate, the hydrophobic moiety can serve to drive the amphiphilic association of the small molecules in aqueous solution.

In certain cases, the hydrophobic moiety can comprise an aromatic moiety that can drive self-assembly of the conjugate in aqueous solution via pi-stacking. For example, the hydrophobic moiety can comprise a polycyclic aromatic moiety, such as a naphthalene, anthracene, pentacene, perylene, or rylene moiety (e.g., perylene, naphthalene, anthracene, pentacene, perylenediimines (PDIs), naphthalene diimides (NDIs), vat red 29 dye, vat red 190, vat red 149, vat red 179, perylene black 31, terrylene, quarterrylene, etc.). In certain cases, the hydrophobic moiety can comprise a heterocyclic moiety, such as a coumarin moiety, quinoline moiety, isoquinoline moiety carbazole moiety, or acridine moiety. In certain cases, the hydrophobic moiety can comprise one or more polymerizable subunits (e.g., acetylene moieties, disulfide bonds, precursors for click chemistry, etc.).

In certain embodiments, the hydrophobic moiety can comprise a hydrophobic drug. The hydrophobic drug can be any drug that is poorly soluble in water, i.e., having a water solubility less than about 10 mg/mL (e.g., less than 1 mg/mL, less than 0.1 mg/mL, or less than 0.01 mg/mL). In some embodiments, the hydrophobic drug can have a c Log P of five or more.

Suitable examples of hydrophobic drugs include, but are not limited to, ROCK inhibitors, SYK-specific inhibitors, JAK-specific inhibitors, SYK/JAK or Multi-Kinase inhibitors, MTORs, STAT3 inhibitors, VEGFR/PDGFR inhibitors, c-Met inhibitors, ALK inhibitors, mTOR inhibitors, PI3K5 inhibitors, PBK/mTOR inhibitors, p38/MAPK inhibitors, antibiotics, antivirals, antifungals, antiparsitic agents, blood pressure lowering agents, cancer drugs, immunosuppressants, psychiatric medications, dermatologic drugs, lipid lowering agents, anti-depressants, anti-diabetics, anti-epileptics, anti-gout agents, anti-hypertensive agents, anti-malarials, antimigraine agents, anti-muscarinic agents, antithyroid gents, anxiolytic, sedatives, hypnotics, neuroleptics, β-blockers, cardiac inotropic agents, diuretics, anti-parkinsonian agents, gastro-intestinal agents, histamine H-receptor antagonists, anti-anginal agents, opioid analgesics, sex hormones, lipophilic bioactive nutrients, and stimulants.

In certain examples, the hydrophobic drug is a steroid. Steroids include for example, fluticasone, hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone, fluocinolone acetonide, flunisolide, fluorometholone, clobetasol propionate, loteprednol, medrysone, rimexolone, difluprednate, halcinonide, beclomethasone, betamethasone, betamethasone sodium phosphate, Ciclesonide, dexamethasone, dexamethasone sodium phosphate, dexamethasone acetate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, prednisolone acetate, prednisolone sodium phosphate, fluoromethalone, fluoromethalone acetate, loteprednol etabonate, and betamethasone phosphate, including the esters and pharmaceutically acceptable salts thereof.

In certain examples, the hydrophobic drug is a nonsteroidal anti-inflammatory drugs NSAID. Suitable NSAIDs can be, for example, bromfenac, diclofenac sodium, flurbiprofen, ketorolac tromethamine, mapracorat, naproxen, oxaprozin, ibuprofen, and nepafenac, including the esters and pharmaceutically acceptable salts thereof.

In still other examples, the hydrophobic drug can be besifloxacin, DE-110 (Santen Inc.), rebamipide, androgens (DHEA, testosterone, analogs, & derivatives having poor water solubility), estrogens (poorly water soluble compounds that are derivatives of estradiol, estriol, and estrone; e.g., estradiol, levonorgesterol, analogs, isomers or derivatives thereof), progesterone and progestins ($1^{(st)}$ through $4^{(th)}$ generation) with poor water solubility (e.g., norethindrone, analogs, and derivatives thereof, medroxyprogesterone, or tagaproget), and pregnenolone. Examples of progestins in various generations include: first generation (estrane) such as norethindrone, norethynodrel, norethindrone acetate, and ethynodiol diacetate; second generation (gonane) such as levonorgestrel, norethisterone, and norgestrel; third generation (gonane) such as desogestrel, gestodene, norgestimate, and drospirenone; and fourth generation such as dienogest, drospirenone, nestorone, nomegestrol acetate and trimegestone.

Other examples of hydrophobic drugs include 10-alkoxy-9-nitrocamptothecin; 17b-estradiol; 3'-azido-3'-deoxythymidine palmitate; 5-amino levulinic acid; ABT-963; aceclofenac; aclacinomycin A; albendazole; alkannin/shikonin; all-trans retinoic acid; alpha-tocopheryl acetate; AMG 517; amprenavir; aprepitant; artemisinin; azadirachtin; baicalein; benzimidazole derivatives; benzoporphyrin; benzopyrimidine derivatives; bicalutamide; BMS-232632; BMS-488043; bromazepam; bropirimine; cabamezapine; candesartan cilexetil; carbamazepine; carbendazim; carvedilol; cefditoren; cefotiam; cefpodoxime proxetil; Cefuroxime axetil; Celecoxib; Ceramide; Cilostazol; Clobetasol propionate; Clotrimazole; Coenzyme Q10; Curcumin; Cyclcoporine; Danazol; Dapsone; Dexibuprofen; Diazepam; Dipyridamole; docetaxel; Doxorubicin; Doxorubicin; Econazole; ER-34122; Esomeprazole; Etoricoxib; Etravirine; Everolimus; Exemestane; Felodipine; Fenofibrate; flurbiprofen; Flutamide; Furosemide; gamma-oryzanol; Glibenclamide; Gliclazide; Gonadorelin; Griseofulvin; Hesperetin; HO-221; Indomethacin; Insulin; Isoniazid; Isotretinoin; Itraconazole; Ketoprofen; LAB687; Limaprost; Liponavir; Loperamide; Mebendazole; Megestrol; Meloxicam; MFB-1041; Mifepristone; MK-0869; MTP-PE; Nabilone; Naringenin; Nicotine; Nilvadipine; Nimesulide; Nimodipine; Nitrendipine; Nitroglycerin; NNC-25-0926; Nobiletin; Octafluoropropane; Oridonin; Oxazepam; Oxcarbazepine; Oxybenzone; Paclitaxel; Paliperidone palmitate; Penciclovir; PG301029; PGE2; Phenytoin; Piroxicam; Podophyllotoxin; Porcine pancreatic lipase and colipase; Probucol; Pyrazinamide; Quercetin; Raloxifene; Retinoids; Resveratrol; Rhein; Rifampicin; Ritonavir; Rosuvastatin; Saquinavir; Silymarin; Sirolimus; Spironolactone; Stavudine; Sulfisoxazole; Tacrolimus; Tadalafil; Tanshinone; Tea polyphenol; Theophylline; Tiaprofenic acid; Tipranavir; Tolbutamide; Tolterodine tartrate; Tranilast; Tretinoin; Triamcinolone acetonide; Triptolide; Troglitazone; Valacyclovir; Verapamil; Vincristine; Vinorelbin-bitartrate; Vinpocetine; Vitamin-E; Warfarin; and XK469.

More examples of suitable hydrophobic drugs include, e.g., amphotericin B, gentamicin and other aminoglycoside antibiotics, ceftriaxone and other cephalosporins, tetracyclines, cyclosporin A, aloxiprin, auranofin, azapropazone, benorylate, diflunisal, etodolac, fenbufen, fenoprofen calcium, meclofenamic acid, mefanamic acid, nabumetone, oxyphenbutazone, phenylbutazone, sulindac, benznidazole, clioquinol, decoquinate, diiodohydroxyquinoline, diloxanide furoate, dinitolmide, furzolidone, metronidazole, nimorazole, nitrofurazone, ornidazole, and tinidazoie.

The hydrophobic drugs suitable for the methods of the invention can also be FDA-approved drugs with c Log P of five or more, such as the following: 2-(4-hydroxy-3,5-diiodobenzyl)cyclohexanecarboxylic Alpha-carotene; Alpha-cyclohexyl-4-hydroxy-3,5-3, 3',4',5-tetrachloro salicylanilide diiodohydrocinnamic acid; 4,6-bis(I-methylpentyl)resorcinol Vitamin E; 4,6-dichloro-2-hexylresorcinol Vitamin E acetate; Acitretin Alverine, Alverine Citrate; Adapalene Amiodarone; Alpha-butyl-4-hydroxy-3,5-diiodohydrocinnamic acid Astemizole Atiprimod dihydrochloride Chlorophyll, chlorophyll unk; Atorvastatin, atorvastatin calcium Chlorotrianisene; Benzestrol Chlorprothixene; Bepridil, bepridil hydrochloride Cholecalciferol Beta-carotene Cholesterol; Bexarotene Choline iodide sebacate; Bithionol Cinacalcet; Bitolterol, bitolterol mesylate Cinnarizine; Clindamycin palmitate, clindamycin; Bromthymol blue palmitate hydrochloride; Buclizine, buclizine hydrochloride Clofazimine; Bunamiodyl sodium Cloflucarban; Clomiphene, enclomiphene; Butenafine, butenafine hydrochloride zuclomiphene, clomiphene citrate; Butoconazole, butoconazole nitrate Clotrimazole; Calcifediol Colfosceril palmitate; Calcium oleate Conivaptan; Calcium stearate Cyverine hydrochloride, cyverine; Desoxycorticosterone trimethylacetate; Candesartan cilexetil desoxycorticosterone pivalate; Captodiame, captodiame hydrochloride Dextromethorphan polistirex; Cetyl alcohol Dichlorodiphenylmethane; Chaulmoogric acid Diethylstilbestrol; Chloramphenicol palmitate Diethylstilbestrol dipalmitate Chlorophenothane Diethylstilbestrol dipropionate Dimestrol Ethylamine oleate; Dimyristoyl lecithin, Etretinate; Diphenoxylate, atropine sulfate; diphenoxylate hydrochloride Fenofibrate; Dipipanone, dipipanone hydrochloride Fenretinide; Docosanol Flunarizine, flunarizine hydrochloride; Docusate sodium Fluphenazine decanoate; Domine Fluphenazine enanthate; Doxercalciferol Fosinopril, fosinopril sodium; Promo stanolone propionate Fulvestrant Dronabinol Gamolenic acid, gammalinolenic acid; Glyceryl stearate, glyceryl; Dutasteride monostearate; Econazole, econazole nitrate Gramicidin; Halofantrine, halofantrine; Vitamin D2, ergocalciferol hydrochloride; Ergosterol, Haloperidol decanoate; Estradiol benzoate Hexachlorophene; Estradiol cypionate Hexestrol; Estradioldipropionate, estradiol; dipropionate Hexetidine; Estradiol valerate Humulus; Estramustine Hydroxyprogesterone caproate; Ethanolamine oleate Hypericin; Ethopropazine, ethopropazine; hydrochloride Implitapide; Ethyl icosapentate, eicosapentaenoic; acid ethyl ester, ethyl Indigosol Indocyanine green Mitotane; locarmate meglumine Mometasone furoate; lodipamide Monoxychlorosene; lodoalphionic acid Montelukast, montelukast sodium; lodoxamate meglumine Motexafin gadolinium; lophendylate Myristyl alcohol; Isobutylsalicyl cinnamate Nabilone Itraconazole Naftifine, naftifine hydrochloride; Levomethadone Nandrolone decanoate; Linoleic acid, Nandrolone phenpropionate; N-myristyl-3-hydroxybutylamine; Lucanthone, lucanthone hydrochloride hydrochloride Img, n myristyl 3; Nonoxynol 9, nonoxynol, nonoxynol; Meclizine, meclizine hydrochloride 10, nonoxynol 15, nonoxynol 30, Meclofenamic acid, meclofenamate; meclofenamate sodium Octicizer; Mefenamic acid Octyl methoxycinnamate; Menthyl salicylate Oleic acid Mercuriclinoleate Omega 3 acid ethyl esters; Mercury oleate Orlistat; Mestilbol 5 mg, mestilbol Oxiconazole, oxiconazole nitrate; Methixene, methixene hydrochloride Oxychlorosene; Mibefradil, mibefradil dihydrochloride Pararosaniline pamoate; Miconazole Penicillin v hydrabamine; Mifepristone Perflubron Perhexiline, perhexiline maleate Rose bengal, rose bengal sodium Permethrin Sertaconazole; Vitamin K, phytonadione Sertraline, sertraline hydrochloride Pimecrolimus Sibutramine, sibutramine hydrochloride; Pimozide Rapamycin, sirolimus, rapamune; Polyethylene, Sitosterol, sitosterols; Sodium beta-(3,5-diiodo-4-; Polyvinyl n-octadecyl carbamate hydroxyphenyl)atropate; Sodium dodecylbenzenesulfonate ng; Porfimer, porfimer sodium dodecylbenzenesulfonic acid; Posaconazole Sodium oleate; Tetradecylsulfate, sodium tetradecyl; Potassium oleate sulfate; Potassium ricinoleate Sorbitan-sesquioleate; Potassium stearate Stearic acid; Prednimustine Sulconazole, sulconazole nitrate; Probucol Suramin, suramin hexasodium; Progesterone caproate Tacrolimus; Promethestrol dipropionate Tamoxifen, tamoxifen citrate; Pyrrobutamine phosphate Tannic acid; Quazepam Tazarotene; Quinacrine, quinacrine hydrochloride Telithromycin Quinestrol Telmisartan; Raloxifene, raloxifene hydrochloride Temoporfin; Ritonavir Temsirolimus, tezacitabine Terbinafine Tyropanoate, tyropanoate sodium; Terconazole Ubidecarenone, coenzyme Q1Q; Terfenadine Verapamil, dexyerapamil; Testosterone cypionate Verteporfin Testosterone enanthate Vitamin A acetate; Vitamin A palmitate; Testosterone phenylacetate; Tetradecylamine lauryl sarcosinate Zafirlukast Thioridazine Cetyl myristate; Thymol iodide Cetyl myristoleate Tioconazole Docosahexanoic acid, doconexent; Tipranavir Hemin Tiratricol Lutein; Tocopherols excipient Chlorophyll b from spinach Tolnaftate Gossypol; Tolterodine Imipramine pamoate; Toremifene, toremifene citrate Iodipamide meglumine; Alitretinoin, isotretinoin, neovitamin A; retinoic acid, tretinoin, 9-cis-retinoic Ondascora; Tribromsalan Zinc stearate; Phenylbutazone, phenylbutazone; Triolein 1125 isomer; Triparanol Bryo statin-1; Troglitazone Dexanabinol; Tyloxapol Dha-paclitaxel Disaccharide tripeptide glycerol; dipalmitoyl Tetraiodothyroacetic acid; and (NZ)—N-[10,13-dimethyl-17-(6-Oxiconazole nitrate methylheptan-2-yl)-Sarsasapogenin.

In a preferred aspect, the hydrophobic drug is Camptothecin or a Camphtothecin analog, 5 Fluorouracil, Taxol, or vinblastin.

Amino Acid Moieties (AA)

The hydrophobic moiety can be linked to a single amino acid residue or an amino acid residue of a peptide. This component is shown as AA in Formula I. The particular amino acid or peptide cab be hydrophilic so that the conjugate will self assemble in aqueous environments to form the nanostructure. When using a peptide, one or more amino acid residues in the peptide can be hydrophobic or neutral, as long as the overall peptide component is hydrophilic.

When a single amino acid residue is present in the conjugate, the preferred residues are arginyl, histidyl, lysyl, aspartyl, glutamyl, seryl, threonyl, cystyl, asparagyl, glutaminyl, prolyl, tyrosyl, methionyl, and tryptophanyl. These moieties can be attached to the hydrophobic by a linker at the amino group, the carboxylate group, or the side chain. In certain, examples, the amino acid residue is a lysyl.

When two amino acid residues are present in the conjugate and they are coupled by a peptide bond, the resulting dipeptide can contain any of the residues in Table 1 as long as the overall dipeptide is hydrophilic. For example, the dipeptide can comprise two arginyls, histidyls, lysyls, aspartyls, glutamyls, seryls, threonyls, cystyls, asparagyls, glutaminyls, prolyls, tyrosyls, methionyls, or tryptophanyls. In other examples the dipeptide comprises at least one of arginyl, histidyl, lysyl, aspartyl, glutamyl, seryl, threonyl, cystyl, asparagyl, glutaminyl, prolyl, tyrosyl, methionyl, or tryptophanyl.

In other examples, the dipeptide can comprise arginyl with alanyl, allosoleucyl, asparagyl, aspartyl, cystyl, glutamyl, glutaminyl, glycyl, histidyl, isolelucyl, leucyl, lysyl, methionyl, phenylalanyl, prolyl, pyroglutamyl, seryl, threonyl, tyrosyl, tryptophanyl, or valyl.

In other examples, the dipeptide can comprise histidyl with alanyl, allosoleucyl, arginyl, asparagyl, aspartyl, cystyl, glutamyl, glutaminyl, glycyl, isolelucyl, leucyl, lysyl, methionyl, phenylalanyl, prolyl, pyroglutamyl, seryl, threonyl, tyrosyl, tryptophanyl, or valyl.

In other examples, the dipeptide can comprise lysyl with alanyl, allosoleucyl, arginyl, asparagyl, aspartyl, cystyl, glutamyl, glutaminyl, glycyl, histidyl, isolelucyl, leucyl, methionyl, phenylalanyl, prolyl, pyroglutamyl, seryl, threonyl, tyrosyl, tryptophanyl, or valyl.

In other examples, the dipeptide can comprise aspartyl with alanyl, allosoleucyl, arginyl, asparagyl, cystyl, glutamyl, glutaminyl, glycyl, histidyl, isolelucyl, leucyl, lysyl, methionyl, phenylalanyl, prolyl, pyroglutamyl, seryl, threonyl, tyrosyl, tryptophanyl, or valyl.

In other examples, the dipeptide can comprise glutamyl with alanyl, allosoleucyl, arginyl, asparagyl, aspartyl, cystyl, glutaminyl, glycyl, histidyl, isolelucyl, leucyl, lysyl, methionyl, phenylalanyl, prolyl, pyroglutamyl, seryl, threonyl, tyrosyl, tryptophanyl, or valyl.

In other examples, the dipeptide can comprise seryl with alanyl, allosoleucyl, arginyl, asparagyl, aspartyl, cystyl, glutamyl, glutaminyl, glycyl, histidyl, isolelucyl, leucyl, lysyl, methionyl, phenylalanyl, prolyl, pyroglutamyl, threonyl, tyrosyl, tryptophanyl, or valyl.

In other examples, the dipeptide can comprise threonyl with alanyl, allosoleucyl, arginyl, asparagyl, aspartyl, cystyl, glutamyl, glutaminyl, glycyl, histidyl, isolelucyl, leucyl, lysyl, methionyl, phenylalanyl, prolyl, pyroglutamyl, seryl, tyrosyl, tryptophanyl, or valyl.

In other examples, the dipeptide can comprise cystyl with alanyl, allosoleucyl, arginyl, asparagyl, aspartyl, glutamyl, glutaminyl, glycyl, histidyl, isolelucyl, leucyl, lysyl, methionyl, phenylalanyl, prolyl, pyroglutamyl, seryl, threonyl, tyrosyl, tryptophanyl, or valyl.

In other examples, the dipeptide can comprise asparagyl with alanyl, allosoleucyl, arginyl, aspartyl, glutamyl, glutaminyl, glycyl, histidyl, isolelucyl, leucyl, lysyl, methionyl, phenylalanyl, prolyl, pyroglutamyl, seryl, cystyl threonyl, tyrosyl, tryptophanyl, or valyl.

In other examples, the dipeptide can comprise glutaminyl with alanyl, allosoleucyl, arginyl, asparagyl, aspartyl, glutamyl, glycyl, histidyl, isolelucyl, leucyl, lysyl, methionyl, phenylalanyl, prolyl, pyroglutamyl, seryl, cystyl threonyl, tyrosyl, tryptophanyl, or valyl.

In other examples, the dipeptide can comprise prolyl with alanyl, allosoleucyl, arginyl, asparagyl, aspartyl, glutamyl, glutaminyl, glycyl, histidyl, isolelucyl, leucyl, lysyl, methionyl, phenylalanyl, pyroglutamyl, seryl, cystyl, threonyl, tyrosyl, tryptophanyl, or valyl.

In other examples, the dipeptide can comprise tyrosyl with alanyl, allosoleucyl, arginyl, asparagyl, aspartyl, glutamyl, glutaminyl, glycyl, histidyl, isolelucyl, leucyl, lysyl, methionyl, phenylalanyl, prolyl, pyroglutamyl, seryl, cystyl, threonyl, tryptophanyl, or valyl.

In other examples, the dipeptide can comprise methionyl with alanyl, allosoleucyl, arginyl, asparagyl, aspartyl, glutamyl, glutaminyl, glycyl, histidyl, isolelucyl, leucyl, lysyl, phenylalanyl, prolyl, pyroglutamyl, seryl, cystyl threonyl, tyrosyl, tryptophanyl, or valyl.

In other examples, the dipeptide can comprise tryptophanyl with alanyl, allosoleucyl, arginyl, asparagyl, aspartyl, glutamyl, glutaminyl, glycyl, histidyl, isolelucyl, leucyl, lysyl, phenylalanyl, prolyl, pyroglutamyl, seryl, cystyl threonyl, tyrosyl, or valyl.

A preferred dipeptide is lysyl-lysyl (KK).

The disclosed conjugate can also comprise three amino acid residues, a tripeptide, linked to the hydrophobic drug. Suitable tripeptides include Xaa-Xbb-Xbb, Xbb-Xaa-Xbb, or Xbb-Xbb-Xaa, where Xaa is arginyl, histidyl, lysyl, aspartyl, glutamyl, seryl, threonyl, cystyl, asparagyl, glutaminyl, prolyl, tyrosyl, methionyl, and tryptophanyl; and wherein each Xbb is independent of the others; alanyl, allosoleucyl, arginyl asparagyl, aspartyl, cystyl, glutamyl, glutaminyl, glycyl, histidyl, isolelucyl, leucyl, lysyl, methionyl, phenylalanyl, prolyl, pyroglutamyl, seryl, threonyl, tyrosyl, tryptophanyl, or valyl.

The disclosed conjugate can also comprise four amino acid residues, a tetrapeptide, linked to the hydrophobic drug. Suitable tetrapeptides include Xaa-Xaa-Xbb-Xbb (SEQ ID NO:2), Xaa-Xbb-Xaa-Xbb (SEQ ID NO:3), Xbb-Xbb-Xaa-Xaa (SEQ ID NO:4), or Xbb-Xaa-Xbb-Xaa (SEQ ID NO:5), where each Xaa is independent of the other, arginyl, histidyl, lysyl, aspartyl, glutamyl, seryl, threonyl, cystyl, asparagyl, glutaminyl, prolyl, tyrosyl, methionyl, and tryptophanyl; and wherein each Xbb is independent of the others, alanyl, allosoleucyl, arginyl asparagyl, aspartyl, cystyl, glutamyl, glutaminyl, glycyl, histidyl, isolelucyl, leucyl, lysyl, methionyl, phenylalanyl, prolyl, pyroglutamyl, seryl, threonyl, tyrosyl, tryptophanyl, or valyl. A preferred tetrepeptide is lysyl-phenylalanyl-lysyl-lysyl (KFKK; SEQ ID NO:1).

In still other examples the conjugate can also comprise five amino acid residues (i.e., a pentapeptide), six amino acid residues (a hexapeptide), seven amino acid residues (a heptapeptide), or eight amino acid residue (an octopeptide). In these examples, the peptide has at least three amino acid residues selected from the group consisting of arginyl, histidyl, lysyl, aspartyl, glutamyl, seryl, threonyl, cystyl, asparagyl, glutaminyl, prolyl, tyrosyl, methionyl, and tryptophanyl.

In many examples herein the conjugate does not contain nine or more amino acid residues.

In each example of the disclosed conjugates, the hydrophobic moiety can be linked to the peptide at the side chain of one of the amino acid residues. Further, the peptide component can be functionalized, at one or more side chains or at the C or N terminus. For example, the N terminus of the peptide or amino group on a side chain can be protected with a benzoyloxycarbonyl groups, tert-butoxycarbonyl groups, acetate, trifluoroacetate, 9-fluorenylmethyloxycarbonyl, or 2-bromobenzyloxycarbonyl, or N-hydroxysuccinimide. In further examples, the C terminus or relevant side chain can be protected with a methyl, ethyl, t-butyl, or benzyl ester. In a preferred example, the N terminus of the peptide is protected with a 9-fluorenylmethyloxycarbonyl. A hydrophobic moiety, as described above, can also be covalently attached to the N terminus of the peptide, the C terminus of the peptide, or a combination thereof.

Linker (L)

The peptide conjugate can comprise a hydrophobic moiety linked to a single amino acid residue or an amino acid residue of a peptide via a linker moiety. The linker moiety is shown as L in Formula I. In some embodiments, the linker can be absent (e.g., the hydrophobic moiety can be directly bound to a single amino acid residue or an amino acid residue of a peptide). In other embodiments, the linker moiety of the disclosed conjugates can arise from any compound (linker) that forms a bond with the hydrophobic moiety and an amino acid residue, linking them together. Thus, when present, a linker typically contains at least two functional groups, e.g., one functional group that can be used to form a bond with the hydrophobic moiety and another functional group that can be used to form a bond with an amino acid residue. Typically, though not necessarily, the functional group on the linker that is used to form a bond with the hydrophobic moiety is at one end of the linker and the functional group that is used to form a bond with the amino acid is at the other end of the linker.

In some aspects, the linker can comprise electrophilic functional groups that can react with nucleophilic functional groups like hydroxyl, thiol, carboxylate, amino, or amide groups on the hydrophobic moiety, forming a bond. Conversely, the linker can comprise nucleophilic functional groups that can react with electrophilic functional groups like carbonyl, halide, or alkoxyl groups on the hydrophobic moiety.

The linker can also have one or more electrophilic groups that can react with and thus form a bond to an amino acid residue.

These bonds can be formed by reaction methods known in the art. For example, the hydrophobic moiety can be first attached to the linker, followed by attaching the amino acid residue. Alternatively, the linker can be first attached to the amino acid residue and then attached to the hydrophobic moiety. Still further, the hydrophobic moiety and amino acid residue can both be attached to the linker simultaneously.

The resulting bond between the linker and the hydrophobic moiety and amino acid residue can be biodegradable. In this way, in embodiments where the hydrophobic moiety comprises a hydrophobic drug, the drug can be released to the individual and act in its intended way. As such, the bond between the drug and linker, and the bond between the linker and the amino acid residue can be, for example an ester, ether, or amide bond. In many examples herein, the linker moiety does not contain a disulfide bond.

The linker moiety can be of varying lengths, such as from 1 to 20 atoms in length. For example, the linker moiety can be from 1, 2, 3, 4, 5, 6, 7, 8, 9, 10, 11, 12, 13, 14, 15, 16, 17, 18, 19, or 20 atoms in length, where any of the stated values can form an upper and/or lower end point of a range. Further, the linker moiety can be substituted or unsubstituted. When substituted, the linker can contain substituents attached to the backbone of the linker or substituents embedded in the backbone of the linker. For example, an amine substituted linker moiety can contain an amine group attached to the backbone of the linker or a nitrogen in the backbone of the linker.

Suitable linker moieties include, but are not limited to, substituted or unsubstituted, branched or unbranched, alkyl, alkenyl, or alkynyl groups, ethers, esters, polyethers, polyesters, polyalkylenes, polyamines, heteroatom substituted alkyl, alkenyl, or alkynyl groups, cycloalkyl groups, cycloalkenyl groups, heterocycloalkyl groups, heterocycloalkenyl groups, and the like, and derivatives thereof, where the point of attachment to the hydrophobic drug and/or amino acid is an ester, ether, carboxylate, amine, or amide bond.

In one aspect, the linker moiety can comprise a $C_1$-$C_6$ branched or straight-chain alkyl, such as methyl, ethyl, n-propyl, iso-propyl, n-butyl, iso-butyl, sec-butyl, tert-butyl, n-pentyl, iso-pentyl, neopentyl, or hexyl. In a specific example, the linker moiety can comprise —$(CH_2)_m$—, wherein m is from 1 to 10, and where the point of attachment to the hydrophobic moiety and/or amino acid is an ester, ether, carboxylate, amine, or amide bond. For example, the linker moiety can be $X^1$—$(CH_2)_m$—$X^2$, wherein m is from 1 to 10, and $X^1$ and $X^2$ are, independent of the other, C(O), C(O)O, C(O)N, NH, or O.

In still another aspect, the linker moiety can comprise a $C_2$-$C_6$ branched or straight-chain alkyl, wherein one or more of the carbon atoms is substituted with oxygen (e.g., an ether) or an amino group. For example, suitable linkers can include, but are not limited to, a methoxymethyl, methoxyethyl, methoxypropyl, methoxybutyl, ethoxymethyl, ethoxyethyl, ethoxypropyl, propoxymethyl, propoxyethyl, methylaminomethyl, methylaminoethyl, methylaminopropyl, methylaminobutyl, ethylaminomethyl, ethylaminoethyl, ethylaminopropyl, propylaminomethyl, propylaminoethyl, methoxymethoxymethyl, ethoxymethoxymethyl, methoxyethoxymethyl, methoxymethoxyethyl, and the like, and derivatives thereof, where the point of attachment to the hydrophobic moiety and/or amino acid is an ester, ether, or amide bond.

In some examples, the linker moiety can be a $C1$-$C_6$ alkyldiester. In a preferred example, the linker moiety is —$C(O)CH_2CH_2C(O)$—, i.e., a succinate ester.

In some embodiments, the biocompatible nanostructure can be formed from self-assembled camptothecin (CPT) peptide conjugate. In these examples, the hydrophobic moiety of the peptide conjugate can comprise CPT or a CPT analog. CPT can be linked to the □-amino group of lysine via a linker such as a succinate ester. CPT- and/or CPT analog-peptide conjugates can self assemble into well-defined nanostructures, including nanotubes.

With CPT or CPT analogs, the amino acid residue can be linked to the CPT or CPT analog via a linker at the 20-position. Esterification of the 20-position hydroxyl group is often used to conjugate CPT to other molecule because this linkage is cleaved under physiological conditions. It has been reported that the free 20-hydroxyl group may facilitate the opening reaction of the E-ring lactone through intramolecular hydrogen bonding with the carbonyl moiety (Fassberg et al., id; Henne et al., Synthesis and activity of a folate peptide camptothecin prodrug. *Bioorg Med Chem Lett* 2006, 16, 5350). Thus, CPT prodrugs esterified at the 20-hydroxyl position generally exhibit greater lactone stability and decreased cytotoxicity compared with unmodified CPT (Cao et al., Alkyl esters of Camptothecin and 9-nitrocamptothecin: Synthesis, in vitro pharmacokinetics, toxicity, and antitumor activity. *J Med Chem* 1998, 41, 31; Vishnuvajjala et al., Tricyclo[4.2.2.02.5]Dec-9-Ene-3,4,7,8-Tetracarboxylic Acid Diimide—Formulation and Stability Studies. *J Pharm Sci* 1986, 75, 301; Conover et al., Camptothecin delivery systems: enhanced efficacy and tumor accumulation of Camptothecin following its conjugation to polyethylene glycol via a glycine linker. *Cancer Chemoth Pharm* 1998, 42, 407; Scheeren et al., Novel 20-carbonate linked prodrugs of camptothecin and 9-aminocamptothecin designed for activation by tumour-associated plasmin. *Bioorg Med Chem Lett* 2002, 12, 2371; Yang et al., Novel camptothecin derivatives. Part 1: Oxyalkanoic acid esters of Camptothecin and their in vitro and in vivo antitumor activity. *Bioorg Med Chem Lett* 2002, 12, 1241; Sinka et al., id). It has also been shown that a succinate linkage at the 20-position system of CPT offers relatively high hydrolytic stability (Dosio et al., Preparation, characterization and properties in vitro and in vivo of a paclitaxel-albumin conjugate. *J Control Release* 1997, 47, 293; Cattel et al., Preparation, characterization and properties of sterically stabilized paclitaxel-containing liposomes. J Control Release 2000, 63, 19; Safavy et al., Site-specifically traced drug release and biodistribution of a paclitaxel-antibody conjugate toward improvement of the linker structure. *Bioconjugate Chem* 2004, 15, 1264; Audus et al., Chemical modification of paclitaxel (Taxol) reduces P-glycoprotein interactions and increases permeation across the blood-brain barrier in vitro and in situ. *J Med Chem* 2005, 48, 832).

In certain examples, the peptide conjugate can be defined by Formula II:

(II)

where n is from 1 to 4, each $R^1$ and $R^2$ is, independent of one another, H, OH, lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen or deuterium, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, or $CO_2H$, or together two $R^1$ or one $R^1$ and $R^2$ can form a fused cycloalkyl or cycloheteroalkyl;

L is absent, or is a linker moiety as described herein; and

AA is a single amino acid or a peptide as described herein.

In some examples the CPT analog can be Topotecan, lonotecan, Exatecan, Lurtotecan, DB 67, DNP 1350, ST 1481, or CKD 602.

In specific examples, the peptide conjugate can be defined by Formula II-A through II-E

II-A

II-B

-continued

-continued

II-C

II-E

II-D

In the conjugates of Formula II, L can be absent, or any of the linker moieties described herein. For example, L can be $X^1$—$(CH_2)_m$—$X^2$, wherein m is from 1 to 10 and $X^1$ and $X^2$ are, independent of the other, C(O), C(O)O, or C(O)N. In other examples, L can be C(O)—$(CH_2)_m$—C(O), where m is from 1 to 6.

In the conjugates of Formula II, AA can be any of the amino acids or peptides disclosed herein. For example, AA can be protected or unprotected lysyl, lysyl-lysyl, lysyl-phenylalanyl-lysyl-lysyl (SEQ ID NO:1).

In some examples, the peptide conjugate can include a compound shown below.

(III)

(IV)

-continued (V)

(VI)

-continued (VII)

In some embodiments, the biocompatible nanostructure can be formed from self-assembled 5-fluorouracil peptide conjugate. In these examples, the hydrophobic moiety of the peptide conjugate can comprise 5-fluorouracil or an analog thereof. Examples of suitable 5-fluorouracil peptide conjugates include the compounds shown below.

(VIII)

(IX)

-continued (X)

In some embodiments, the biocompatible nanostructure can be formed from self-assembled naphthalene diimide-based (NDI-based) peptide conjugate. In these examples, the hydrophobic moiety of the peptide conjugate can comprise an NDI-based moiety (e.g., NDI or a derivative thereof). Examples of suitable NDI-based peptide conjugates include the compounds shown below.

(XI)

(XII)

-continued (XIII)

(XIV)

In some embodiments, the biocompatible nanostructure can be formed from self-assembled diacetylene peptide conjugate. In these examples, the hydrophobic moiety of the peptide conjugate can comprise a diacetylene moiety. Examples of suitable diacetylene peptide conjugates include the compounds shown below.

(XV)

(XVI)

In some embodiments, the biocompatible nanostructure can be formed from self-assembled coumarin peptide conjugate. In these examples, the hydrophobic moiety of the peptide conjugate can comprise a coumarin moiety. Examples of suitable coumarin peptide conjugates include the compounds shown below.

(XVII)

(XVIII)

(XIX)

(XX)

-continued (XXI-AAC2)

In some embodiments, the biocompatible nanostructure can be formed from the self-assembly of an oligopeptide. Oligopeptides that can form self-assembled nanostructures in aqueous solutions are known in the art. In certain examples, the oligopeptide can include from three to eight amino acid residues.

For example, the oligopeptide can comprise a tripeptide. Suitable tripeptides include Xaa-Xbb-Xbb, Xbb-Xaa-Xbb, or Xbb-Xbb-Xaa, where Xaa is arginyl, histidyl, lysyl, aspartyl, glutamyl, seryl, threonyl, cystyl, asparagyl, gluta-minyl, prolyl, tyrosyl, methionyl, and tryptophanyl; and wherein each Xbb is independent of the others; alanyl, allosoleucyl, arginyl asparagyl, aspartyl, cystyl, glutamyl, glutaminyl, glycyl, histidyl, isolelucyl, leucyl, lysyl, methio-nyl, phenylalanyl, prolyl, pyroglutamyl, seryl, threonyl, tyrosyl, tryptophanyl, or valyl.

The oligopeptide can also comprise a tetrapeptide. Suit-able tetrapeptides include Xaa-Xaa-Xbb-Xbb (SEQ ID NO:2), Xaa-Xbb-Xaa-Xbb (SEQ ID NO:3), Xbb-Xbb-Xaa-Xaa (SEQ ID NO:4), or Xbb-Xaa-Xbb-Xaa (SEQ ID NO:5), where each Xaa is independent of the other, arginyl, histidyl, lysyl, aspartyl, glutamyl, seryl, threonyl, cystyl, asparagyl, glutaminyl, prolyl, tyrosyl, methionyl, and tryptophanyl; and wherein each Xbb is independent of the others, alanyl, allosoleucyl, arginyl asparagyl, aspartyl, cystyl, glutamyl, glutaminyl, glycyl, histidyl, isolelucyl, leucyl, lysyl, methio-nyl, phenylalanyl, prolyl, pyroglutamyl, seryl, threonyl, tyrosyl, tryptophanyl, or valyl. A preferred tetrepeptide is lysyl-phenylalanyl-lysyl-lysyl (KFKK).

In still other examples the oligopeptide can also comprise five amino acid residues (i.e., a pentapeptide), six amino acid residues (a hexapeptide), seven amino acid residues (a heptapeptide), or eight amino acid residue (an octopeptide). In these examples, the peptide can have at least three amino acid residues selected from the group consisting of arginyl, histidyl, lysyl, aspartyl, glutamyl, seryl, threonyl, cystyl, asparagyl, glutaminyl, prolyl, tyrosyl, methionyl, and tryp-tophanyl.

In many examples herein the conjugate does not contain nine or more amino acid residues.

In each example of the oligopeptides described above, the oligopeptide can be functionalized at one or more side chains and/or at the C and/or N terminus. For example, the N terminus of the oligopeptide or amino group on a side chain can be protected with a benzoyloxycarbonyl groups, tert-butoxycarbonyl groups, acetate, trifluoroacetate, 9-fluo-renylmethyloxycarbonyl, 2-bromobenzyloxycarbonyl, or N-hydroxysuccinimide groups. In further examples, the C terminus or relevant side chain can be protected with a methyl, ethyl, t-butyl, or benzyl ester. In preferred oligo-peptides, the N terminus of the oligopeptide is protected with a 9-fluorenylmethyloxycarbonyl. In certain examples, the N terminus of the oligopeptide is protected with a 9-fluorenylmethyloxycarbonyl group, and an amino group on a side chain of the oligopeptide is protected with a benzoyloxycarbonyl group, a tert-butoxycarbonyl group, an acetate group, a trifluoroacetate group, a 9-fluorenylmeth-yloxycarbonyl group, a 2-bromobenzyloxycarbonyl group, or an N-hydroxysuccinimide group.

Examples of suitable oligopeptides include the com-pounds shown below.

(XXII)

(XXIII)

(XXIV)

(XXV)

57

Self-assembled, biocompatible nanostructures formed from the compounds above can have therapeutic properties as antioxidants and scavengers of reactive oxygen species and oxidized metabolites, such as reactive aldehyde species, reactive ketones. Other therapeutic properties of self-assembled, biocompatible nanostructures can emerge from their role in improving stability and lowering degradation of endogenous metabolites and bioactive biologicals.

Self-assembled, biocompatible nanostructures formed from the compounds above can be non-covalently associated with a therapeutic or diagnostic peptide or peptidomimetic. The therapeutic or diagnostic peptide or peptidomimetic can be any suitable therapeutic or diagnostic peptide or peptidomimetic. Suitable peptides and peptidomimetics that can be administered to a subject for therapeutic and/or diagnostic effect are known in the art, and include, for example, vasopressin, oxytocin, melanocyte stimulating hormones, adrenocorticotropic hormones, growth hormones; hypothalamic hormones such as growth hormone releasing factor, corticotropin releasing factor, prolactin releasing peptides, gonadotropin releasing hormone and its associated peptides, luteinizing hormone release hormones, thyrotropin releasing hormone, orexin, and somatostatin; thyroid hormones such as calcitonins, calcitonin precursors, and calcitonin gene related peptides; parathyroid hormones and their related proteins; pancreatic hormones such as insulin and insulin-like peptides, glucagon, somatostatin, pancreatic polypeptides, amylin, peptide YY, and neuropeptide Y; digestive hormones such as gastrin, gastrin releasing peptides, gastrin inhibitory peptides, cholecystokinin, secretin, motilin, and vasoactive intestinal peptide; natriuretic peptides such as atrial natriuretic peptides, brain natriuretic peptides, and C-type natriuretic peptides; neurokinins such as neurokinin A, neurokinin B, and substance P; renin related peptides such as renin substrates and inhibitors and angiotensins; endothelins, including big endothelin, endothelin A receptor antagonists, and sarafotoxin peptides; and other peptides such as adrenomedullin peptides, allatostatin peptides, amyloid beta protein fragments, antibiotic and antimicrobial peptides, apoptosis related peptides, bag cell peptides, bombesin, bone Gla protein peptides, CART peptides, chemotactic peptides, cortistatin peptides, fibronectin fragments and fibrin related peptides, FMRF and analog peptides, galanin and related peptides, growth factors and related peptides, Gtherapeutic peptide-binding protein fragments, guanylin and uroguanylin, inhibin peptides, interleukin and interleukin receptor proteins, laminin fragments, leptin fragment peptides, leucokinins, mast cell degranulating peptides, pituitary adenylate cyclase activating polypeptides, pancreastatin, peptide T, polypeptides, virus related peptides, signal transduction reagents, toxins, and miscellaneous peptides such as adjuvant peptide analogs, alpha mating factor, antiarrhythmic peptide, antifreeze polypeptide, anorexigenic peptide, bovine pineal antireproductive peptide, bursin, C3 peptide P16, tumor necrosis factor, cadherin peptide, chromogranin A fragment, contraceptive tetrapeptide, conantokin G, conantokin T, crustacean cardioactive peptide, C-telopeptide, cytochrome b588 peptide, decorsin, delicioius peptide, delta-sleep-inducing peptide, diazempam-binding inhibitor fragment, nitric oxide synthase blocking peptide, OVA peptide, platelet calpain inhibitor (P1), plasminogen activator inhibitor 1, rigin, schizophrenia related peptide, serum thymic factor, sodium potassium Atherapeutic peptidease inhibiro-1, speract, sperm activating peptide, systemin, thrombin receptor agonist, thymic humoral gamma2 factor, thymopentin, thymosin alpha 1, thymus factor, tuftsin, adipokinetic hormone, uremic pentapeptides, and combinations thereof. Other examples of suitable peptides and peptidomimetics include aptamers, decoy receptors, soluble receptors, antibodies, antibody fragments (e.g., single chain antibodies, such as scFv fragments), fusion proteins, and combinations thereof.

In certain embodiments, the peptide or peptidomimetic can be a thermogenesis inducing peptide or peptidomimetic, such as epiregulin, insulin-like growth factor-binding protein 4 (IGFBP4), insulin-like growth factor-binding protein 7 (IRBP7), glia maturation factor beta (GMFB), ephrin A5, ADAMT S9, semaphorin 3E, or a combination thereof.
Methods of Treatment Disclosed is a method for treating or preventing a condition in a subject selected from the group consisting of visceral fat accumulation (e.g., Crohn's disease associated with visceral fat accumulation), obesity, diabetes, pre-diabetes, hypothermia, age-related dementia, and chronic inflammation, comprising administering to the subject an effective amount of a composition comprising 1, 2, 3, 4, 5, 6, or 7 molecules selected from the group consisting of epiregulin, IGFBP4, IGFBP7, GMFB, ephrin A5, ADAMT S9, and semaphorin 3E.

Also disclosed is a method for promoting glucose uptake in insulin deficient conditions and in patients developing tolerance and side effects to insulin therapy, comprising administering to the subject an effective amount of a composition comprising 1, 2, 3, 4, 5, 6, or 7 molecules selected from the group consisting of epiregulin, IGFBP4, IGFBP7, GMFB, ephrin A5, ADAMT S9, and semaphorin 3E.

Also disclosed is a method for promoting glucose uptake in peripheral tissues (e.g., adipocytes and muscles) of a subject, comprising administering to the subject an effective amount of a composition comprising 1, 2, 3, 4, 5, 6, or 7 molecules selected from the group consisting of epiregulin, IGFBP4, IGFBP7, GMFB, ephrin A5, ADAMT S9, and semaphorin 3E. In some embodiments, the method further involves administering to the subject a therapeutically effective amount of an epidermal growth factor receptor (EGFR) inhibitor, an ErbB receptor inhibitor, a MAPK inhibitor, or a combination thereof.

In some embodiments, the subject is resistant to insulin. In some embodiments, the subject has diminished insulin production. In some embodiments, the subject is obese.

Also disclosed is a method for enhancing nerve innervation in a subject, comprising administering to the subject an effective amount of a composition comprising 1, 2, 3, 4, 5, 6, or 7 molecules selected from the group consisting of epiregulin, IGFBP4, IGFBP7, GMFB, ephrin A5, ADAMT S9, and semaphorin 3E. In some cases the method involves administering to the subject a composition comprising Complement C3 factor.

The disclosed molecules, such as epiregulin, are also shown herein to be effective activators of PI3 kinase. Therefore, also disclosed is a method for activating PI3 kinase in cell, comprising contacting the cell with a composition comprising epiregulin.

The disclosed molecules, such as epiregulin, are also shown herein to be effective at inducing leptin secretion. Therefore, also disclosed is a method for inducing leptin secretion by an adipocyte, comprising contacting the adipocyte with a composition comprising epiregulin.

In some cases, it is advantageous to decrease thermogenesis of adipocytes in a subject. For example, cachexia or wasting syndrome is loss of weight, muscle atrophy, fatigue, weakness, and significant loss of appetite in someone who is not actively trying to lose weight. Therefore, a method is disclosed that involves administering to the subject an effective amount of a composition that inhibits 1, 2, 3, 4, 5, 6, or 7 molecules selected from the group consisting of epiregulin, IGFBP4, IGFBP7, GMFB, ephrin A5, ADAMT S9, and semaphorin 3E. For example, the inhibitor can be an antibody that binds and inactivates the molecule. In some cases, the inhibitor is a decoy molecule, soluble receptor, or the like. In some cases, the inhibitor is a gene silencing functional nucleic acid, such as an antisense DNA, RNAi, siRNA, shRNA, or miRNA. In some case, the inhibitor is a small molecule shown to inhibit one or more activities of the molecule.

Also disclosed is a method of treating cancer in a subject, comprising administering to the subject a self-assembled, biocompatible nanostructure disclosed herein. In some embodiments, the nanostructure is self-assembled from compound III, IV, V, VI, VII, VIII, IX, X, or any combination thereof. The cancer of the disclosed methods can be any cell in a subject undergoing unregulated growth, invasion, or metastasis. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

Also disclosed is a method for promoting glucose uptake in a subject, comprising administering to the subject a self-assembled, biocompatible nanostructure disclosed herein. Therefore, also disclosed is a method of treating diabetes in a subject, comprising administering to the subject a self-assembled, biocompatible nanostructure disclosed herein. In some embodiments, the subject has type I diabetes, type 2 diabetes, gestational diabetes, or a metabolic syndrome. In some embodiments, the nanostructure is self-assembled from compound II.

Also disclosed is a method for inhibiting inflammation in a subject, comprising administering to the subject a self-assembled, biocompatible nanostructure disclosed herein. Therefore, also disclosed is a method of binding of reactive aldehyde species to lysines group on nanostructures and lipid mediators of inflammation to hydrophobic portions of nanostructures, comprising administering to the subject a self-assembled, biocompatible nanostructure disclosed herein. In some embodiments, the nanostructure is self-assembled from compound II. In some embodiments, the nanostructure is self-assembled from compound III, IV, V, VI, VII, VIII, IX, X, XI, XII, XIII, XIV, XV, XVI, XVII, XVIII, XIX, XX, XXI, XXII, XXIII, XXIV, XXV, or any combination thereof.

Also disclosed is a method for inhibiting glucose uptake in cancers, comprising administering to the subject a self-assembled, biocompatible nanostructure disclosed herein in combination with antibodies to EREG, IGFBP4, IGFBP7, EFNA5, insulin, or any combination thereof. In some embodiments, the nanostructure is self-assembled from compound XI, XII, XIII, XIV, XV, XVI, XVII, XVIII, XIX, XX, XXI, XXII, XXIII, XXIV, XXV, or any combination thereof.

Administration

The herein disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, in visceral fat (intravisceral), intracavity, or transdermally. The compositions may be administered orally, parenterally (e.g., intravenously), by intramuscular injection, by intravisceral injection, by intraperitoneal injection, transdermally, extracorporeally, ophthalmically, vaginally, rectally, intranasally, topically or the like, including topical intranasal administration or administration by inhalant.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained. See, e.g., U.S. Pat. No. 3,610,795, which is incorporated by reference herein.

The compositions disclosed herein may be administered prophylactically to patients or subjects who are at risk for obesity, diabetes, cachexia, or any other disease treatable by the compositions disclosed herein. Thus, the method can further comprise identifying a subject at risk for a disease disclosed herein prior to administration of the herein disclosed compositions.

The exact amount of the compositions required will vary from subject to subject, depending on the species, age, weight and general condition of the subject, the severity of the allergic disorder being treated, the particular nucleic acid or vector used, its mode of administration and the like. Thus, exact amount for every composition will be specified for patients and depend on their diagnosis, age, sex and ethnicity. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389.

In some embodiments, the disclosed composition is administered in a dose equivalent to parenteral administration of about 0.1 ng to about 100 g per kg of body weight, about 10 ng to about 50 g per kg of body weight, about 100 ng to about 1 g per kg of body weight, from about 1 μg to about 100 mg per kg of body weight, from about 1 μg to about 50 mg per kg of body weight, from about 1 mg to about 500 mg per kg of body weight; and from about 1 mg to about 50 mg per kg of body weight. Alternatively, the amount of composition administered to achieve a therapeutic effective dose is about 0.1 ng, 1 ng, 10 ng, 100 ng, 1 μg, 10 μg, 100 μg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Secretome from Thermogenic Adipocytes Regulates Axonal Growth and Innervation of White Adipose Tissue Results Identification of Axon Guiding Molecules in Thermocytes The levels of innervation were examined in intra-abdominal (iAb) fat the model of WAT thermogenesis Adh1a1$^{-/-}$ compared to WT mice. The functional thermogenesis in these mice has been established (Yasmeen, R. et al. Diabetes. 62(1):124-36 (2013); Yang, F., et al. Biomaterials 33:5638-5649 (2012); Ziouzenkova, O., et al. Nature medicine 13:695-702 (2007); Kiefer, F. W., et al. Nature medicine 18:918-925 (2012)). Consistent with the obligatory role of innervation in thermogenesis, there was higher protein expression of peripherin and tyrosine hydroxylase (TH), markers of peripheral and sympathetic neurons, in thermogenic intra-abdominal (iAb) fat of Aldh1a$^{-/-}$ compared to WT mice (FIG. 1A, Table 1, Study 1).

TABLE 1

Body weight and adipose tissue weights in mice from animal studies 1-5

Study 1. WT and Aldh1a1$^{-/-}$ (A1KO) mice on a high-fat (HF) diet

| Study group | Body Wt. (g) M | F | Sub Fat (g) M | F | iAb Fat (g) M | F | Brown Fat (g) M | F |
|---|---|---|---|---|---|---|---|---|
| WT (HF) (n = 10) | 52.76 ± 3.68 | 40.43 ± 3.51# | 2.85 ± 0.58 | 3.22 ± 0.85 | 1.75 ± 0.12 | 2.84 ± 0.91 | 0.35 ± 0.07 | 0.15 ± 0.04# |
| A1KO (HF) (n = 9) | 28.75 ± 1.88* | 22.92 ± 2.04#* | 0.92 ± 0.35* | 0.55 ± 0.13* | 1.23 ± 0.33* | 0.65 ± 0.20#* | 0.11 ± 0.04* | 0.09 ± 0.02* |

P < 0.05, Male vs. Female;
*P < 0.05, WT vs. A1KO, Mann-Whithney U test

Study 2. Comparison of lean and obese mice with dietary and genetic obesity

| Study group | Body Wt. (g) M | F | Sub Fat (g) M | F | iAb Fat (g) M | F | Brown Fat (g) M | F |
|---|---|---|---|---|---|---|---|---|
| WT (n = 14) | 28.7 ± 0.9 | 22.3 ± 1.8# | 0.26 ± 0.11 | 0.3 ± 0.2 | 0.4 ± 0.1 | 0.4 ± 0.2 | 0.07 ± 0.02 | 0.06 ± 0.01 |
| Ob/Ob (n = 9) | 48.7 ± 2.2* | 45.7 ± 2.1* | 2.55 ± 0.15* | 2.8 ± 0.2* | 3.2 ± 0.3* | 4.0 ± 0.9* | 0.39 ± 0.11* | 0.38 ± 0.09* |

P < 0.05, Male vs. Female;
*P < 0.05, WT vs. Ob/Ob (both Mann-Whithney U test,
** P < 0.05, paired t-test Study 3. WT mice on a high-fat (HF) diet treated with encapsulated WT and Aldh1a1$^{-/-}$ (A1KO) cells

| Study group | Body Wt. (g) WT Veh | WT encWT | WT encAIKO | Sub Fat (g) WT Veh | WT encWT | WT encAIKO | iAb Fat (g) WT Veh | WT encWT | WT encAIKO |
|---|---|---|---|---|---|---|---|---|---|
| Host: (n = 18) Injected with: | | | | | | | | | |
| WT | 41.0 ± 4.8 | 38.5 ± 7.8 | 37.0 ± 6.3 | 2.7 ± 0.9 | 2.0 ± 0.8 | 2.3 ± 0.6 | 4.1 ± 1.0 | 4.6 ± 1.7 | 4.1 ± 1.2 | n.s. within groups (Veh, encWT, and encA1KO)

Study 4. Comparison of WT and Aldh1a1$^{-/-}$ (A1KO) mice on a regular chow diet

| Study group | Body Wt. (g) M | F | Sub Fat (g) M | F | iAb Fat (g) M | F | Brown Fat (g) M | F |
|---|---|---|---|---|---|---|---|---|
| WT baseline (n = 14) | 28.72 ± 0.88 | 22.26 ± 1.81# | 0.26 ± 0.11 | 0.3 ± 0.2 | 0.42 ± 0.10 | 0.4 ± 0.2 | 0.07 ± 0.02 | 0.10 ± 0.01 |
| A1KO baseline (n = 13) | 22.60 ± 1.84* | 19.18 ± 1.84#* | 0.22 ± 0.05 | 0.3 ± 0.1 | 0.19 ± 0.05* | 0.2 ± 0.02* | 0.19 ± 0.30 | 0.05 ± 0.01* |

P < 0.05, Male vs. Female;

TABLE 1-continued

Body weight and adipose tissue weights in mice from animal studies 1-5

*P < 0.05, WT vs. A1KO, Mann-Whithney U test
Study 5. Ephrin A5 (EFNA5) effects on Brainbow (BB) mice fed a high-fat (HF) diet

| Study group | Body Wt. (g) | | Sub Fat (g) | | iAb Fat (g) | | Brown Fat (g) | |
|---|---|---|---|---|---|---|---|---|
| | PBS | EA5 | PBS | EA5 | PBS | EA5 | PBS | EA5 |
| BB (n = 7) | 29.5 ± 2.6 | 28.7 ± 3.2 | 1.2 ± 0.1 | 1.0 ± 0.4** | 1.3 ± 0.5 | 1.2 ± 0.5 | 0.11 ± 0.03 | 0.1 ± 0.03 | n.s. within groups (PBS vs. EA5)
Study 1. WT and Aldh1a1$^{-/-}$ (A1KO) mice on a high-fat (HF) diet

| Study group | Body Wt. (g) | | Sub Fat (g) | | iAb Fat (g) | | Brown Fat (g) | |
|---|---|---|---|---|---|---|---|---|
| | M | F | M | F | M | F | M | F |
| WT (HF) (n = 10) | 52.76 ± 3.68 | 40.43 ± 3.51# | 2.85 ± 0.58 | 3.22 ± 0.85 | 1.75 ± 0.12 | 2.84 ± 0.91 | 0.35 ± 0.07 | 0.15 ± 0.04# |
| A1KO (HF) (n = 9) | 28.75 ± 1.88* | 22.92 ± 2.04#* | 0.92 ± 0.35* | 0.55 ± 0.13* | 1.23 ± 0.33* | 0.65 ± 0.20#* | 0.11 ± 0.04* | 0.09 ± 0.02* |

P < 0.05, Male vs. Female;
*P < 0.05, WT vs. A1KO, Mann-Whithney U test
Study 2. Comparison of lean and obese mice with dietary and genetic obesity

| Study group | Body Wt. (g) | | Sub Fat (g) | | iAb Fat (g) | | Brown Fat (g) | |
|---|---|---|---|---|---|---|---|---|
| | M | F | M | F | M | F | M | F |
| WT (n = 14) | 28.7 ± 0.9 | 22.3 ± 1.8# | 0.26 ± 0.11 | 0.3 ± 0.2 | 0.4 ± 0.1 | 0.4 ± 0.2 | 0.07 ± 0.02 | 0.06 ± 0.01 |
| Ob/Ob (n = 9) | 48.7 ± 2.2* | 45.7 ± 2.1* | 2.55 ± 0.15* | 2.8 ± 0.2* | 3.2 ± 0.3* | 4.0 ± 0.9* | 0.39 ± 0.11* | 0.38 ± 0.09* |

P < 0.05, Male vs. Female;
*P < 0.05, WT vs. Ob/Ob (both Mann-Whithney U test,
** P < 0.05, paired t-test
Study 3. WT mice on a high-fat (HF) diet treated with encapsulated WT and Aldh1a1$^{-/-}$ (A1KO) cells

| Study group | Body Wt. (g) | | | Sub Fat (g) | | | iAb Fat (g) | | |
|---|---|---|---|---|---|---|---|---|---|
| Host: (n = 18) Injected with: | WT Veh | WT encWT | WT encAIKO | WT Veh | WT encWT | WT encAIKO | WT Veh | WT encWT | WT encAIKO |
| WT | 41.0 ± 4.8 | 38.5 ± 7.8 | 37.0 ± 6.3 | 2.7 ± 0.9 | 2.0 ± 0.8 | 2.3 ± 0.6 | 4.1 ± 1.0 | 4.6 ± 1.7 | 4.1 ± 1.2 | n.s. within groups (Veh, encWT, and encA1KO)
Study 4. Comparison of WT and Aldh1a1$^{-/-}$ (A1KO) mice on a regular chow diet

| Study group | Body Wt. (g) | | Sub Fat (g) | | iAb Fat (g) | | Brown Fat (g) | |
|---|---|---|---|---|---|---|---|---|
| | M | F | M | F | M | F | M | F |
| WT baseline (n = 14) | 28.72 ± 0.88 | 22.26 ± 1.81# | 0.26 ± 0.11 | 0.3 ± 0.2 | 0.42 ± 0.10 | 0.4 ± 0.2 | 0.07 ± 0.02 | 0.10 ± 0.01 |
| A1KO baseline (n = 13) | 22.60 ± 1.84* | 19.18 ± 1.84#* | 0.22 ± 0.05 | 0.3 ± 0.1 | 0.19 ± 0.05* | 0.2 ± 0.02* | 0.19 ± 0.30 | 0.05 ± 0.01* |

P < 0.05, Male vs. Female;
*P < 0.05, WT vs. A1KO, Mann-Whithney U test
Study 5. Ephrin A5 (EFNA5) effects on Brainbow (BB) mice fed a high-fat (HF) diet

| Study group | Body Wt. (g) | | Sub Fat (g) | | iAb Fat (g) | | Brown Fat (g) | |
|---|---|---|---|---|---|---|---|---|
| | PBS | EA5 | PBS | EA5 | PBS | EA5 | PBS | EA5 |
| BB (n = 7) | 29.5 ± 2.6 | 28.7 ± 3.2 | 1.2 ± 0.1 | 1.0 ± 0.4** | 1.3 ± 0.5 | 1.2 ± 0.5 | 0.11 ± 0.03 | 0.1 ± 0.03 | n.s. within groups (PBS vs. EA5)

Figure 7A:
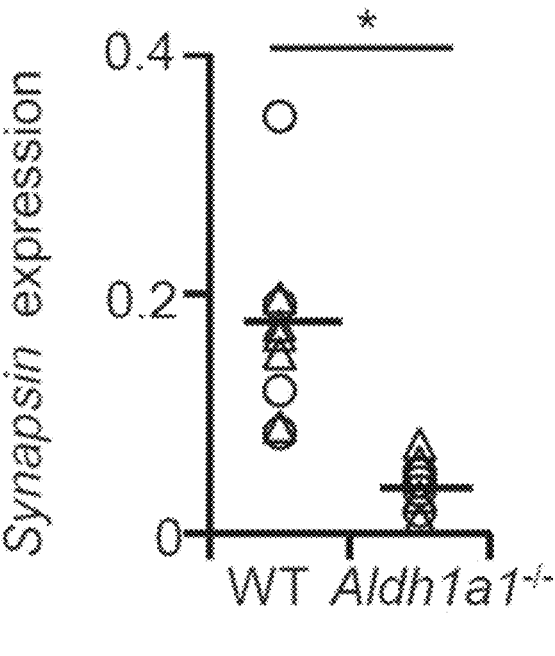
FIG. 7A: Relative expression of synopsin measured by TaqMan in iAb from WT and Aldh1a1$^{-/-}$ males (triangle) and females (circle). The expression was normalized to TATA box protein (TBP). An asterisk indicates a significant difference between WT and Aldh1a1$^{-/-}$ groups (P<0.05). LTA axon guiding gene expression was analyzed in iAb fat pads of WT lean mice (white circles), WT mice with HF diet-induced obesity (black circles), and Ob/Ob mice (black squares) using the NanoString mouse innervation panel (Table 1, Study 2). The Pearson test was used for correlation analysis.
Figure 7B:
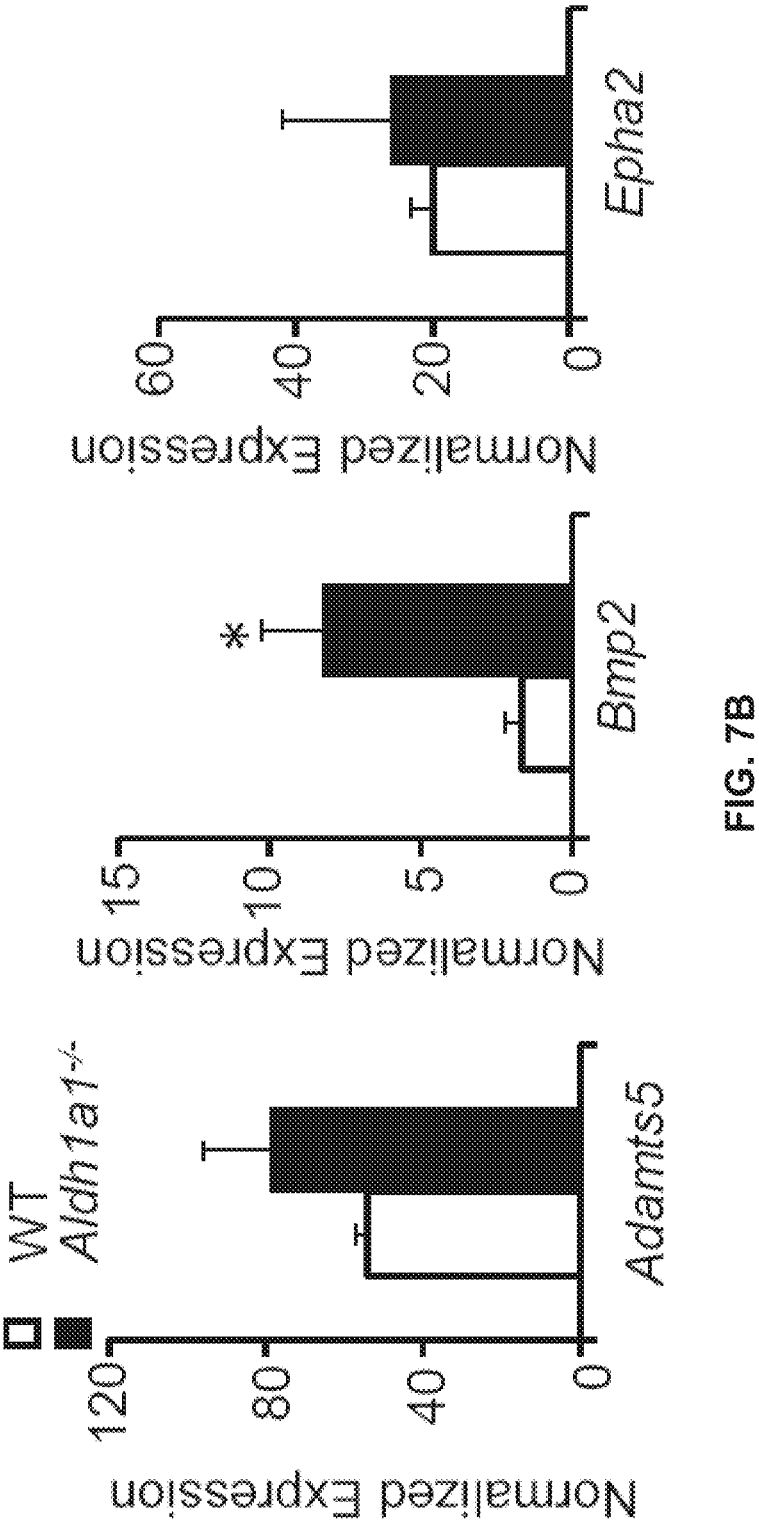
FIGS. 7B and 7C: WT (white bars) and Aldh1a1$^{-/-}$ (black bars) preadipocytes (n=3) were differentiated for 4 days. Gene expression was measured in purified mRNA samples using a customized NanoString mouse panel including markers for adipogenesis, thermogenesis, and axon guidance genes. Data represent mean±SD. An asterisk indicates P<0.05; Mann Whitney U test.
Figure 7C:
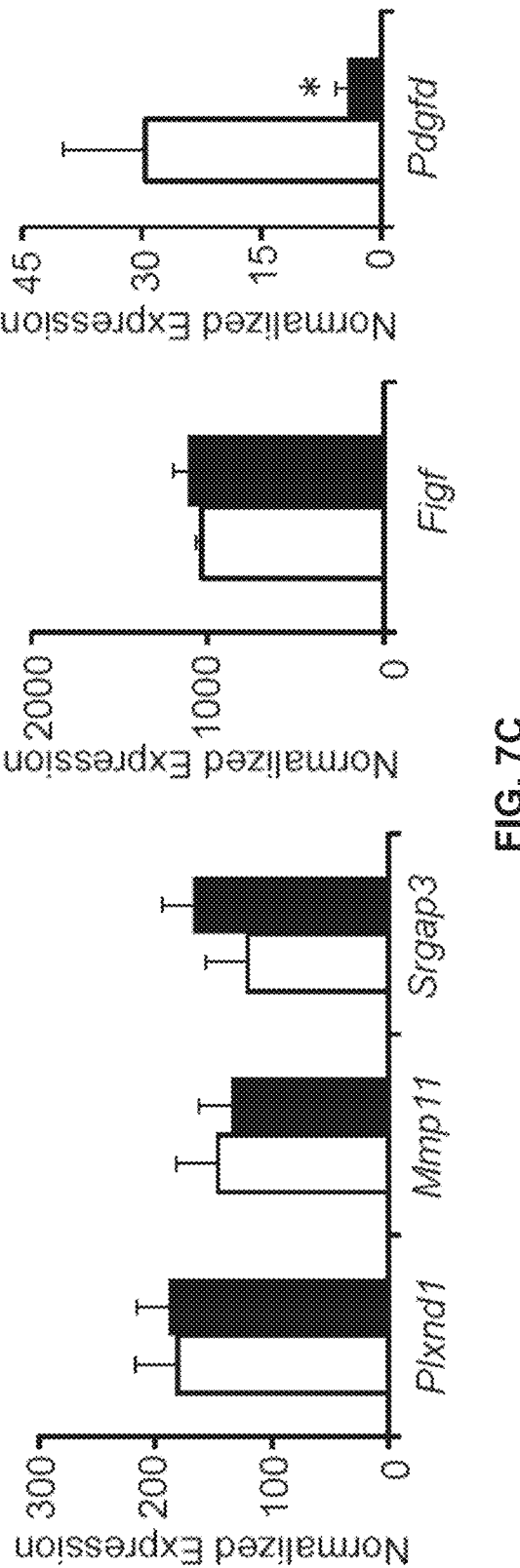
Figure 7D:
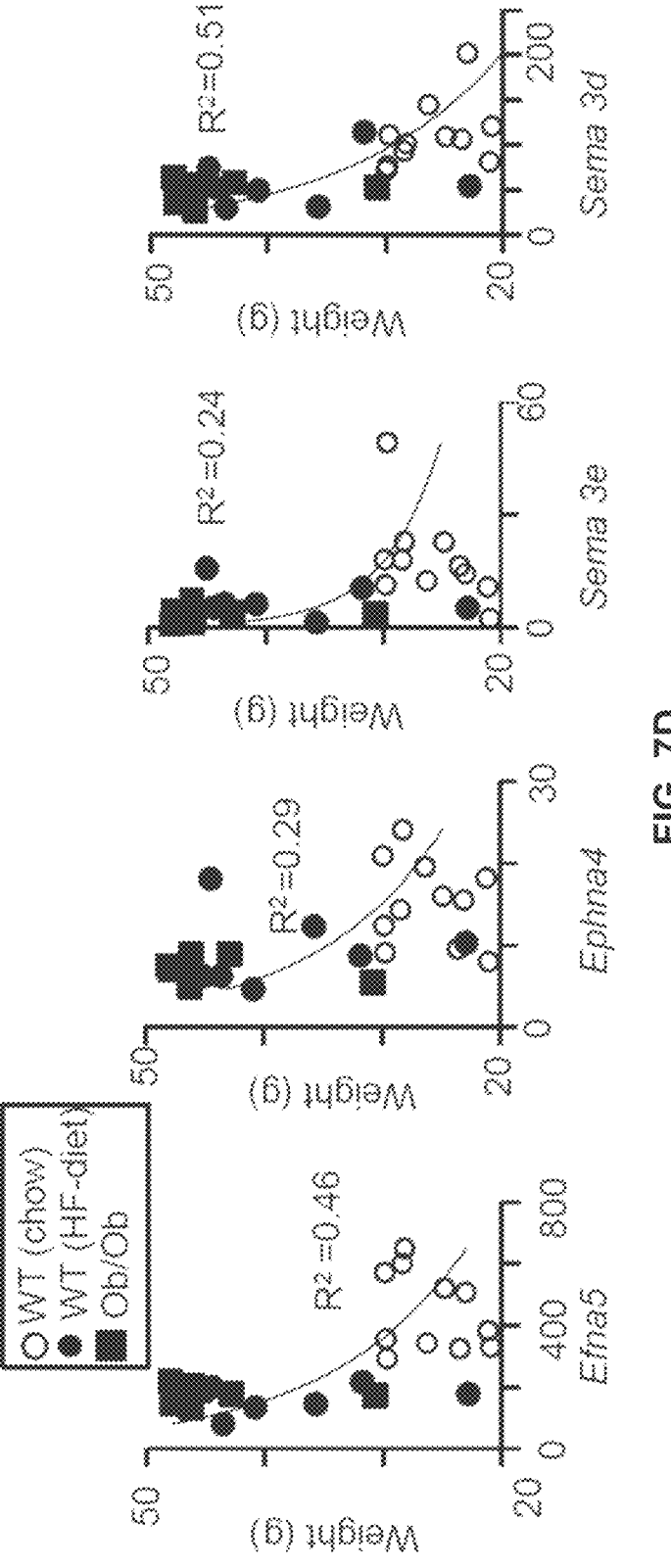
FIG. 7D: Correlation between weight and LTA axon guiding gene expression in iAb fat. LTA axon guiding gene expression was analyzed in iAb fat pads of WT lean mice (white circles), WT mice with HF diet-induced obesity (black circles), and Ob/Ob mice (black squares) using NanoString mouse innervation panel (Table 1, Study 2). The Pearson test was used to examine significance by correlation analysis.

The increase in peripheral innervation in adult mice could be result of elevated levels of neural precursors, enhanced neurogenesis of neural precursors and/or fibroblasts, or axon outgrowth. However, analysis of the whole iAb fat pad revealed similar expression of the mature neuron marker Rbfox3 and significantly reduced expression of the neuronal precursor marker nestin and synapsin (FIG. 1b,c, FIG. 7a) in Adh1a1$^{-/-}$ compared to WT mice. These data argue against a major role of neuronal precursor recruitment or neurogenesis in the increased innervation of iAb fat in Aldh1a1$^{-/-}$ mice. Retinoic acid (RA) is required for the induction of neurogenesis (Yu, S., et al. The Journal of biological chemistry 287:42195-42205 (2012)); however, RA generation is diminished by 70% in Aldh1a1$^{-/-}$ vs. WT adipocytes (Reichert, B., et al. Mol Endocrinol 25:799-809 (2011)) and in the circulation (Molotkov, A., et al. The Journal of biological chemistry 278:36085-36090 (2003)) in Aldh1a1$^{-/-}$ vs. WT mice. Given the reported role of NGF in WAT (Bullo, M., et al. Eur J Endocrinol 157:303-310 (2007); Peeraully, M. R., et al. Endocrinology and metabolism 287:E331-339 (2004)), correlation of plasma NGF levels with obesity (Bullo, M., et al. Eur J Endocrinol 157:303-310 (2007)), NGF regulation by RA (Wion, D., et al. Biochem Biophys Res Commun 149: 510-514 (1987)), and stimulation of adrenergic neuronal differentiation by NGF in other tissues (Liesi, P., et al. Nature 306:265-267 (1983)), the plasma levels of NGF was also examined in WT and Aldh1a1$^{-/-}$ mice (FIG. 1$d$). NGF levels in circulation were similar between these genotypes. Both WT and Aldh1a1$^{-/-}$ adipocytes secreted similar levels of NGF (FIG. 1$e$). Fibroblasts can also develop neuron-like morphology in vitro (Ladewig, J., et al. Nat Methods 9:575-578 (2012)) that could depend on retinoic acid receptor (RAR) (Shi, Z., et al. J Biol Chem 289:6415-6428 (2014)). Neurogenic morphology was induced in 3T3-L1 and WT fibroblasts, but did not alter morphology of Aldh1a1$^{-/-}$ fibroblasts using a standard neurogenic differentiation medium (FIG. 1$f$). These experiments confirm the lack of neurogenic potential in Aldh1a1$^{-/-}$ preadipocytes in vitro and in WAT from Aldh1a1$^{-/-}$ mice (FIG. 1$b$-$f$).

Figure 2H:
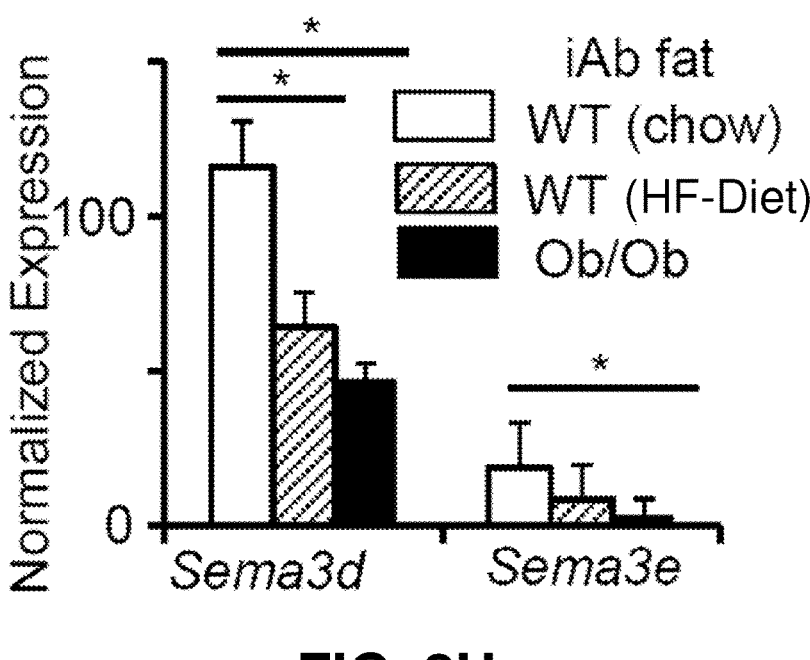

To elucidate all potential functions of adipocytes in the innervation of iAb fat, gene array analysis was performed in immortalized WT and Aldh1a1$^{-/-}$ preadipocytes (FIG. 1$f$). Increased lipolysis and thermogenesis, measured as increase UCP1 and ATGL protein expression, was a signature of Aldh1a1$^{-/-}$ thermocytes compared to WT adipocytes (Bostrom, P., et al. Nature 481:463-468 (2012); Rao, R. R., et al. Cell 157:1279-1291 (2014)). More genes expressed in thermogenic beige adipocytes such as Cidea (Wu, J., et al. Cell 150:366-376 (2012)) and Ucp2 lowering inner mitochondrial membrane potential and ATP:ADP ratio (Vozza, A., et al. Proc Natl Acad Sci USA 111:960-965 (2014)) were identified in gene microarray analysis and validated by Nanostring (FIG. 2$a$; Yasmeen, R. et al. Diabetes. 2013 January; 62(1):124-36; Yang, F., et al. Biomaterials 33:5638-5649 (2012)). However, pathway analyses of gene array data revealed that axon guidance was the primary pathway altered in Aldh1a1$^{-/-}$ thermocytes vs. WT adipocytes. Therefore, this axon guidance cluster of genes in Aldh1a1$^{-/-}$ adipocytes was termed as 'lipolysis thermogenesis associated' (LTA)-axon guidance molecules. The validation of LTA-axon guiding cluster demonstrated higher expression of GPI-anchored ephrin A5 ligand (Efna5) and its receptor Epha4 (FIG. 2$b$), which belongs to the family of ephrin tyrosine kinase receptors. Genes associated with the ephrin pathway, such as integrin alpha 3 (Itga3) (Moreno-Bravo, J. A. et al. Brain Struct Funct. 221(1):665-78 (2016); Mertens-Walker, I., et al. BMC cancer 15:164 (2015)) and phospholipase C (Plce1), were also induced (Hornberger, M. R., et al. Neuron 22:731-742 (1999)) (FIG. 2$c$). The axon guidance molecules semaphorin 3E (Sema3e) and 3D (Sema3d) and their co-regulatory molecule Robo1 (Hernandez-Miranda, L. R., et al. J Neurosci. 31:6174-6187 (2011)) were also upregulated (FIG. 2$d$). The expression of the repellant, Slit1, which binds to ROBO1 was decreased (Moreno-Bravo, J. A. et al. Brain Struct Funct. 221(1):665-78 (2016)). Another regulatory molecule, Hhip, which is involved in repulsive axon guidance in other tissues, was also down-regulated (Wilson, N. H., et al. Neuron 79:478-491 (2013)) (FIG. 2$e$). Previously, the expression of these molecules was reported in brain and other tissues, where they regulate axon guidance (Zaheer, A., et al. Neurochemical research 31:579-584 (2006); Zaheer, A., et al. Neuroscience letters 265:203-206 (1999); Chauvet, S., et al. Neuron 56:807-822 (2007); Overman, J. J., et al. Proc Natl Acad Sci USA 109:E2230-2239 (2012); Marler, K. J., et al. J Neurosci. 28(48):12700-12 (2008); Cooper, M. A., et al. Dev Neurobiol. 69:36-46 (2009)). SEMA3E and EFNA5 have repulsive or attractive activity (Cooper, M. A., et al. Dev Neurobiol. 69:36-46 (2009)) on axonal growth depending on the type of neurons and cellular cues (Chauvet, S., et al. Neuron 56:807-822 (2007); Overman, J. J., et al. Proc Natl Acad Sci USA 109:E2230-2239 (2012); Marler, K. J., et al. J Neurosci. 28(48):12700-12 (2008); Cooper, M. A., et al. Dev Neurobiol. 69:36-46 (2009); Bellon, A., et al. Neuron 66:205-219 (2010)). Overexpression of SEMA3E together with plexin-D1 in WAT increases inflammation and induces obesity and insulin resistance (Shimizu, I., et al. Cell Metab 18:491-504 (2013)). However, in Aldh1a1$^{-/-}$ thermocytes, only Sema3e was upregulated; perhaps it acts via alternative pathways. Axon growth is dependent on proteolysis that enables remodeling of matrix proteins and cleavage-dependent activation and secretion of ephrin ligands (Janes, P. W., et al. Cell 123:291-304 (2005); Hattori, M., et al. Science 289:1360-1365 (2000)). Within LTA-axon guidance pathway, there was significantly increased expression of the proteases AdamtS9, matrix metallopeptidase 10 (Mmp10), and Mmp13 in Aldh1a1$^{-/-}$ thermocytes compared to WT adipocytes (FIG. 2$f$). Finally, in Aldh1a1$^{-/-}$ thermocytes, G protein signaling pathways underwent significant changes. Guanine nucleotide-binding protein G(i) subunit (Gnai) was the predominantly expressed G protein in Aldh1a1$^{-/-}$ adipocytes whereas expression of Gnao1 and Gng11 were suppressed compared to WT adipocytes (FIG. 2$g$). Gnai is coupled G protein-coupled receptors (GPCR) activated by neurotransmitters and required for activation of specific adenylyl cyclases for cAMP-dependent activation of lipolysis and thermogenesis (Brust, T. F., et al. Eur J Pharmacol. 763(Pt B):223-32 (2015)). The validation analysis of the remaining molecules, which were not altered or associated only indirectly with axon guidance pathways are shown in FIGS. 7$b$ and 7$c$. Thus, thermocytes express molecules integrating stimulation of axon growth with matrix remodeling and neurotransmitter pathways in adipocytes.

LTA Secretome is Downregulated in Mouse Obesity Models

Figure 2I:
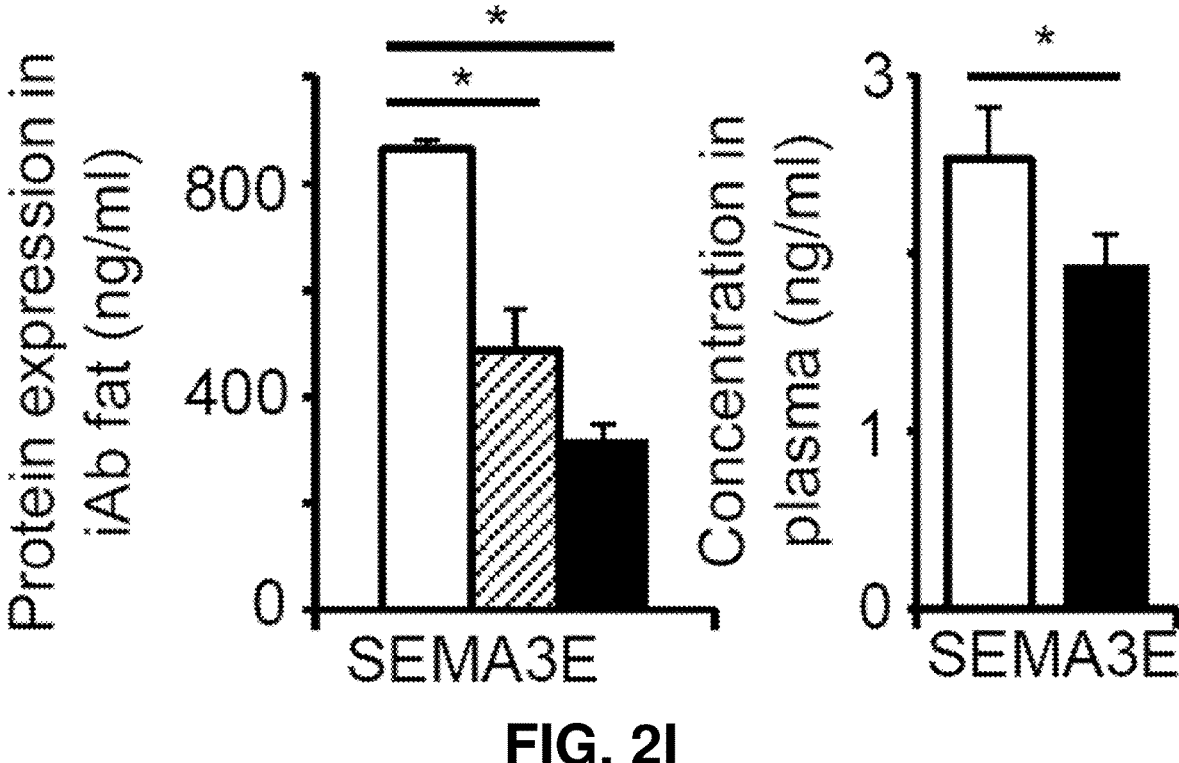
FIG. 2I: SEMA3E levels in iAb fat and plasma were examined by ELISA.
Figures 2J, 2K, 2L, 2M:
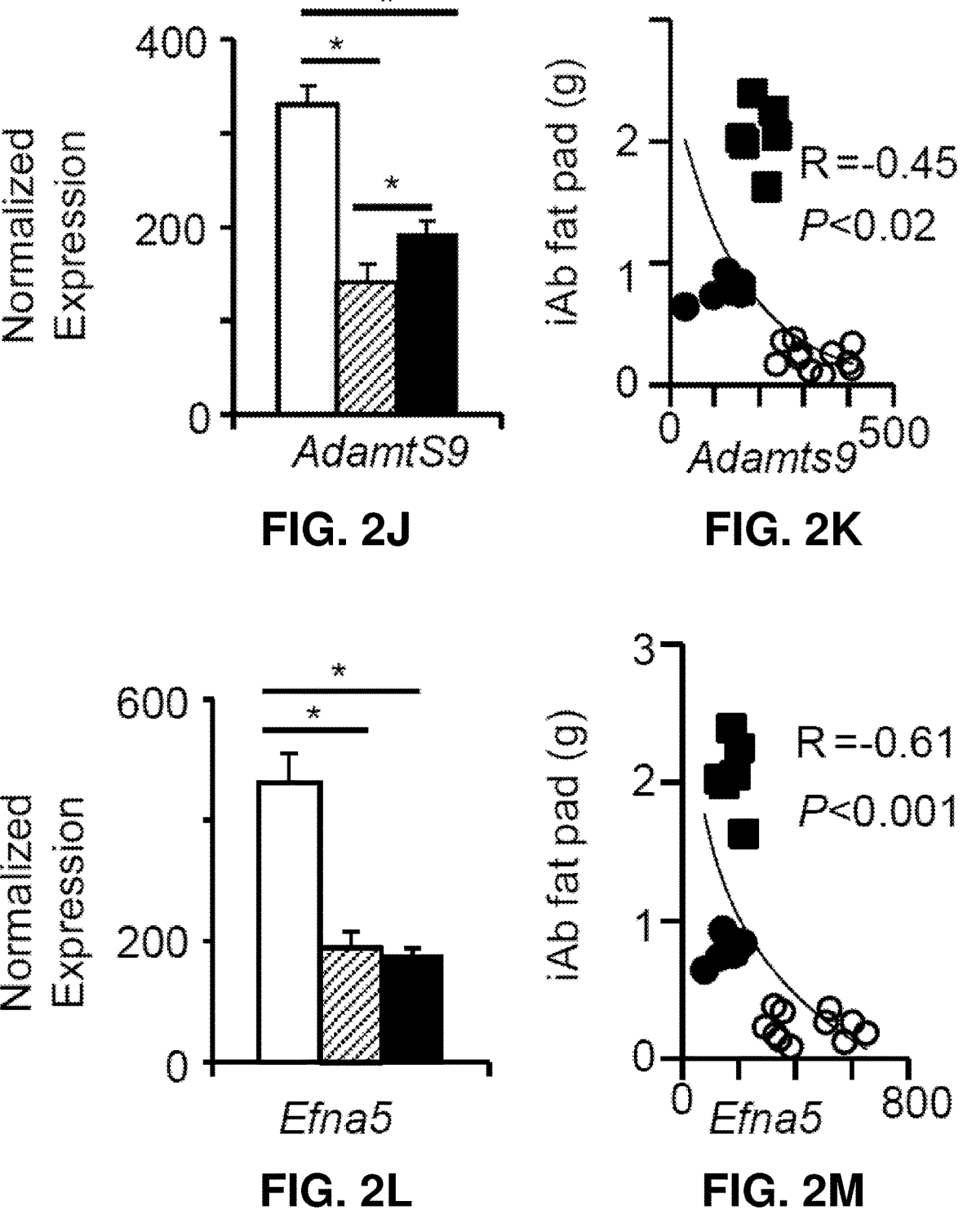

To examine if obesogenic processes are associated with impaired expression of LTA axon guidance molecules, the expression of these molecules was tested in diet-induced and genetic models of obesity (FIG. 2$h$-$o$, Table 1, Study 2). The expression of molecules comprising the secretome, including Sema3e and Sema3d (FIG. 2$h$), protein levels of SEMA3E in iAb fat and plasma (FIG. 2$i$), expression of AdamtS9 (FIG. 2$j$), and Efna5 (FIG. 2I) and its receptor Epha4 (FIG. 2$n$), were markedly suppressed in iAb fat of obese mice and inversely correlated with iAb fat pad mass and body weight (FIG. 2$k$, 2$m$, 2$o$, FIG. 7$d$). These data demonstrated that expression of all secreted LTA axon guidance molecules (secretome) was inhibited in obesity.

Figure 8C:
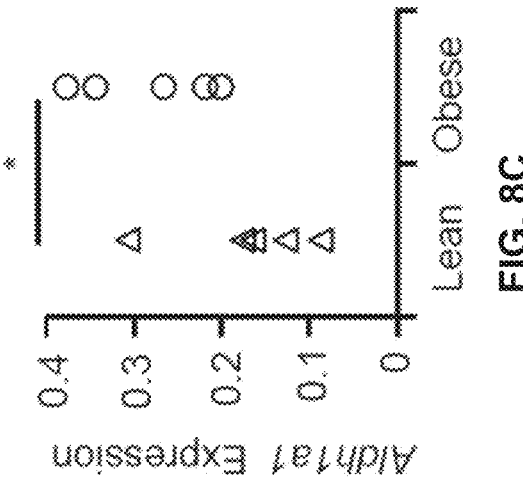
FIGS. 8A to 8C show expression of Efna5 (FIG. 8A), Epha4 (FIG. 8B), and Aldh1a1 (FIG. 8C) in human subcutaneous adipose, examined using RT-PCR. Tissues were isolated from lean (n=5) and obese (n=5) Caucasian women (Table 3). An asterisk indicates P<0.05, Mann-Whitney U test.
Figure 8B:
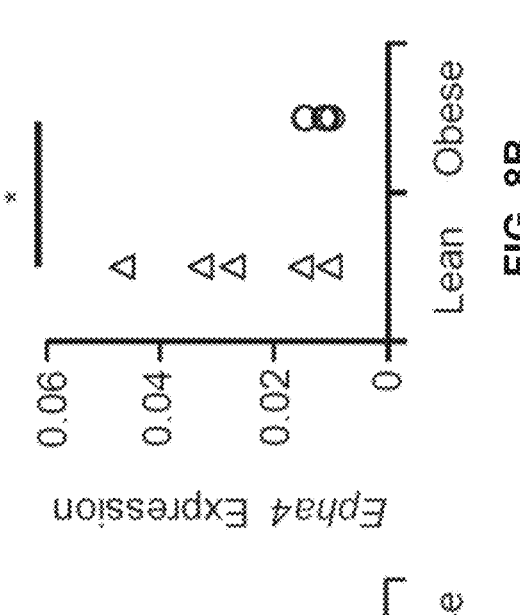
Figure 8A:
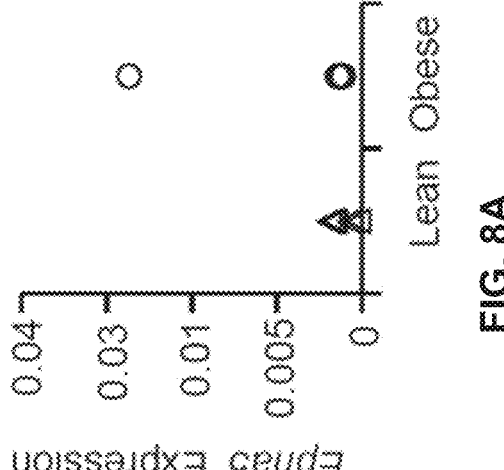

Both differentiated and non-differentiated human iAb (omental) adipocytes, iAb and subcutaneous fat also express LTA axon guidance molecules (Table 2, FIG. 8). In small number of participants, the inverse association with obesity was found only for EphA4 receptor in subcutaneous WAT from obese vs lean patients expressing significantly higher levels of Aldh1a1 (FIG. 8).

TABLE 2

Gene expression of visceral adipose tissue and isolated non-differentiated (ND) and differentiated (D) visceral adipocytes from obese patients. Data is shown as mean ± S.D.

| | iAb (omental) Adipocytes (N = 5) | | iAb Tissue |
|---|---|---|---|
| Gene | ND | D | (N = 8) |
| Adamts5 | 192.0 ± 83.7 | 114.0 ± 46.5 | 660.0 ± 247.3 |
| Adamts9 | 19.8 ± 25.4 | 62.6 ± 32.2 | 871.4 ± 1191.9 |
| Epha4 | 197.0 ± 109.0 | 237.4 ± 122.9 | 297.1 ± 109.2 |
| Epha2 | 282.8 ± 118.1 | 179.6 ± 47.2 | 114.8 ± 74.8 |
| Efna5 | 75.2 ± 50.5 | 67.8 ± 66.8 | 190.1 ± 50.6 |
| Gnai1 | 789.2 ± 233.5 | 924.2 ± 217.0 | 2372.6 ± 796.3 |
| Gnao1 | 11.6 ± 15.8 | 15.2 ± 28.5 | 17.5 ± 12.3 |
| Gng11 | 1000.8 ± 434.3 | 1429.8 ± 602.4 | 4673.0 ± 749.7 |
| Hhip | 81.6 ± 67.4 | 6.8 ± 12.4 | 94.4 ± 64.2 |
| Itga3 | 785.4 ± 573.6 | 188.0 ± 231.8 | 148.8 ± 57.2 |
| Mmp10 | 3.4 ± 3.9 | d.l. | 11.4 ± 7.9 |
| Mmp11 | 10.4 ± 5.9 | 7.2 ± 5.5 | 12.4 ± 12.0 |
| Mmp13 | 2.0 ± 1.7 | 1.6 ± 1.3 | 105.5 ± 81.3 |
| Plce1 | 29.8 ± 23.3 | 16.0 ± 17.2 | 168.6 ± 39.4 |
| Robo1 | 241.6 ± 50.5 | 363.8 ± 138.5 | 271.4 ± 48.3 |
| Slit2 | 283.6 ± 87.5 | 329.4 ± 155.2 | 278.8 ± 67.7 |
| Bmp2 | 182.8 ± 196.0 | 125.6 ± 88.9 | 319.4 ± 135.0 |
| Sema3d | 104.8 ± 60.5 | 177.8 ± 302.3 | 604.1 ± 264.8 |
| Sema3e | 27.4 ± 32.9 | 7.0 ± 12.9 | 123.6 ± 89.2 |
| Plxnd1 | 135.6 ± 49.5 | 308.4 ± 50.5 | 394.9 ± 170.1 |
| Srgap3 | 1.2 ± 0.4 | 2.4 ± 3.1 | 53.9 ± 35.0 |
| Figf | 9.8 ± 4.2 | 154.0 ± 298.2 | 175.5 ± 166.6 |
| Pdgfd | 869.4 ± 565.5 | 4292.8 ± 1187.9 | 639.0 ± 308.6 |

TABLE 3

Description of lean and obese human patients

| | BMI | Age | Glucose | Race | Gender |
|---|---|---|---|---|---|
| Lean | 24.69 ± 1.18 | 43 ± 10.63 | 86.60 ± 7.44 | W | F |
| Obese | 42.98 ± 5.17 | 50 ± 10.05 | 111.80 ± 16.21 | W | F |
| p-value | 0.00006 | 0.315845 | 0.013 | | |

Figure 3A:
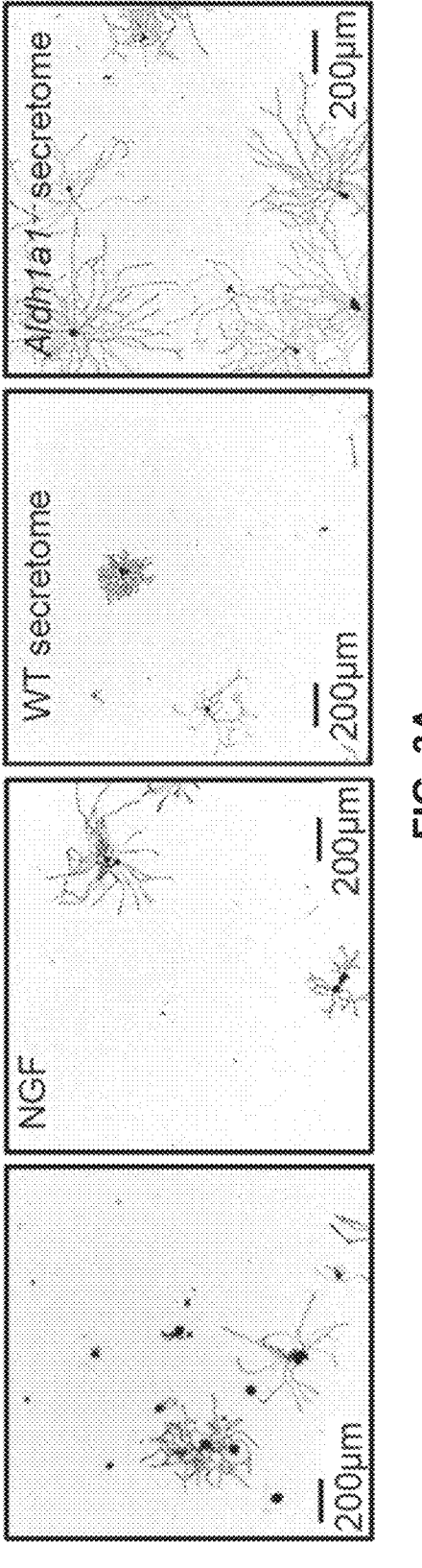
Figure 3B:
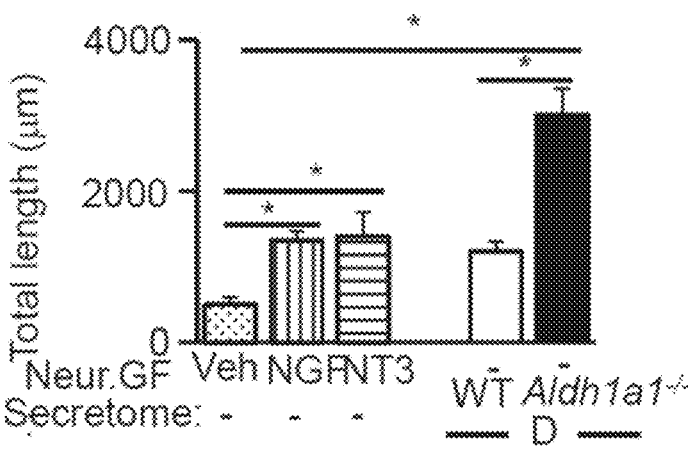
Figure 3C:
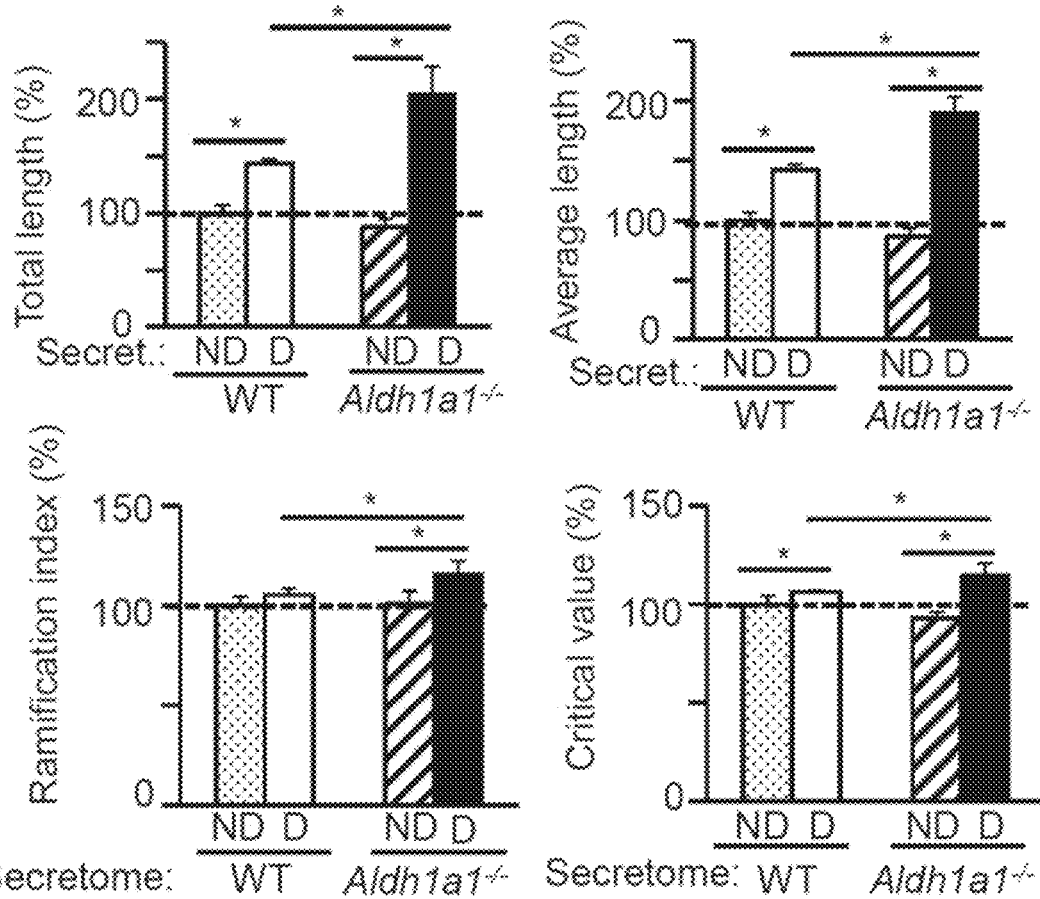
Figure 9A:
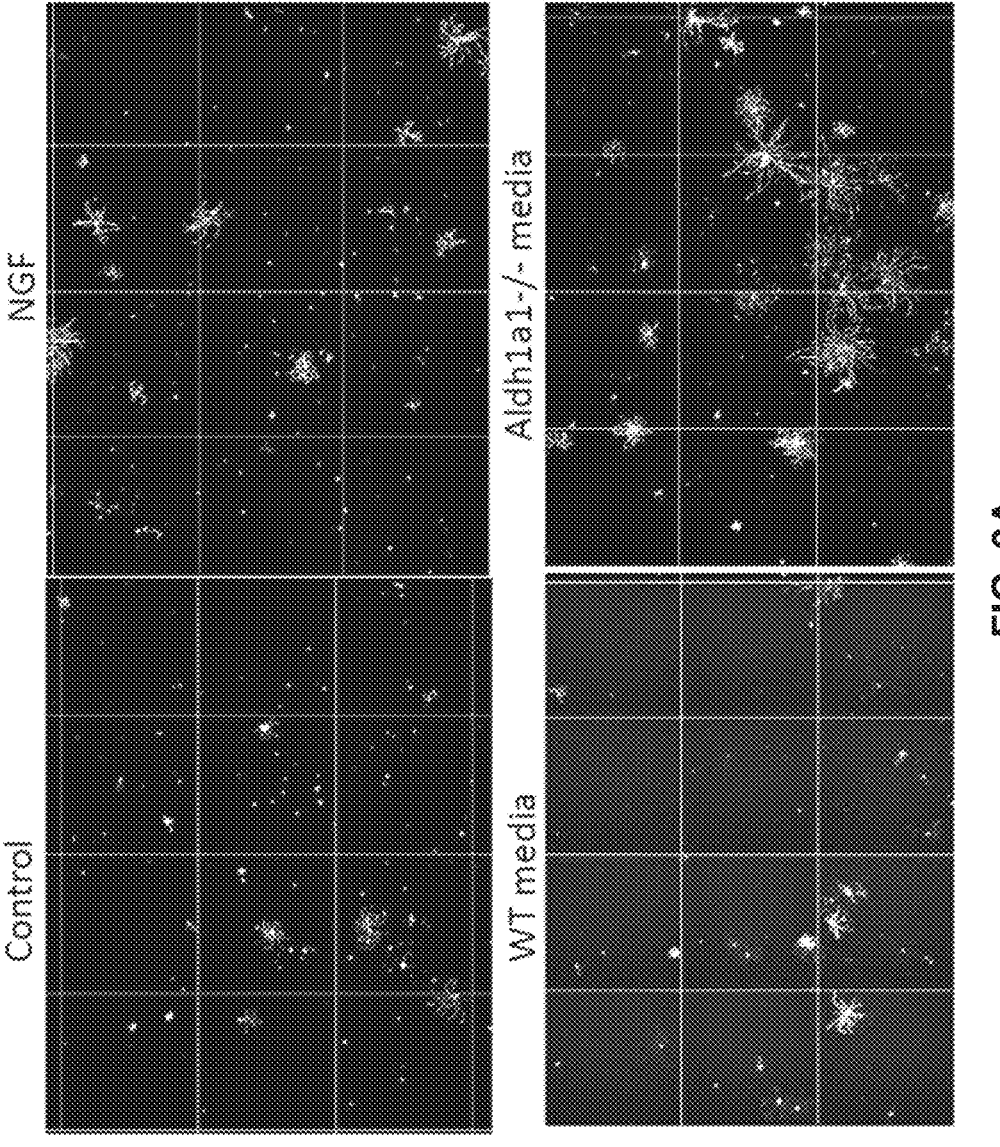
FIGS. 9A to 9D show DRG neurons (500 neurons per well) cultured in DRG culture medium only, or DRG culture medium with NT-3 (1 ng/mL), with NGF (10 ng/mL), with WT secretome (1/1, v/v), or with Aldh1a1$^{-/-}$ secretome (1/1, v/v) for 24 hours. WT and Aldh1a1$^{-/-}$ adipocytes differentiated for 5 days. Secretome is the media collected from these cells for 24 h. Neurite outgrowth parameters were assayed using the Thermo Scientific™ ArrayScan™ XTI Live High Content microscope and analyzed with the Neuronal Profiling Algorithm (ThermoFisher). Nine independent experiments were performed using DRG from three mice. Each DRG batch was analyzed in triplicate. Data are shown as mean±SD obtained with one DRG batch. Asterisks indicate P<0.05 between different groups; Mann-Whitney U test.

Thermocytes' axon guiding secretome is functional and induces neurite outgrowth Next experiments were conducted to determine if the changes in expression of secreted LTA-axon guidance cluster could functionally influence neurons. DRG neurons innervate WAT (Murphy, K. T., et al. Endocrinology and metabolism 304:E1338-1347 (2013)). For all experiments equal numbers of 500 neurons per well were used. Stimulation of primary murine DRG neurons with the medium obtained from differentiated WT and Aldh1a1$^{-/-}$ adipocytes led to marked induction of axonal growth (representative images are shown in FIG. 3a, 9). Axonal growth was quantified by length, branching points, and total neurite outgrowth in the presence of media from Aldh1a$^{-/-}$ thermocytes vs. WT adipocytes (FIG. 3b-e). The axonal growth in media from Aldh1a1$^{-/-}$ thermocytes was significantly higher than that seen in the presence of the classic inducers NGF and neurotrophin 3 (NT3) (FIG. 3a,b). Media from WT adipocytes and Aldh1a1$^{-/-}$ thermocytes contained similar levels (0.1 ng/mL) of secreted endogenous NGF (FIG. 1E) compared to 10 ng/mL of recombinant NGF used for positive control (10 ng/mL). The secretomes from WT and Aldh1a1$^{-/-}$ differentiated cells promote axonal growth more efficiently than the secretome from non-differentiated cells (FIG. 3b), in agreement with the higher expression of axon guiding molecules during differentiation (FIG. 2). EFNA5 antibody prevent outgrowing of neurites and their maximal length stimulated by Aldh1a1$^{-/-}$ media, while other parameter such as branching were not influenced by this treatment. Thus, EFNA5 mediates some of the effects attributed to LTA secretome (FIG. 3f); however, the whole secretome is responsible for axon guidance promoting effect of Aldh1a1$^{-/-}$ secretome.

Thermocyte Engraftment Induces Innervation of iAb Fat In Vivo

Experiments were next conducted to determine if the secretome from Aldh1a1$^{-/-}$ thermocytes can induce innervation in vivo. Engrafting WT adipocytes and Aldh1a1$^{-/-}$ thermocytes within the alginate poly-L-lysine polymer provides protection from the immune system and promotes long-term survival of adipocytes (Yang, F., et al. Biomaterials 33:5638-5649 (2012)). In vivo encapsulated cells survive in mice for 80 days (Yang, F., et al. Biomaterials 33:5638-5649 (2012)) and in humans for up to 9 years (Brust, T. F., et al. Eur J Pharmacol. 763(Pt B):223-32 (2015)). The semipermeable poly-L-lysine membrane allows only the exchange of low molecular weight molecules (<36 kD). This model (Yang, F., et al. Biomaterials 33:5638-5649 (2012)) allows testing the effect of the secretome on host adipocytes. Previous studies showed that engrafting of Aldh1a1$^{-/-}$ preadipocytes, but not WT preadipocytes induces thermogenesis and lipolysis iAb, accompanied by long-term increase in metabolic rate in obese WT mice (Yang, F., et al. Biomaterials 33:5638-5649 (2012); Xu L, et al. J Vis Exp. (100):e52806 (2015)).

Figure 4A:
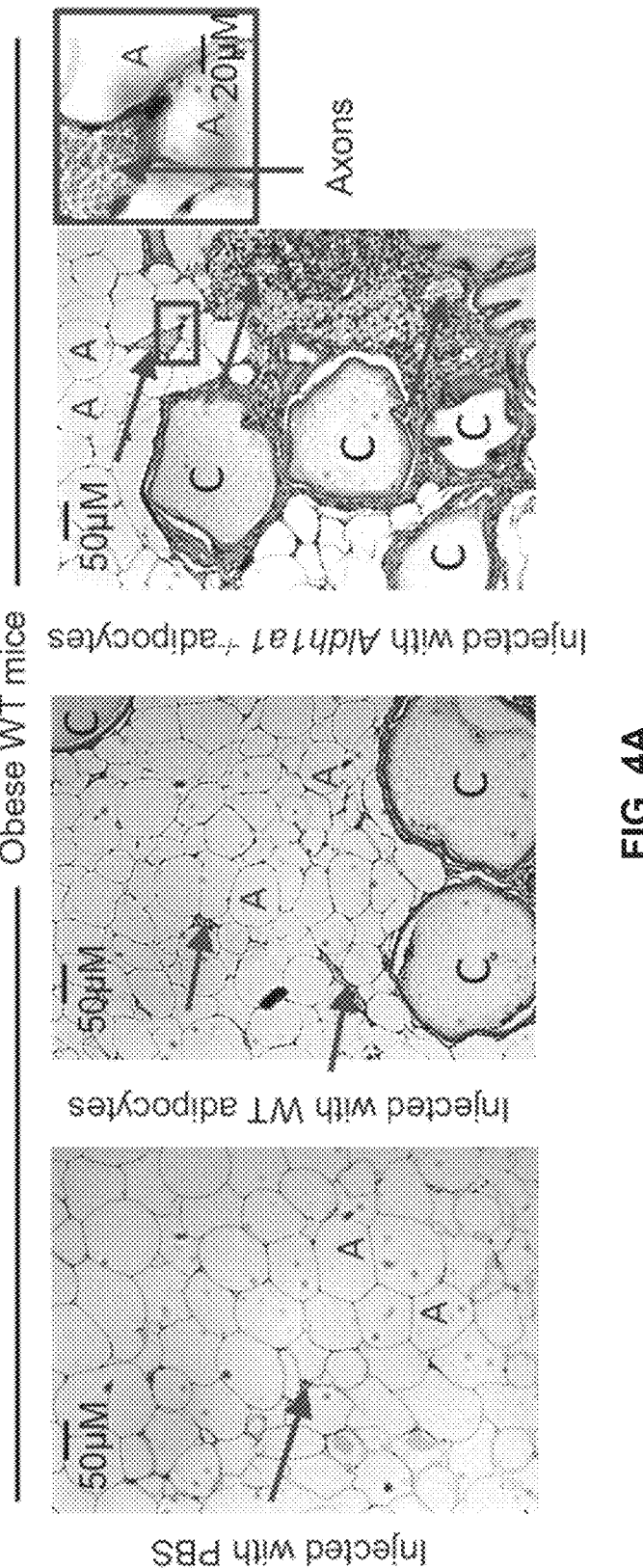
FIGS. 4A to 4C show secretome from engrafted encapsulated Aldh1a1$^{-/-}$ thermocytes promotes innervation in WT obese mice. Obese WT mice (n=18) on a HF diet were treated with acellular (n=3) microcapsules or micro capsules containing WT adipocytes (n=5) or Aldh1a1$^{-/-}$ thermocytes (n=5) or remained untreated (n=5) (Table 1, Study 3).
Figure 4B:
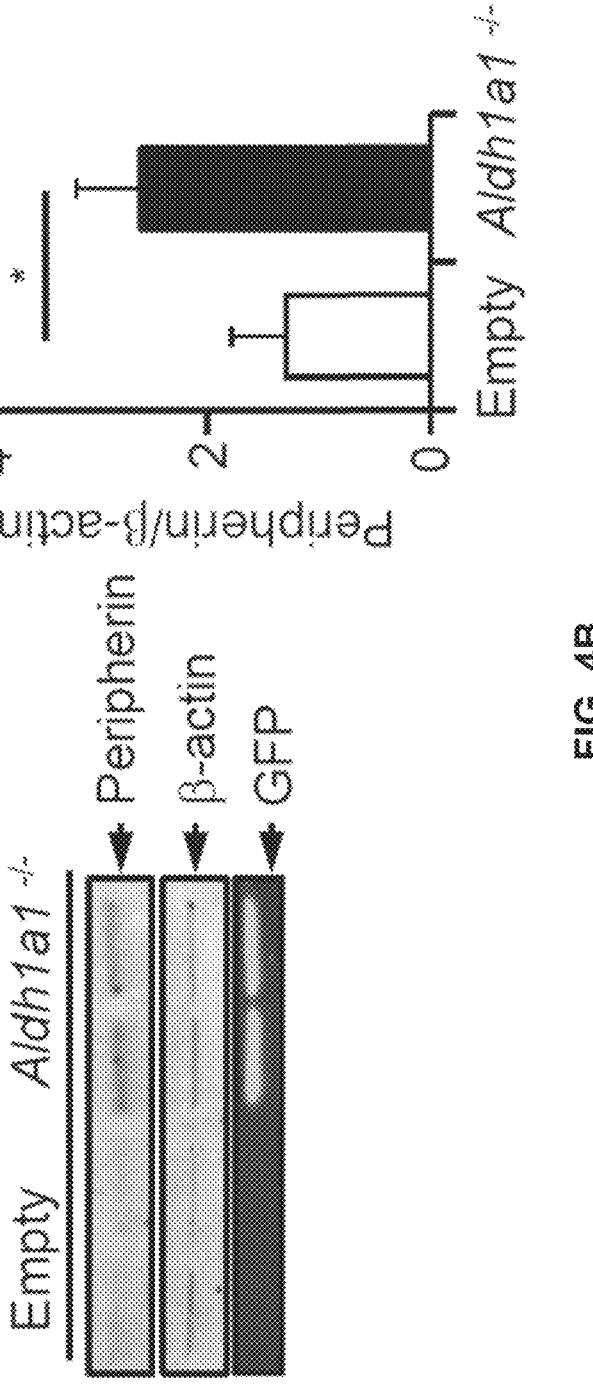
Figure 4C:
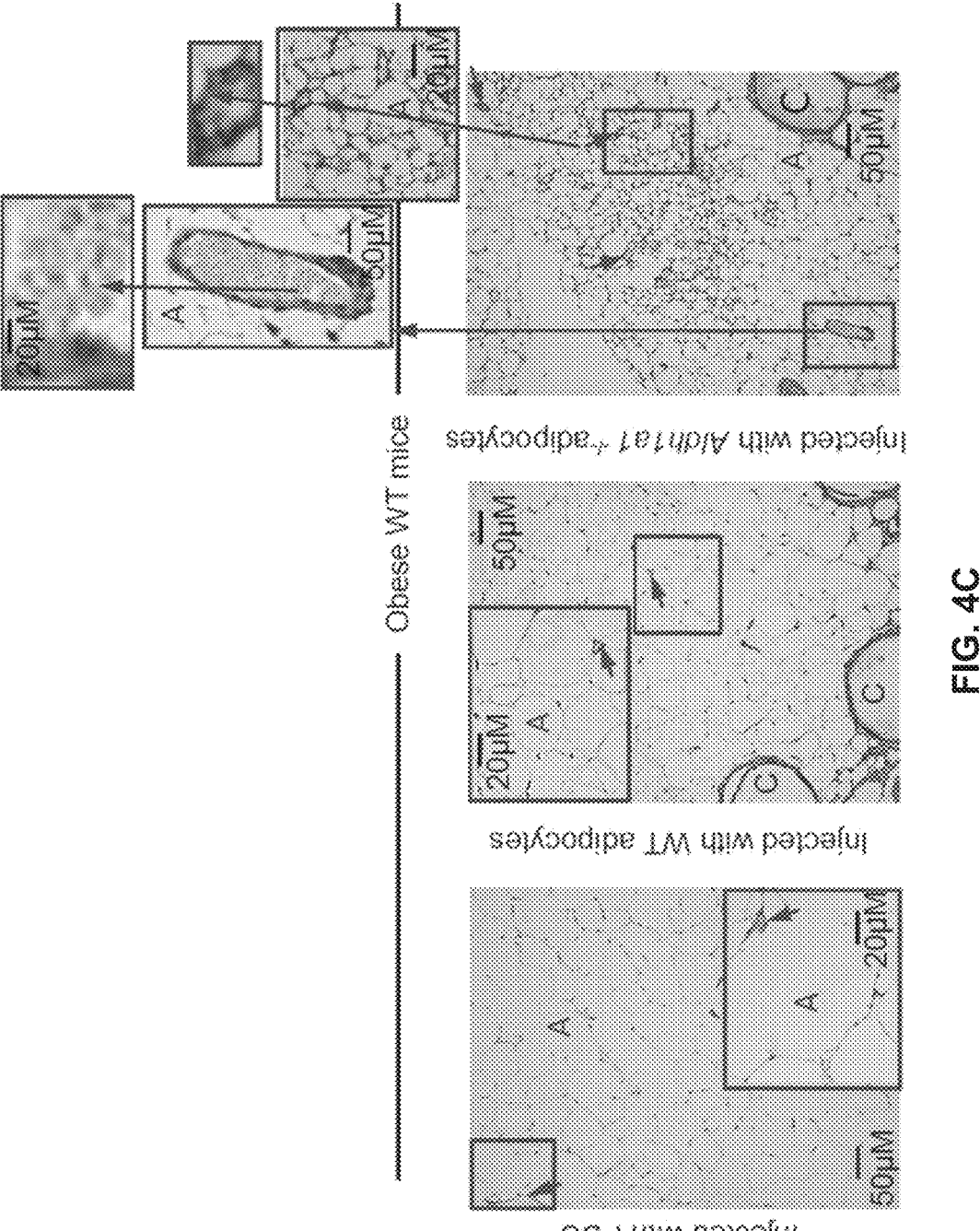

To address the question if functional thermogenesis is accompanied by remodeled innervation, the encapsulated WT and Aldh1a1$^{-/-}$ preadipocytes were injected into iAb fat of WT mice with high-fat diet-induced obesity (Table 1, Study 3). The engrafting of encapsulated Aldh1a1$^{-/-}$ thermocytes, but not WT adipocytes, stimulated development of peripherin positive axons around engrafts (FIG. 4a). Peripherin was expressed at significantly higher levels compared to iAb fat injected with empty capsules (FIG. 4b). Tyrosine hydroxylase positive sympathetic axons were also present around Aldh1a1$^{-/-}$ thermocyte engrafts, but not in the proximity of encapsulated WT adipocytes (FIG. 4c). The host WT adipocytes in areas surrounding Aldh1a1$^{-/-}$ thermocyte engrafts were of smaller size and had a multilocular structure consistent with previously reported lipolysis and thermogenesis localized to these areas (Yang, F., et al. Biomaterials 33:5638-5649 (2012)). Thus, the LTA-axon guidance secretome released from encapsulated Aldh1a1$^{-/-}$ thermocytes contributes to innervation of iAb fat in an autonomous manner.

Figure 5A:
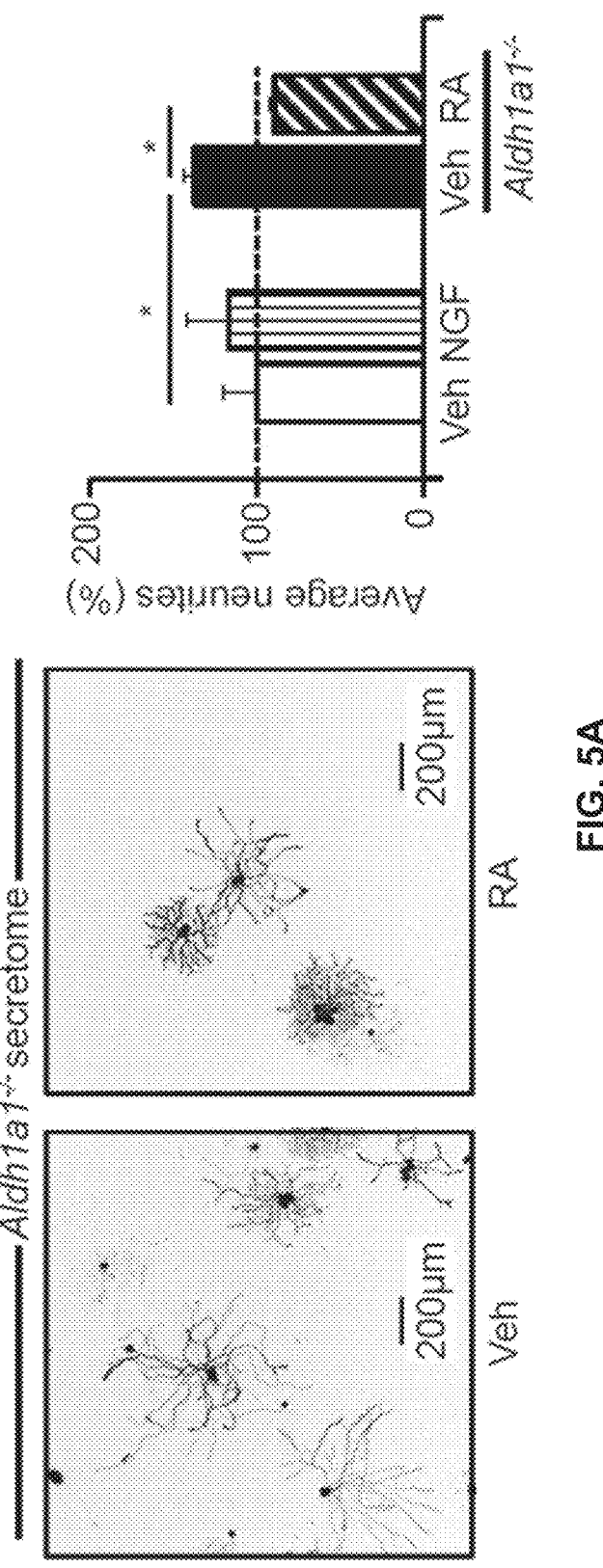
Figure 5C:
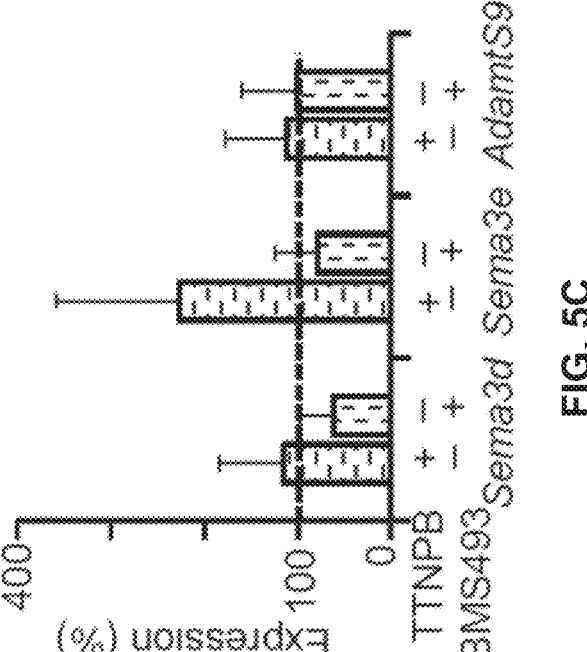
Figure 5B:
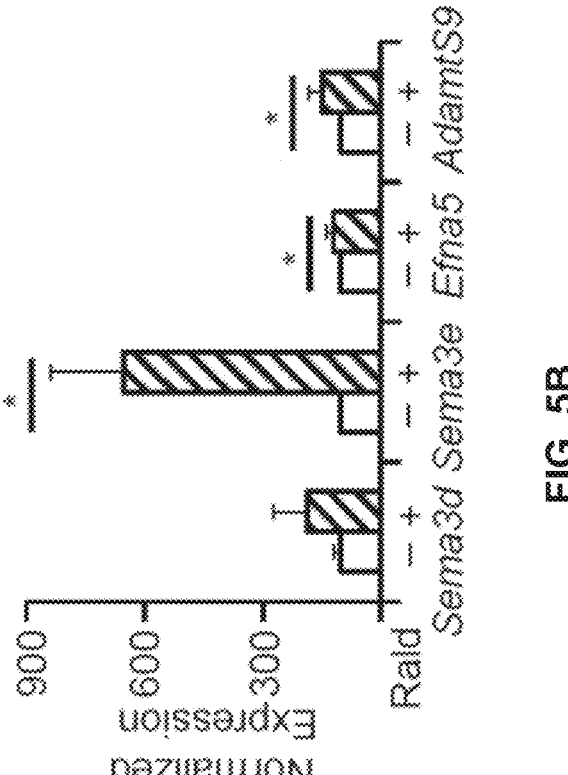
Figure 5G:
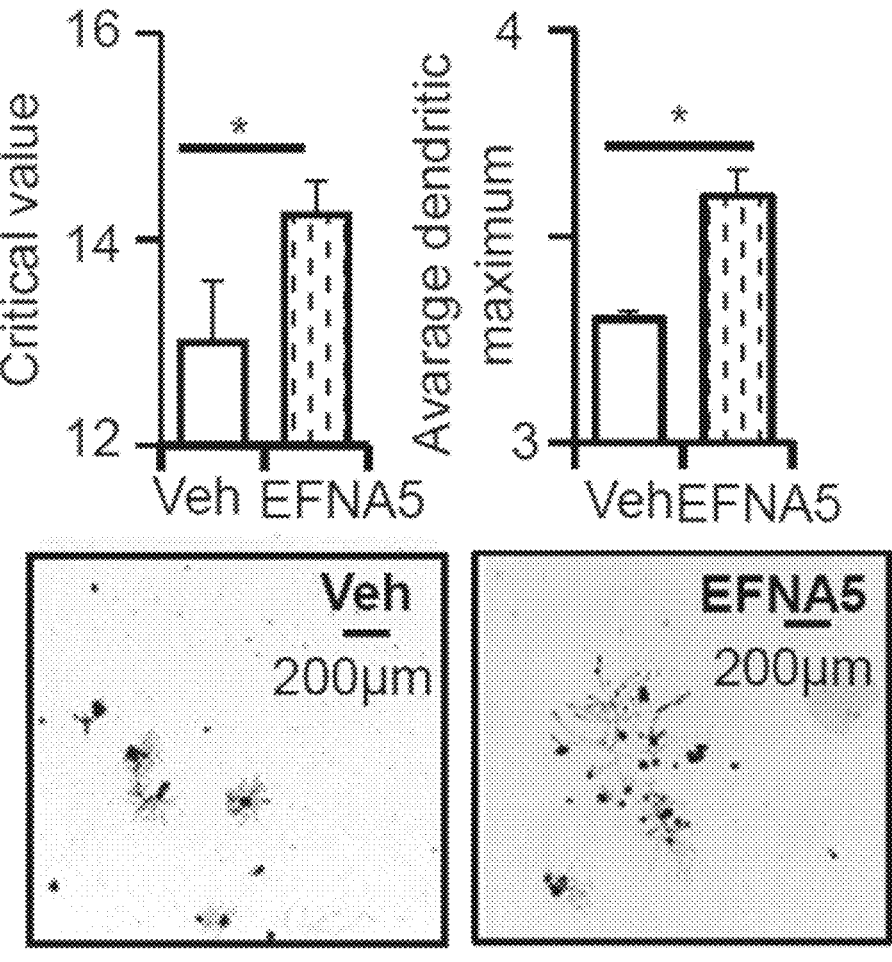
Figure 5H:
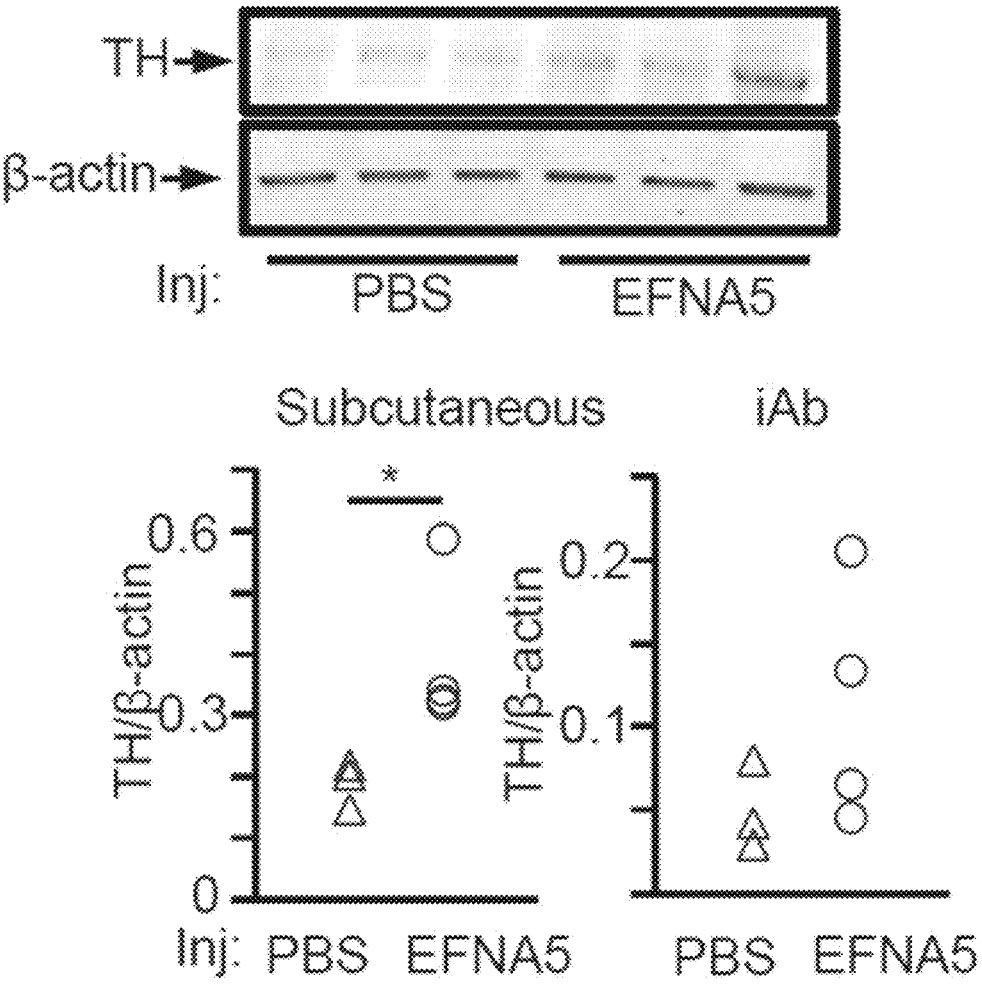
Figure 5I:
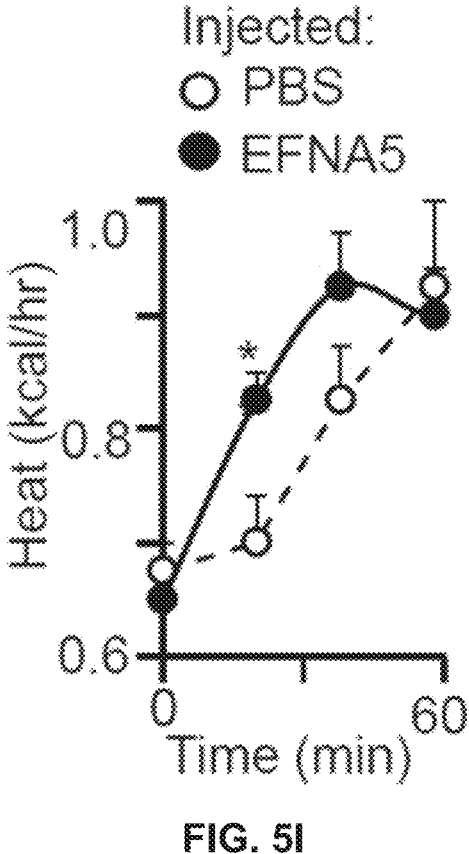
Figures 9B, 9D:
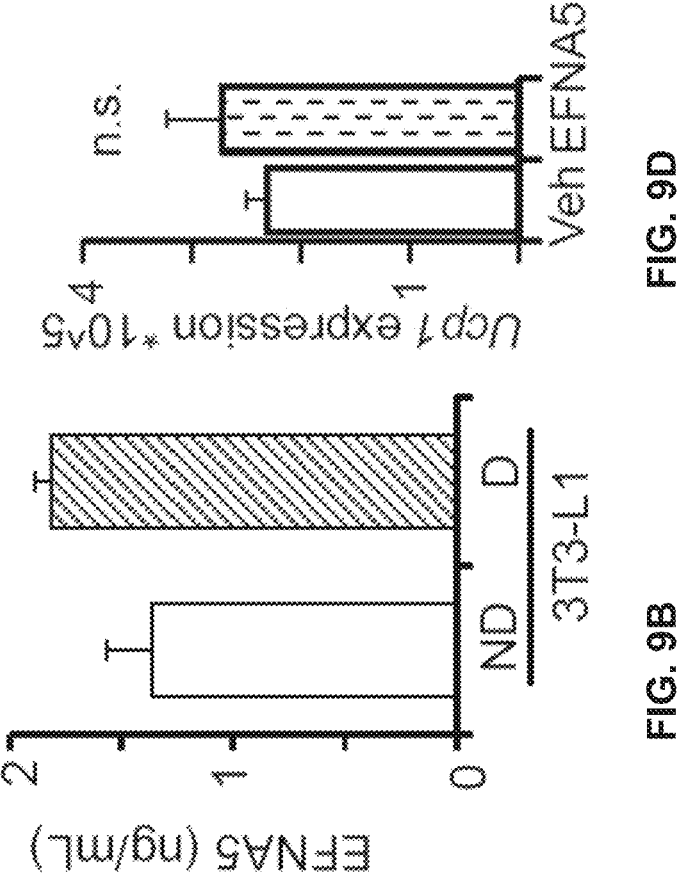
Figure 9C:
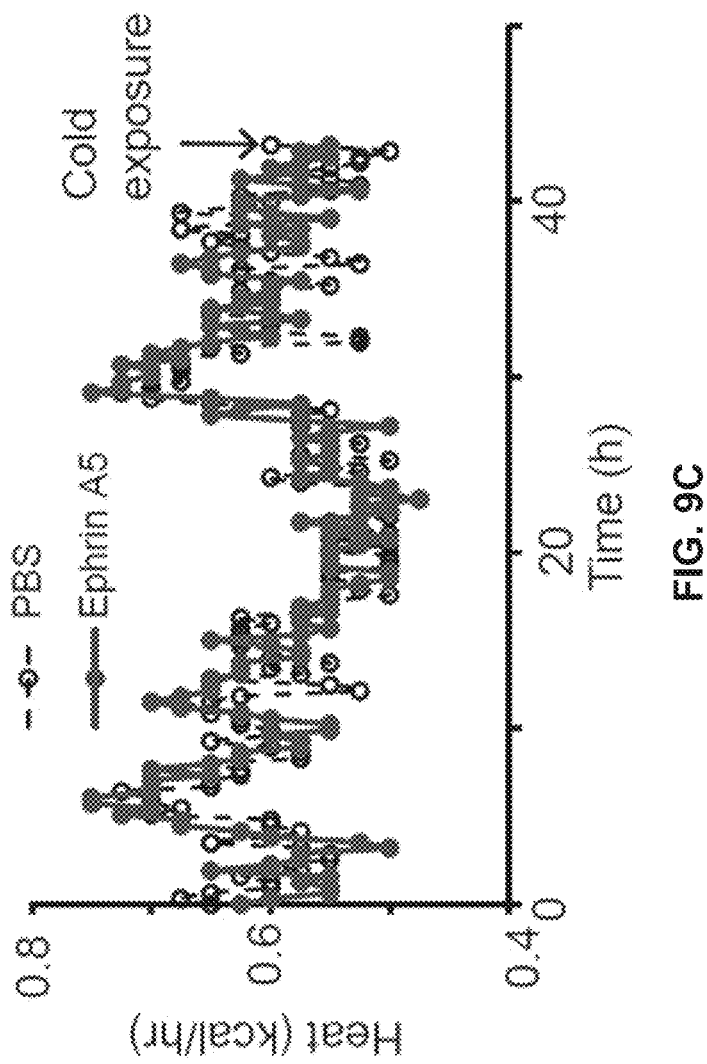
Figure 10A:
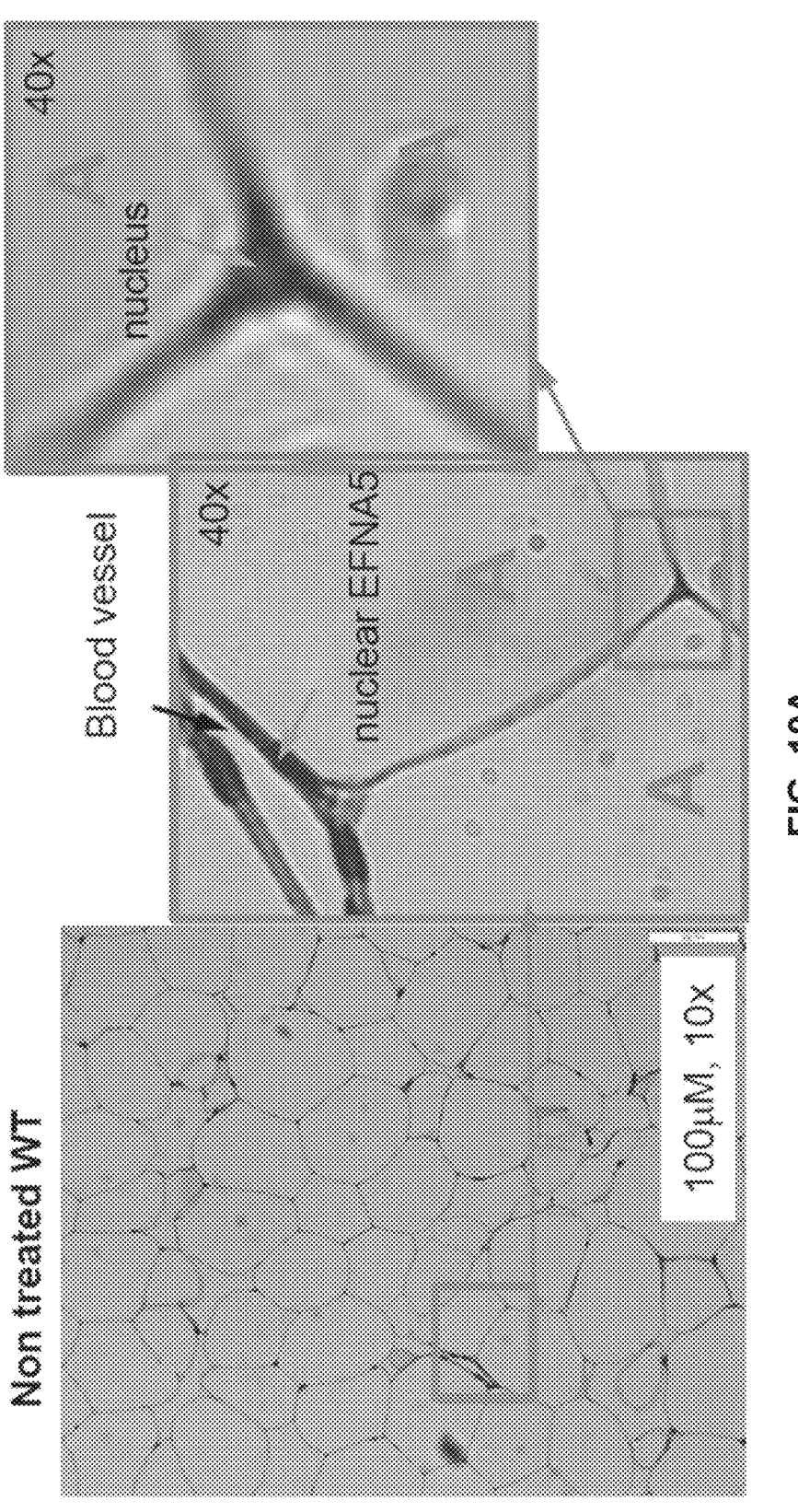
FIGS. 10A to 10C show obese WT mice (n=18) on a HF diet that were not treated (n=3) (FIG. 10A), were treated with micro capsules containing WT adipocytes (n=5) (FIG. 10B) or Aldh1a1$^{-/-}$ thermocytes (n=5) (FIG. 10C) (Table 1, Study 3). Representative images show ENFA5 immunoreactive areas in blood vessels, nerves, and adipocytes ('A' letters) found in paraffin-embedded iAb fat from mice injected with vehicle and encapsulated WT and Aldh1a1$^{-/-}$ cells at 10× magnification or at 40× magnification in the inserts. Arrows indicate examples of ENFA5-positive nucleus or perinuclear area. 'C' indicates empty core of microcapsules because encapsulated cells are attached at the inner surface of capsules.
Figure 10B:
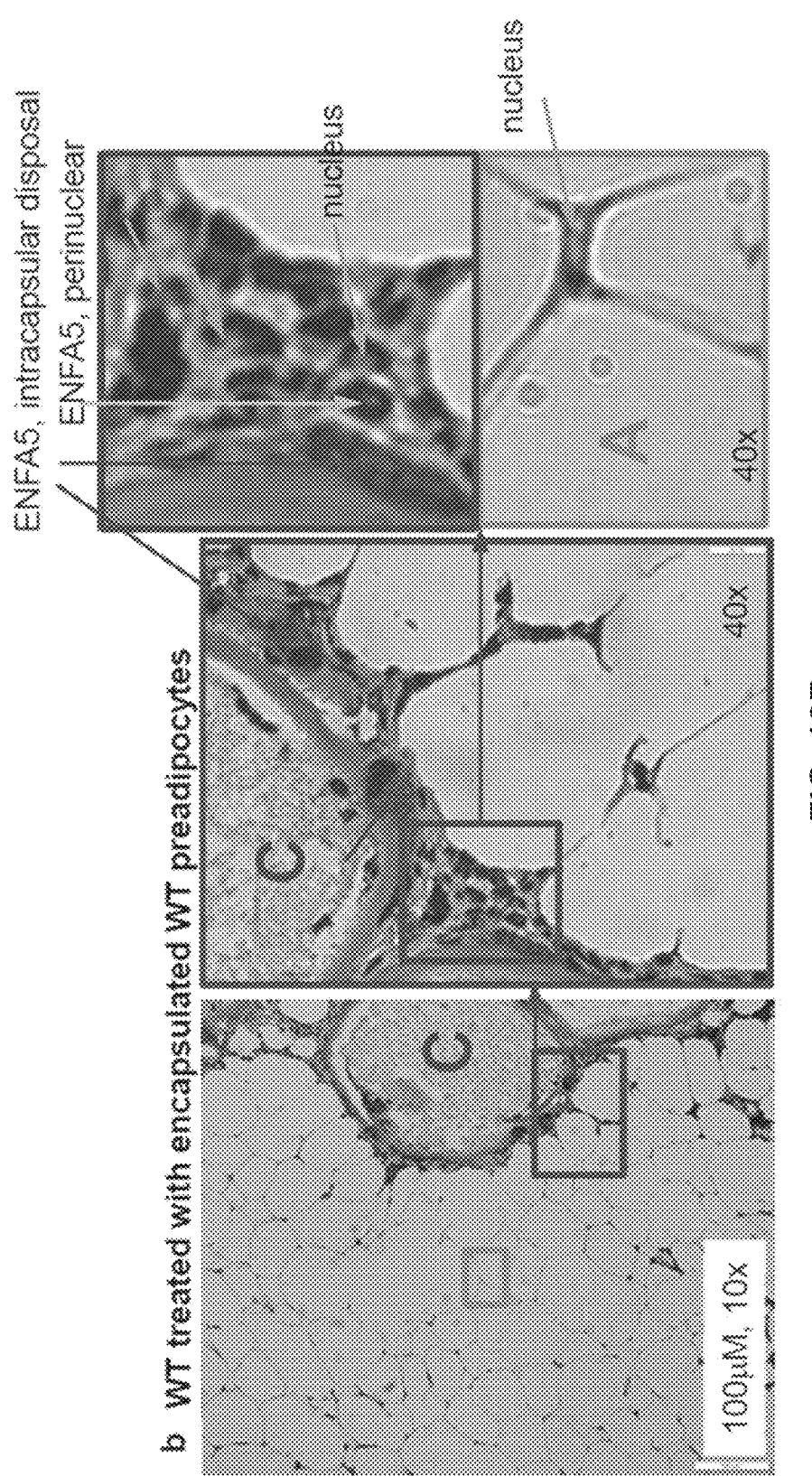
Figure 10C:
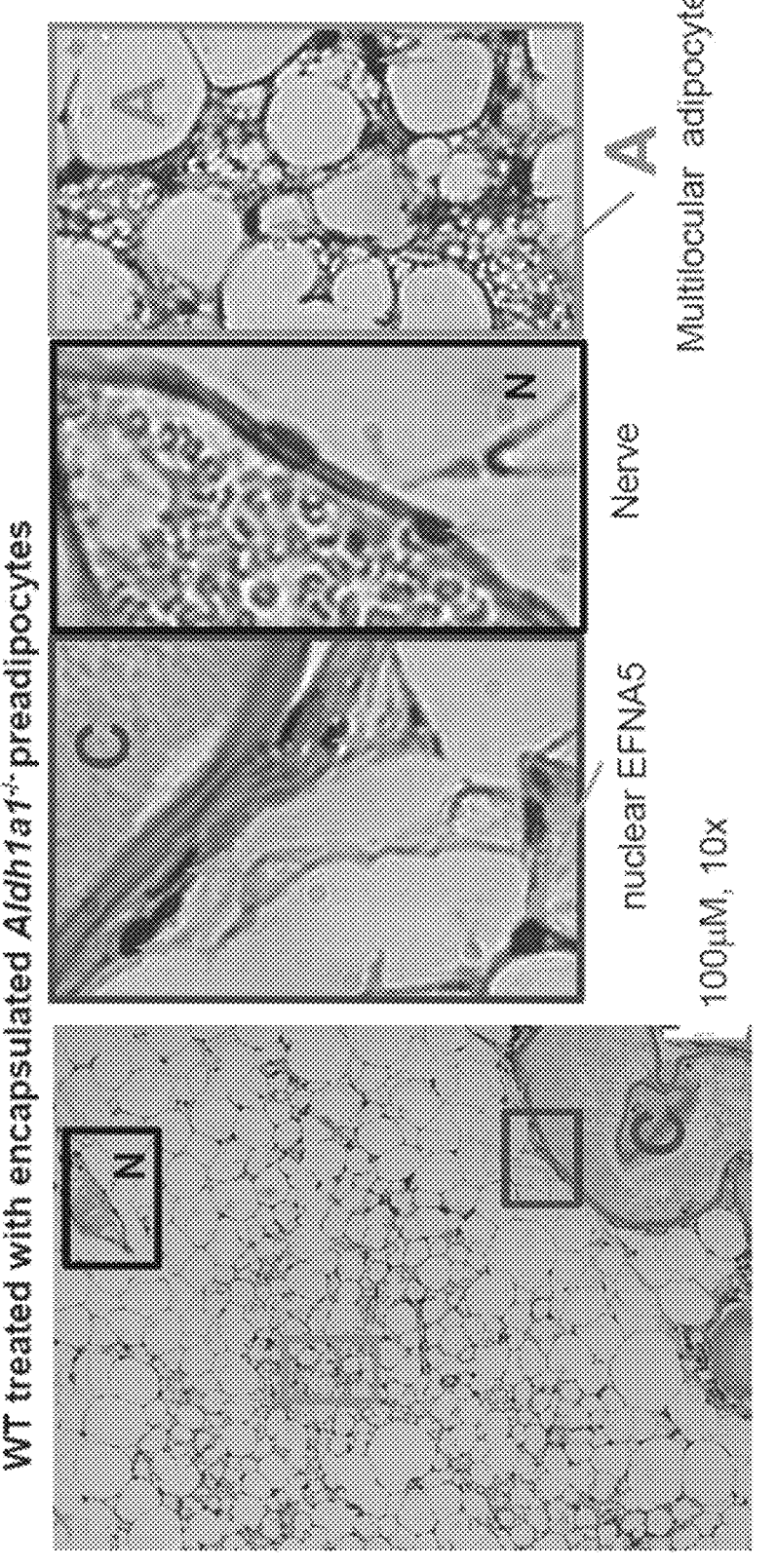

Retinoic Acid Receptor is a Negative Regulator of Ephrin A5 Pathway and Axon Guidance A mechanism by which ALDH1A1 influences specific expression of LTA axon guidance molecules could depend on its enzymatic products. ALDH1A1 is a key enzyme in the production of RA from retinaldehyde in adipocytes under physiological conditions (Reichert, B., et al. Mol Endocrinol 25:799-809 (2011)), although ALDH1A1 can catalyze other reactions including oxidation of 3-deoxyglucosone (Collard, F., et al. Biochimie 89:369-373 (2007)). To test if RA regulate properties of Adh1a1$^{-/-}$ secretome, Adh1a1$^{-/-}$ thermocytes were differentiated in presence and absence of RA and medium used to stimulate primary DRG neurons. RA-conditioned Aldh1a1$^{-/-}$ secretome inhibited growth of DRG axons mediated by Aldh1a1$^{-/-}$ secretome (FIG. 5a). These data indicate a key inhibitory role of RA against the LTA-axon-guiding secretome. In contrast, stimulation of 3T3-L1 adipocytes with precursor retinaldehyde significantly increased expression of molecules associated with the LTA-axon guidance secretome (FIG. 5b). However, among all tested LTA-axon-guiding factors only Efna5 and Epha4 expression was regulated in a RA receptor (RAR)-dependent manner (FIG. 5c, d). Efna5 and Epha4 were suppressed by the RAR agonist TTNPB and induced by the RAR antagonist BMS429. Aldh1a1 also influenced protein levels and secretion of the EFNA5 ligand. EFNA5 protein was produced by 3T3-L1 adipocytes (FIG. 9b), WT, and Aldh1a1$^{-/-}$ cells (FIG. 5e). However, EFNA5 secretion was associated predominantly with differentiated Aldh1a1$^{-/-}$ thermocytes. Consistent with this expression, significantly higher levels of EFNA5 were found in plasma from Aldh1a1$^{-/-}$ vs. WT mice fed regular chow (FIG. 5f, Table 1, Study 4). EFNA5 has been implicated in the regulation of axon growth that was promoted (Cooper, M. A., et al. Dev Neurobiol. 69:36-46 (2009)) or inhibited (Overman, J. J., et al. Proc Natl Acad Sci USA 109:E2230-2239 (2012)) in different tissues via protease-dependent forward and reverse signaling (Xu, N. J., et al. Semin Cell Dev Biol 23:58-64 (2012)). Stimulation of DRG neurons with recombinant EFNA5 increased dendritic maximum and critical value in neurons, suggesting that EFNA5 contributes to the axon growth-promoting activity of Aldh1a1$^{-/-}$ thermocytes (FIG. 5g). Recombinant EFNA5 was also injected into iAb fat of mice with HF-diet-induced obesity. After 2 weeks of treatment, tyrosine hydroxylase protein levels were increased in WAT in mice injected with EFNA5 vs. PBS (FIG. 5h, Table 1, Study 5). Cold exposure of these mice also led to an increased metabolic rate in EFNA5- vs. PBS-injected mice, suggesting that sympathetic innervation is increased by recombinant EFNA5 (FIG. 5i; basal metabolic rate is shown in FIG. 9c). EFNA5 stimulation has no direct effect on regulation of expression of thermogenic genes in 3T3-L1 adipocytes (FIG. 9d). Increased EFNA5 expression was found in the thermogenic multilocular iAb fat and adjacent nerves after treatment of WT mice with encapsulated Aldh1a1$^{-/-}$ thermocytes, compared to monolocular fat of non-treated WT mice or mice treated with encapsulated WT adipocytes (FIG. 10). Thus, EFNA5 is under RAR control and contributes to axon guiding in vitro and possibly in vivo.

Discussion

Figure 6A:
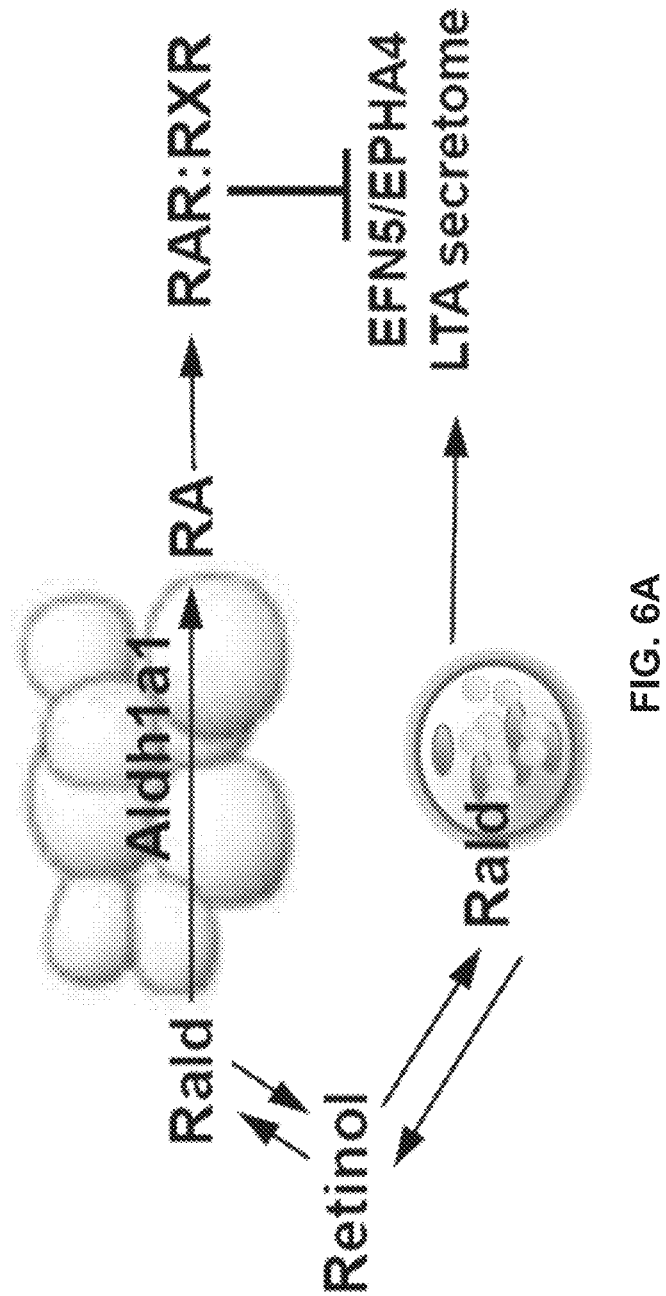
FIGS. 6A and 6B illustrate that inhibition of the LTA axon guiding secretome is associated with obesity in mice and humans.
Figure 6B:
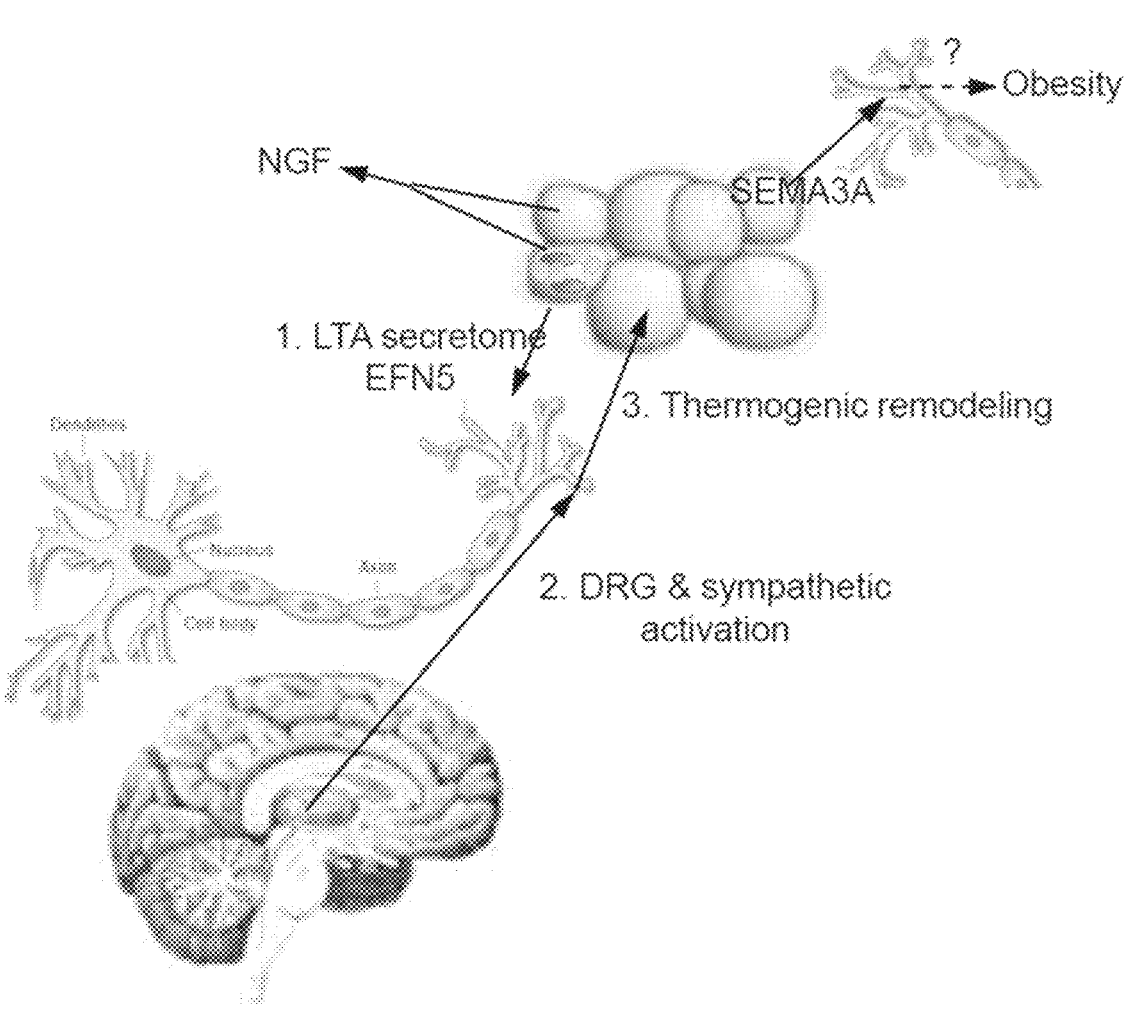

Studies in animal models of obesity as well as epidemiologic and clinical evidence suggest a pathophysiologic relationship between neuropathy and metabolic syndrome (Cortez, M., et al. Handbook of clinical neurology 126:109-122 (2014)). Researchers have identified that monolocular adipocytes in WAT contribute to the production of axon guiding molecules such, as NGF (Bullo, M., et al. Eur J Endocrinol 157:303-310 (2007); Peeraully, M. R., et al. Endocrinology and metabolism 287:E331-339 (2004)) and SEMA3A (Giordano, A., et al. J Neurocytol 32:345-352 (2003)). Their levels are increased in obese patients and are associated with obesity (Giordano, A., et al. J Neurocytol 32:345-352 (2003); Bullo, M., et al. Eur J Endocrinol 157:303-310 (2007)). Many empirical studies have indicated that adipose tissue can improve recovery from a spinal cord injury that was attributed to the presence of stem cells in adipose tissue (Kang, S. K., et al. Stem Cells Dev 15:583-594 (2006)). Here evidence is provided for a regulatory paradigm in which thermogenic adipocytes populations produce distinct guidance cues and establish distinct peripheral innervation that contributes to metabolic control of lipolysis and thermogenesis by the CNS (FIG. 6). Two approaches were used to show that differentiated thermocytes are key inducers of axonal growth and that this growth is mediated by secreted molecules. First, the secretome from Aldh1a1$^{-/-}$ thermocytes was sufficient to induce axonal growth in SDG neurons in vitro and its activity exceeded effects of the classic inducers, NGF and NT-3. Second, the unique properties of encapsulation model allowing slow release of secretome in vivo was used. In this model, the LTA-secretome of Aldh1a1$^{-/-}$ thermocytes, but not WT adipocytes stimulates innervation in iAb fat of obese WT host mice in vivo. The adjacent to encapsulated Aldh1a$^{-/-}$ thermocytes nerves were TH-positive. This enzyme is expressed in sympathetic neurons, although not all types of axons were characterized in WAT. These sympathetic axons were functional and induced multilocular pattern in WT host adipocytes from obese animals. Previously, these multilocular adipocytes have increased lipolysis and thermogenesis (Yang, F., et al. Biomaterials 33:5638-5649 (2012)). Based on these data, there may be a paracrine function of thermocytes in iAb adipose tissue that enables innervation and remodeling of this tissue.

High-fat and high-cholesterol diets induce Aldh1a1 expression in adipocytes (Yasmeen, R. et al. Diabetes. 2013 62(1):124-36) and hepatocytes (Huq, M. D., et al. EMBO J 25:3203-3213 (2006)) leading to obesity and iAb accumulation (Yasmeen, R. et al. Diabetes. 2013 62(1):124-36). Shown here in is a role of ALDH1A1 in suppression of axon growth-dependent innervation associated with lipolysis and thermogenesis. This function of ALDH1A1 in the regulation of axon growth is more important for induction of thermogenesis than intracrine effects of ALDH1A1 in adipocytes (Kiefer, F. W., et al. Nature medicine 18:918-925 (2012)), because an engraft of encapsulated Aldh1a1$^{-/-}$ thermocytes induced massive thermogenesis in WT mouse, it occurs distally from capsules and co-localized with TH-positive, possibly sympathetic neurons (FIG. 4). This locally increased thermogenesis decreases obesity and improves glucose tolerance in these animals (Yang, F., et al. Biomaterials 33:5638-5649 (2012)). The axon-dependent effects of the whole LTA secretome and EFNA5 on lipolysis and thermogenesis offer directions for development of tissue-specific therapies against obesity in the future. More studies needed to clarify if all thermocytes in WAT and BAT have similar axon guiding characteristics. Other researchers noticed innervation of implants of cells with thermogenic properties in mice without explaining mechanism of these phenomena (Kir, S., et al. Nature 513:100-104 (2014)). In white adipocytes, ALDH1A1 acts as a switch preventing sprouting of sympathetic axons and axons from DRG that depends on the intracrine production of RA. RA downregulates the ephrin A5/A4 pathway, whereas retinaldehyde induces expression of Sema3e, Sema3d and AdamtS9. Recombinant EFNA5 at physiological nanomolar concentrations partially reproduced the axon guiding properties related to the LTA secretome in vitro and in vivo, whereas antibodies against EFNA5 partially suppress neurite outgrowth mediated by Aldh1a1$^{-/-}$ secretome. Although axon guidance activities of EFN5 was identified in the context of iAb WAT, the treatment with recombinant protein was the most efficacious in subcutaneous tissue, possibly due to its extensive sympathetic innervation. However, other guiding molecules and activating-proteases in the LTA secretome appear to be necessary to achieve the full LTA axon-guiding potential related to the Aldh1a1$^{-/-}$ secretome.

The bidirectional regulation of nervous and adipose tissues provides an insight into genesis and remodeling of innervation in peripheral tissues of in adult organisms. This bidirectional regulation may contribute to development of metabolic syndrome and, possibly, neuropathies associated with the metabolic syndrome. The axon guiding cues supporting lipolysis and thermogenic remodeling can be candidates for developing therapeutic interventions for the treatment of obesity and re-innervation of damaged tissues.

Experimental Procedures

Human Studies

The study was approved by the Mayo Clinic Institutional Review Board for Human Research. All subjects provided written informed consent. Subcutaneous fat was obtained from overnight fasted Caucasian women (n=10). Equal numbers of lean (BMI<30) and in obese subjects (BMI≥40) were studied (Table 2). Institutional review board-approved informed consents were obtained for the subjects' medical records. Subcutaneous adipose tissue samples were obtained. Tissue specimens were washed in PBS before processing for mRNA isolation and protein extraction.

Animal Studies

Animal studies were approved by the Institutional Animal Care and Use Committee of The Ohio State University (OSU). Data for all studies are summarized in Table 1.

Study 1. WT and Aldh1a1$^{-/-}$ Mice on a High-Fat (HF) Diet

Aldh1a1$^{-/-}$ deficient mice were constructed and provided by G. Duester and colleagues (Fan, X., et al. Molecular and cellular biology 23:4637-4648 (2003)) and their metabolic profile was analyzed (Yasmeen, R. et al. Diabetes. 2013 62(1):124-36; Yang, F., et al. Biomaterials 33:5638-5649 (2012); Ziouzenkova, O., et al. Nature medicine 13:695-702 (2007)); Reichert, B., et al. Mol Endocrinol 25:799-809 (2011); Gushchna, L., et al. Arch Biochem Biophys. 539(2): 239-47 (2013)). C57BL/6J (WT) mice were initially purchased from The Jackson Laboratory (Bar Harbor, ME) and are breed at OSU. Eight-month old WT (n=10, 5 males and 5 females) and Aldh1a1$^{-/-}$ (n=9, 5 males and 4 females) were fed a high fat diet (HF, 45% kcal from fat, D12451, Research Diet Inc., New Brunswick, NJ) for 180 days. Visceral (intra-abdominal (i-Ab); gonadal) fat were collected for protein, mRNA, and histology.

Study 2. Comparison of Lean and Obese Mice with Dietary and Genetic Obesity

Three groups of mice were studied. Group 1: 4-month-old WT mice (n=14) fed regular chow (n=14, 7 males and 7 females). Group 2: 3-month-old WT mice fed with HF diet (n=11, 5 males and 6 females). Mice with diet induced obesity (60% HF for 2 weeks) were purchased from The Jackson Laboratory and continued on 45% HF for 3 weeks. Group 3: Ob/Ob (B6.V-Lepob/J strain containing spontaneous mutation in the gene encoding leptin congenic on C57BL6/J) mice were obtained from The Jackson Laboratory (n=9, 5 males and 4 females). 11 week old mice were analyzed. WAT were collected from all mice for protein, mRNA, and histology.

Study 3. WT Mice on a High-Fat (HF) Diet Treated with Encapsulated WT Adipocytes and Aldh1a1$^{-/-}$ Thermocytes Eighteen 3-month old WT female mice were fed a HF diet for 90 days. Encapsulation into alginate-poly-L-lysine and injection procedure were performed as previously described (Yang, F., et al. Biomaterials 33:5638-5649 (2012)). Then mice were randomly assigned into four groups:

1) injected with vehicle (1 mL sterile PBS, n=5);
2) acellular 'empty' capsules (n=3);
3) encapsulated WT fibroblasts (0.5×10$^6$ cells in 1 mL PBS per iAb depot, n=5); and
4) encapsulated Aldh1a1$^{-/-}$ fibroblasts (0.5×10$^6$ cells in 1 mL PBS per iAb depot, n=5).

Mice were injected with vehicle or encapsulated cells into both iAb depots, and maintained on the same HF diet for 80 days. Whole iAb fat, containing all encapsulated and host cells, was collected for protein analysis. Another iAb fat pad was embedded into paraffin for histological examination.

Study 4. Comparison of WT and Aldh1a1$^{-/-}$ (A1KO) Mice on a Regular Chow Diet 5-month old WT (n=14, 7 males and 7 females) and Aldh1a1l (n=13, 7 males and 6 females) were fed a regular chow diet (Harlan Teklad, Madison, WI). WAT and EDTA-plasma were collected for analysis and stored at −80° C.

Study 5. Ephrin A5 (EFNA5) Effects on Brainbow Mice Fed a HF Diet

Brainbow (BB) B6.Cg-Tg(Thy1-Brainbow1.0)HLich/J mice were purchased from The Jackson Laboratory (n=7, females). 5-week old BB mice were fed a HF for 140 days. Then mice were randomly assigned into groups injected with PBS (n=3) and recombinant EFNA5 (n=4). Mice were individually housed for all treatment periods. Mice were injected into both iAb fat depots with 100 µL PBS/iAb depot or with PBS containing recombinant EFNA5 (Life Technologies, 45 ng/mL) every other day for 1 month. Metabolic measurements were performed. WAT were collected for protein, mRNA, and histology.

Metabolic Measurements

Metabolic parameters were measured by indirect calorimetry (CLAMS, Columbus Instruments, Columbus, OH) at ambient temperature (22° C.) with 12 h light/dark cycles. Animals were fed the same HF diet and water was provided ad libitum. Mice were placed individually and allowed to acclimatize in the chambers for 12 h. Oxygen consumption, $CO_2$ production, energy expenditure, and locomotor activity were measured for at least 24 h. Based on these data, respiratory quotient or exchange ratio ($V_{CO2}/V_{O2}$) and Δ heat values were calculated by CLAMS. For cold exposure the temperature was changed to 4° C. for 6 h.

Cell Culture Studies.

Stromal Vascular Fraction (SVF) and Immortalized Cell Line Development

SVF was isolated from subcutaneous fat of one-month-old WT and Aldh1a1$^{-/-}$ female mice fed regular chow. Fibroblasts (preadipocytes) from SVF were immortalized.

Differentiation of Mouse Fibroblasts in Neurogenic Medium

3T3-L1, WT, and Aldh1a1$^{-/-}$ fibroblasts (n=3/group) were cultured in DMEM medium containing 10% calf serum until cells were 80% confluent (Day 0). Then this medium: was replaced with MACS Neuro Media (Miltenyi Biotec Inc., San Diego, CA) with and without forskolin (10 µM, Cayman Chemical Company, Ann Arbor, MI) (Day 1). Two days later, the medium was replaced with neuronal differentiation medium MACS Neuro Media (Miltenyi Biotec Inc., San Diego, CA), containing 2% NeuroBrew 21 (Miltenyi Biotec Inc., San Diego, CA), 1% N2 supplement, and NGF (50 ng/mL, Life Technologies, Grand Island, NY) (Day 3). Morphology of cells was analyzed on Day 4.

Preparation and Stimulation of Adult Mouse Dorsal Root Ganglion (DRG) Neurons

Single cell suspensions from cervical, thoracic, and lumbar DRG neurons were isolated from terminally anesthetized C57BL/6 adult female mice (12-16 weeks old, The Jackson Laboratory). Dissected DRGs were enzymatically digested in a solution of collagenase type 2 (200 U/mL; Sigma, St. Louis, MO) and dispase I (5 U/mL; Sigma) on a shaker for 45 min at 37° C. (Davies et al., 1999). Enzyme solution was aspirated and cells were washed twice in Hank's Balanced Salt Solution 1× (HBSS; Mediatech Inc., Manassas, VA) before incubating in DNase I type II (5 mg/mL; Worthington Biochemical, Lakewood, NJ) for 5 min at room temperature. DRGs were triturated in HBSS with Pasteur pipette until cells were well dissociated, then passed through a Falcon 70 µm cell strainer (Corning Inc., Corning, NY) to remove myelin debris and centrifuged at 3,000 rpm for 3 min to pellet the cells. The neuron-enriched pellet was resuspended in DRG culture medium (DMEM/F12, 1% N2 supplement, and 0.05% Gentamicin) and live cells were counted on a hemocytometer using trypan blue exclusion. Cells were plated at 500 cells/well in a 24-well plate (Corning Inc.) previously coated with poly-D-lysine (25 ug/mL; Sigma) and laminin (10 µg/mL; Life Technologies, Grand Island, NY). DRG neurons were incubated at 37° C./5% $CO_2$ in DRG culture medium only, DRG culture medium with NT-3 (1 ng/mL), with NGF (10 ng/mL), with WT secretome with DRG medium (1:1, v/v), and with Aldh1a1$^{-/-}$ secretome with DRG medium (1:1, v/v) for 24 hours. To assess neurite outgrowth and neuronal morphology, cells were fixed with 4% paraformaldehyde for 25 min (Gensel et al., 2009) and washed in 0.1 M PBS, then incubated in blocking solution (4% BSA/0.3% Tx-100/PBS) for 1 hr at room temperature. Cells were immunostained with B-tubulin III antibody diluted in blocking solution (1:1000; Sigma) at 4° C. overnight, then washed incubated in Alexa Fluor® 546 secondary (1:1000; Life Technologies) for 1 hr at RT. Cells were automatically imaged using a Thermo Scientific™ Array-Scan™ XTI Live High Content microscope and analyzed with the Neuronal Profiling algorithm (ThermoFisher) (Lerch et al., 2014). Total neurite length, average neurite length, number of branch points, critical value, dendrite maximum, and ramification index were averaged across all neurons detected per well, with 3 wells included per treatment. Three experimental replicates were performed using DRGs from three mice (total: n=9). Dendrite maximum and critical value are parameters determined based on Scholl analysis, and are automatically generated by the software. Dendrite maximum corresponds to the maximum number of dendrite crossings at a given radius from the cell body, and the critical value describes the radius at which the dendrite max occurs. The ramification index of a neuron is the dendrite max value divided by the number of primary dendrites. Percent of neurons with neurites was calculated as the ratio of the number of neurons with neurite extension to the total number of neurons per well. Significant growth differences were calculated in GraphPad Prism 5.0 (Graph-Pad Software) using well averages in a one-way ANOVA followed by a Tukey post-hoc analysis. Differences were significant for p<0.05.

Adipocyte Differentiation

Murine preadipocyte (3T3-L1, WT and Aldh1a1$^{-/-}$) lines were cultured and maintained in standard culture medium (DMEM containing 10% calf serum and 0.1% 50 mg/mL gentamicin. Adipogenesis was induced (Day 0) in confluent preadipocytes using differentiation medium I containing 3-isobutyl-1-methylxanthine (0.5 mM), dexamethasone (1 µM), insulin (1.7 µM), 10% FBS, and 0.1% gentamicin in DMEM. Differentiation medium II containing 10% FBS, insulin (1.7 µM), and 0.1% gentamicin in DMEM was replaced every 48 hours after adding differentiation medium I.

Gene Expression Analysis

Affymetrix GeneChip mRNA was isolated by RNeasy (Qiagen, Valencia, CA). RNA integrity was interrogated using the Agilent 2100 Bioanalyzer (Agilent Technologies). A 100 ng aliquot of total RNA was linearly amplified. Then, 5.5 µg of cDNA was labeled and fragmented using the GeneChip WT PLUS reagent kit (Affymetrix, Santa Clara, CA) following the manufacturer's instructions. Labeled cDNA targets were hybridized to Affymetrix GeneChip Mouse Gene ST 2.0 arrays for 16 h at 45° C. rotating at 60 rpm. The arrays were washed and stained using the Fluidics Station 450 and scanned using a GeneChip Scanner 3000. Signal intensities were quantified by Affymetrix Expression Console version 1.3.1. Background correction and quantile normalization were performed to adjust for technical bias, and probe-set expression levels were calculated by the RMA method. After filtering above noise cutoff, there are 9,528 probe-sets that were tested by linear model. A variance smoothing method with fully moderated t-statistic was employed for this study and was adjusted by controlling the mean number of false positives. With a combined cutoff of 2-fold change and p-value of 0.0001 (controlling 1 false positive over all probe-sets), 500 probe-sets were declared as differential gene expression between Aldh1a1$^{-/-}$ and WT preadipocytes. GEO file: 'QS wild type and Aldh1a1 KO preadipocytes 2015'.

NanoString nCounter Gene Expression Assay

NanoString's nCounter analysis (NanoString Technologies) system performed direct detection of target molecules from a single sample using color-coded molecular barcodes, giving a digital quantification of the number of target molecules as described before (Shen et al., 2015, PMID: 25620076). A custom panel containing axon guidance molecules was designed and used for simultaneous quantification of 32 axon guidance genes and 5 housekeeping genes. All data were normalized to 5 housekeeping genes quantified in the same samples. Total mRNA (100 ng in 5 µl) was hybridized overnight with nCounter Reporter (20 µl) probes in hybridization buffer and in an excess of nCounter Capture probes (5 µL) at 65° C. for 16-20 h. The hybridization mixture containing target/probe complexes was allowed to bind to magnetic beads containing complementary sequences on the Capture Probe. After each target found a probe pair, excess probes were washed followed by sequential binding to sequences on the Reporter Probe. Biotinylated capture probe-bound samples were immobilized and recovered on a streptavidin-coated cartridge. The abundance of specific target molecules was then quantified using the nCounter Digital Analyzer. Individual fluorescent barcodes and target molecules present in each sample were recorded with a CCD camera by performing a high-density scan (600 fields of view). Images were processed internally into a digital format and were normalized using the NanoString nSolver software analysis tool. Counts were normalized for all target RNAs in all samples based on the positive control RNA to account for differences in hybridization efficiency and post-hybridization processing, including purification and immobilization of complexes. The average was normalized by background counts for each sample obtained from the average of the eight negative control counts. Subsequently, a normalization of mRNA content was performed based on six internal reference housekeeping genes Gapdh, Gusb, Hprt1, Pgk1, and Tubb, using nSolver Software. Similar custom Nanosting panel was used for validation of LTA genes in human samples (Table 2).

Semi-Quantitative mRNA Analysis mRNA was isolated from WAT or adipocyte cultures according to the manufacturer's instructions (Qiagen; Valencia, CA). cDNA was prepared from purified mRNA and analyzed using a 7900HT Fast Real-Time PCR System, TaqMan fluorogenic detection system, and validated primers (Applied Biosystems; Foster City, CA). Comparative real time PCR was performed in triplicate, including no-template controls. The mRNA expression of genes of interest was normalized by 18S expression level using the comparative cycle threshold (Ct) method.

Protein Analysis

Immunohistochemistry

Fat pads were embedded into paraffin for immune-histochemical analysis. Sections were stained with hematoxylin and eosin (H&E) using a modified hematoxylin procedure followed by dehydration in graded alcohol or with peripherin and tyrosine hydroxylase polyclonal rabbit antibodies (Abcam, Cambridge, MA) at 1:1000 dilution. Images were obtained using Olympus M081 IX50 and Pixera Viewfinder 3.0 software.

Western Blot

Cell/tissue protein lysates normalized by protein content (BCA, ThermoFisher). Medium was collected from cells plated at similar numbers. Protein lysate or medium were separated on 10% acrylamide gel under reducing conditions. After transfer to a polyvinylidene fluoride membrane (Immobilon-P; Millipore), proteins were analyzed using an Odyssey Infrared Imaging System (LI-COR Biosciences). Peripherin and tyrosine hydroxylase polyclonal rabbit antibodies (Abcam, Cambridge, MA) were used at 1:1000 dilution.

Enzyme-Linked Immunosorbent Assay (ELISA)

Plasma samples were collected from WT and Aldh1a1$^{-/-}$ (A1KO) mice in Study 3. Medium was collected from differentiated and non-differentiated 3T3-L1. Samples were analyzed for ephrin A5 using an ELISA Kit (Cedarlane, Burlington, NC) Elisa according to manufacturer's instructions. Absorbance (450 nm) was measured using a Synergy H1 Hybrid Multi-Mode Microplate Reader. NGF Elisa was purchased from Abnova (Walnut, CA) and used for measurement media from WT and Aldh1a1$^{-/-}$ adipocytes and plasma from WT and Aldh1a1$^{-/-}$ mice.

Statistical Analysis

All data are shown as mean±SD. Number of samples is indicated in Figure legends or described in Supplementary tables 1 and 2. Group comparisons were assessed using Mann Whitney U test or using ANOVA models. P<0.05 was considered to be statistically significant and is presented as*. Trends were examined using Pearson correlation analysis tests.

Figures 11A, 11B, 11C:
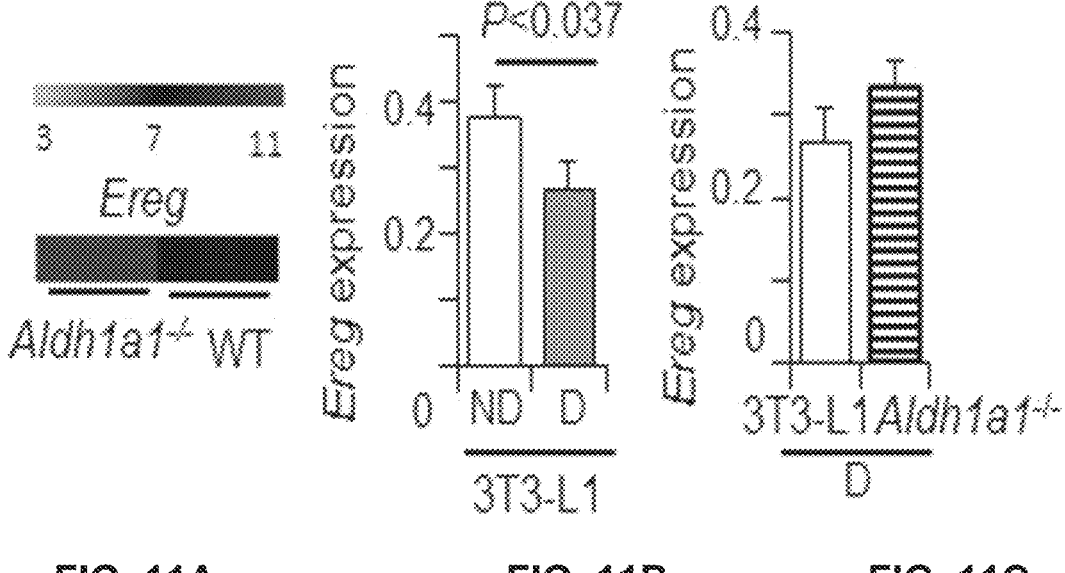
FIGS. 11A to 11I show adipokine Ereg is bilaterally associated with obesity and thermogenesis and activates PPARα.
Figure 11D:
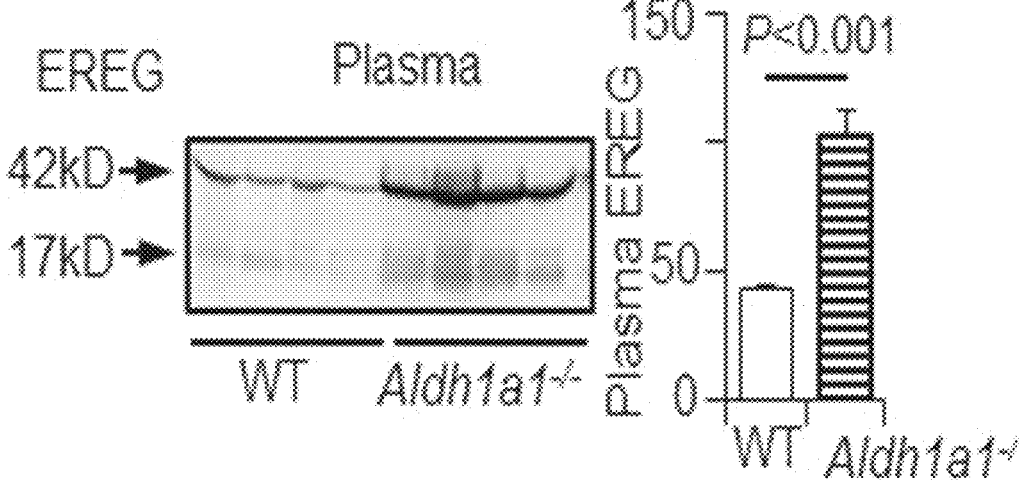
Figure 11E:
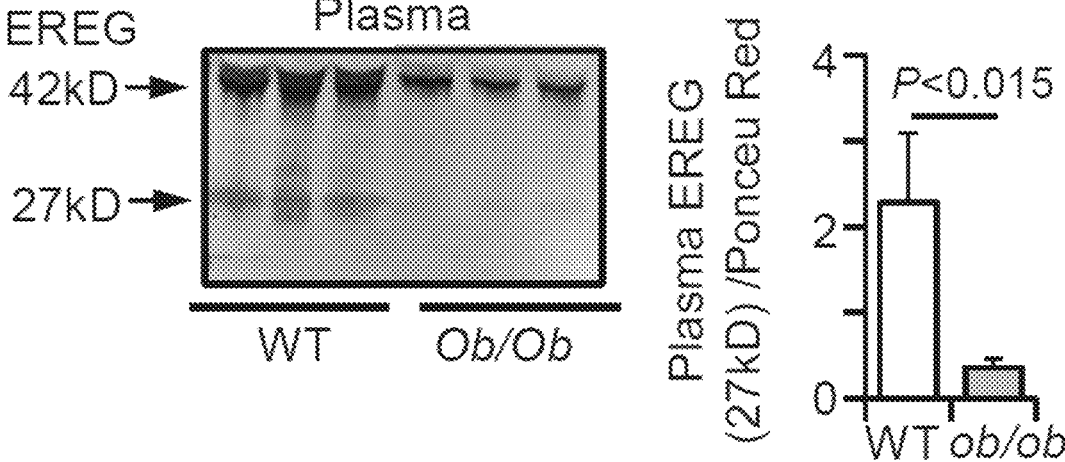
Figure 11F:
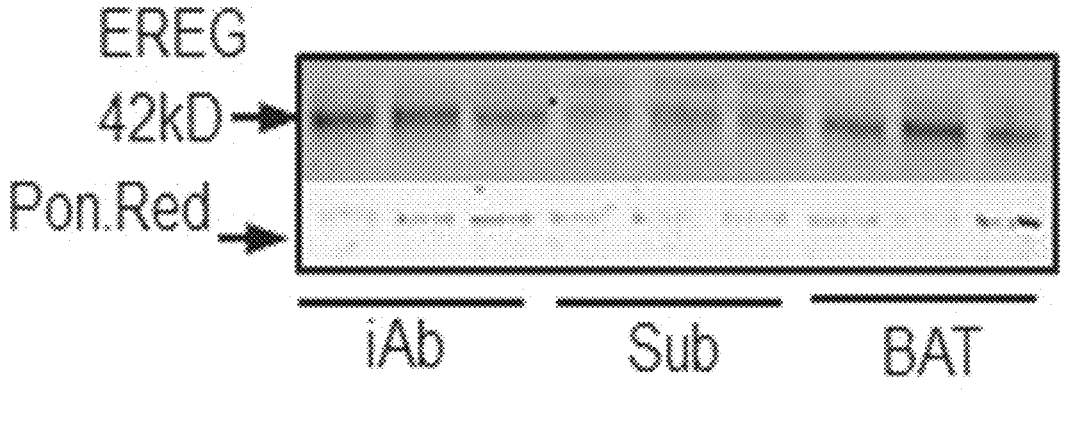

Example 2: Epiregulin Mitigates Visceral Obesity and Promotes Thermogenesis and Glucose Utilization Via EGFR Independent Mechanism Results Identification of EREG as a Preadipokine The strategy for identification of intrinsic thermogenic adipokine(s) was based on comparison of both gene and protein expression as well as the secretion of protein into the circulation across several thermogenic and obesogenic preadipocytes cell lines; WAT and BAT tissues; and published cachexia data. Given that encapsulated Adh1a1$^{-/-}$ preadipocytes induced browning of iAb WAT in obese WT mice, gene expression was compared in WT and Adh1a1$^{-/-}$ preadipocytes. The EFGR ligand EREG was expressed at significantly higher levels in Adh1a$^{-/-}$ than in WT preadipocytes (FIG. 11A). EREG was described as non-significant contributor to thermogenesis in cachexia and inducer of mitochondrial oxidation in oocytes, therefore, this cytokine was examined as a candidate for physiologic thermoadipokines. Ereg was expressed at higher levels in preadipocytes than in adipocytes (FIG. 11B). In differentiated adipocytes Ereg expression was moderately higher in thermogenic Adh1a1$^{-/-}$ adipocytes (FIG. 11C). In contrast circulating plasma levels of EREG were 2-fold higher in Adh1a1$^{-/-}$ then in WT mice (FIG. 11D). In plasma, EREG was present in both precursor (42 kD) and active cleaved (17 kD). In contrast, in ob/ob mice the plasma levels of EREG precursor and particularly cleaved form was markedly diminished (FIG. 11E). All types of WAT and BAT expressed EREG and can potentially contribute to its levels in plasma (FIG. 11F).

Figure 11G:
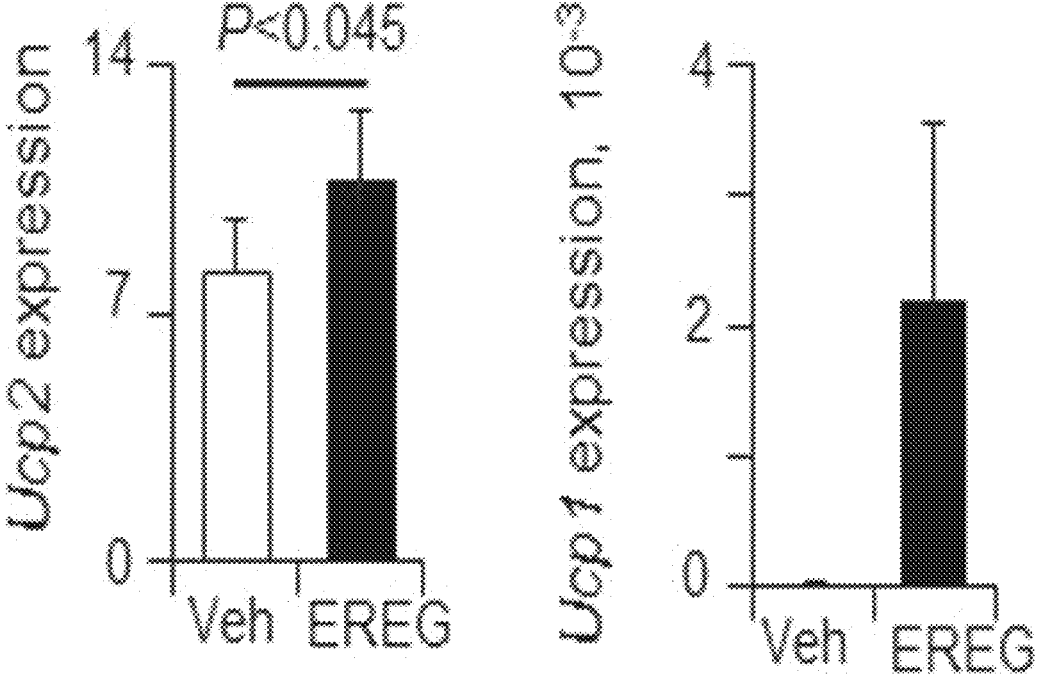
Figure 11H:
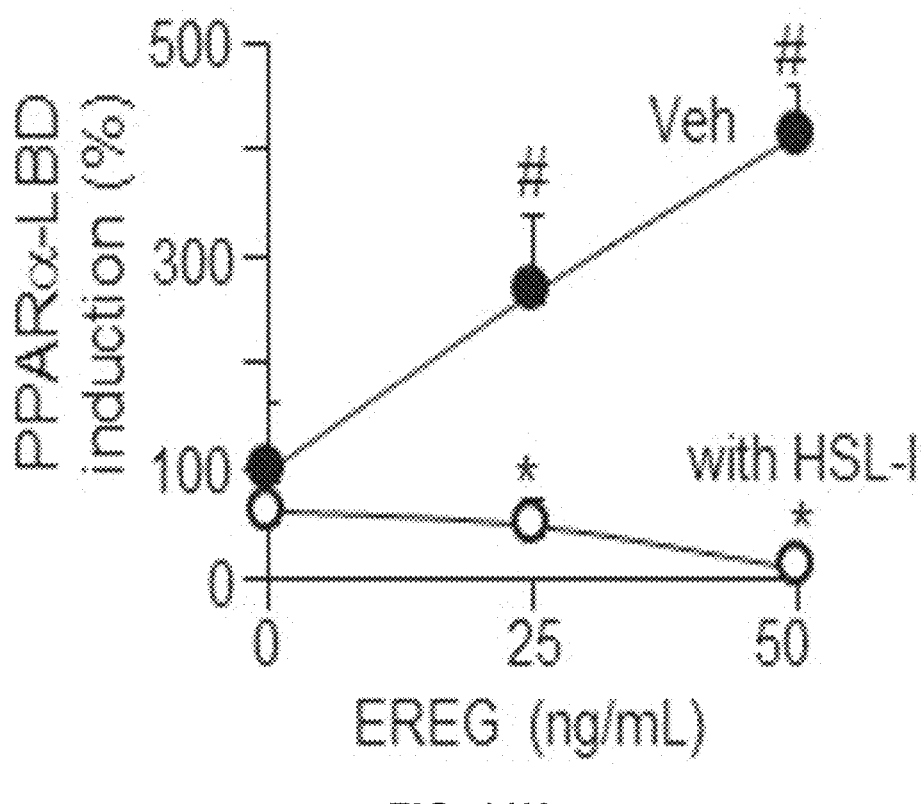
Figure 11I:
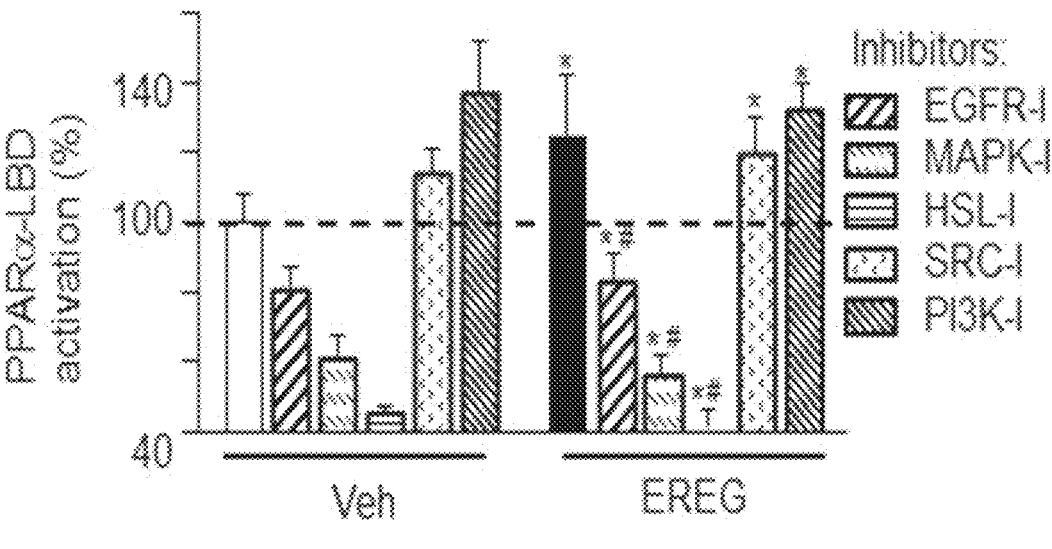

Next, the mechanism for EREG contribution to regulation of thermogenic and mitochondrial genes, which are controlled by nuclear receptor PPARα, was examined. In 3T3-L1 adipocytes, recombinant EREG induced Ucp1 and Ucp2 expression in agreement with previously published data (FIG. 11G). The transcriptional activity of PPARα is induced by free long-chain fatty acids that could be hydrolyzed from lipid droplet by lipases. Stimulation of HEK293 cells transfected with PPARα-ligand binding domain (LBD) with EREG lead to rapid dose dependent induction of PPARα (FIG. 11H); however, this response was abolished by inhibitor of hormone sensitive lipase (HSL). EGFR, a principal receptor for EREG could contribute to lipolysis via activation of MAPK, PI3, or SRC kinases. This relation was examined using inhibitors to MAPK and SRC kinases and EGFR (FIG. 11I). EREG-dependent PPARα-LBD activation was abolished in the presence of specific EGFR inhibitor AF-1478, a MAPK inhibitor, and HSL inhibitor. In contrast inhibitors of SRC and PI3 kinases had now effect. Together, in vitro data supported EREG role as an adipokine suggesting its functional role in thermogenesis via activation of EGFR/MAPK/HSL/PPARα axes.

Figure 12A:
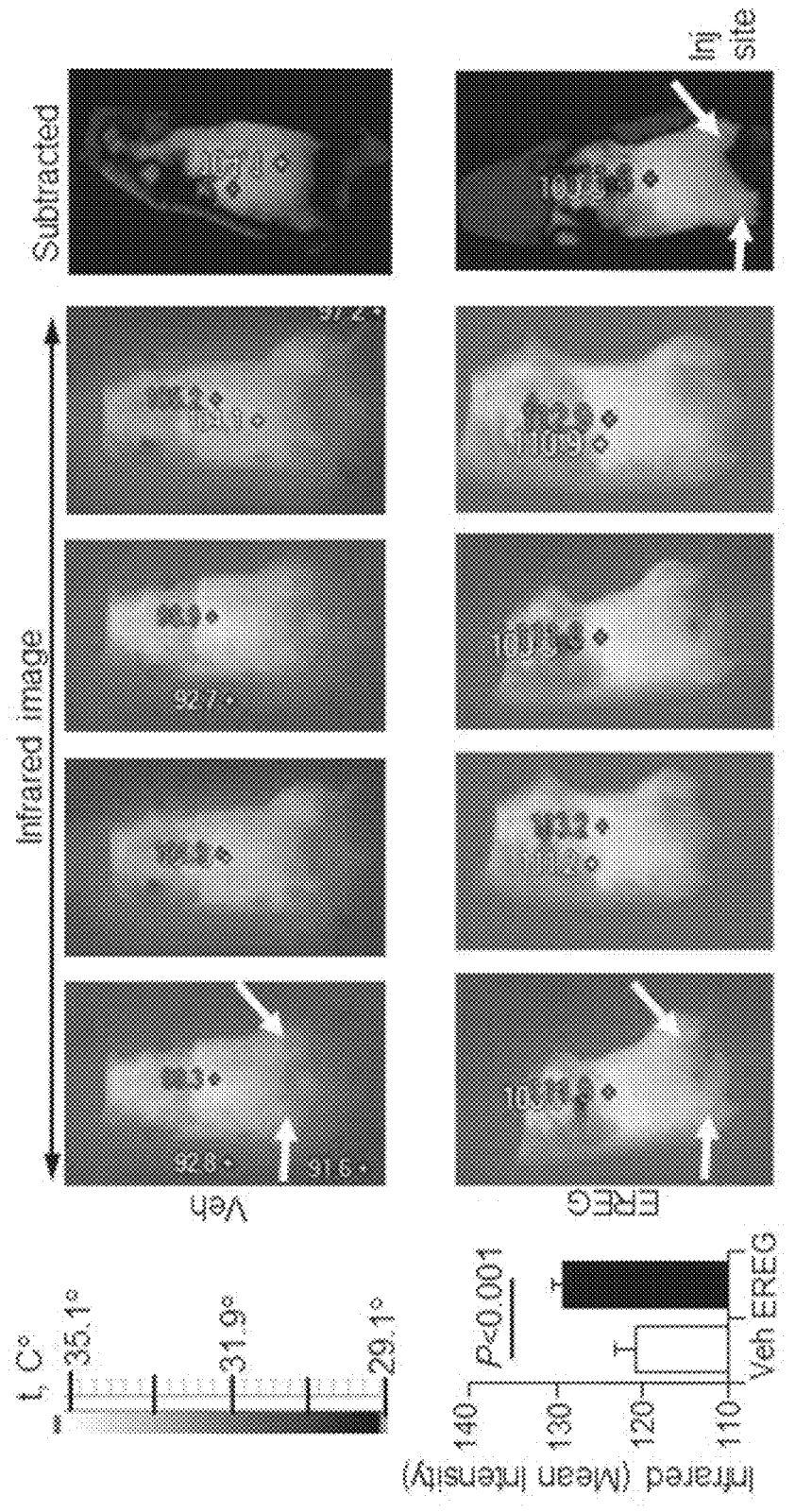
FIGS. 12A to 12E show EREG induces thermogenesis and metabolic rate in DIO mice.
Figure 12B:
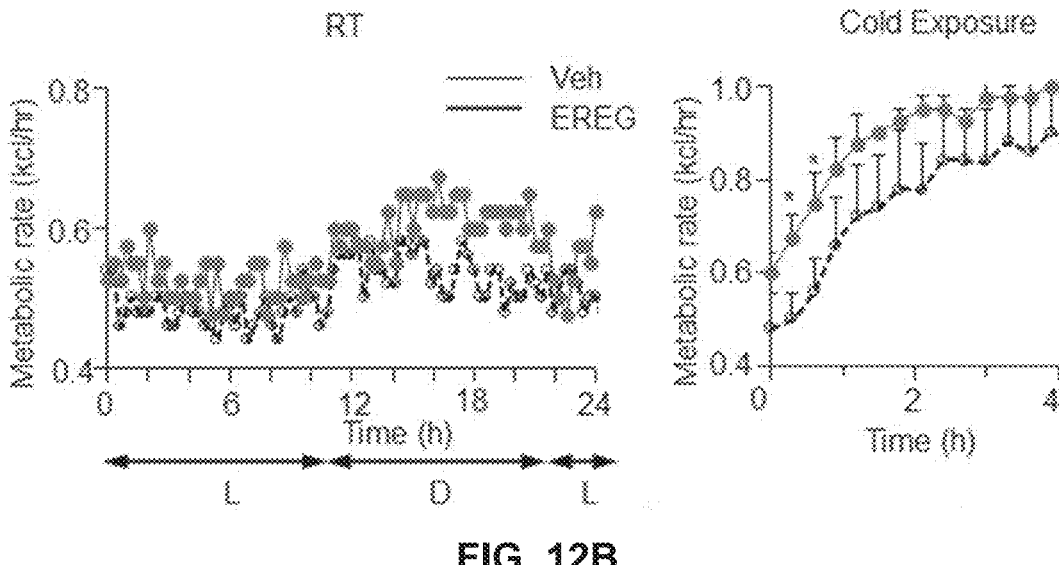
Figure 12C:
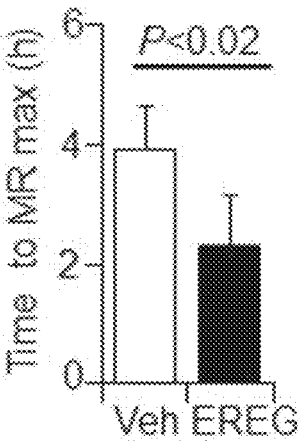
Figure 12D:
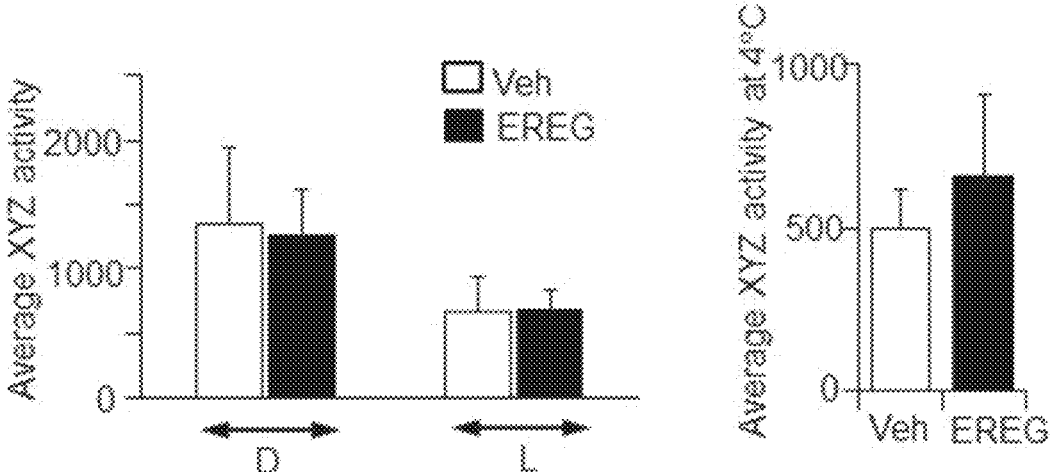
Figure 12E:
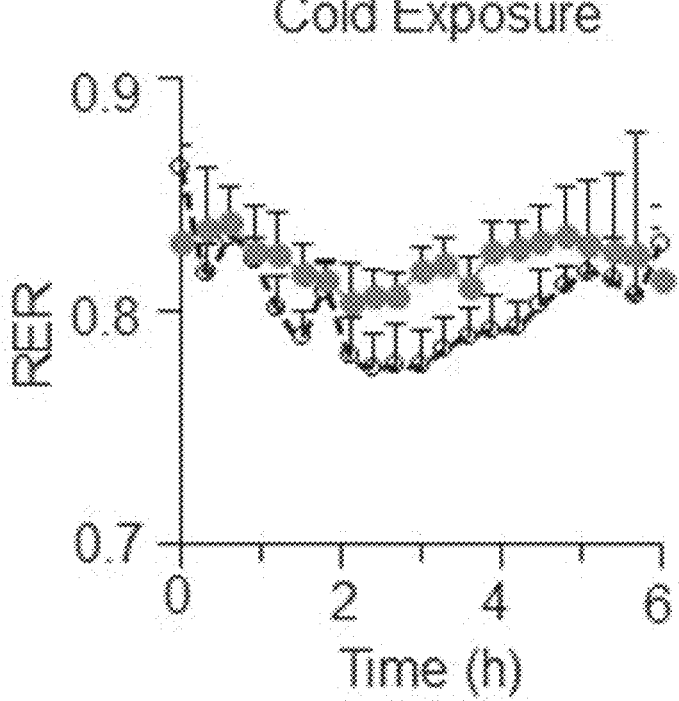

EREG Stimulates Thermogenesis and iAb Fat Loss in Mice with Diet-Induced Obesity In vivo effects of recombinant EREG were elucidated in WT mice with a high-fat diet-induced obesity (DIO mice). EREG injections into iAb fat for 2 weeks had profound effects on body temperature in the abdominal area in DIO mice (FIG. 12A). The increase in local body temperature was co-localized with the sides of injection that were seen in the original infrared images. The injection regions with high local body temperature were highlighted after subtraction of temperatures before and after cold exposure (FIG. 12B). This increase in body temperature in DIO mice was achieved after only 6 treatments with EREG without change in a high fat diet regimen. The data obtained in metabolic cages further validate that EREG treatments led to an increase in metabolic rate at an ambient temperature and after the cold exposure. The EREG-treated DIO mice reached maximal metabolic rate plateau at a significantly shorter period of time compared to the control group during the cold exposure (FIG. 12C). EREG treatment did not influence light and dark period activity in DIO that remains similar in treated and control group before and after cold exposure (FIG. 12D). In these experiments, RER was similar between treated and non-treated groups (FIG. 12E).

Figure 13A:
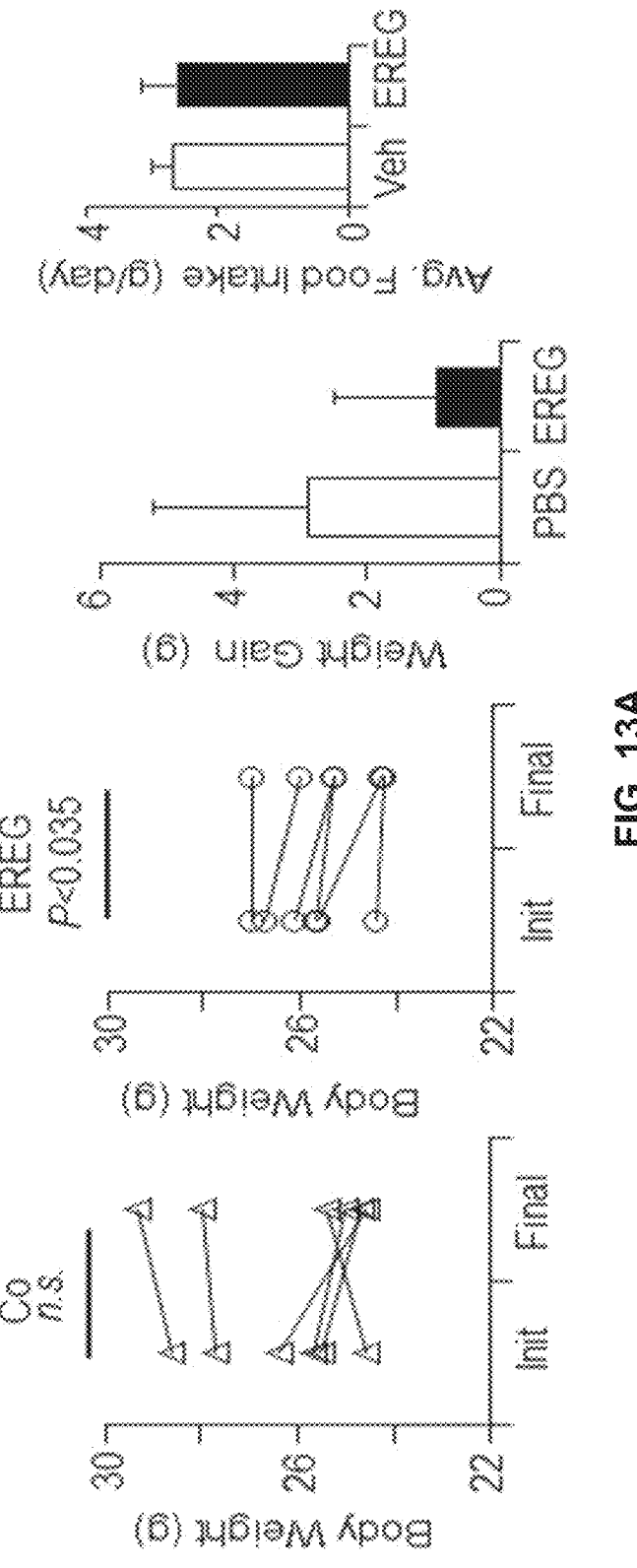
FIGS. 13A to 13F show EREG suppresses iAb obesity and stimulates lipolysis in vivo.
Figure 13B:
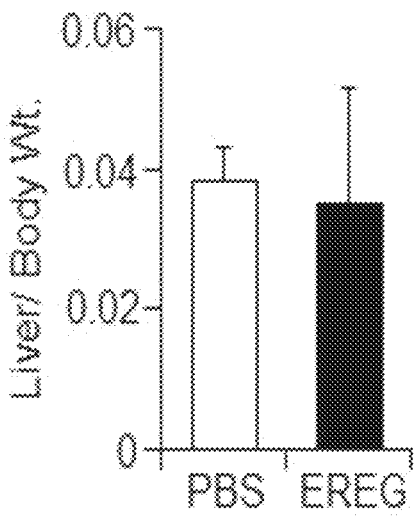
Figure 13C:
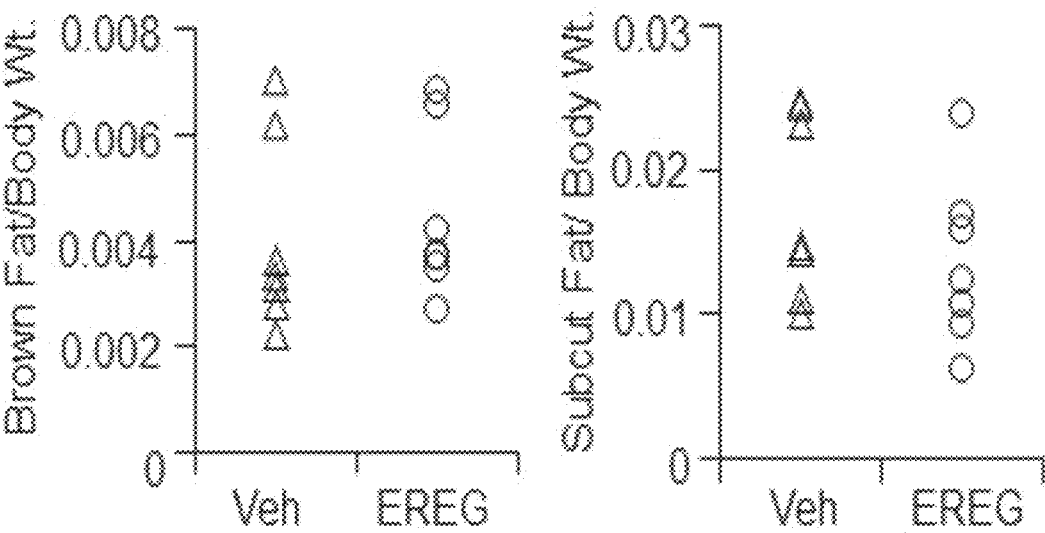
Figure 13D:
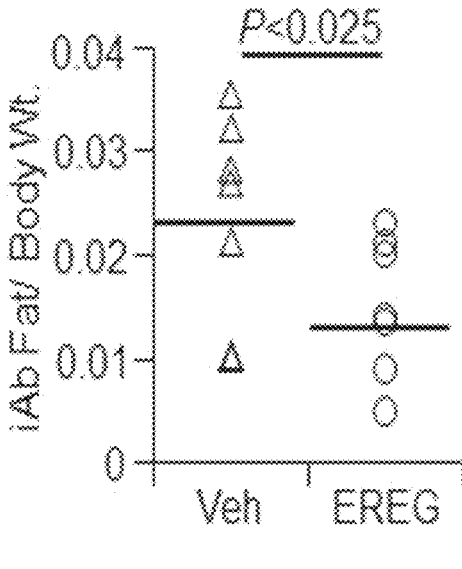
Figure 13E:
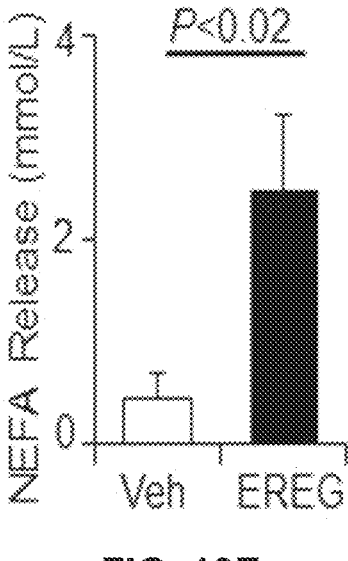
Figure 13F:
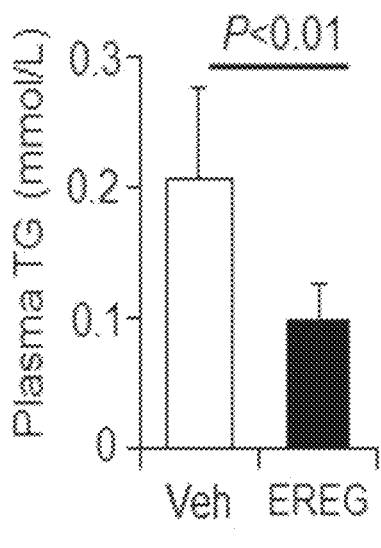

The increase body temperature and metabolic rate prevented weight gain in the EREG treated DIO (FIG. 13A). These effects were not dependent on food consumption that was similar in both groups. EREG treatments did not influence liver (FIG. 13B), BAT and subcutaneous WAT weight (FIG. 13C). However, EREG treated had 32% less iAb fat than non-treated mice (FIG. 13C). Consistent with the expected increase in lipolysis and PPARα activation, EREG-treated mice have 580% increase in non-esterified fatty acid in the circulation (FIG. 13E), while their circulating triglyceride levels were decreased (48%) compared to control group (FIG. 13F).

Figure 14A:
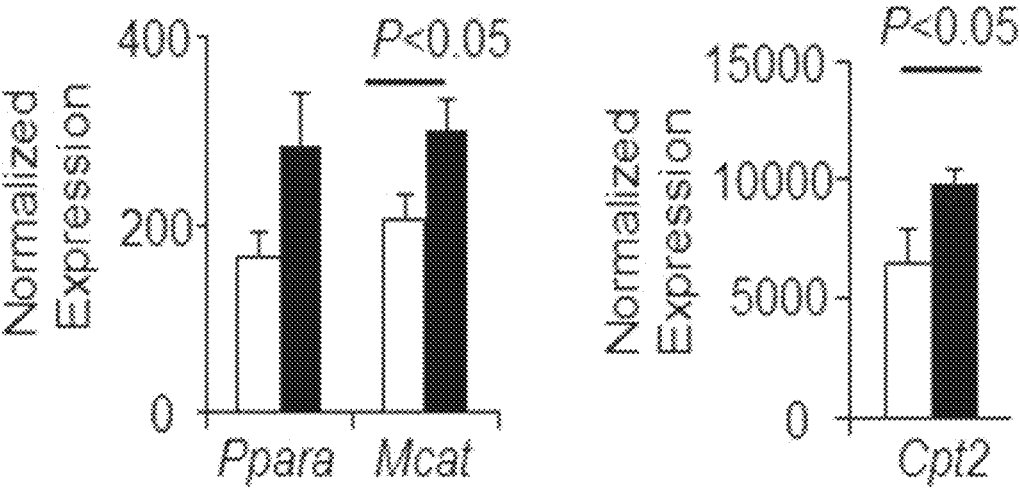
FIGS. 14A to 14N show EREG induces expression of thermogenic and PPARα-target genes, suppresses inflammatory genes, and stimulates leptin secretion.
Figures 14E, 14F:
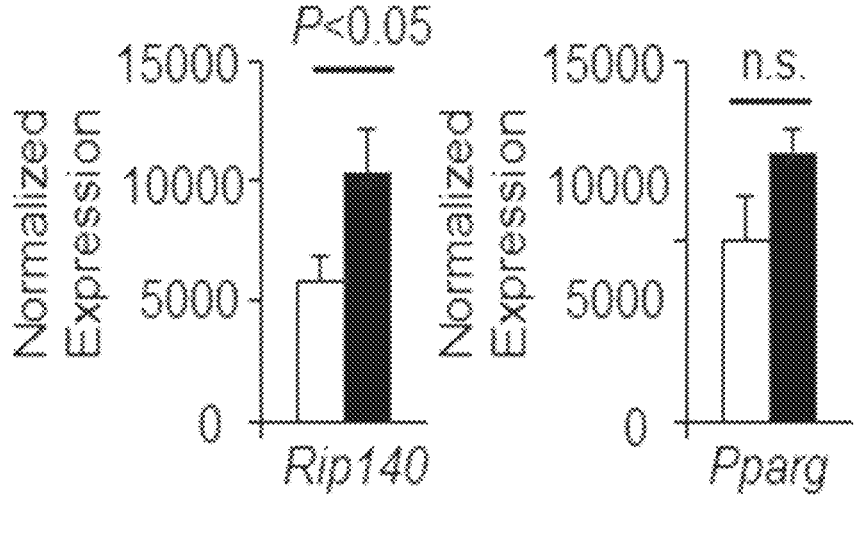
Figure 14G:
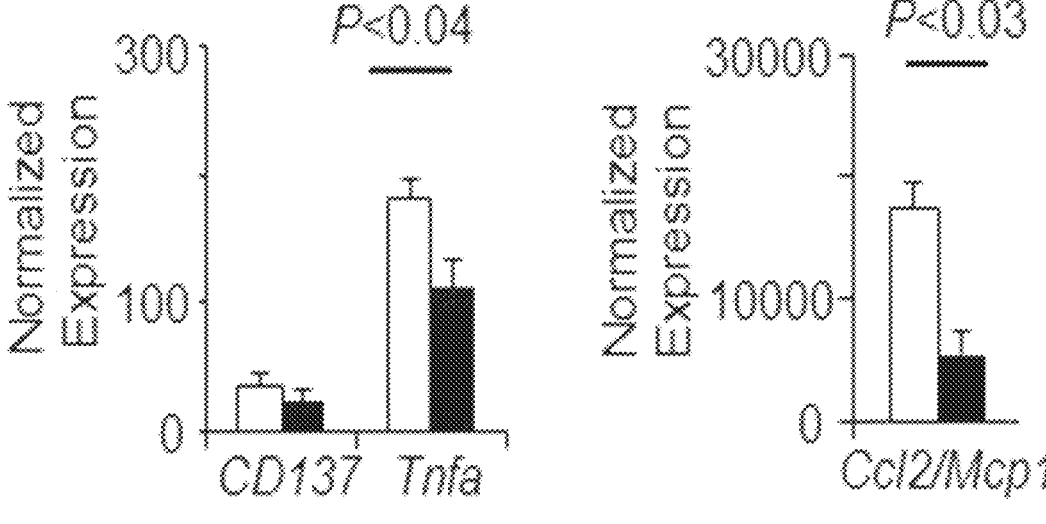
Figures 14H, 14I:
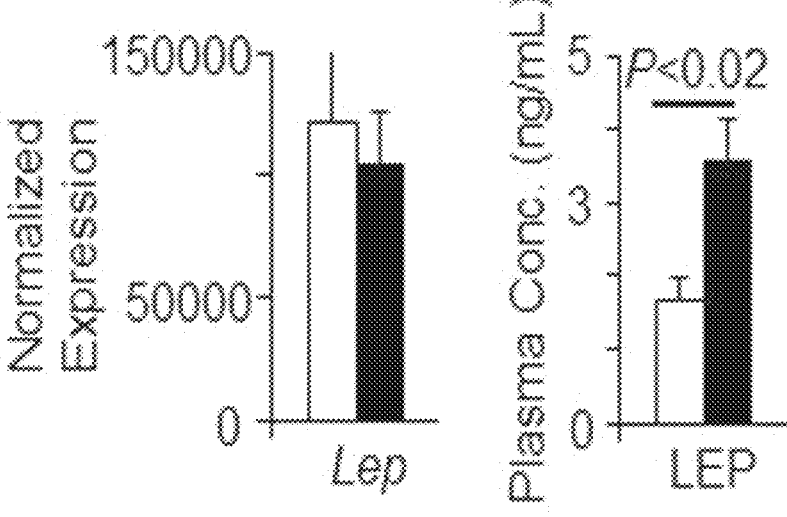

EREG Induces Expression of Thermogenic and PPARα Target Genes and Secretion of Leptin Analysis of gene expression in iAb fat showed that EREG treatment compared to non-treated controls, increased expression of PPARα target genes Mcat and Cpt2, although an increase in PPARα expression did not reach statistical significance (FIG. 14A). The levels of BAT marker Prdm16 was similar between groups, however thermogenic genes (Dio2, Pgc1a, Cidea, Rip140) and genes involved in oxidative phosphorylation (CoxIV) were significantly increased in EREG treated compared to non-treated group (FIG. 14B-E). An increase in Ucp1 and Pparg (FIG. 14F) did not reach statistical significance. The expression of pro-inflammatory genes Tnfa and Mcp1 were suppressed in EREG vs control group suggesting that EREG treatment was not associated with inflammation (FIG. 14G). Given the reported PPARα ligand-induced LEP production and Lep's function in systemic regulation of energy expenditure, both Lep expression and its levels in the circulation were measured (FIG. 14H). Lep expression was similar between groups; however, the levels of secreted LEP were 215% higher in EREG-treated vs non-treated mice.

Figure 14J:
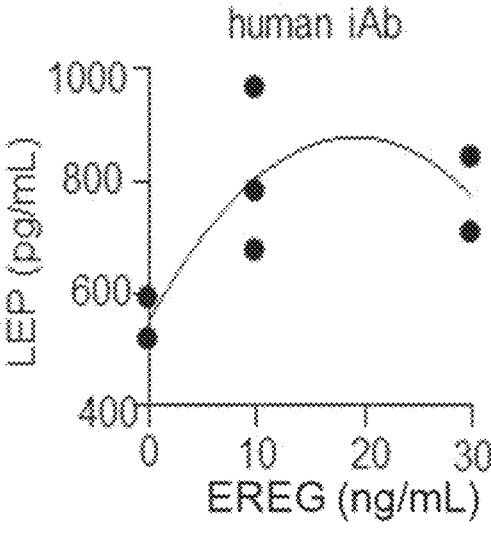
FIG. 14J: LEP release after stimulation with different concentrations of recombinant human EREGs was measured in explants of iAb (omental) tissue obtained from an obese insulin resistant patient.
Figure 14K:
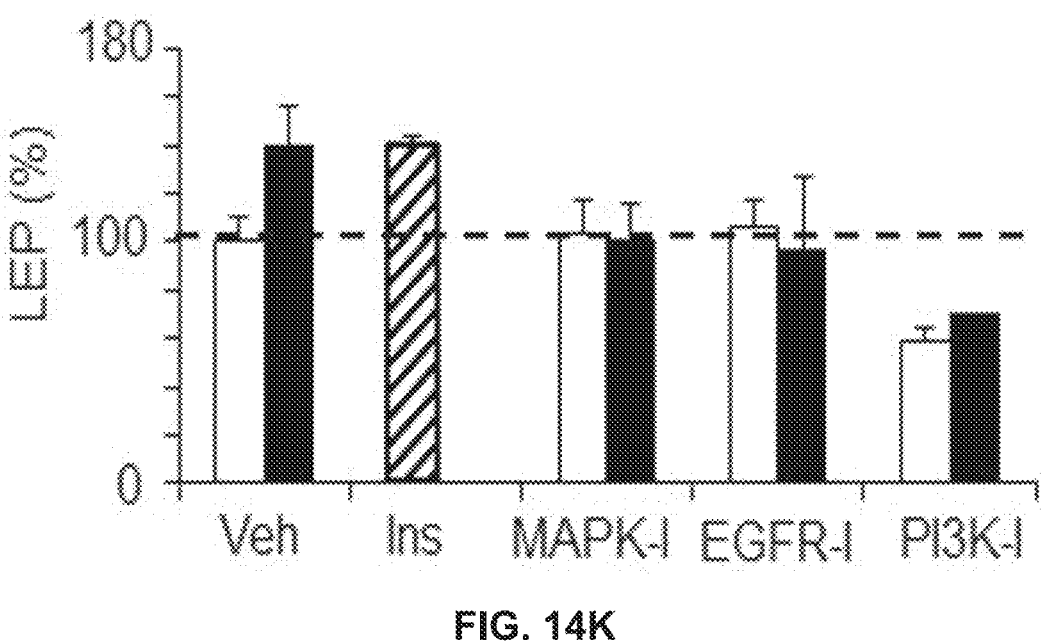
FIG. 14K: LEP release after stimulation of explants from same donor with and without EREG (50 ng/mL) in the presence and absence of insulin (Ins, 10 µg/mL), MAPK-I, EGFR-I, PI3K-I. Inhibitors concentrations were described in FIG. 1.
Figure 14L:
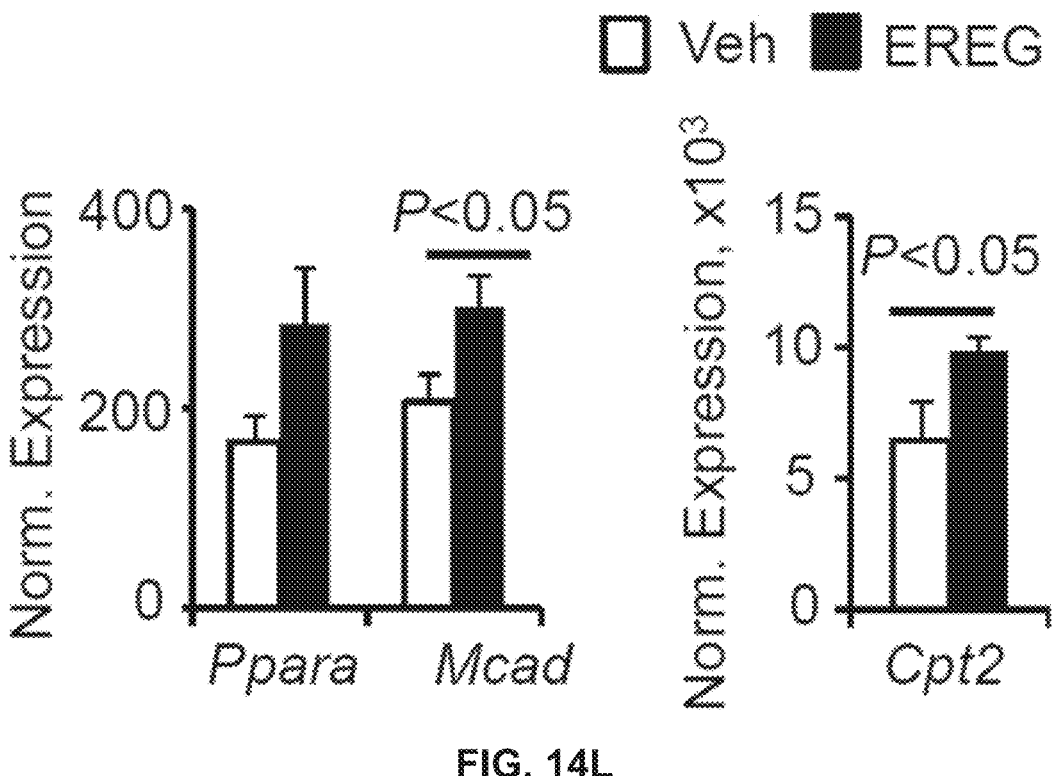
Figures 14M, 14N:
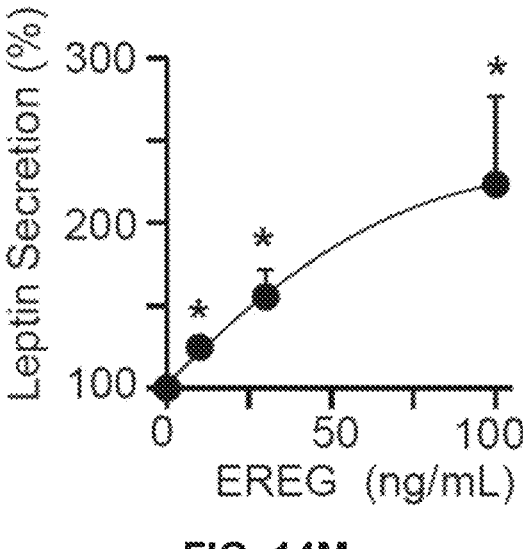
FIG. 14M: LEP release after stimulation of iAb fat explants (2 h) from WT mice with different concentrations of recombinant mouse EREG. Experiment was repeated in three different WT mice. Data (mean±SD) are shown as percent to control (Veh, 100%).

To investigate if LEP secretion was directly mediated by EREG and it is relevant for human iAb (omental) WAT, effects of EREG in the fat explants from an obese patient were studied (FIG. 14I). EREG induced dose dependent release of LEP from iAb fat explants. EREG and insulin mediated similar LEP release, which was inhibited by inhibitors of EGFR, MAPK and PI3K. Inhibition of PI3 kinase (65%) had the most profound impact on LEP release by EREG compared to all EGFR, MAPK (100%) (FIG. 14J). The expression data suggest that EREG stimulated energy expenditure; however, these effects could be mediated by PPARα, leptin, or both.

EREG Increases iAb Weight Loss and Energy Expenditure in Lep-Dependent Manner

Figure 15A:
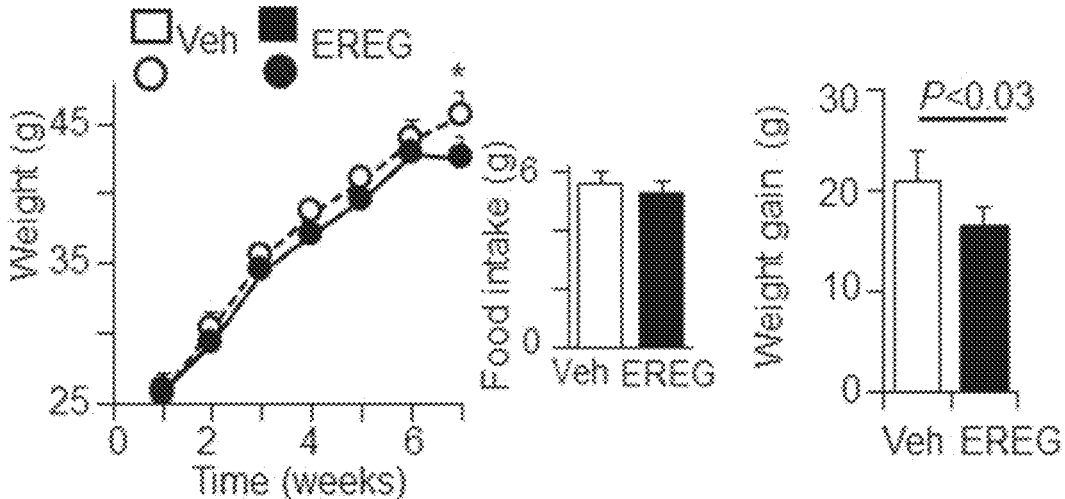
Figure 15B:
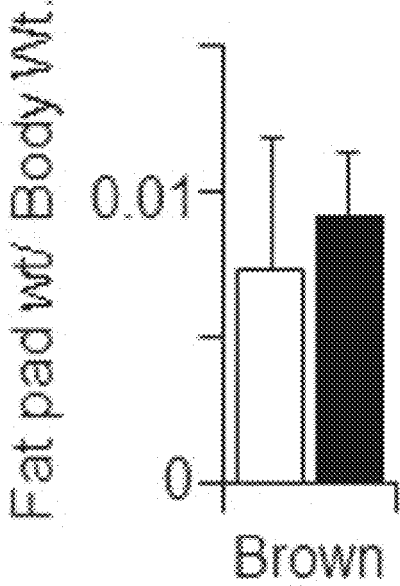
Figure 15F:
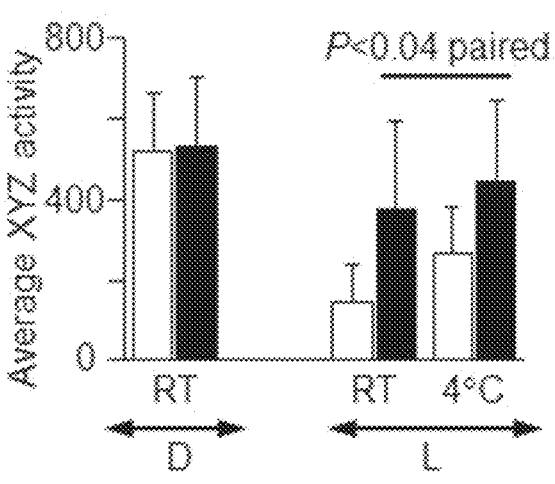
Figure 15G:
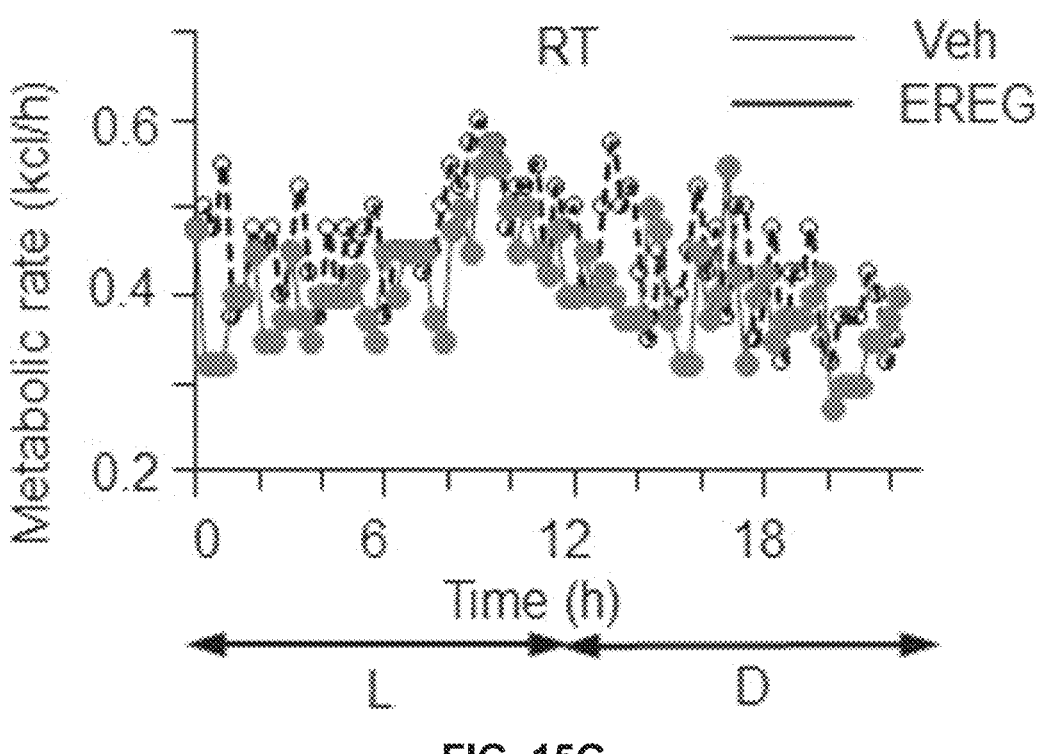
Figure 15H:
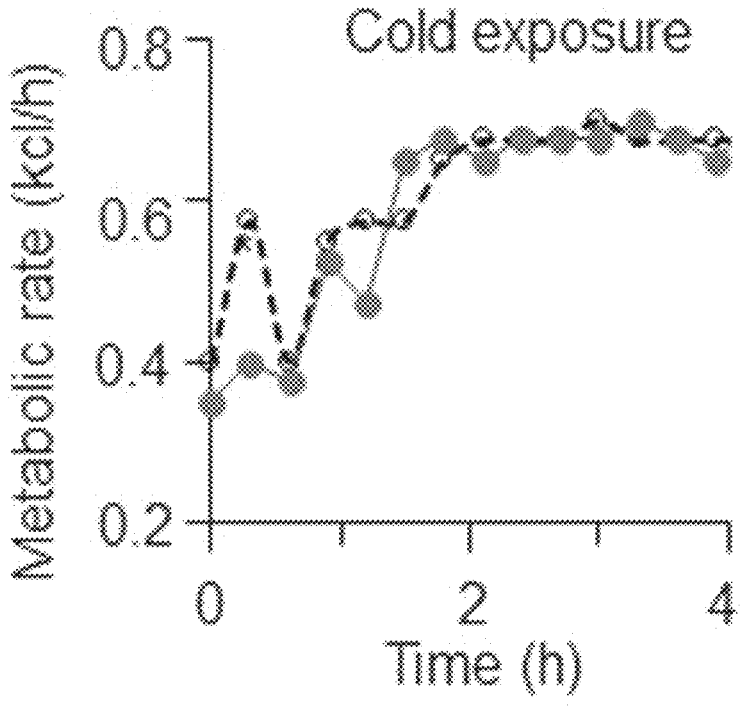
Figure 15I:
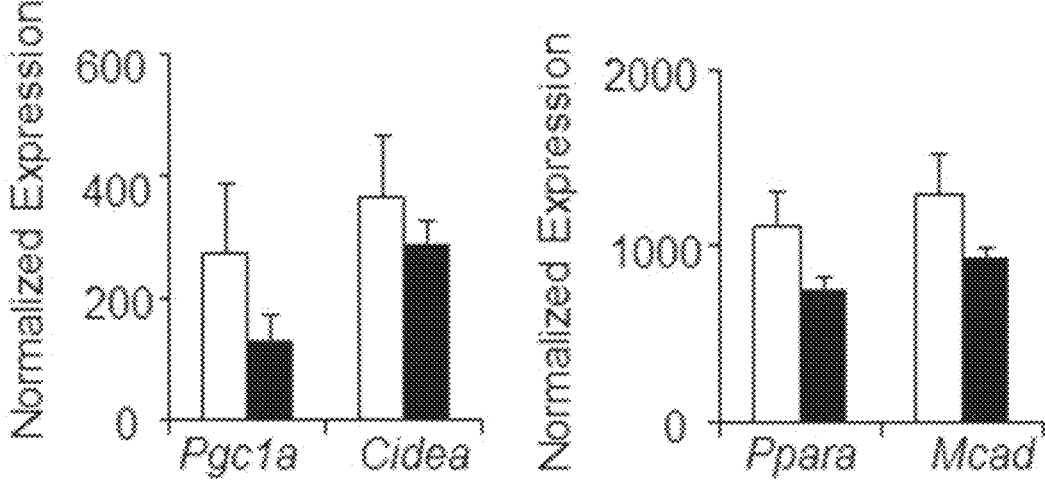

To elucidate weather EREG acts via Lep, ob/ob mice were treated with recombinant EREG. After 6 weeks of treatment with EREG, mice had reduced weight gain, although their food intake remained identical (FIG. 15A). Surprisingly, this weight loss was not associated with significant changes in weight in any investigated tissue, including BAT, WAT depot, and liver (FIG. 15B-D). The EREG-treated vs control ob/ob group had significantly lower RER during the light cycle and higher activity after transition from ambient temperature to the cold (FIG. 15E,F). However, metabolic rate remained identical between groups before and during cold exposure (FIG. 15G,H). In agreement, the expression of all PPARα target genes and mitochondrial genes involved in thermogenesis and oxidative phosphorylation was similar between these groups (FIG. 15I). It was concluded that EREG mediates energy expenditure effects systemically, specifically via induction of LEP secretion.

EREG Improves Glucose Uptake in Mice and Humans in EGFR-Independent Manner

Figures 16A, 16B:
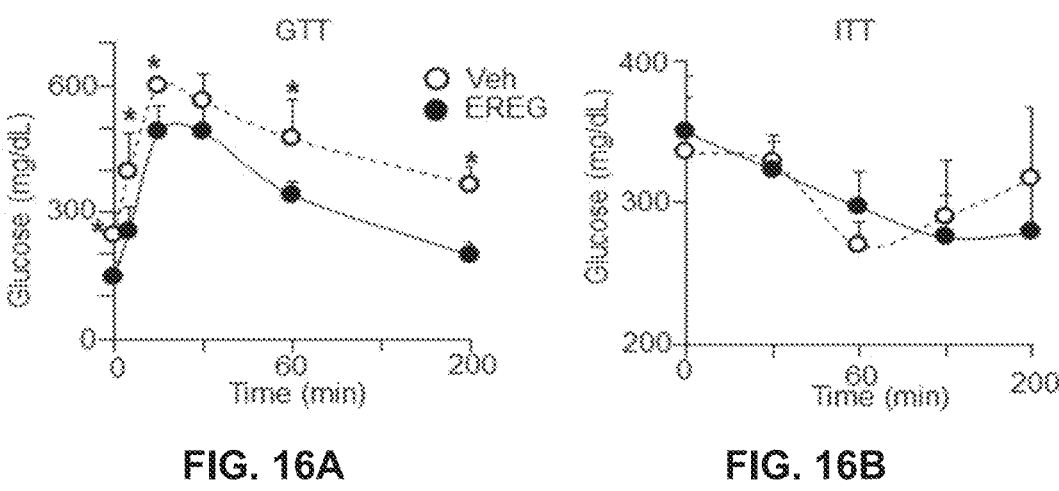
Figures 16C, 16D:
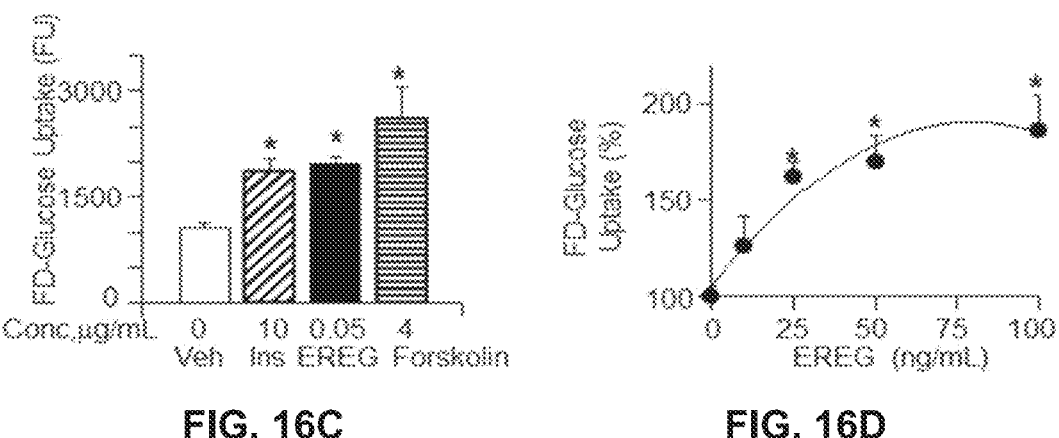
Figures 16E, 16F:
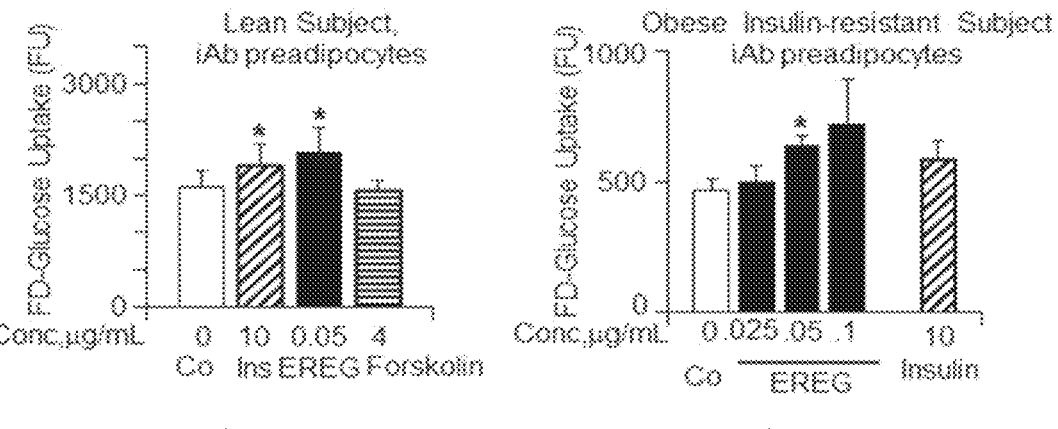
Figure 16J:
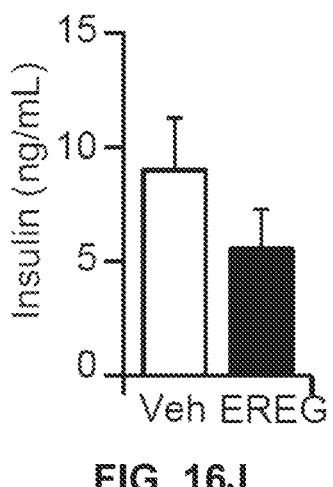
Figure 16K:
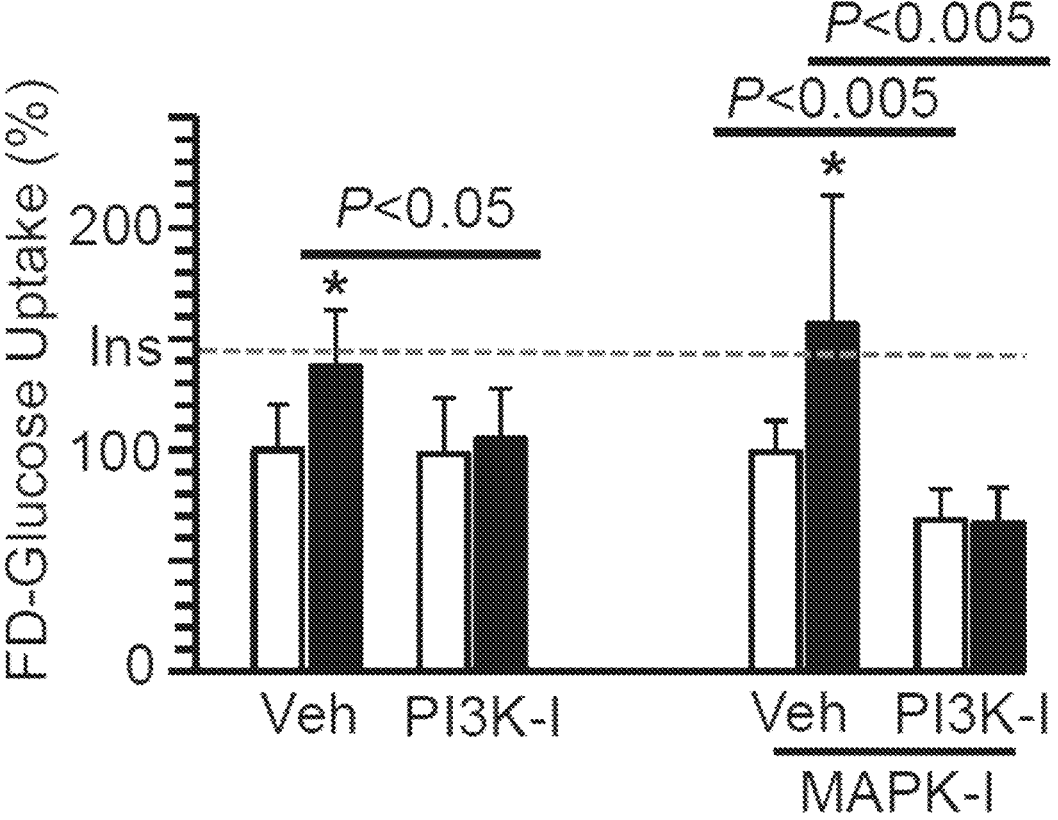
Figure 16L:
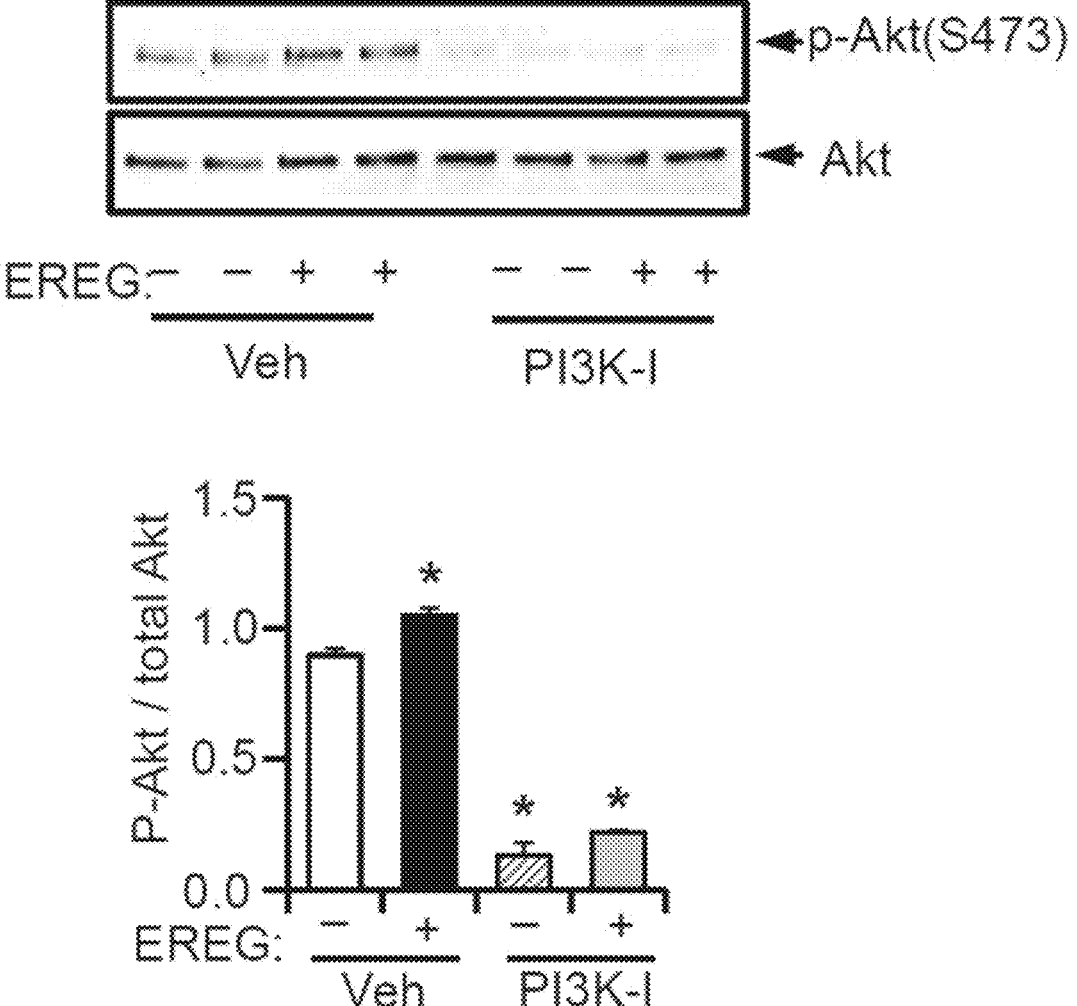
Figure 16M:
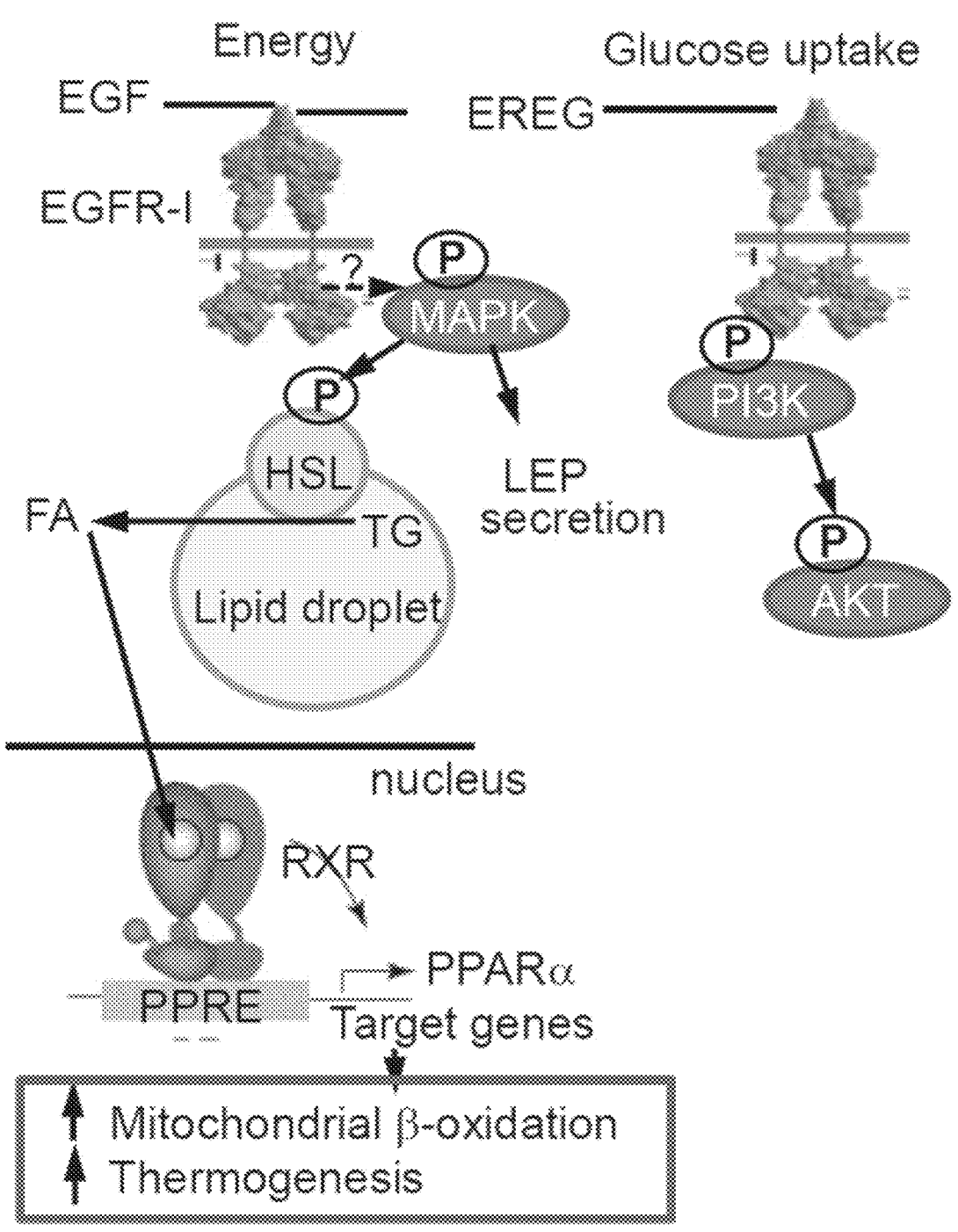
Figure 17:
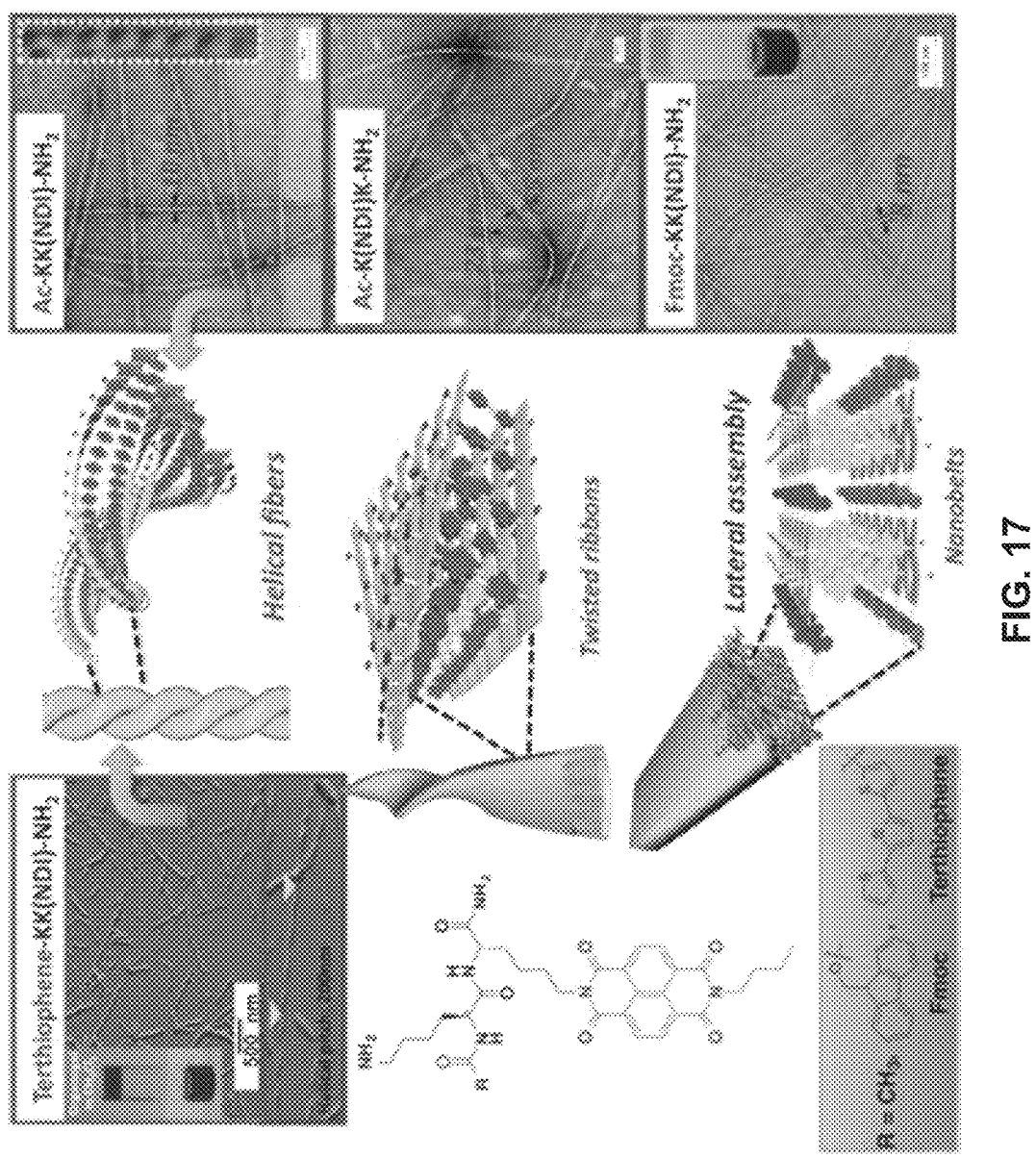
FIG. 17 shows β-sheet assembly of functionalized dilysine peptides.
Figure 18A:
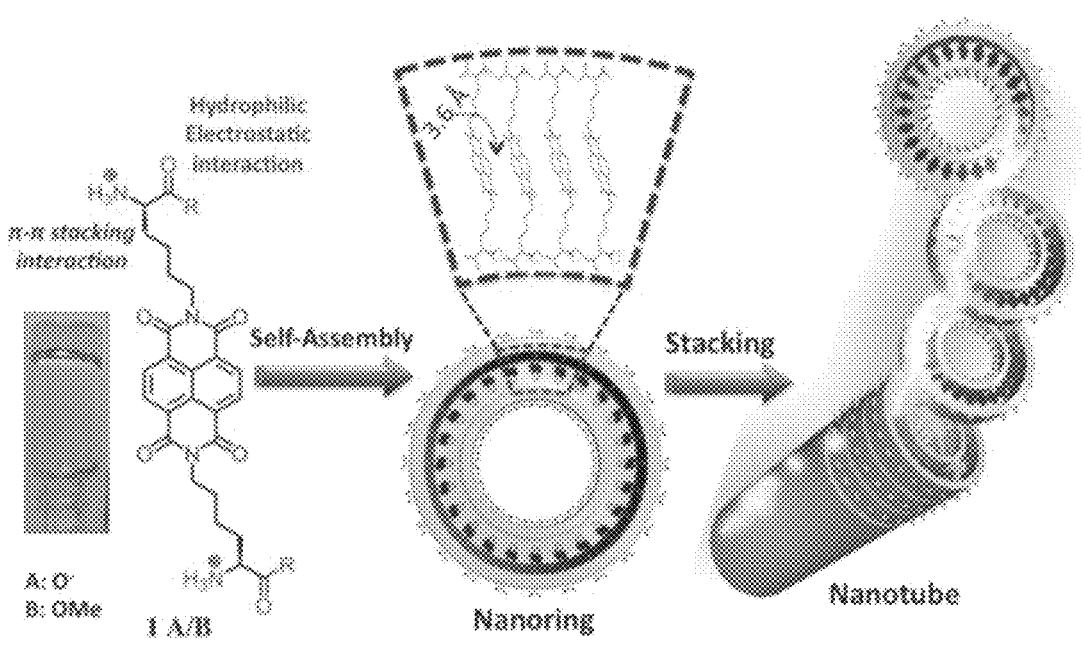
FIG. 18A: Self-assembly and structure of NDI-dilysine Bola 1A.
Figure 18B:
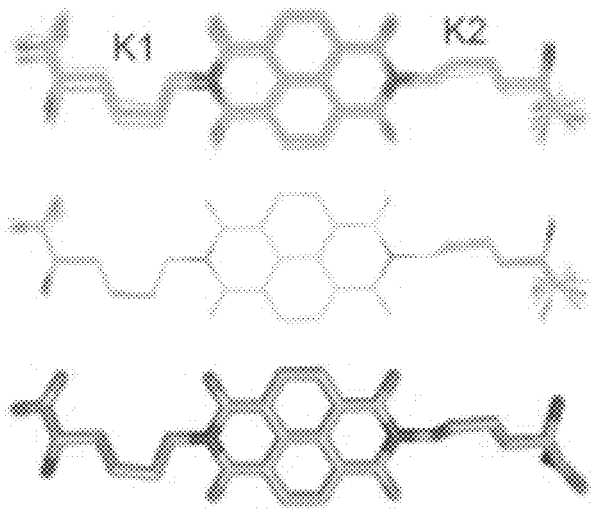
FIGS. 18B to 18E: Structural model of bolaamphiphilic nanotubes by MAS solid-state NMR.
Figure 18C:
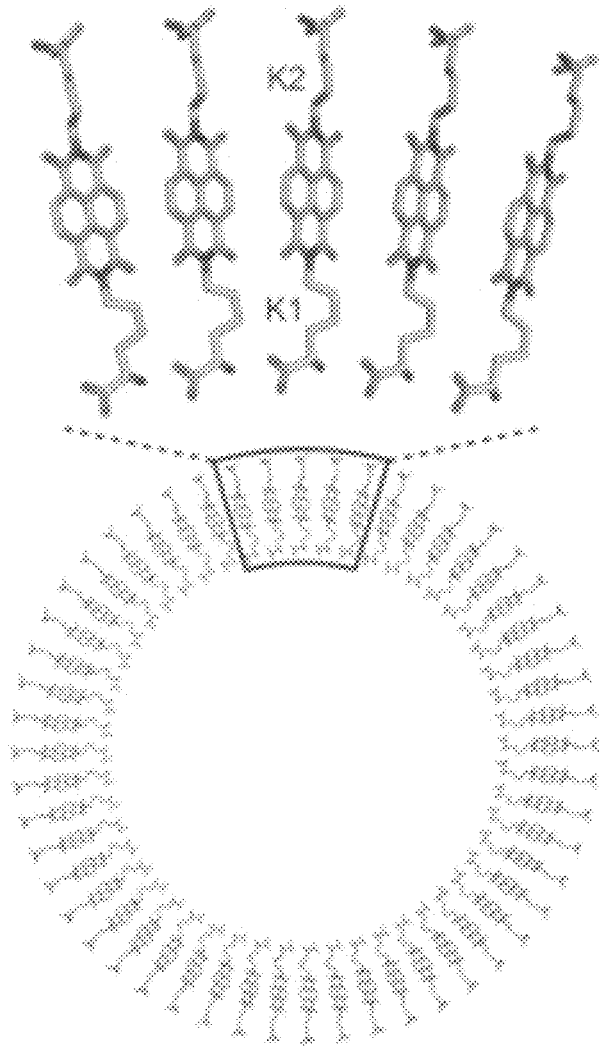
Figure 18D:
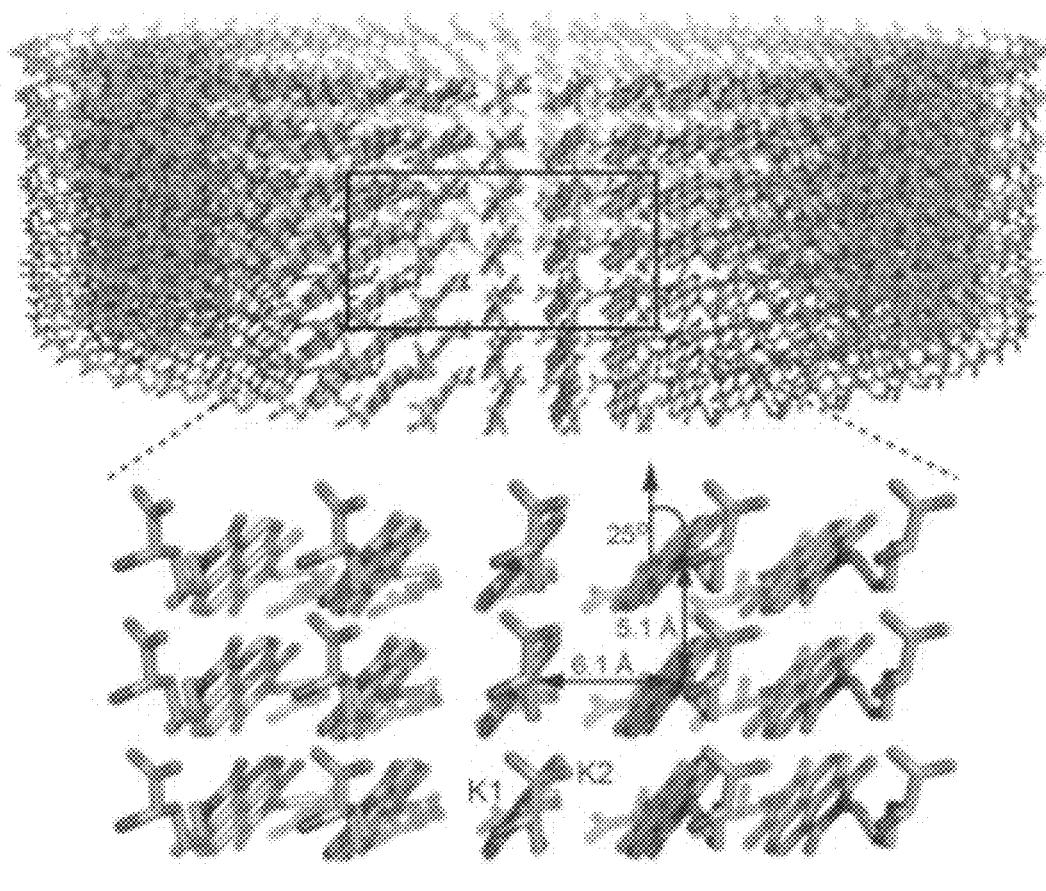
Figure 18E:
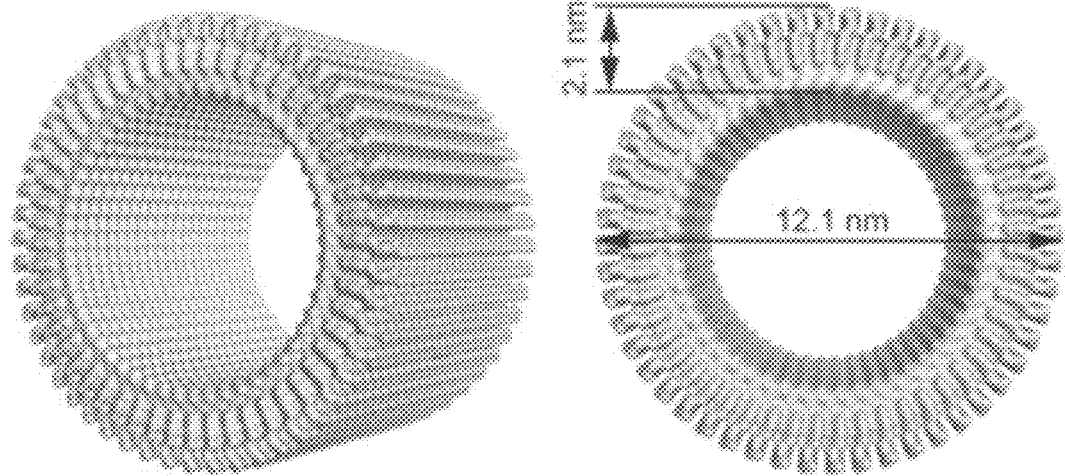
Figure 20:
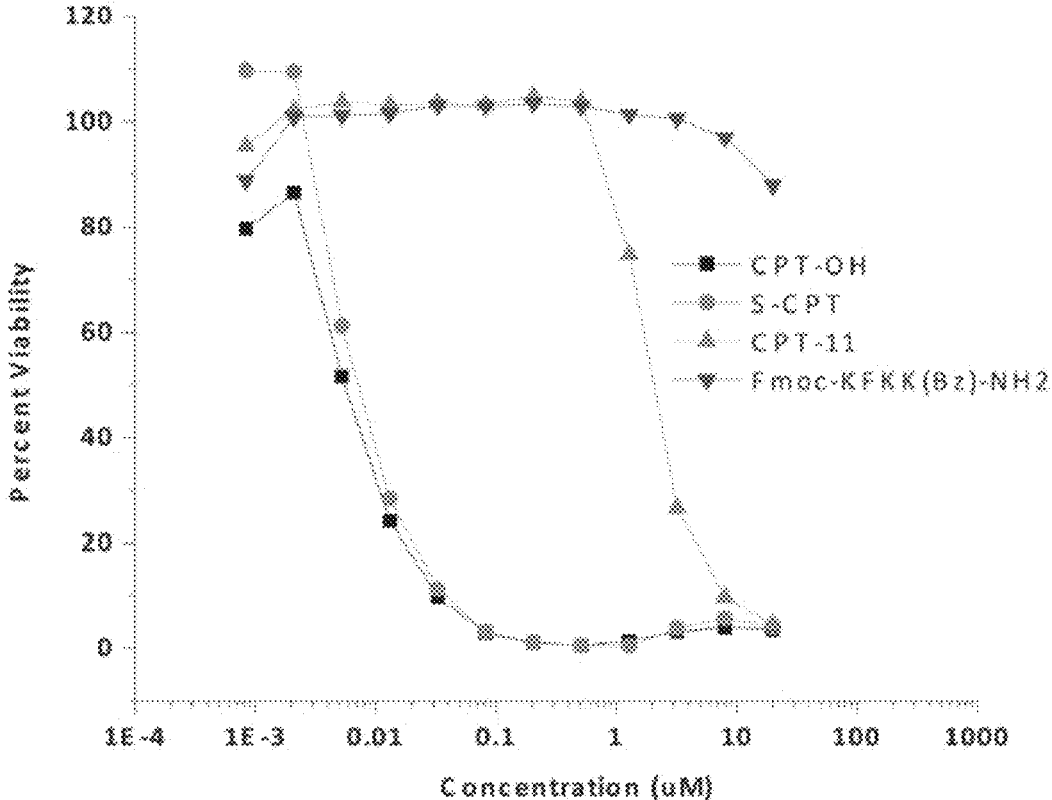
FIG. 20 shows viability of HT-29 colorectal cancer cells as a function of the concentration of Fmoc-KFKK(Bz)-NH$_2$ (SEQ ID NO:1 for underlined portion).

Although EREG treatment did not influenced metabolic rate and thermogenesis in ob/ob mice, the glucose tolerance test (GTT) showed markedly improved glucose tolerance compare to non-treated group (FIG. 16A). The response to insulin was similar between groups (FIG. 16B). EREG has been previously shown to improve pancreatic beta cell functions. Experiments were conducted to determine whether EREG has a direct effect on murine and human preadipocytes. EREG, insulin and forskolin stimulation significantly increased glucose uptake (187%, 174%, 245%, respectively) compared to non-stimulated 3T3-L1 preadipocytes (FIG. 16C). EREG stimulated glucose uptake in these preadipocytes in dose-dependent fashion (FIG. 16D). EREG and insulin induced similar glucose uptake also in human preadipocytes isolated from lean insulin-sensitive patients (FIG. 16E). Furthermore, in preadipocytes isolated from an insulin resistant patient, EREG induced glucose uptake in dose-dependent fashion (FIG. 16F), whereas stimulatory effect of insulin was not significant. To elucidate if EREG effect on glucose uptake was mediated by EGFR, glucose uptake was examined with and without inhibitors of EGFR and MAPK (FIG. 16G). The inhibition of EGFR markedly increased glucose uptake (268%) compared to non-treated preadipocytes (100%) as well 212% compared to insulin response (100%) in this experiment. These data demonstrate the role of EREG in glucose metabolism in WAT that was independent on it is insulin-stimulating role in pancreatic beta-cells. EREG acted via alternative pathways to EGFR that streamline and augment effects of EREG by EGFR inhibition.

Experimental Procedures

Reagents

All reagents were purchased from Sigma (St. Louis, MO) and all cell culture mediums from Life technologies (Life technologies, Grand Island, NY) unless otherwise indicated. Grand Island, New York Mouse monoclonal anti-EREG antibody was purchased from Santa Cruz Biotechnology (Dallas, Texas) and secondary antibody from LI-COR Biosciences (Lincoln, NE). Mouse recombinant EREG was obtained from Sino Biological (Beijing, China) and human recombinant EREG from R&D Systems (Minneapolis, MN). HSL (CAY10499), PI3K (Wortmannin) inhibitors were purchased from Cayman Chemical (Ann Arbor, MI), MAPK (U0126), SRC (AZM475271) inhibitors were from Tocris Bioscience (Bristol, UK), and EGFR (Tyrphostin AG1478) inhibitor from Sigma-Aldrich (St. Louis, MO).

Human Studies

This study was approved by the Ohio State University Institutional Review Board for Human Research. All subjects provided written informed consent. Abdominal fat was obtained from overnight fasted men and women (n=10). The data from lean (BMI<30) and obese subjects (BMI≥40) are shown in Table 3. Institutional review board-approved informed consent was obtained for access to subjects' medical records.

Animal Studies

Animal studies were approved by the Institutional Animal Care and Use Committee of The Ohio State University (OSU).

Study 1. Comparison of WT and Aldh1a1$^{-/-}$ Mice on a Regular Chow Diet

Aldh1a1$^{-/-}$ mice were constructed and metabolic profile was analyzed. C57BL/6J (WT) mice were initially purchased from The Jackson Laboratory (Bar Harbor, Maine) and bred at OSU. 5-month old WT (n=14, 7 males and 7 females) and Aldh1a1$^{-/-}$ (n=13, 7 males and 6 females) were fed a regular chow. WAT and plasma EDTA were collected for analysis and stored at −80° C.

Study 2. Comparison of Lean and Obese Mice with Dietary and Genetic Obesity

Three groups of mice were studied. Group 1: 4-month-old WT mice (n=14) fed regular chow (n=14, 7 males and 7 females). Group 2: 3-month-old WT mice fed with HF diet (n=11, 5 males and 6 females). Mice with diet induced obesity (60% HF for 2 weeks) were purchased from Jackson laboratories and continue on 45% HF for 3 weeks. Group 3: 10-week old Ob/Ob (B6.V-Lepob/J strain containing spontaneous mutation in the gene encoding leptin congenic on C57BL6/J) mice were purchased from The Jackson Laboratory (n=9, 5 males and 4 females). Visceral (intra-abdominal (i-Ab); gonadal) fat were collected for protein, mRNA, and histology.

Study 3. EREG Effects on WT Mice Fed a High-Fat (HF) Diet 6-week old C57BL6/J male mice (WT) were fed a high fat diet (HF, 45% kcal from fat, D12451, Research Diet Inc., New Brunswick, NJ) for 30 days. Then mice were randomly assigned for 1) a control group injected with 0.1 mL sterile phosphate buffered saline (PBS) into both epididymal iAb fat (n=7), and 2) EREG-treated group injected with 20 ng EREG per epididymal iAb fat depot (n=7). Mice were injected with 0.1 mL sterile PBS, containing 200 ng EREG/mL.

Mice were individually housed and pair fed when injection started. Mice were injected every other day for 2 weeks. Metabolic measurements were performed as described in 2.5. WAT were collected for protein, mRNA, and histology.

Study 4. EREG Effects on Ob/Ob Mice Fed a High-Fat (HF) Diet 6-week old Ob/Ob male mice, purchased from the Jackson laboratory (n=10), were fed a high fat diet (HF, 45% kcal from fat, D12451, Research Diet Inc., New Brunswick, NJ) for 30 days and then randomly assigned into two groups:

1) a control group injected with 0.1 mL sterile PBS into both epididymal iAb fat (n=5), and 2) EREG-treated group injected with 60 ng EREG per epididymal iAb fat depot (n=5). Mice were injected with 0.1 mL sterile PBS, containing 600 ng EREG/mL.

These mice were pair fed and individually housed during injections. Mice were injected every other day for 2 weeks. Metabolic measurements were performed as described in 2.5. WAT were collected for protein, mRNA, and histology.

Metabolic Measurements.

Metabolic parameters in study 2.3 and 2.4 were measured by indirect calorimetry (CLAMS, Columbus Instruments, Columbus, OH) at ambient temperature (22° C.) with 12 h light/dark cycles. Animals were fed the same HF diet and water provided ad libitum. Mice were placed individually and allowed to acclimatize in the chambers for 12 h, and $O_2$ consumption, $CO_2$ production, energy expenditure, and locomotor activity were measured for 24 h. Then temperature was changed to 4° C. for 6 h. Based on this data, respiratory quotient, activity, exchange ratio ($V_{CO2}/V_{O2}$) and $\Delta$ heat values were calculated by CLAMS.

Glucose Tolerance Test (GT7) and Insulin Tolerance Tests (ITT).

GTT was performed in overnight fasted Ob/Ob mice (study 4, N=5 per group) by intraperitoneal injection of 0.004 mL 25% glucose/g body weight. One week after GTT, an ITT test was performed in same overnight fasted mice. They were injected with a single intraperitoneal insulin dose (1 mU of insulin/g body weight). Blood glucose was measured from mouse tails by One Touch Ultra glucometer (LifeScan, Wayne, PA).

Cell Culture Studies.

Human and Murine Adipocyte Differentiation

Murine preadipocyte (3T3-L1, WT and Aldh1a1$^{-/-}$) lines were cultured and maintained in standard culture medium (DMEM containing 10% calf serum and 0.1% 50 mg/mL Gentamicin). Adipogenesis was induced (Day 0) in confluent preadipocytes using differentiation medium I containing 3-isobutyl-1-methylxanthine (0.5 mM), dexamethasone (1 μM), insulin (1.7 μM), 10% FBS, and 0.1% gentamicin in DMEM. Differentiation medium II containing 10% FBS, insulin (1.7 μM), and 0.1% gentamicin in DMEM was replaced every 48 hours after induction of adipogenesis.

Human stromal vascular fraction (SVF) was isolated from iAb (omental) fat of lean and obese men and women as described before and maintained in preadipocyte culture media (Lonza, Allendale, NJ). Differentiation was carried out for 9-10 days using preadipocyte culture media supplemented with insulin, dexamethasone, IBMX and indomethacin (Lonza, Allendale, NJ).

Human Tissue Explants

Abdominal fat tissue obtained from a male obese patient was excised into 35 mg sections for stimulation with EREG. Explants were stimulated with EREG in DMEM containing 1% FBS for 2 h. Media was collected after 2 h, lyophilized and reconstituted in 120 μL deionized water for leptin detection using ELISA kit (Alpco, Salem, NH).

Gene Expression

Affymetrix GeneChip mRNA was isolated by RNeasy (Qiagen, Valencia, CA). RNA integrity was interrogated using the Agilent 2100 Bioanalyzer (Agilent Technologies). A 100 ng aliquot of total RNA was linearly amplified. Then, 5.5 ug of cDNA was labeled and fragmented using the GeneChip WT PLUS reagent kit (Affymetrix, Santa Clara, CA) following the manufacturer's instructions. Labeled cDNA targets were hybridized to Affymetrix GeneChip Mouse Gene ST 2.0 arrays for 16 h at 45° C. rotating at 60 rpm. The arrays were washed and stained using the Fluidics Station 450 and scanned using a GeneChip Scanner 3000. Signal intensities were quantified by Affymetrix Expression Console version 1.3.1. Background correction and quantile normalization were performed to adjust for technical bias, and probe-set expression levels were calculated by the RMA method. After filtering above noise cutoff, there are 9,528 probe-sets that were tested by linear model. A variance smoothing method with fully moderated t-statistic was employed for this study and was adjusted by controlling the mean number of false positives. With a combined cutoff of 2-fold change and p-value of 0.0001 (controlling 1 false positive over all probe-sets), 500 probe-sets were declared as differential gene expression between Aldh1a1$^{-/-}$ and WT preadipocytes. GEO file: 'QS wild type and Aldh1a1 KO preadipocytes 2015'.

NanoString nCounter Mouse Metabolic Expression Assay (NanoString Technologies)

NanoString's nCounter analysis system performed direct detection of target molecules from a single sample using color-coded molecular barcodes, giving a digital quantification of the number of target molecules. A custom panel containing Ereg, thermogenic genes, and PPARα-target genes was designed and used for simultaneous quantification of 37 genes including housekeeping genes. All data were normalized to 3 housekeeping genes Gapdh, Pgk1, and Tubb quantified in the same samples using nSolver Software. Total mRNA (100 ng in 5 μl) was hybridized overnight with nCounter Reporter (20 μl) probes in hybridization buffer and in an excess of nCounter Capture probes (5 μL) at 65° C. for 16-20 h. The hybridization mixture containing target/probe complexes was allowed to bind to magnetic beads containing complementary sequences on the Capture Probe. After each target found a probe pair, excess probes were washed followed by sequential binding to sequences on the Reporter Probe. Biotinylated capture probe-bound samples were immobilized and recovered on a streptavidin-coated cartridge. The abundance of specific target molecules was then quantified using the nCounter Digital Analyzer. Individual fluorescent barcodes and target molecules present in each sample were recorded with a CCD camera by performing a high-density scan (600 fields of view). Images were processed internally into a digital format and were normalized using the NanoString nSolver software analysis tool. Counts were normalized for all target RNAs in all samples based on the positive control RNA to account for differences in hybridization efficiency and post-hybridization processing, purification, and immobilization of complexes. The average was normalized by background counts (the average of the eight negative control counts) for each sample. Subsequently, a normalization of mRNA content was performed based on Gapdh, Pgk1, and Tubb internal reference housekeeping genes.

Semi-Quantitative mRNA Analysis mRNA was isolated from adipocyte cultures according to the manufacturer's instructions (Qiagen; Valencia, CA). cDNA was prepared from purified mRNA and analyzed using 7900HT Fast Real-Time PCR System, TaqMan fluorogenic detection system and validated primers (Applied Biosystems; Foster City, CA). Comparative real time PCR was performed in triplicate, including no-template controls. The mRNA expression of interested genes was normalized by 18S expression level using the comparative cycle threshold (Ct) method.

Transfections

HEK293 cells ($2.3 \pm 10^4$ cells, 24-well plates) were used for transient transfection experiments. Cells were transfected with human PPARα-LBD construct, yeast UASTK luciferase reporter (SwitchGear Genomics, Menlo Park, CA), using Fugene (Roche Applied Science, Indianapolis, IN). Transfections were carried out in OptiMeM (Invitrogen, Carlsbad, CA) medium for 12 hours as described previously. Luciferase was measured using Promega assay according to manufacturer's instructions Western Blot Cell/tissue protein lysates normalized by protein content and medium were separated on 10% acrylamide gel under reducing conditions. After transfer to a polyvinylidene fluoride membrane (Immobilon-P; Millipore), proteins were analyzed using an Odyssey Infrared Imaging System (LI-COR Biosciences).

Non Esterified Fatty Acids (NEFA) and Triglyceride (TG) Assays

Plasma FFA and TG were measured in plasma samples from study 3, using kits from Wako Diagnostics (Mountain View, CA).

Glucose Uptake Assay

Glucose uptake assay was performed using glucose uptake cell-based assay kit (Cayman Chemical, Ann Arbor, MI). 3T3-L1 or human preadipocytes were cultured at a density of $5 \times 10^4$ per well into a 96-well plate (n=7) in high glucose media and grown overnight. Old cell culture medium was removed the next day and washed with PBS to remove residual glucose. Supplied 2-deoxy-2-[(7-nitro-2,1, 3-benzoxadiazol-4-yl)amino]-D-glucose) (2-NBDG) was diluted to 150 µg/mL in DMEM medium without glucose, phenol red, L-glutamine, sodium pyruvate, and HEPES (Life technologies, Grand Island, New York). 100 µL of 2-NBDG glucose free medium with or without recombinant EREG and other treatments was added to the plated cells. After incubating at 37° C. for 30 minutes, cells were washed gently two times with 200 µL of glucose assay buffer. 100 µL of the assay buffer was added to each well and measured for fluorescence at an excitation/emission of 485/535 nm.

Enzyme-Linked Immunosorbent Assay (ELISA)

Plasma samples were collected from mice in Study 3 and analyzed using a mouse leptin ELISA Kit (Alpco, Salem, NH) according to manufacturer's instruction. The absorbance (450 nm) was measured using Synergy H1 Hybrid Multi-Mode Microplate Reader. Insulin levels were measured in plasma from mice in Study 4 using an ultra-sensitive mouse insulin ELISA kit (Crystal Chem, Downers Grove, IL) according to manufacturer's instruction.

Human plasma samples obtained from lean and obese patients were used to determine plasma EREG concentrations using a human EREG ELISA kit (R&D Systems, Minneapolis, MN).

Statistical Analysis

All data are shown as mean±SD. Number of samples is indicated in Figure legends. Group comparisons were assessed using Mann Whitney U test or using ANOVA models. P<0.05 was considered to be statistically significant and is presented as an asterisk. Trends were examined using Pearson correlation analysis tests.

Example 3: Thermogenic Biologicals Treatment of Obesity and Improvement of Insulin Resistance This example describes the immobilization of epiregulin by self-assembled nanostructures. These nanostructures enhance the stability of epiregulin and increases its efficacy in mediating adipocyte cell differentiation. The approach described for epiregulin appears to be generally applicable to other biomolecules including other enzymes, cytokines and other biomolecules. Studies have been conducted on nanofibers formed by the β-sheet assembly of the tetrapeptide, <u>KFKK</u>(Bz)-NH$_2$ (SEQ ID NO:1 for underlined portion).

Results

Nanofibers were formed by the self-assembly of the Fmoc-protected tetrapeptide, Fmoc-<u>KFKK</u>(Bz)-NH$_2$ (SEQ ID NO:1 for underlined portion) having one lysine side-chain capped with as a benzamide group (FIG. 19, top). Self-assembly was performed by incubating the peptide in PBS (2.5 mM) then imaging by TEM (FIG. 19). TEM imaging shows the formation of well-defined nanostructures comprised of twisted nanoribbons and nanofibers. FT-IR spectra exhibited peaks at 1674 cm$^{-1}$, due to the benzamide carbonyl, and at 1620 cm$^{-1}$, which is characteristic of β-sheet structure. Deconvolution of the IR absorption data indicated that the peptide structure was comprised of 26% random coil and 74% β-sheet.

Cytotoxicity assay data indicated that the peptide, Fmoc-<u>KFKK</u>(Bz)-NH$_2$ (SEQ ID NO:1 for underlined portion) has no efficacy against human colorectal cell line in vitro.

Figures 21, 22:
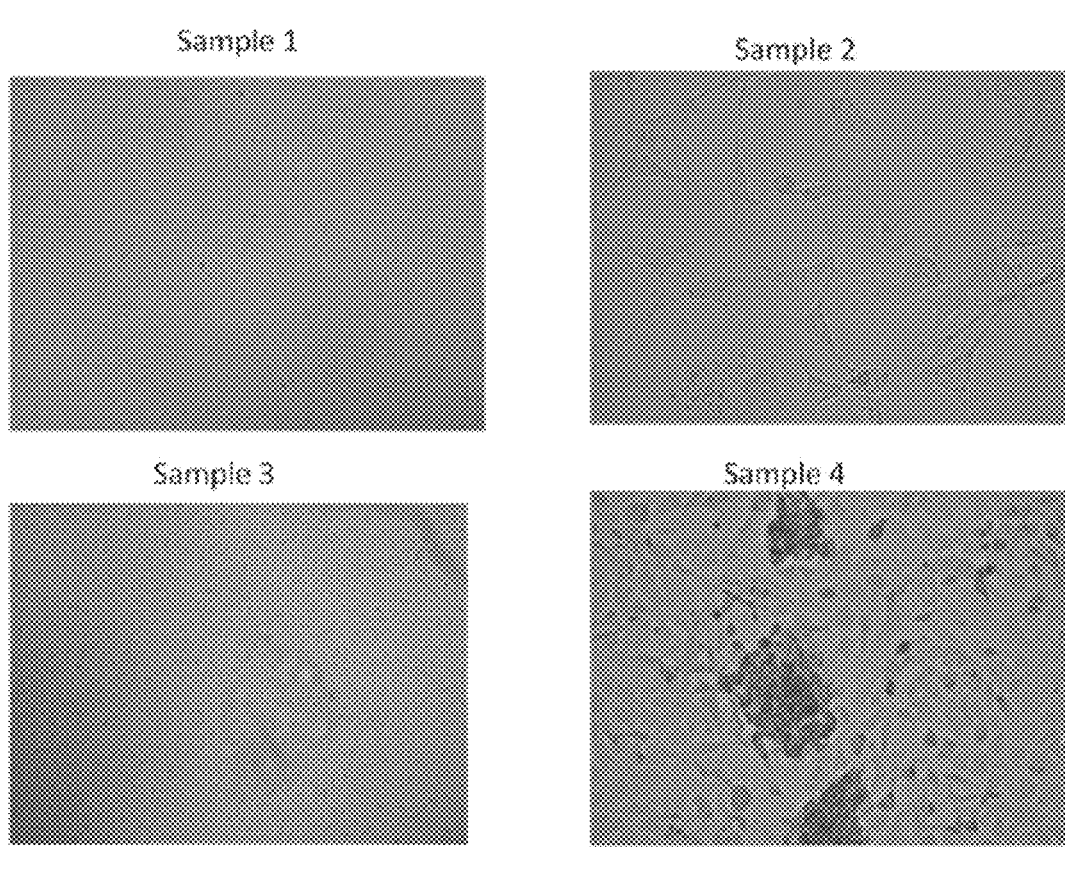
FIG. 21 shows microscopy images of adipocyte cell differentiation under several conditions after incubation in 5% CO2 at 37° C.: (1) 3T3-L1 preadipocyte cells in 3 mL differentiation medium. (Blank Control); (2) 3T3-L1 preadipocyte cells with 100 ng EREG in 3 mL differentiation medium; (3) 3T3-L1 preadipocyte cells with nanofiber in 3 mL differentiation medium; (4) 3T3-L1 preadipocyte cells with EREG binded nanofiber in 3 mL differentiation medium.
FIG. 22 shows stimulation of 3T3-L1 adipocytes with EREG, nanofibers, or EREG bound to nanofibers increases expression of thermogenic gene Pgc1a. 3T3-L1 fibroblasts were stimulated with 10 ng/ml of recombinant EREG (Sino Biological Ins). Pgc1a expression was measured by TaqMan and normalized to TATA box.
Figure 24:
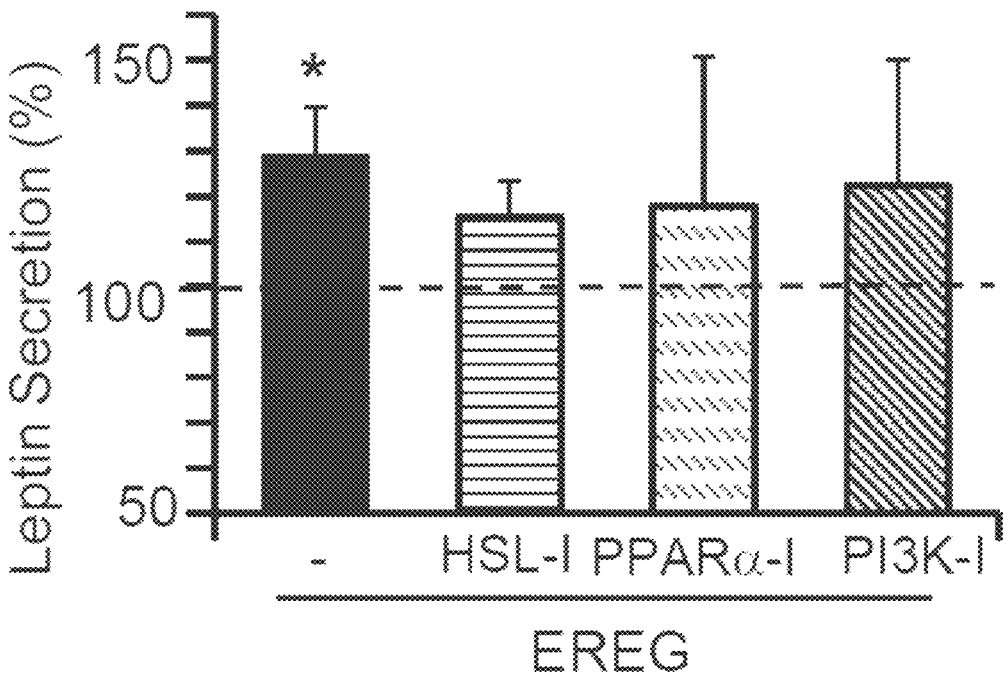
FIG. 24 shows LEP release quantified by ELISA following stimulation of mouse explants with and without EGF (50 ng/mL) in the presence and absence of inhibitors of HSL (10 μM), PPARα (10 μM), and PI3K (100 nM) for 2 h. Data (mean±SD) are shown as percent to control (Veh, 100%) and is indicated as a dashed line.
Figure 25A:
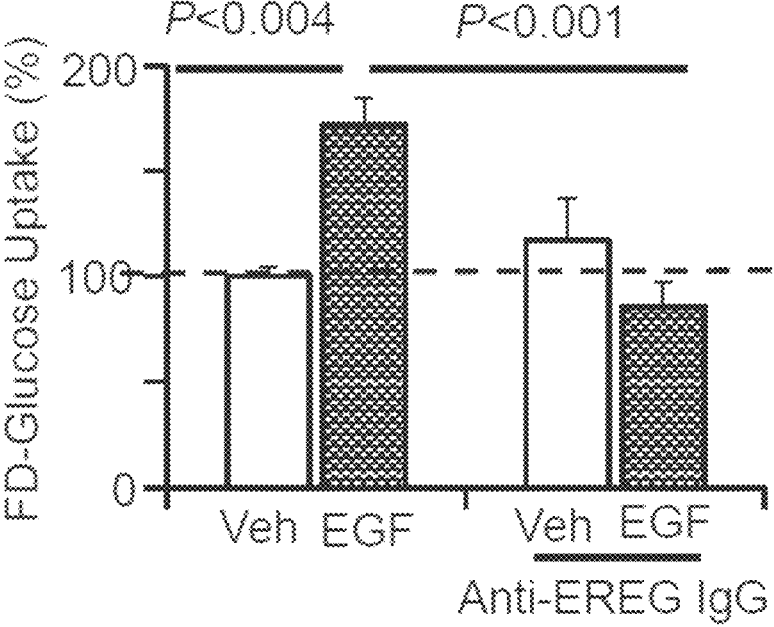
FIG. 25A: FD-glucose uptake was measured in mouse 3T3-L1 preadipocytes with or without EGF (50 ng/mL) in the presence and absence of anti-EREG antibody (10 μg/mL). Data (mean±SD) are shown as percent to control (Veh 100%). P<0.05 indicate significant differences between treatments.
Figure 25B:
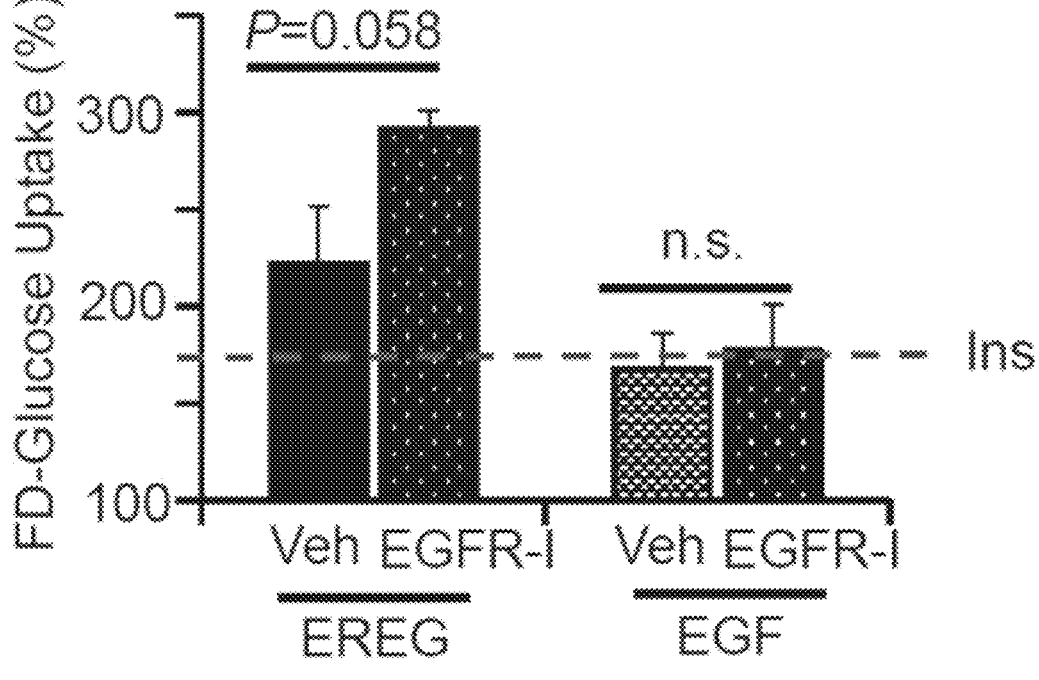
FIG. 25B: FD-glucose uptake comparison in mouse 3T3-L1 preadipocytes with and without EGFR inhibitor (10 μM), in the presence and absence of EREG or EGF (50 ng/mL, each). Data (mean±SD) are shown as percent to control (Veh 100%). Dashed line shows FD glucose uptake mediated by insulin (Ins, 10 μg/mL). n.s. indicated not significant.
Figure 26:
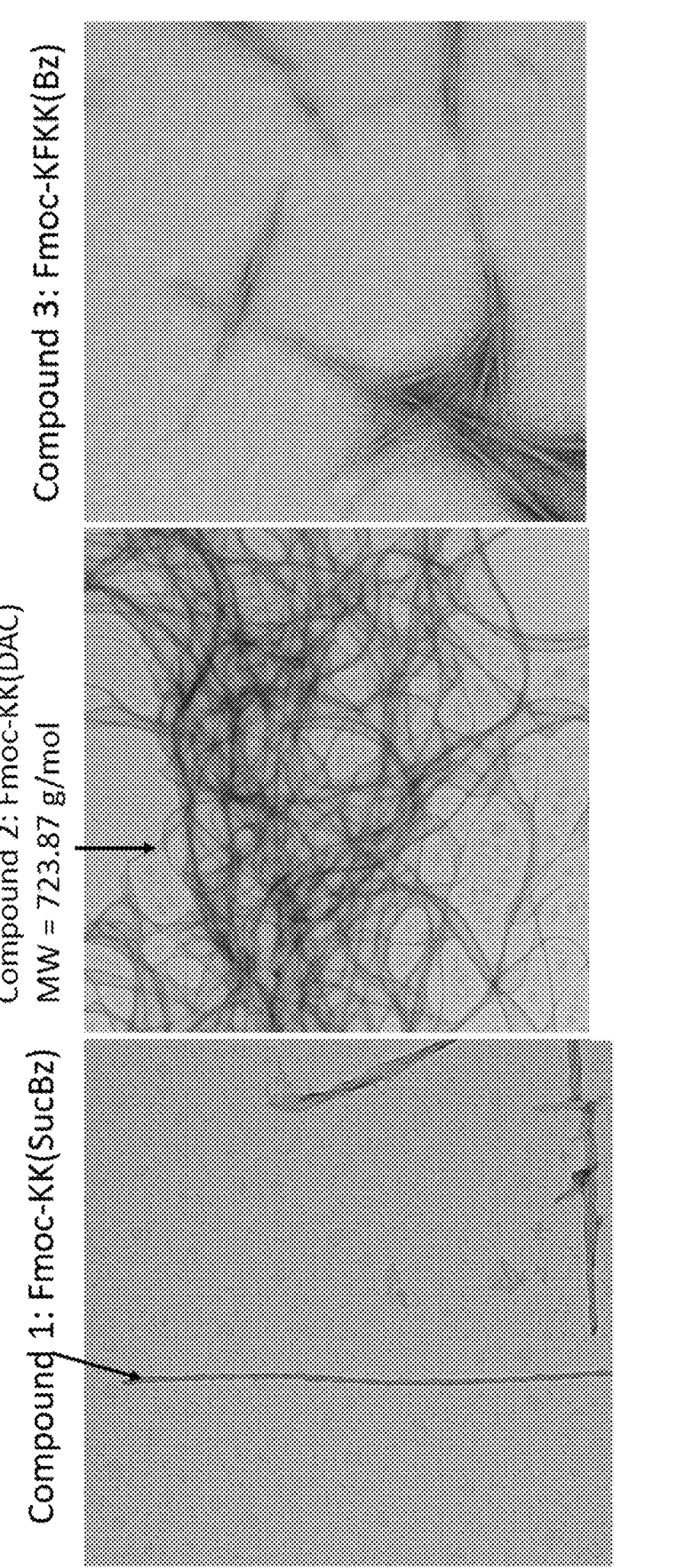
FIG. 26 shows electron microscopy of self-assembled nanoscaffolds #1 (Fmoc-KK(SucBz)), #2 (Fmoc-KK (DAC)), and #3 (Fmoc-KFKK(Bz)).
Figure 27:
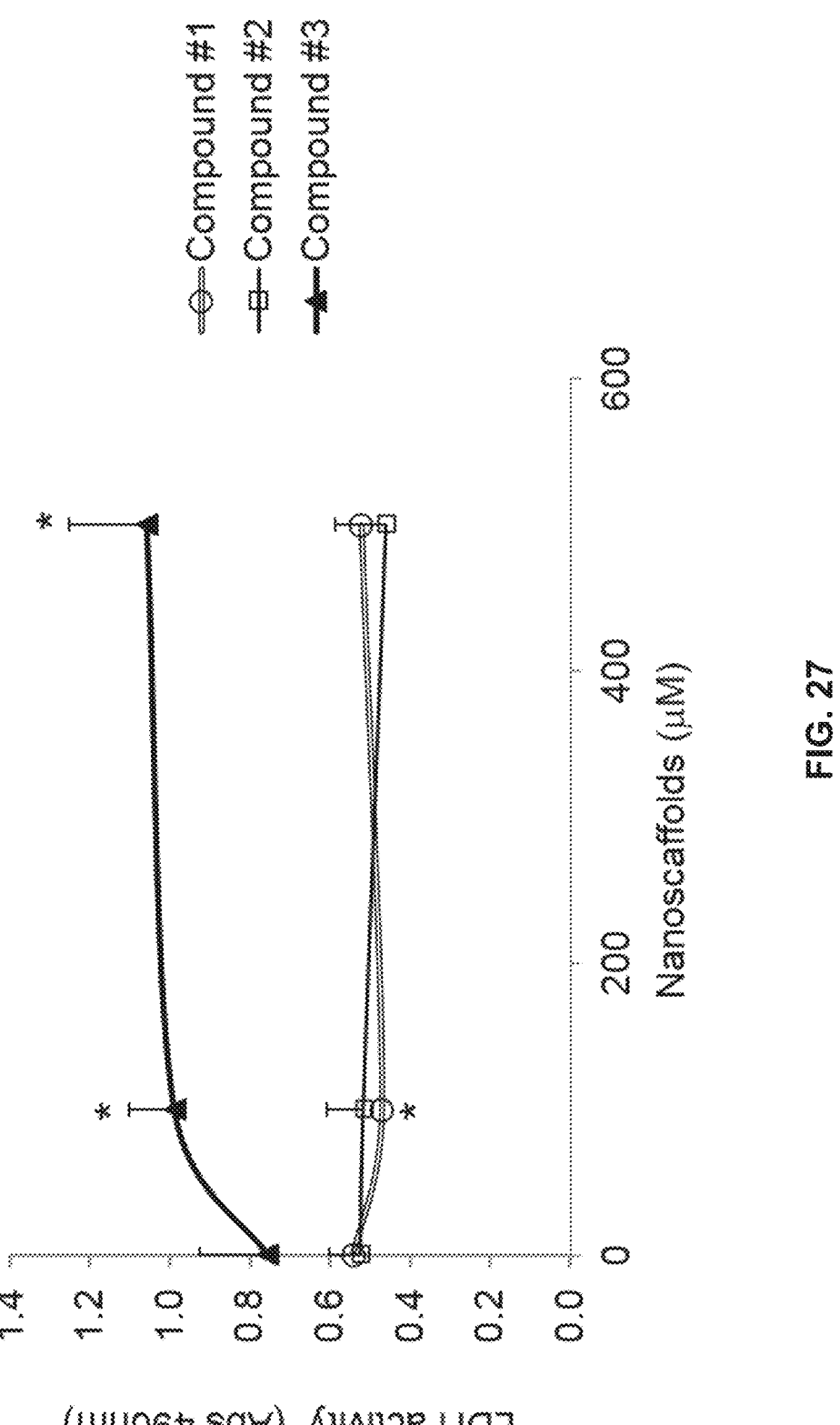
FIG. 27 shows that nanoscaffolds #1 and #2 are not toxic. Non-differentiated, 90% confluent 3T3-L1 cells were incubated with different concentrations of nanoscaffolds #1, #2, or #3 for 6 hours. Cytotoxicity was measured the lactate dehydrogenase (LDH), released upon cell lysis using The CytoTox 96 assay (Promega, Cat #G1780). Asterisks showed the significant difference (P<0.05) compared to cells treated with PBS control.
Figures 28A, 28B:
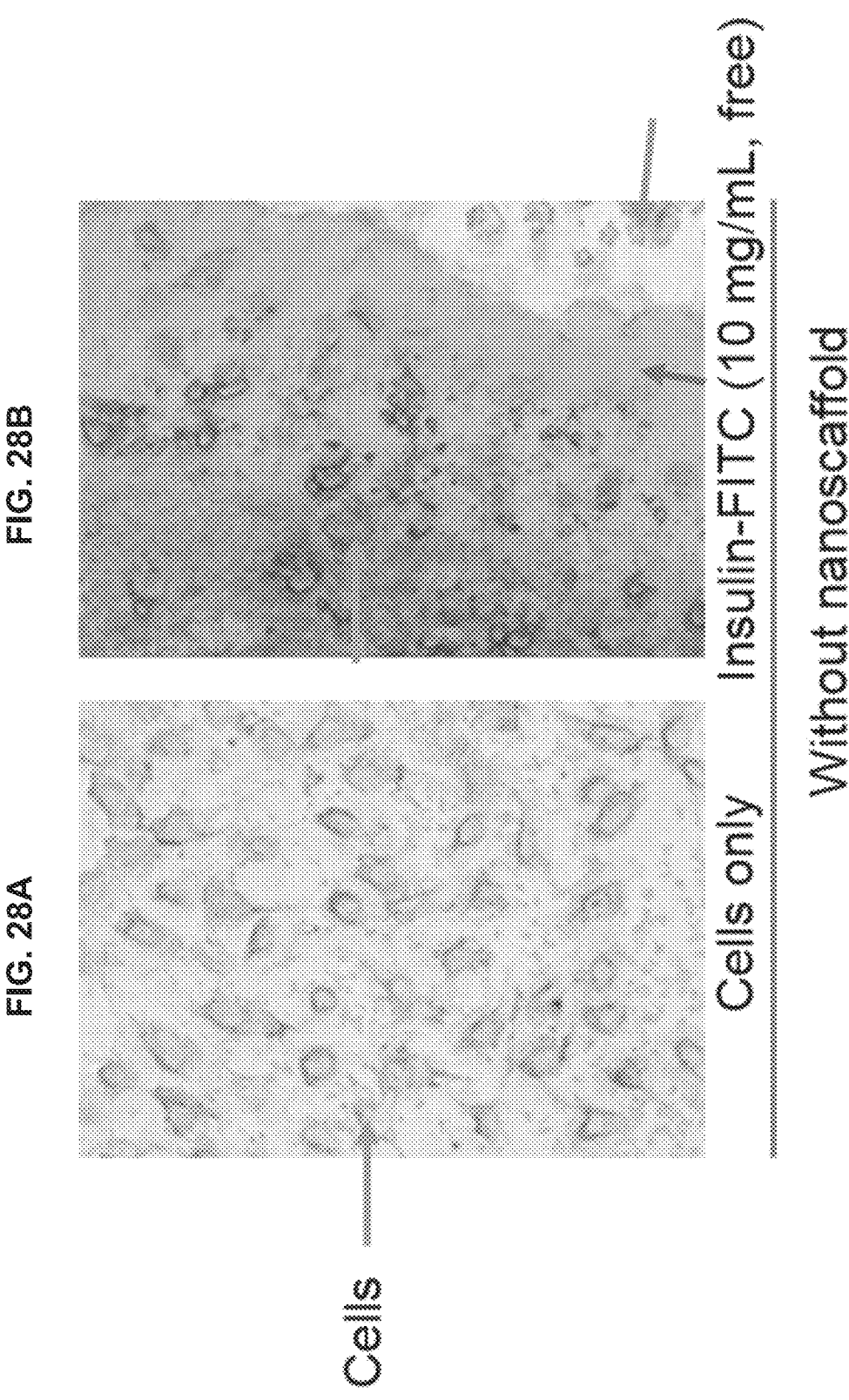
FIGS. 28A to 28D show nanoscaffold #2 binds insulin and creates microenvironment. The surface interaction among cells, nanoscaffold 2, and protein were demonstrated using laser scanning microscopy. (KEYENCE America, VK-X260K model) Non-differentiated, 3T3-L1 cells were cultured on the cover glass.
Figures 28C, 28D:
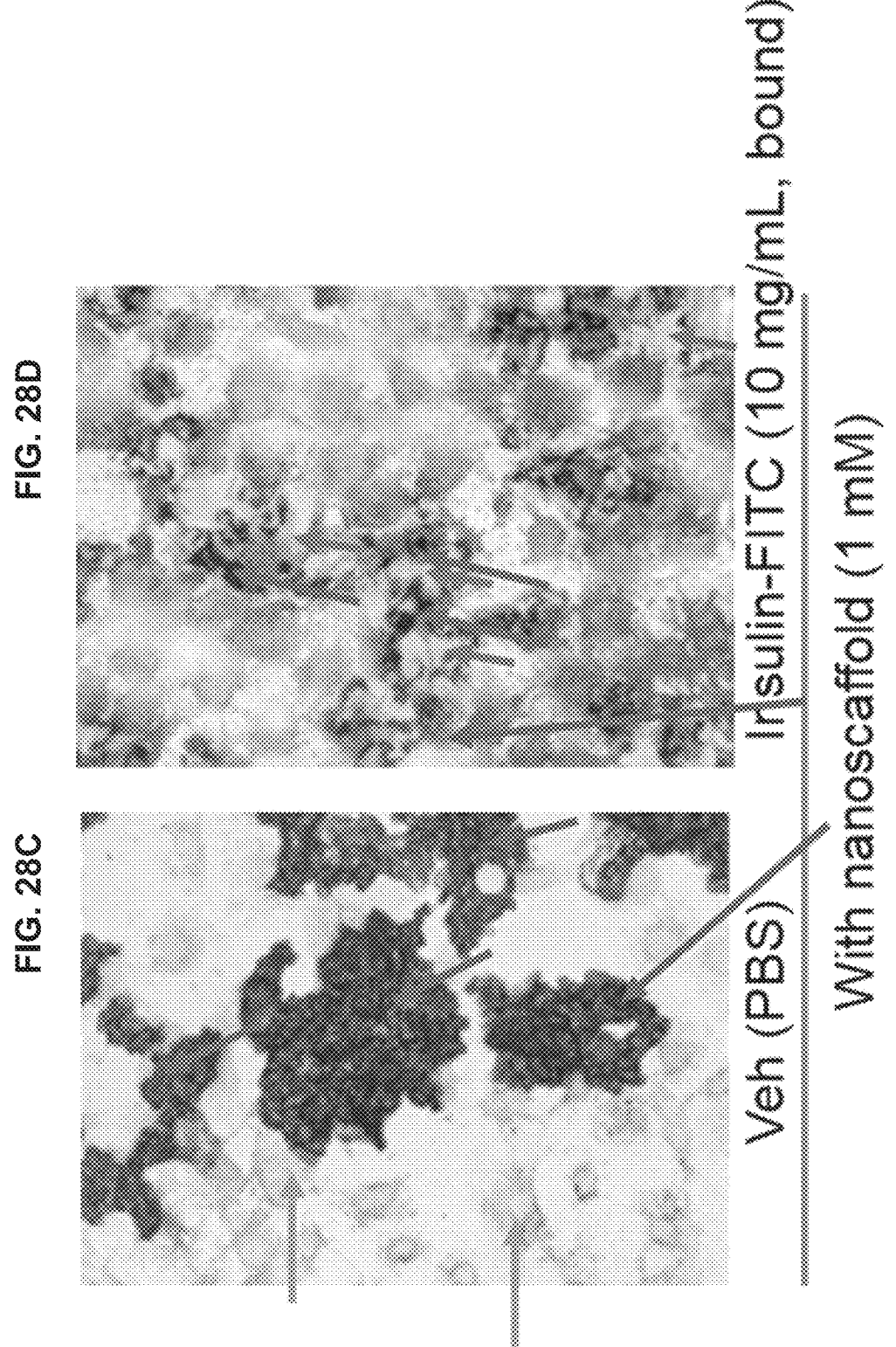
Figure 29A:
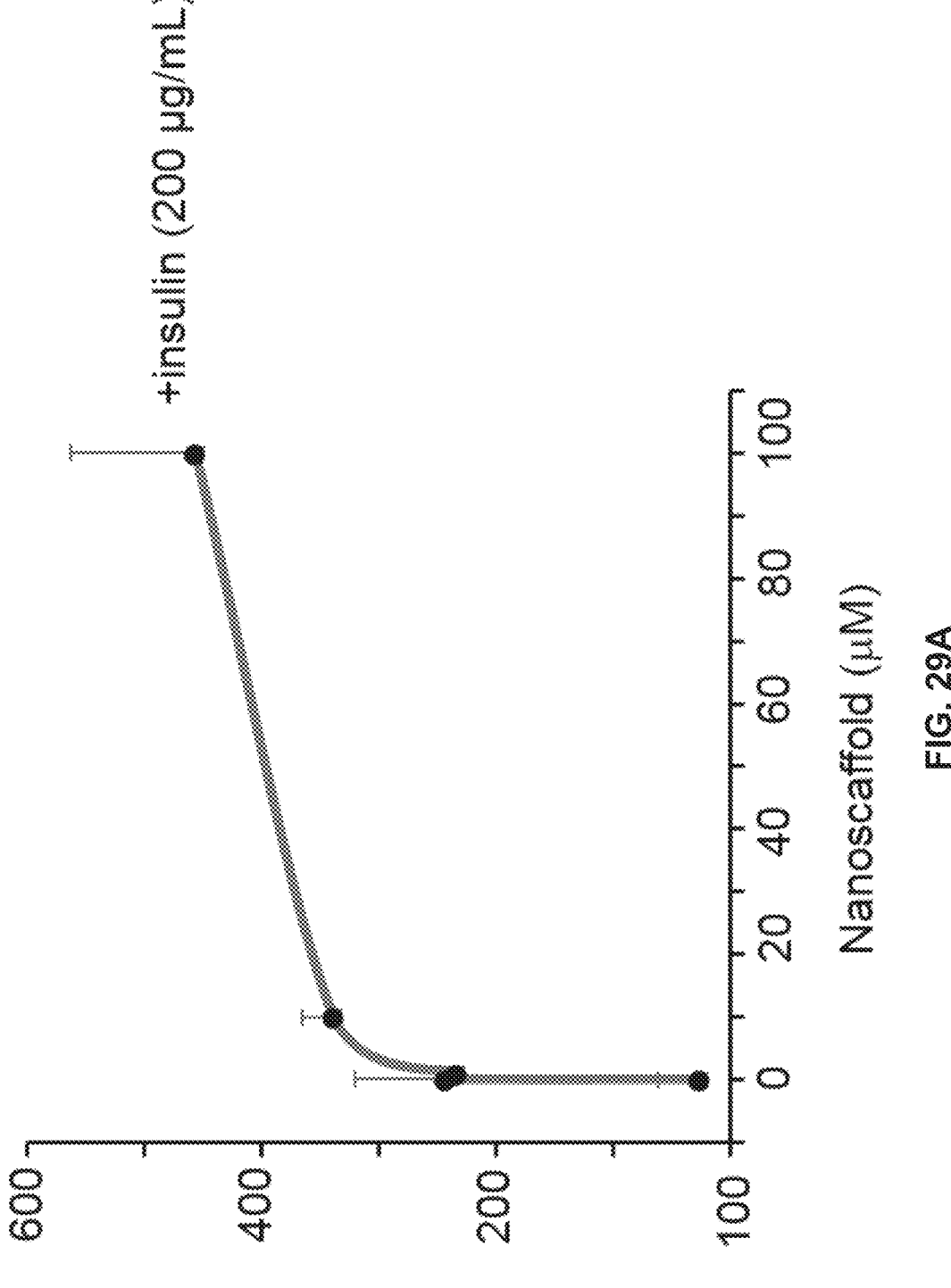
FIG. 29A shows nanoscaffold improves 5-fold efficacy and stability of insulin. Non-differentiated, 90% confluent 3T3-L1 cells were starved with glucose-deprived medium for 40 min. Then cells were treated in the presence and absence of different concentrations of nanoscaffold #2 and bovine insulin (200 μg/mL), all of reagents dissolved in the same glucose-deprived medium but containing fluorescent-D (FD)-glucose for 80 min. Thereafter, the FD glucose uptake was measured according to manufacturer's instructions (Cayman Chemical, USA, cat #600471).
Figure 29B:
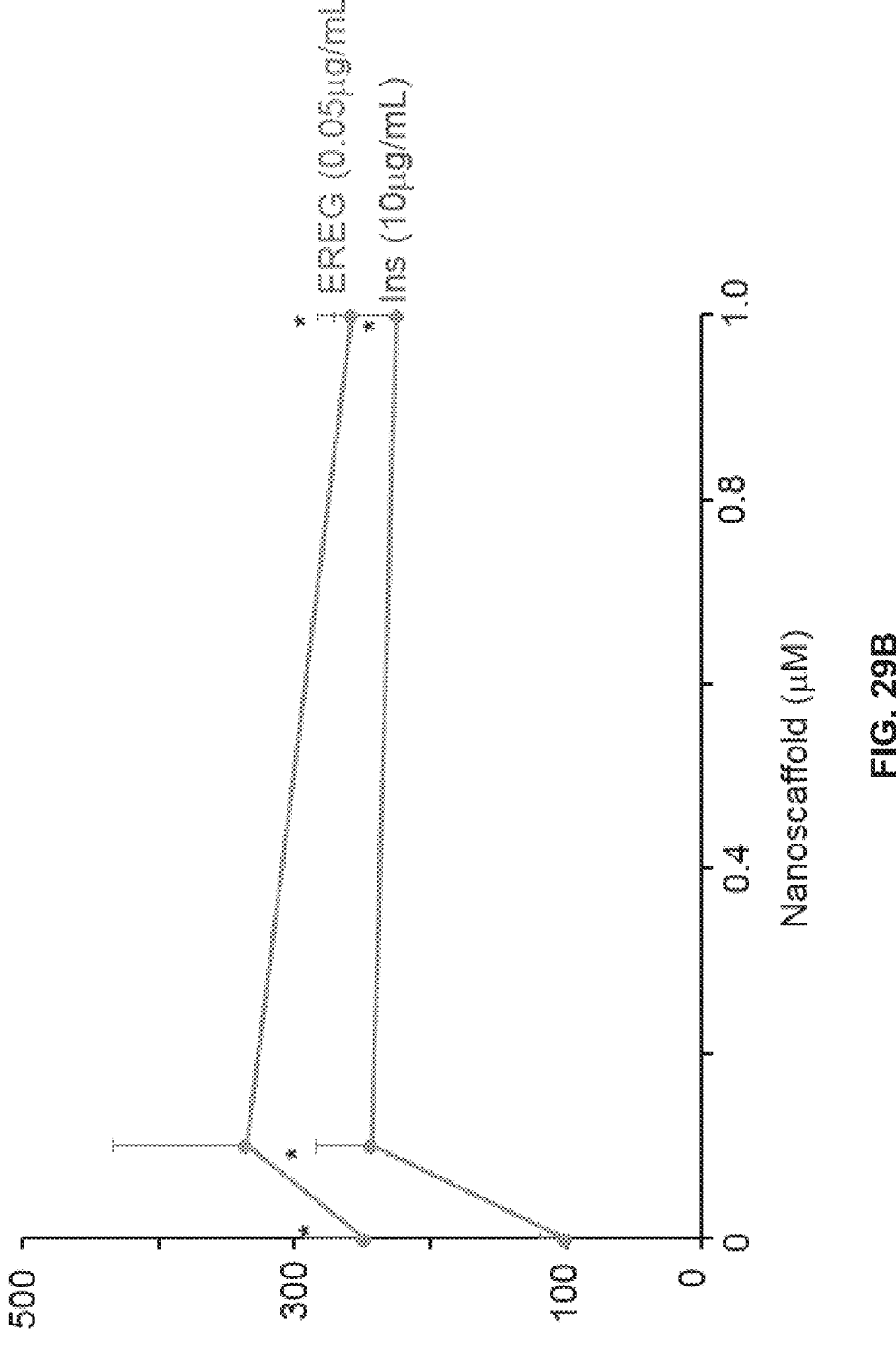
FIG. 29B shows Long-term effect of scaffold on efficacy and stability of insulin and EREG. Non-differentiated, 90% confluent 3T3-L1 cells treated in the presence and absence of different concentrations of nanoscaffold #2 and bovine insulin (10 μg/mL) or mouse epiregulin (EREG, 0.05 μg/mL) and incubated for 24 h. Then cells were starved with glucose-deprived medium for 40 min and, then incubated with fluorescent-D (FD)-glucose for 80 min. Thereafter, the FD glucose uptake was measured according to manufacturer's instructions (Cayman Chemical, USA, cat #600471). Data are shown as percent of uptake in the presence of insulin (100%). Asterisk shows the statistical difference compared to insulin (100%, n=4 per condition, mean±SD, P<0.05, Student's t-test)
Figures 30A, 30B:
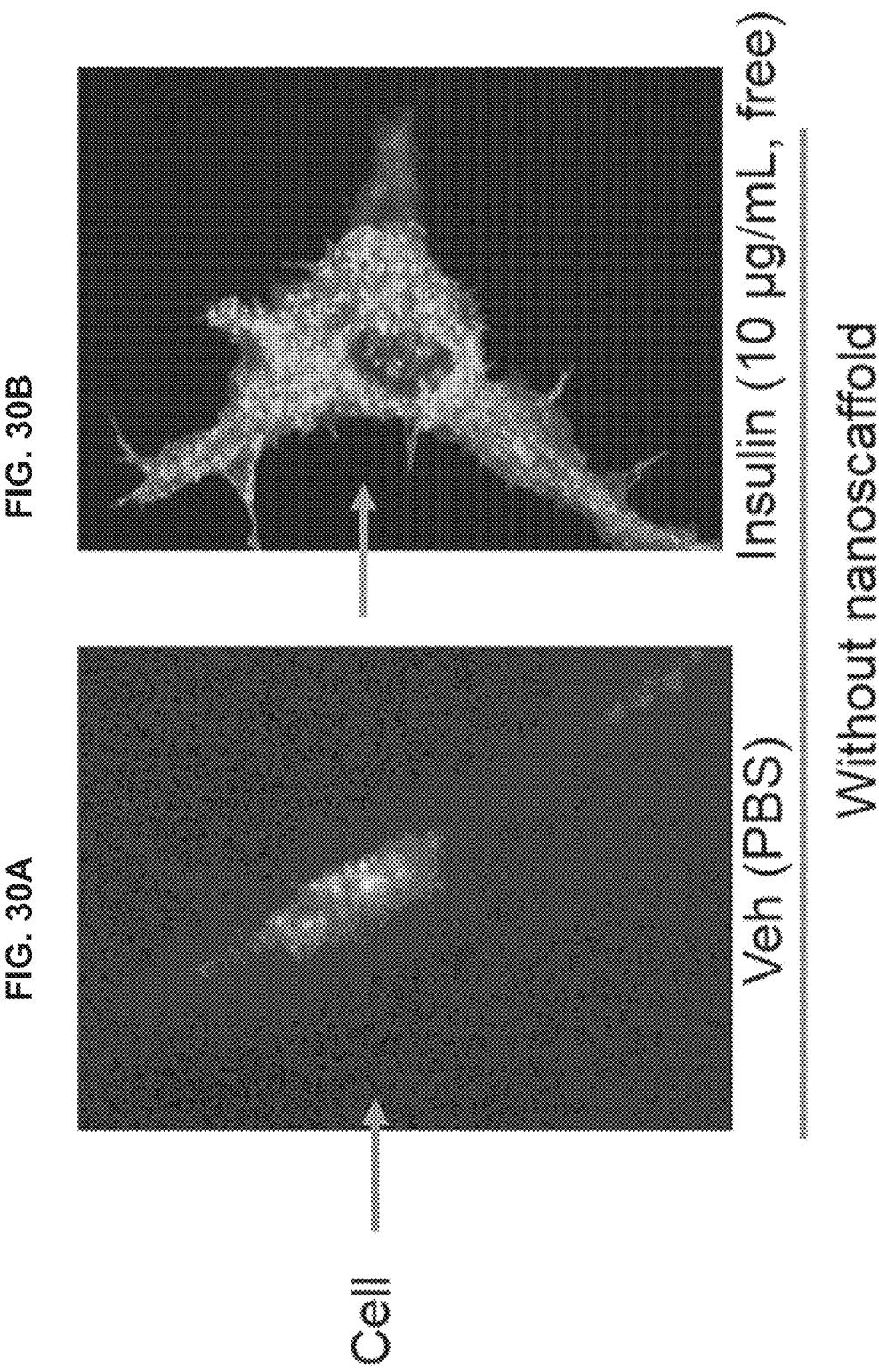
FIGS. 30A to 30D show translocation of GLUT4 (the major glucose transporter of adipocytes). Non-differentiated NIH-3T3 cells were transiently transfected with GLUT4-GFP plasmid (Addgene #52872) on Petri-35 dishes with coverslip (MatTek, cat #P35G-1.5-14-C, USA). Translocation of GLUT4 in the transfected NIH-3T3 cells was demonstrated using confocal microscopy (Olympus FV10i).
Figures 30C, 30D:
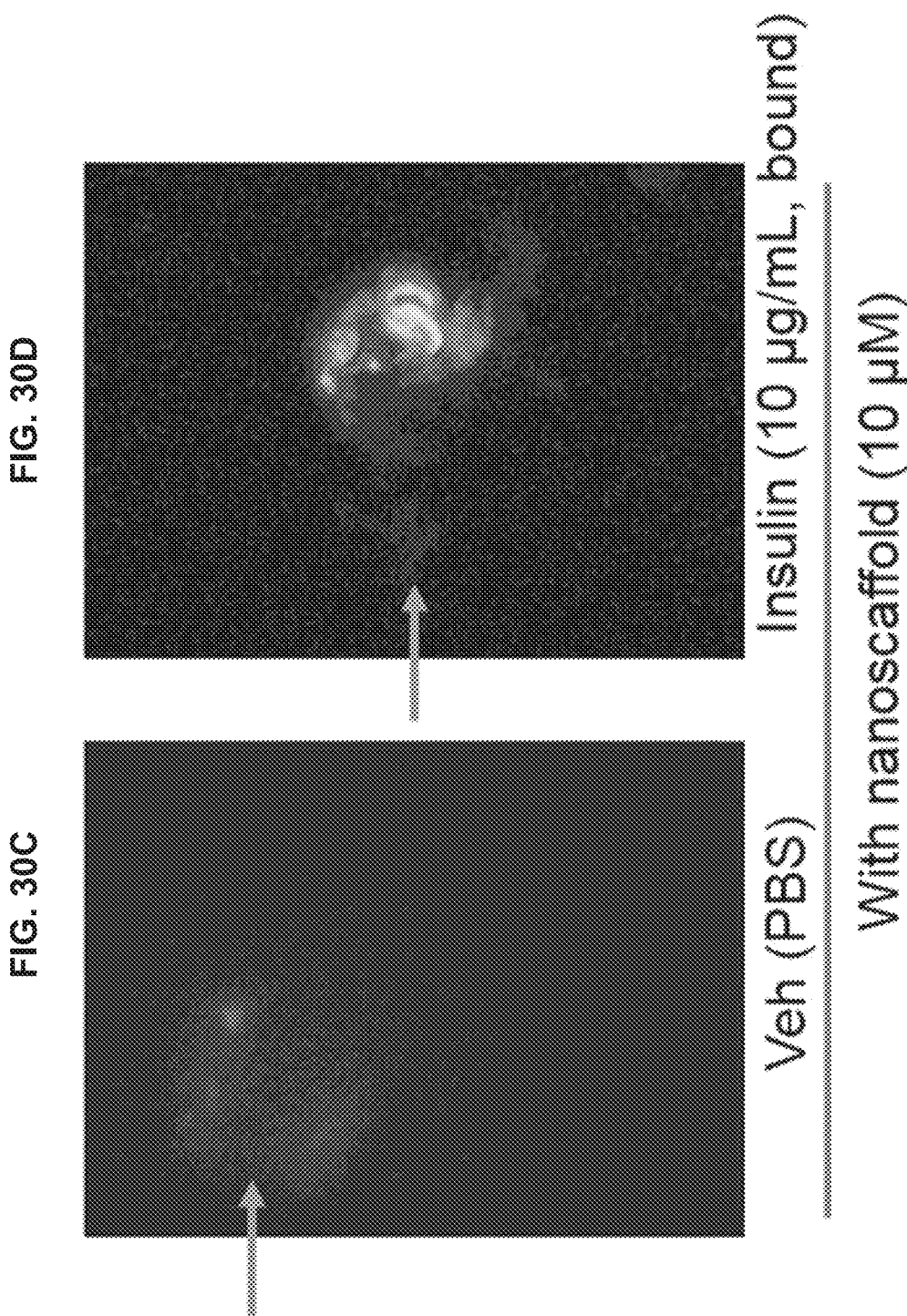

Epiregulin was immobilized onto the nanostructures by the following protocol. Fmoc-<u>KFKK</u>(Bz) (SEQ ID NO:1 for underlined portion) was incubated at 2.5 mM in PBS (pH=7.4) for 3 days prior to ultracentrifugation (80,000 RPM, 1 h, 4° C.) to separate the nanostructures from the monomeric peptide in solution. The pellet was resuspended in PBS with 0.4 µg (4 µl of 400 ng/ml) epiregulin (EREG), and the solution was incubated for one day at 4° C. to allow immobilization of the EREG by the nanostructures. The mixture was then used to investigate the differentiation of adipocyte cells (FIG. 21).

Example 4: Self-Assembly of a Reduction-Sensitive Tetrapeptide Camptothecin Conjugates into Nanotubes The ultimate objective of targeted drug delivery system is to shuttle therapeutic payloads into specific destination without any pre-release, requiring the delivery system remaining robust and stable before reaching the disease site and releasing the therapeutic agents. It then raises the requirements for the delivery system to be highly selective and respond to different cellular signals and environments. Over the past few decades, targeted drug delivery systems that respond to stimulus such as pH, temperature, ionic strength, and light, have been widely proposed and investigated for cancer therapy. The drug release kinetics could be controlled by adjusting relative parameters. However, most of the circumstantial differences between the tumor sites and the normal tissue were tiny and hard to differentiate by chemical techniques.

In recent years, increasing efforts have been devoted to the development of intracellular stimuli-responsive nanocarriers that are generally stable under extracellular conditions (e.g., in blood circulation) but rapidly release the loaded payloads after entering into tumor cells, which could result in markedly enhanced therapeutic efficacy and reduced side effects and toxicity. In particular, researchers have paid much attention to the disulfide bond as a linkage of the prodrug system because it can be cleaved in the presence of reducing agents. In the targeted tumor cells, the disulfide bonds are cleaved as the result of reaction with endogenous thiols such as glutathione (GSH) and thioredoxin (Trx) which are overexpressed in cancer cells. Glutathione is the most abundant biological reducing agent in body. It has been demonstrated that the body fluids (e.g., blood) and normal extracellular matrices possess a low GSH concentration (2-20 μM), while the cytosol and the nucleus have a high redox potential with GSH concentrations ranging from 2 to 10 mM. The presence of a high redox potential difference between the oxidizing extracellular space and the reducing intracellular space makes the disulfide bond intriguing as a potential delivery tool. Therefore, it is a very promising strategy to construct disulfide containing drug delivery systems for reduction-triggered active drug release within tumor cells. Additionally, crosslinked disulfide bonds could provide extra stability for self-assembled system, enabling the nanostructure to remain stable even under low concentration or harsh condition. This example tests self-assembly of a Camptothecin (CPT) tetrapeptide into well-defined nanotubes. These tetrapeptides can be crosslinked into disulfide bonds upon oxidation, which then gain the ability of reduction-triggered drug release.

Figure 31:
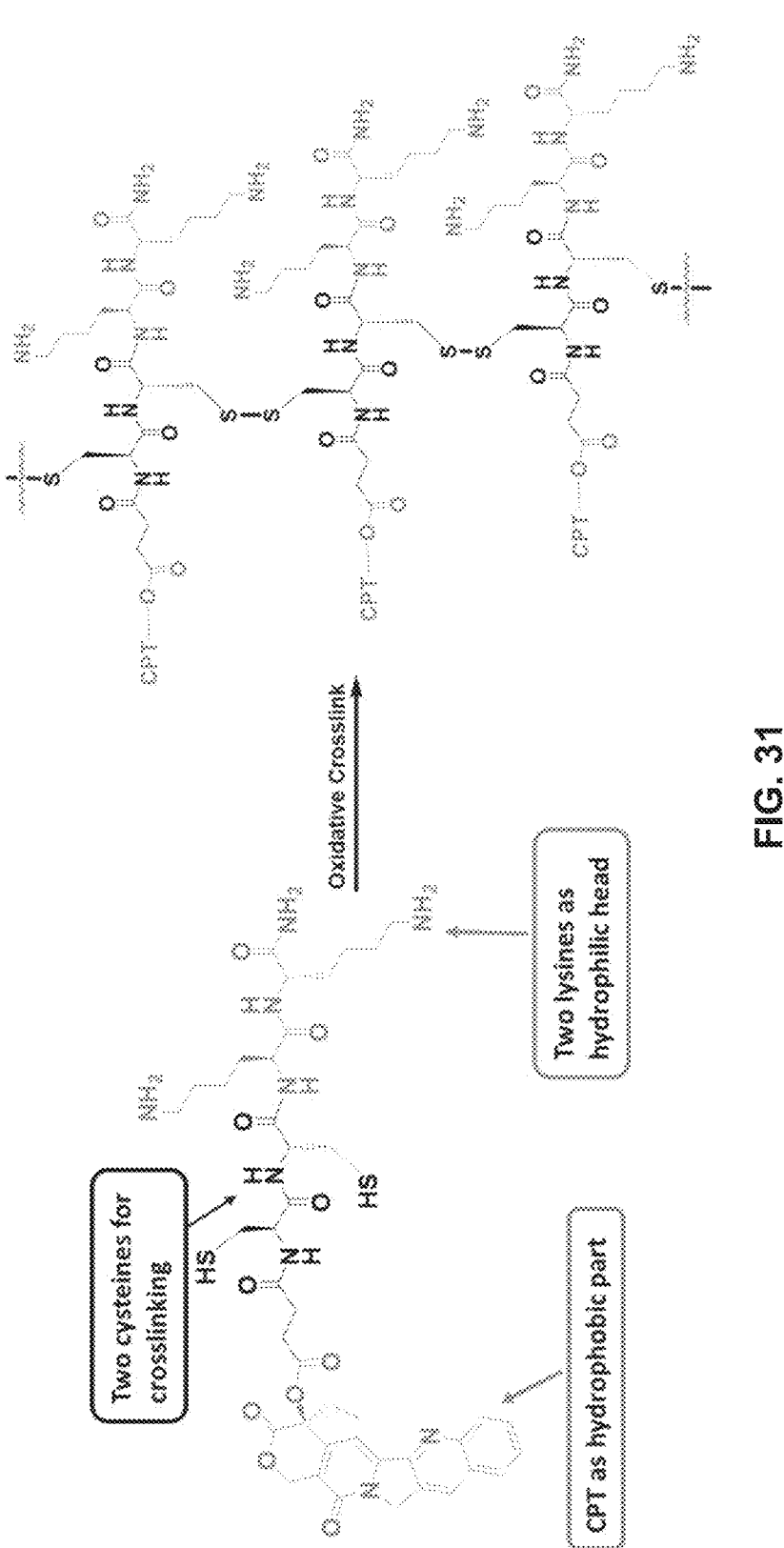
FIG. 31 shows a structural design of compound VI and crosslinking via disulfide bond formation between cysteines.

The design of the CPT-tetrapeptide A ("compound VI") (FIG. 31) was based on the theory of self-assembly of small molecules. Generally, the balance of molecular force within the assembly monomer molecules is required. CPT was conjugated onto the α-amino group of tetrapeptide chain via a succinic acid linkage which is designed to be cleaved and release the active CPT. While CPT can act as hydrophobic part of the entire molecule, two hydrophilic amino acids lysines were adopted in the peptide sequence as the hydrophilic part on the C terminus. In order to enable the nanostructure with reduction stimulus ability, two cysteines were also incorporated into the peptide structures to support the ability of crosslinking by forming disulfide bonds between peptide molecules. Cysteines motif here were also regarded as a flexible linkage between rigid CPT structure and dilysine amino acids, enabling the entire molecule to be able to adopt flexible molecular conformation for self-assembly. Since only amino acids lysine and cysteine were used to construct the delivery vehicle, it can be generally recognized as safe (GRAS). The synthesis of compound VI was based on Fmoc-protected solid phase peptide synthesis on resin. CPT was first converted into CPT-succinic acid via the reaction between CPT and succinic anhydride as reported before. The resulted carboxylic acid functional group can be conjugated with N-terminus of the cysteine. Fmoc-protected lysine and cysteine with either Boc or Trt protected side chain were used on the solid phase peptide synthesis. All four protecting groups can be removed in the final stage of cleavage from the solid resin by high concentration of TFA. The obtained nanotube ("CPT-CCKK") has a drug loading percentage of 38.1%, which was much higher than most of the polymer based CPT conjugates.

Figures 32A, 32B:
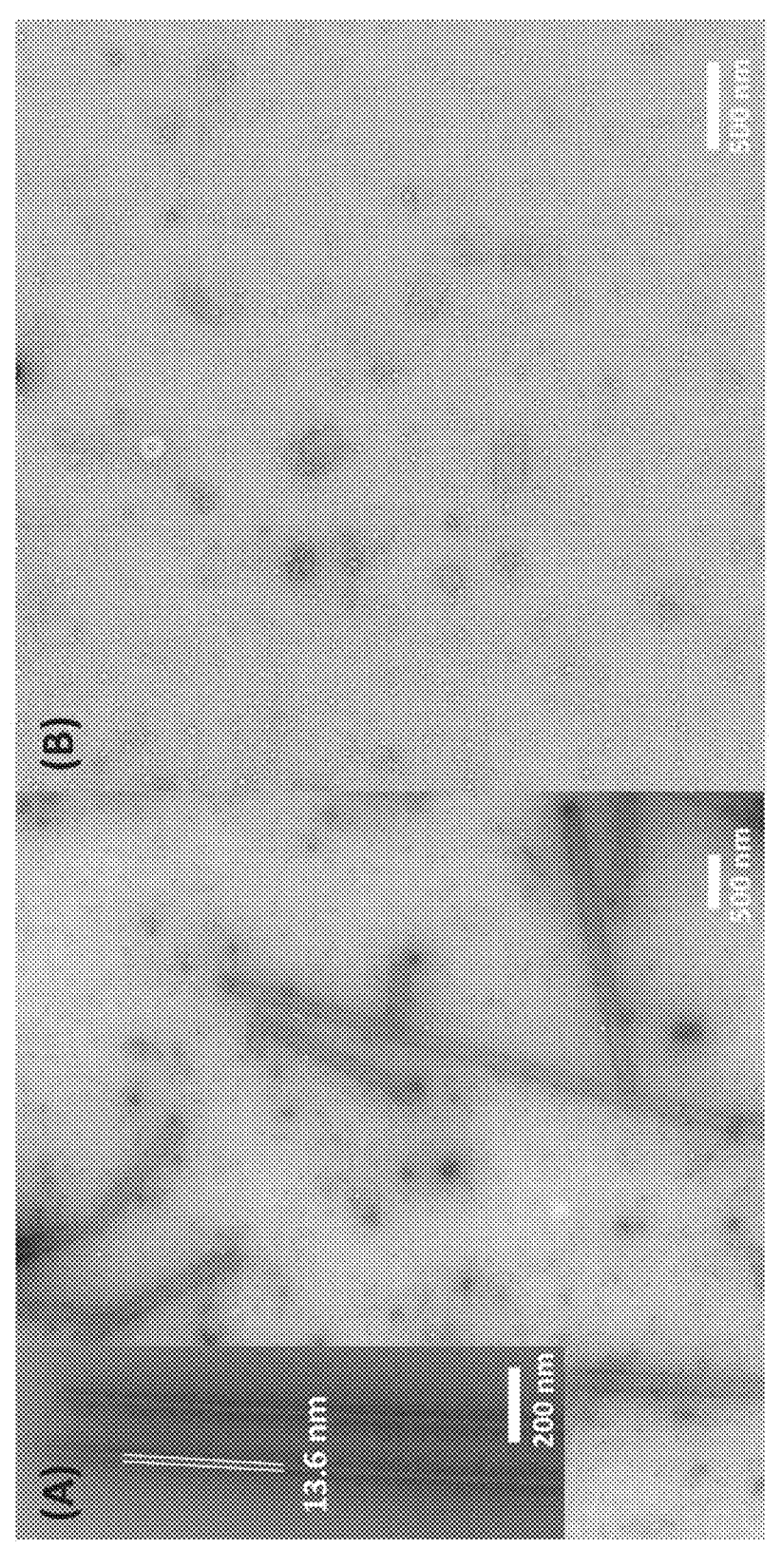
FIG. 32A shows self-assembly of compound VI into mature nanotubes in PBS (pH=7.4).
FIG. 32B shows self-assembly of compound VI in pure water (pH=7.0) to form short and less organized nanostructure.
Figures 34A, 34B:
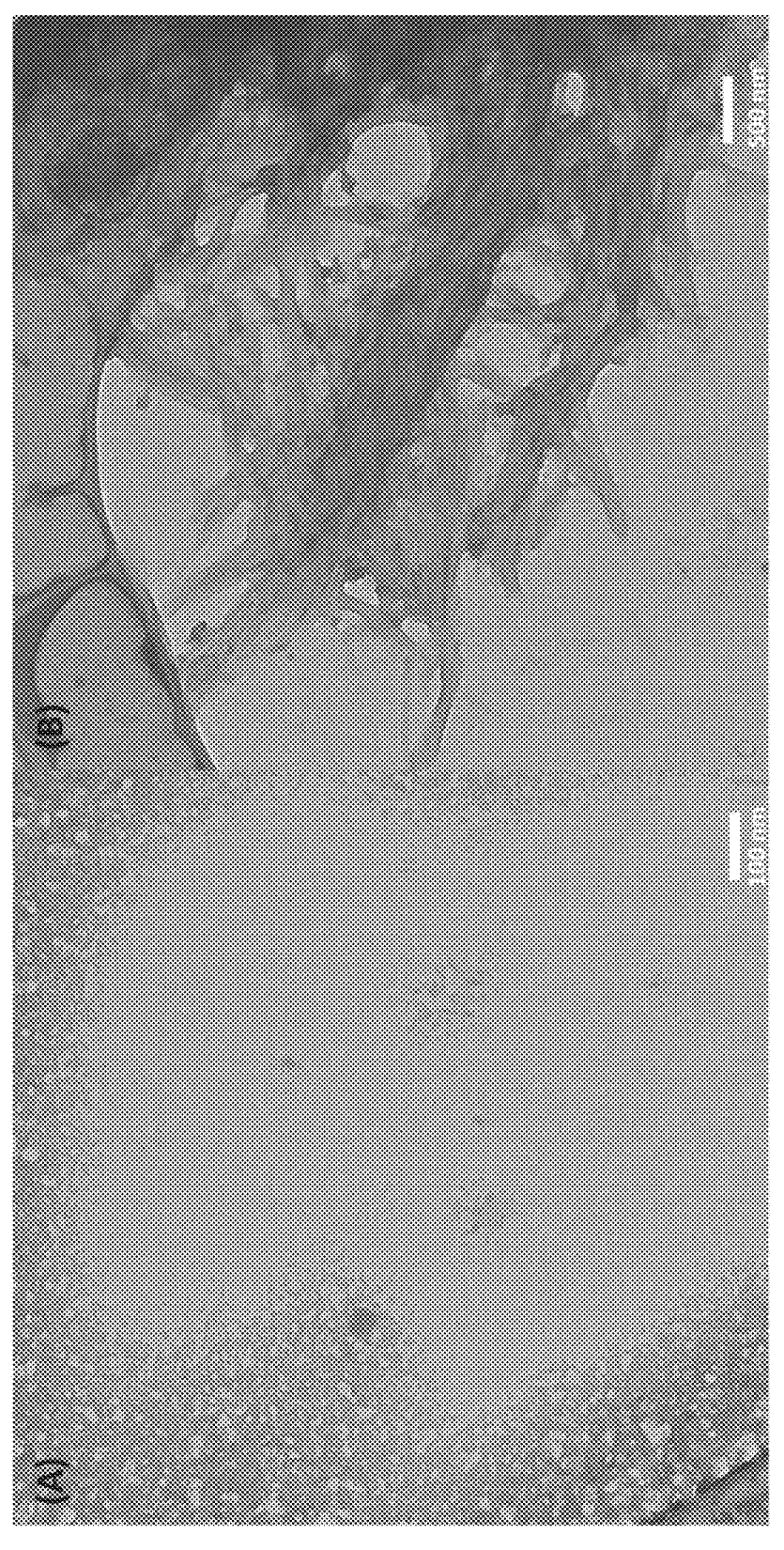
FIG. 34A shows a TEM of compound VI in trifluoroethanol (TFE) without crosslinking.
FIG. 34B shows a TEM of nanotubes after oxidative crosslinking in TFE.

The self-assembly morphology of compound VI was exploited by transmission electron microscopy (TEM) in PBS buffer (pH=7.4) and pure water (pH=7.0). Compound VI was aged under 10 mM for 72 hours before diluted to 1 mM for morphology checking. From the TEM picture, it can be observed that A was able to self-assemble into nanotubes in both ionic buffer PBS and pure water with different dimension size. The self-assembly of compound VI in PBS yielded uniform and long nanotubes with diameter around 190 nm with length up to several micrometers (FIG. 32). As comparison, the assembly structure in water were less mature and only short and narrow nanotubes with can be seen. The diameter is reduced to around 135 nm and the length is usually shorter than 1 micrometer (FIG. 32). Aging under high concentration is a key factor for the successful self-assembly process. Less concentrated sample would move the equilibrium towards the monomer side instead of assembly side. Samples that are aged under 0.2 mM will not be able to form organized nanostructures with only random aggregates which indicated that the self-assembly process of peptides is an equilibrium between monomer and nanostructure. Trifluoroethanol (TFE) was also used to evaluate the self-assembly process of compound VI. As is known, hydrogen bonding is crucial for self-assembly of peptides and peptide conjugates, especially at the initial stage to form the β-sheet structures of peptides. TFE is a strong polar solvent and can disrupt the hydrogen bond formation between assembly molecules, thus destroying the self-assembled nanostructure. TEM pictures of the TFE solution of compound VI confirmed the result as no self-assembly structures can be observed even under high concentration of 10 mM (FIG. 34).

From the TEM pictures of some less-mature solution samples (aged for only 24 hours), the intermediate of self-assembly can be witnessed as the coiled ribbons. The thickness of the nanotube walls (~13.6 nm), as measured by TEM imaging, suggested multiple bilayer structures comprised of around 8 molecules of A in an extended conformation (1.7 nm). The UV-Vis spectra of A revealed bands at 350 and 368 nm in PBS that were decreased in amplitude and slightly red-shifted compared with solutions measured in TFE, indicative of J-type aggregation of the CPT chromophores in PBS.

The crosslinking of nanotubes formed by compound VI was then studied to enable extra stability for the self-assembled nanostructures. Two adjacent cysteines within the molecular structure ensured the possibility of forming crosslinked disulfide bonds. Numerous methods have been reported to oxidize adjacent thiol groups into disulfide bonds, while each of them has certain merits and is suitable under specific conditions. Atmospheric oxygen is commonly used to oxidize thiols into disulfide bonds. The reaction condition usually requires high diluted condition under slightly alkaline conditions. This widely used approach may be subject to some of the following limitations as dimerization, inadequate solubility for basic or hydrophobic peptides, very long times (up to 5 days), difficulty in controlling oxidations and so on. In contrast to air oxidation, oxidation of thiols to disulfides promoted by dimethyl sulfoxide (DMSO) can also be carried out under a mild condition and suitable in a wider range of pH environment (3-8). A higher DMSO concentration leads to faster reaction, but also to reduced selectivity. Problems in removing DMSO from the final products have been observed in some cases. For self-assembly system, the influence of DMSO on the nano-structures should also be taken into consideration.

Figure 35A:
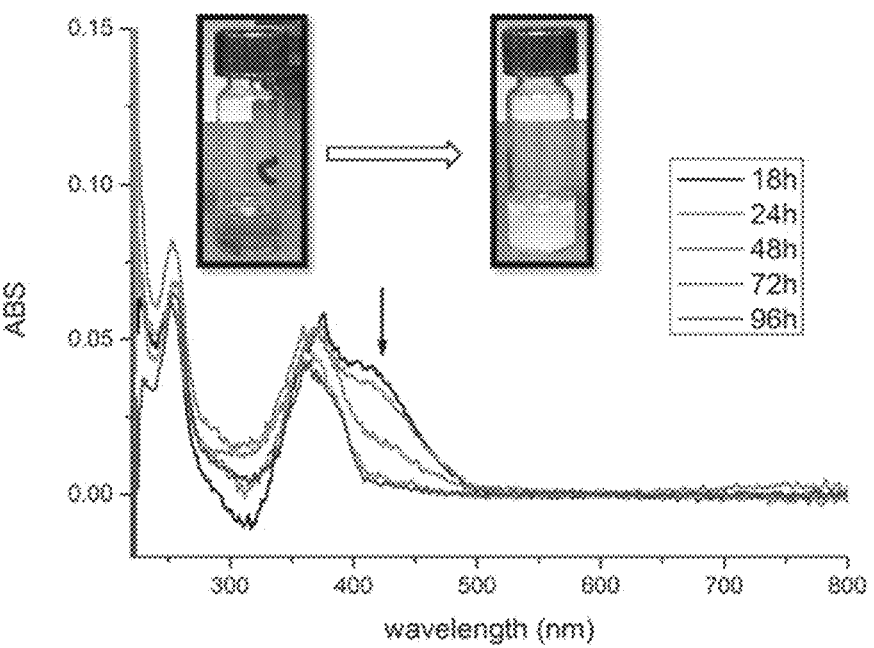
FIG. 35A shows a UV spectrum nanotube solution reacting with DTNB. The decrease of absorption at 415 nm indicated the completion of oxidative crosslinking.
Figure 35B:
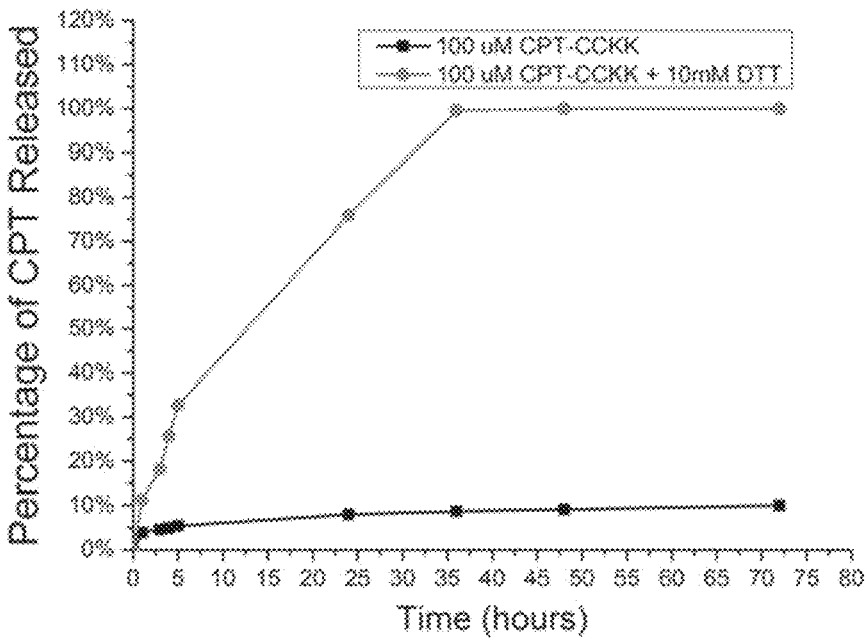
FIG. 35B shows release of active CPT from crosslinked nanotube with or without reducing agent DTT.

Here we adopted the DMSO oxidation to form disulfide bonds between peptide monomers. 10% DMSO was adopted to add into the maturely formed nanotube solution with stirring for one day. The free thiol group in the solution was monitored by Ellman's reagent, 5,5'-dithiobis-(2-nitroben-zoic acid) or DTNB. DTNB reacts with free thiols, cleaving the disulfide bond to give 2-nitro-5-thiobenzoate (TNB2-), which ionizes to the TNB2-dianion in water at neutral and alkaline pH. The TNB2- is quantified in a spectrophotometer by measuring the absorbance of visible light at 412 nm according to previous reports. Therefore, the completion of disulfide forming can be monitored by UV-Vis spectrum. Results from oxidation of CPT-CCKK nanotube with DMSO showed the disappearance of peak at 415 nm over 3 days, indicating that no existing of free thiol groups after 3 days of oxidation with DMSO (FIG. 35). One of the advan-tage of the designed peptide here is the improved stability upon the formation of disulfide bonds between cysteine amino acids. It is proposed that the covalent linkage between peptide monomers can effectively protect the mature nano-tubes from dissociating into monomers when the solvent changes or the concentration decreases. To assess the sta-bility of the crosslinked structure, the oxidized CPT-CCKK nanotubes were isolated by ultracentrifugation under 80K rpm. The obtained pellets were then dissolved in TFE and sonicated for 30 seconds to yield a homogeneous solution. While dilution of non-crosslinked nanotubes into TFE and aging sample of free CPT-CCKK in TFE resulted in no observation of nanotubes, crosslinked nanotubes were very robust and can still maintain the nano morphology even after staying in TFE for 72 hours (FIG. 34). Therefore, a conclu-sion can be made that such a crosslinking via thiols can largely improve the stability of self-assembled nanostruc-tures, which can not only find applications in targeted drug delivery but also in some other field such as heat-treatment protection or robust materials production.

The self-assembly of CPT-CCKK into nanotubes seques-ters the hydrophobic CPT structure within the hydrophobic regions, protecting the 20-O-succinyl linkage from the hydrolytic aqueous environment. Nanotube formation could effectively slow down the release of active CPT. Since self-assembly process described here is a dynamic process, diluting the solution will accelerate the dissociation of nanotubes into monomer form, which then can be cleaved and release CPT. Here the influence of reduction reagent DTT on the release of CPT from oxidized CPT-CCKK nanotubes was studied in PBS. Very interesting, even if diluted to low concentration as 0.1 mM, crosslinked CPT-CCKK nanotube was still able to protect the CPT from being released. Only less than 10% CPT was released from nano-tube after 3 days, presumably from those crosslinked oli-gomers of CPT-CCKK. The result here confirmed the hypothesis that CPT will only be released from monomer CPT-CCKK but not CPT-CCKK nanotubes. Once the nano-tube is stabilized and crosslinked by disulfide bonds, much less CPT-CCKK monomer will be found in the solution and the release of CPT was dramatically slowed down. However, once the reductive agent such as DTT was added into the solution of crosslinked CPT-CCKK nanotube, the release of CPT was accelerated to a great extent. Almost 100% CPT was fully released after 36 hours (FIG. 35). The drastic difference between release manner of oxidized CPT-CCKK and non-oxidized CPT-CCKK demonstrated the ability of the nanostructures here to be responsive to the reduction environment, and can be further utilized as a targeted drug delivery system.

Figure 36A:
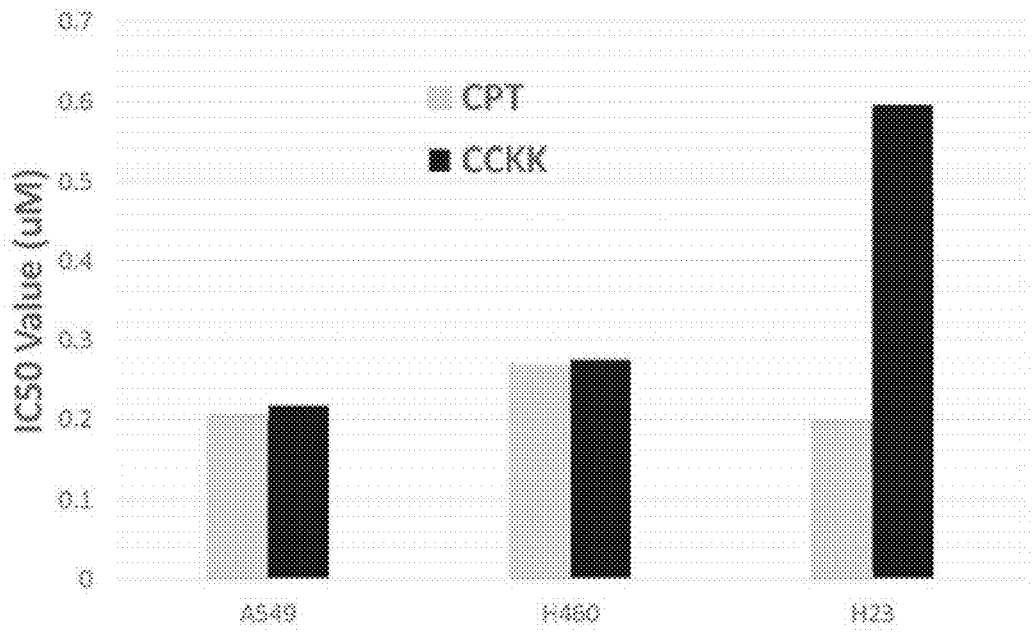
FIG. 36A shows cytotoxicity of non-crosslinked nanotube A and CPT against human non-small cell lung cancer (NSCLC) cell lines A549, NCI-460, and NCI-H23.
Figure 36B:
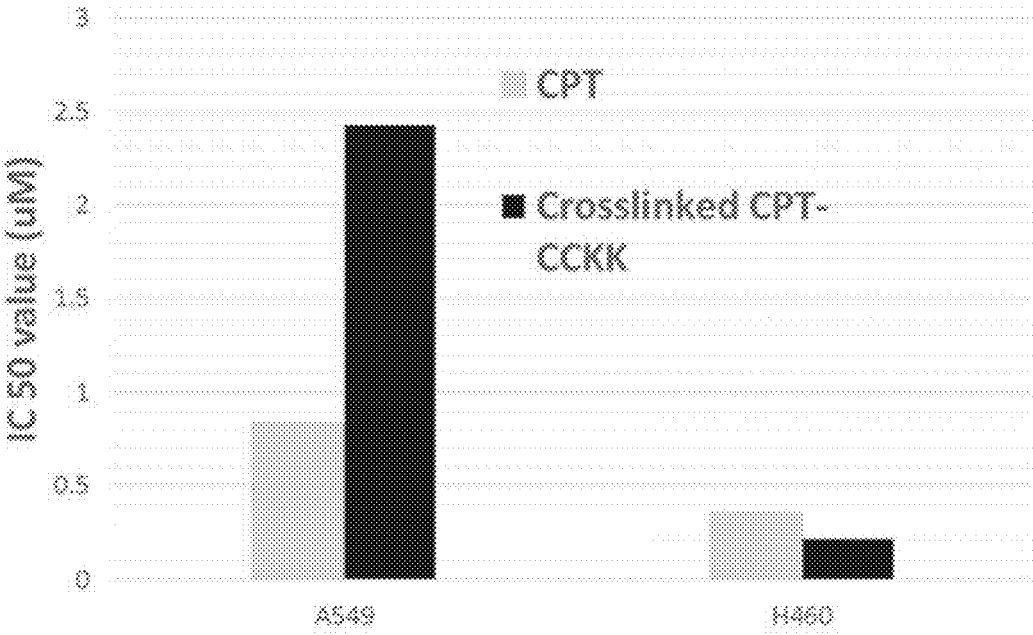
FIG. 36B shows cytotoxicity of crosslinked nanotube and CPT against A549, NCI-460 cancer cell lines.
Figures 37A, 37B:
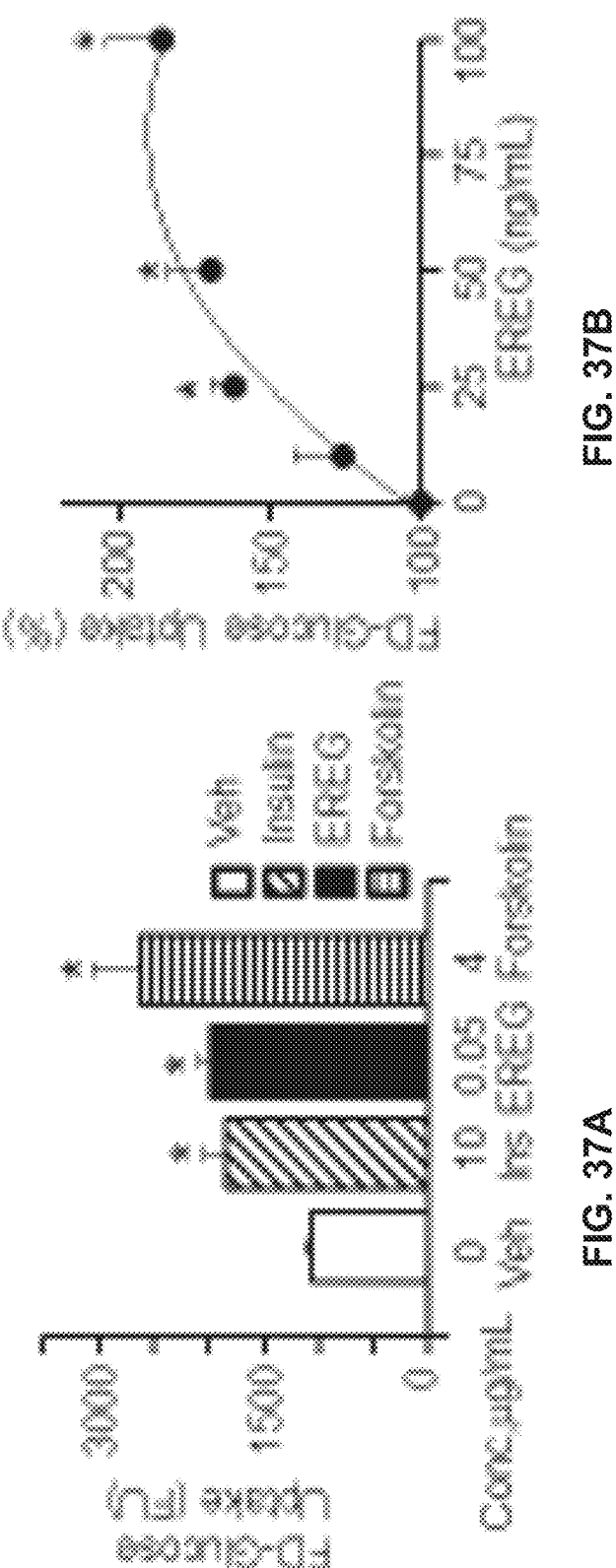
FIGS. 37A and 37B show fluorescently-labelled (FD) glucose uptake measured in mouse 3T3-L3 preadipocytes. Preadipocytes were treated with vehicle, insulin (ins, 10 μg/ml), EREG (50 ng/ml) and forskolin (4 μg/ml) for 30 mins.
Figure 37C:
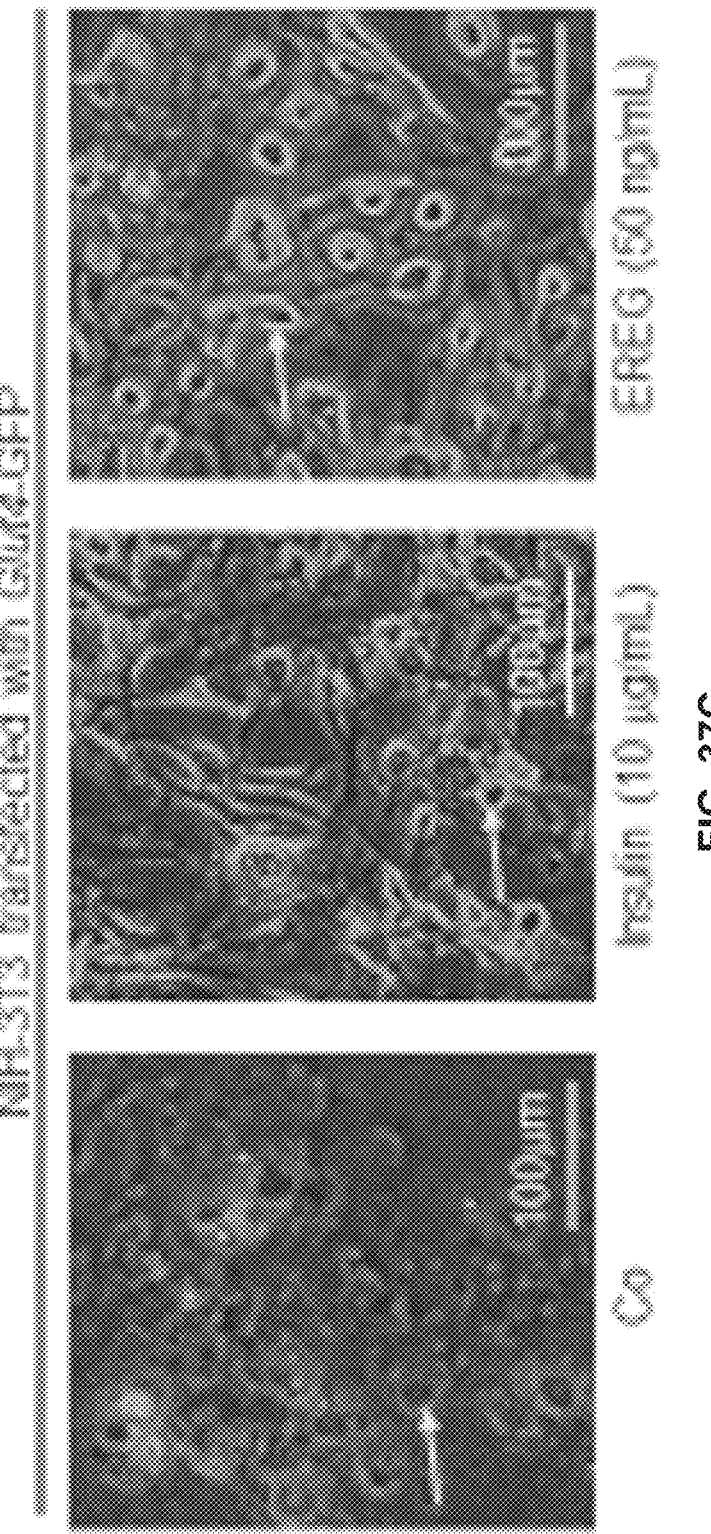
FIG. 37C shows NIH-3T3 preadipocytes transiently transfected with pB-Glut4-7myc-GFP and stimulated with vehicle, insulin (ins, 10 μg/ml), EREG (50 ng/ml) for 60 min. Data shows representative fluorescent images of GFP-labeled GLUT4 selected from three independent experiments. 10× magnification. Yellow arrow shows GFP-labeled GLUT4 that was translocated to the cellular membrane.
Figures 37D, 37E:
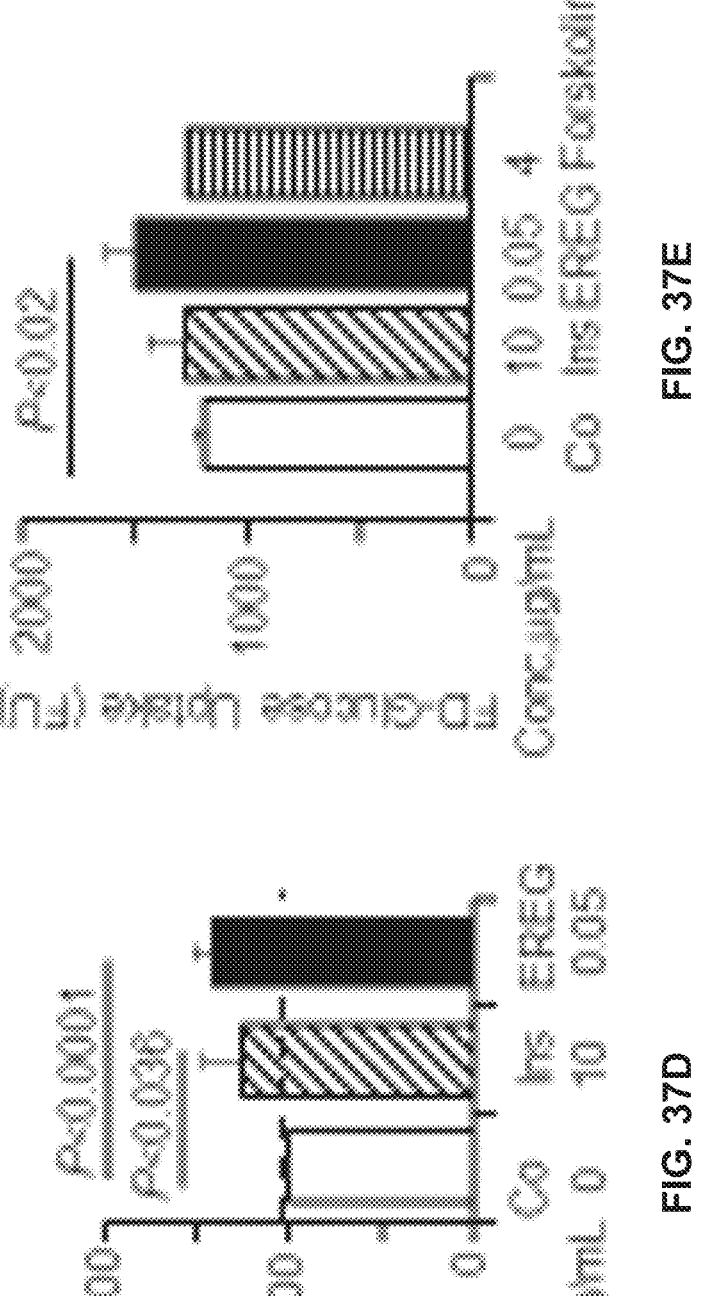
FIG. 37D shows inter-individual variability in FD-glucose uptake measured in omental iAb preadipocytes. Five batches of preadipocytes were isolated from five individual donors (BMI 19.4-48). Preadipocytes from each donor were treated with insulin (10 μg/ml) or EREG (50 ng/ml). One-way ANOVA was used for group comparison.
FIG. 37E shows FD-glucose uptake measured (n=3 independent experiments, mean±SD) in omental iAb preadipocytes isolated from a lean subject. Preadipocytes were stimulated with insulin (10 µg/ml), EREG (50 ng/ml), and forskolin (4 µg/ml). One-way ANOVA.
Figure 37F:
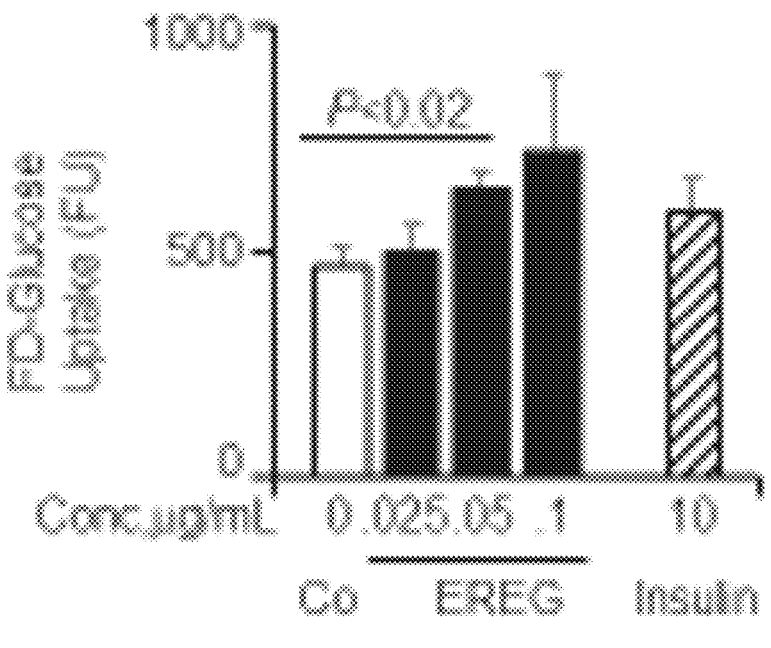
FIG. 37F shows FD-glucose was measured (n=6 independent experiments) in omental iAb preadipocytes isolated from an obese insulin-resistant subject stimulated by different doses of EREG or insulin (10 µg/ml). One-way ANOVA.
Figure 38:
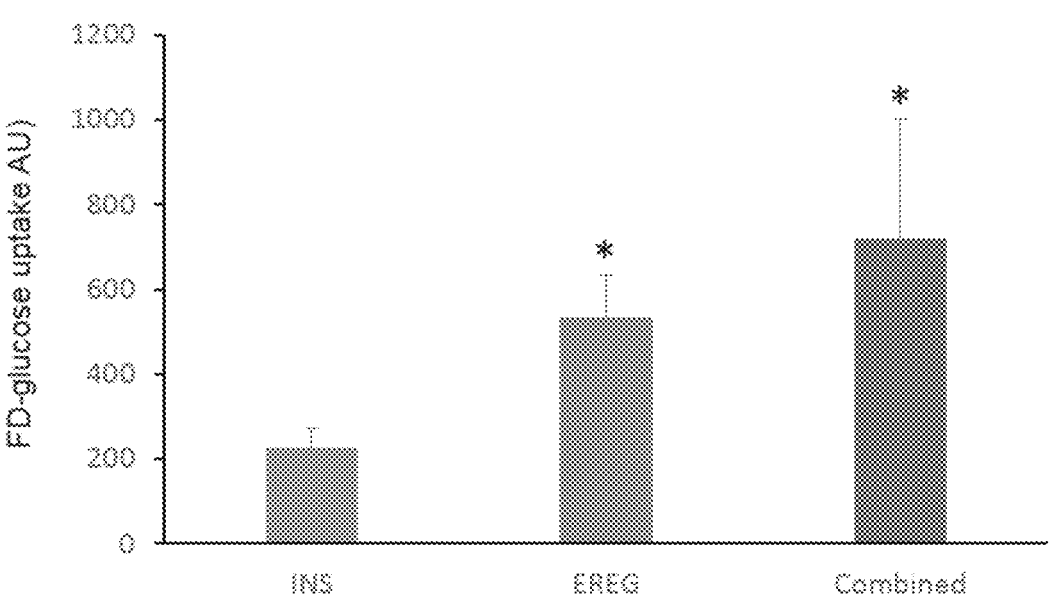
FIG. 38 shows additive effect of insulin and EREG on glucose uptake. Non-differentiated, 90% confluent 3T3-L1 cells treated in the presence of bovine insulin (10 µg/mL), mouse epiregulin (EREG, 0.05 µg/mL), or their combinations and incubated for 24 h. Then cells were starved with glucose-deprived medium for 40 min and, then incubated with fluorescent-D (FD)-glucose for 80 min. Thereafter, the FD glucose uptake was measured according to manufacturer's instructions (Cayman Chemical, USA, cat #600471). Asterisk shows the statistical difference compared to cells stimulated with insulin (P<0.05, n=4 per condition, mean±SD, Student's t-test).
Figure 39:
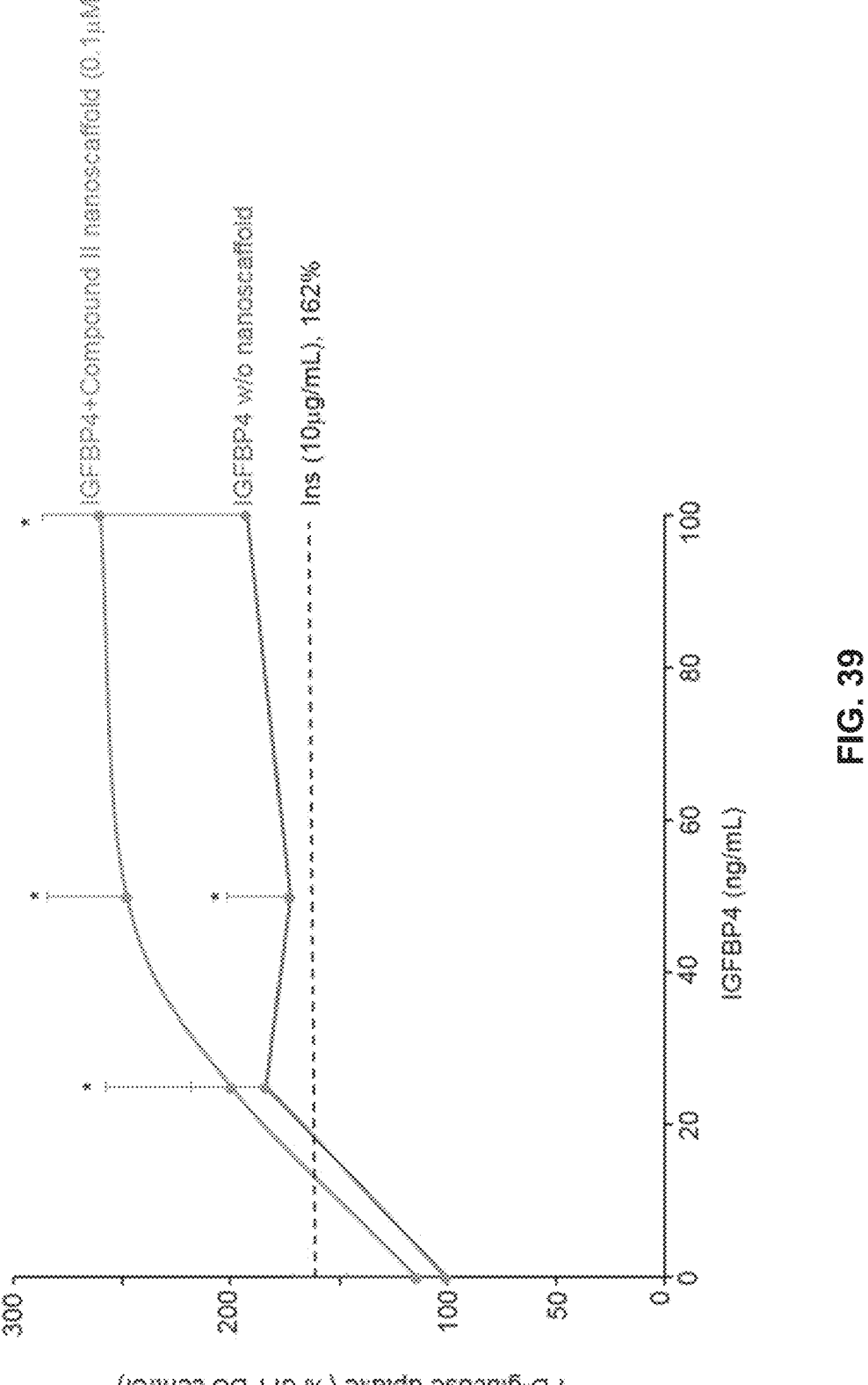
FIG. 39 shows IGFBP4 improves glucose uptake at 100 lower concentration than insulin and its efficacy is improved by nanoscaffold compound 2. Non-differentiated, 90% confluent 3T3-L1 cells were starved with glucose-deprived medium for 50 min. Then cells were treated in the presence and absence of different concentrations of mouse recombinant IGFBP4 with and without nanoscaffold #2 and human insulin (10 µg/mL). All of reagents were dissolved in the same glucose-deprived medium but containing fluorescent-D (FD)-glucose for 90 min. Thereafter, the FD glucose uptake was measured according to manufacturer's instructions (Cayman Chemical, USA, cat #600471). Asterisk shows the statistical difference compared to cells stimulated with PBS control (P<0.05, n=4 per condition, mean±SD, Student's t-test). Dashed lines shows glucose uptake in the presence of insulin.
Figures 40A, 40B:
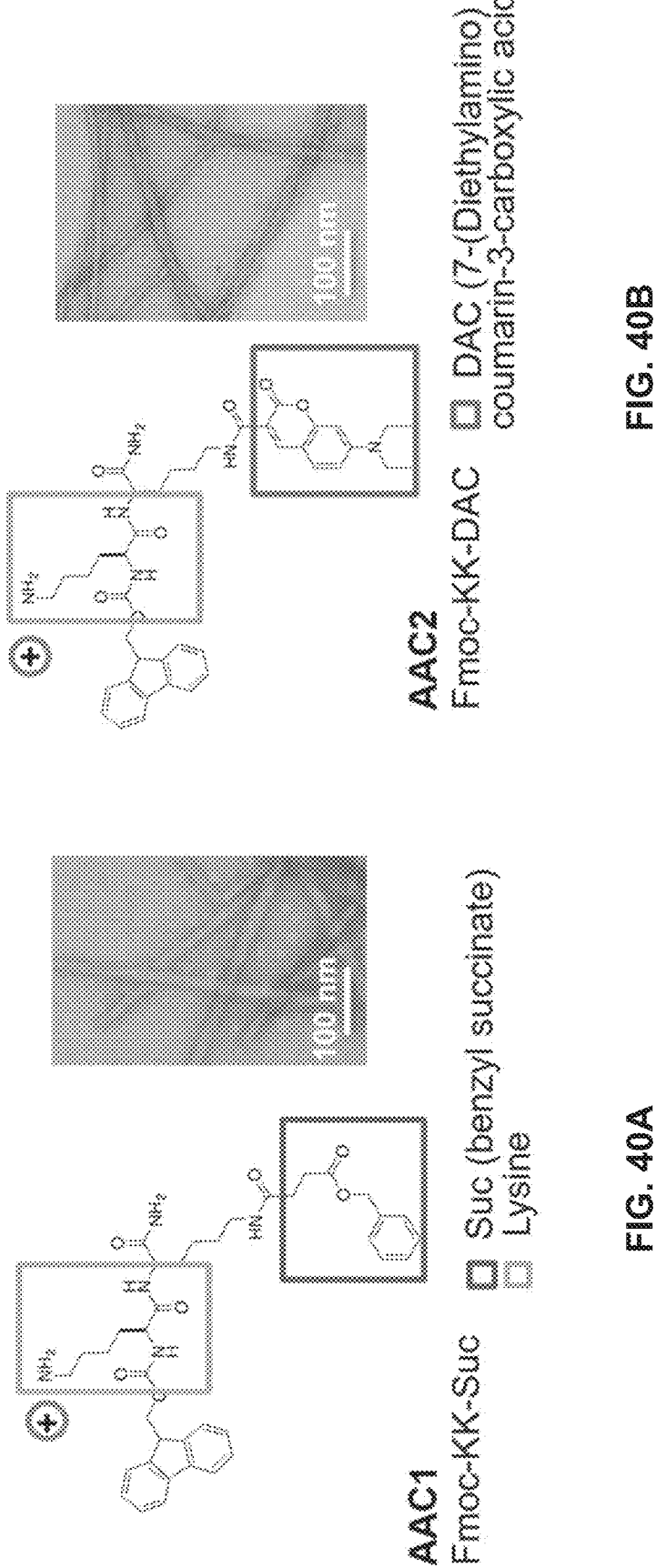
Figure 40D:
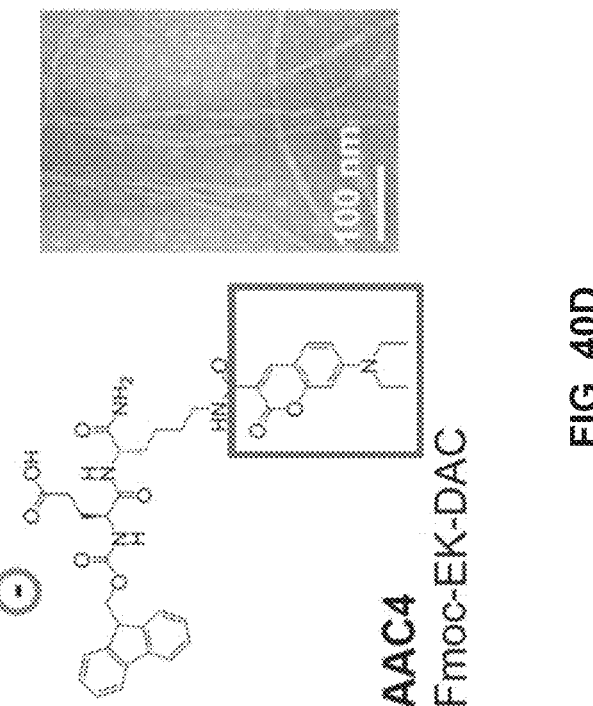
Figure 40C:
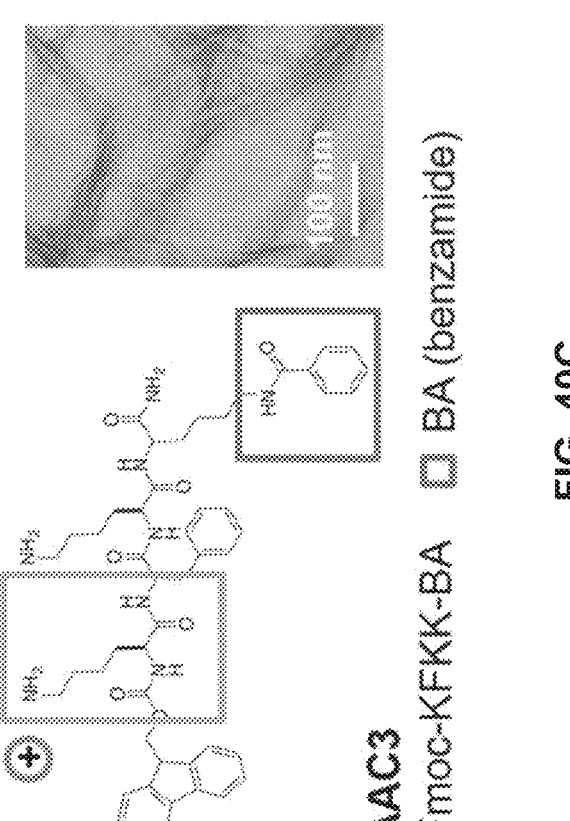

The non-oxidized CPT-CCKK nanotube was assessed for cytotoxic efficacy against human non-small cell lung cancer (NSCLC) cell lines A549, NCI-460, and NCI-H23, which were selected according to the indications of approved CPT derivative Topotecan. The cytotoxic activity was assayed using MTT-assay over the course of a 96 h incubation period and the IC50 values were 0.22 $\mu$M, 0.28 $\mu$M, 0.60 $\mu$M for CPT-CCKK, and 0.20 $\mu$M, 0.27 $\mu$M, and 0.19 $\mu$M for CPT, respectively (FIG. 36). CPT-CCKK exhibits comparable cytotoxicity with parental drug CPT on cells lines A549 and H460, and roughly 3 folds less cytotoxic on H23 cell lines. The explanation for the cytotoxicity results could be that CPT-CCKK release active CPT in a time-dependent manner, and the entire true concentration for CPT in the cell medium is less than that of free CPT. Very interestingly, the cross-linked disulfide containing nanotubes behaved differently on the cytotoxicity assay against non-small cell lung cancer (NSCLC) cell lines A549 and NCI-460. For A549 cancer cell lines, crosslinked CPT-CCKK nanotubes were less toxic with an $IC_{50}$ value of 2.43 $\mu$M while the parental drug CPT has an $IC_{50}$ value around 0.83 $\mu$M. However, results from cancer cell lines H460 demonstrated that crosslinked CPT-CCKK had stronger cell killing ability with the $IC_{50}$ value of 0.21 $\mu$M compared that of free CPT at 0.35 $\mu$M. While the cytotoxicity study of non-oxidized CPT-CCKK showed comparable efficacy on A549 and H460 cancer cells, the difference in cytotoxicity observed on crosslinked CPT-CCKK nanotubes could result from the different intracellu-lar levels of GSH. It has been reported before that the GSH level in H460 was almost twice higher than that in A549. Therefore, higher concentration of GSH in H460 accelerated the breakage of the disulfide bonds within the crosslinked CPT-CCKK nanotubes, leading to faster release of active CPT and higher in vitro cytotoxicity.

In summary, disclosed in this example is the design, synthesis, and evaluation of a Camptothecin tetrapeptide that self-assembles into well-defined nanotubes with diam-eters of 190 nm. Due to the functionality of incorporated cysteine, the self-assembled nanotubes can be oxidized to form the crosslinked disulfide bonds within the nanostruc-tures. The resulted crosslinked nanotubes exhibited a reduc-tion triggered release manner of CPT, in which oxidized nanotubes barely not release free CPT even the concentra-tion is as low as 0.1 mM for 72 hours. The addition of reductive reagent DTT, which was used to simulate the reduction environment of cancer cells, was able to strongly accelerate the release of CPT to a great extent. It was demonstrated here that incorporation of cysteine groups into the self-assembled peptide sequence can be utilized to stabilize the nanostructures, which may find numerous applications in drug delivery and material production. The yielded non-crosslinked nanotubes also displayed a compa-rable cytotoxicity with CPT on cancer cell lines A549, H460 and H23, while the crosslinked CPT nanotubes demon-strated better cytoxicity in cells with higher GSH concen-tration. These results made the disulfide crosslinked CPT nanotube a great candidate for further exploration in targeted and controlled drug delivery.

Example 2: Comparison of AAC1-7

FIGS. 40A to 40G show chemical structures and charge of AAC1-7 molecules and their electron microscopy nano-structure after self-assembly.

Figure 41A:
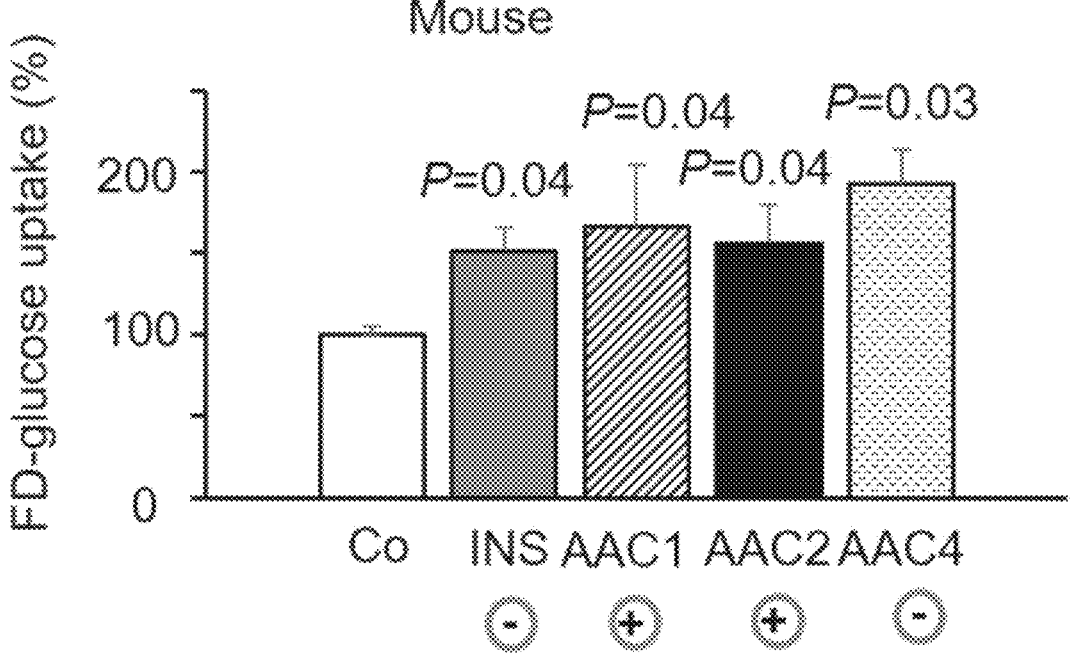
FIGS. 41A to 41C show glucose uptake efficacy of different AAC in mouse (FIG. 41A) and human (FIG. 41B, 41C) cells representing peripheral cells
Figure 41B:
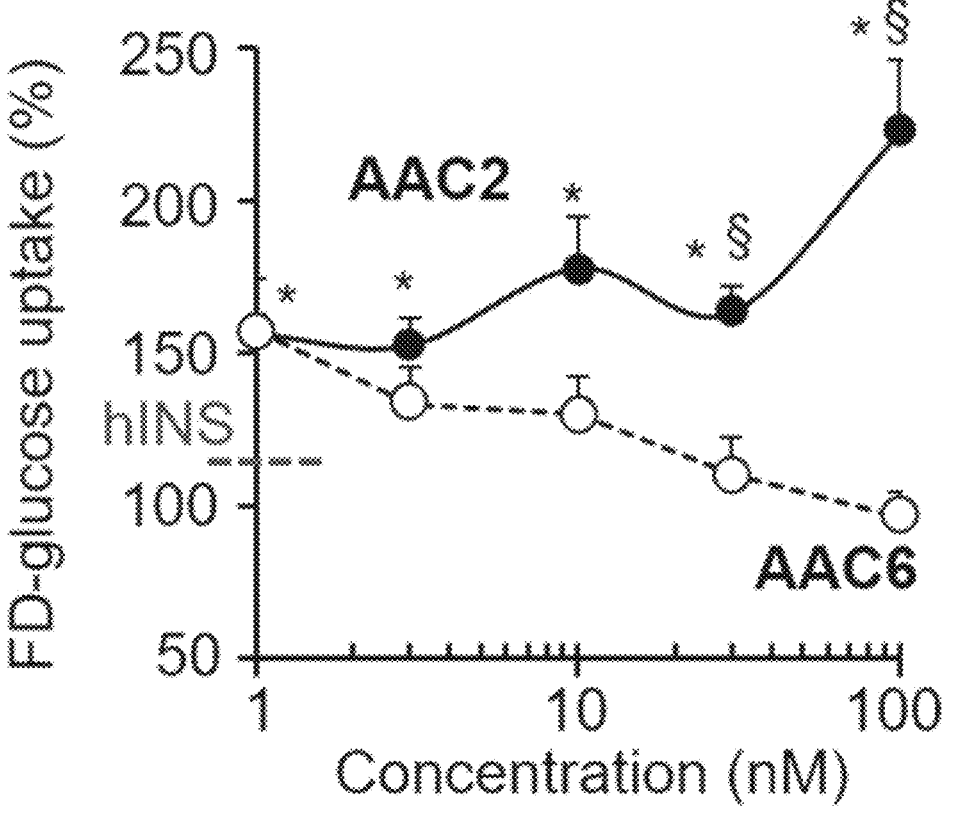
Figure 41C:
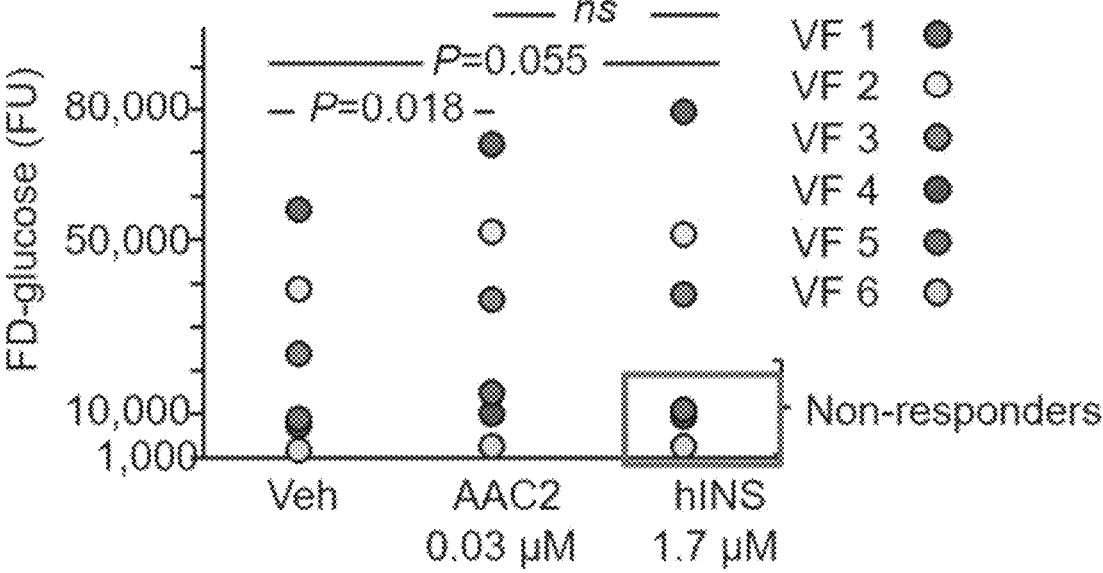

FIGS. 41A to 41C show glucose uptake efficacy of different AAC in mouse (FIG. 41A) and human (FIG. 41B, 41C) cells representing peripheral or central nervous system (CNS) cells.

AAC1, AAC2, and AAC4 increase glucose uptake in mouse 3T3-3L1 preadipocyte representing peripheral adipose tissue response (FIG. 41A). Fluorescence glucose uptake (FD-glucose assay) was performed as described PMID: 32065973, using insulin, 1.7 µM and different AACs at concentration 0.1 µM.

FIG. 41B shows dose-dependent FD-glucose uptake in SVF cells stimulated with AAC2 (closed circles) and AAC6 (open circle). SVF were collected from an individual donor. Data (n=8 per treatment) was normalized to FD-glucose uptake in non-stimulated cells (% compared to Veh). Red dashed line shows FD-glucose uptake cells stimulated with human insulin (hINS; 1.7 µM). Student's independent t-test. Asterisks, P<0.05 compared to Control (PBS). §, P<0.05 comparison between AAC2 vs. AAC6.

AAC2 improves glucose uptake in insulin-resistant and insulin-sensitive preadipocytes (FIG. 41C). FD-glucose uptake in non-treated (Veh) SVF cells or stimulated with AAC2 (0.03 µM), or hINS (1.7 µM) for 80 min. SVF were isolated from 6 different subjects (circles, Supplementary Table 1) Data are shown as mean±SEM of fluorescence units (FU) from n=8/subjects/treatment. Student's paired t-test.

Figures 42A, 42B:
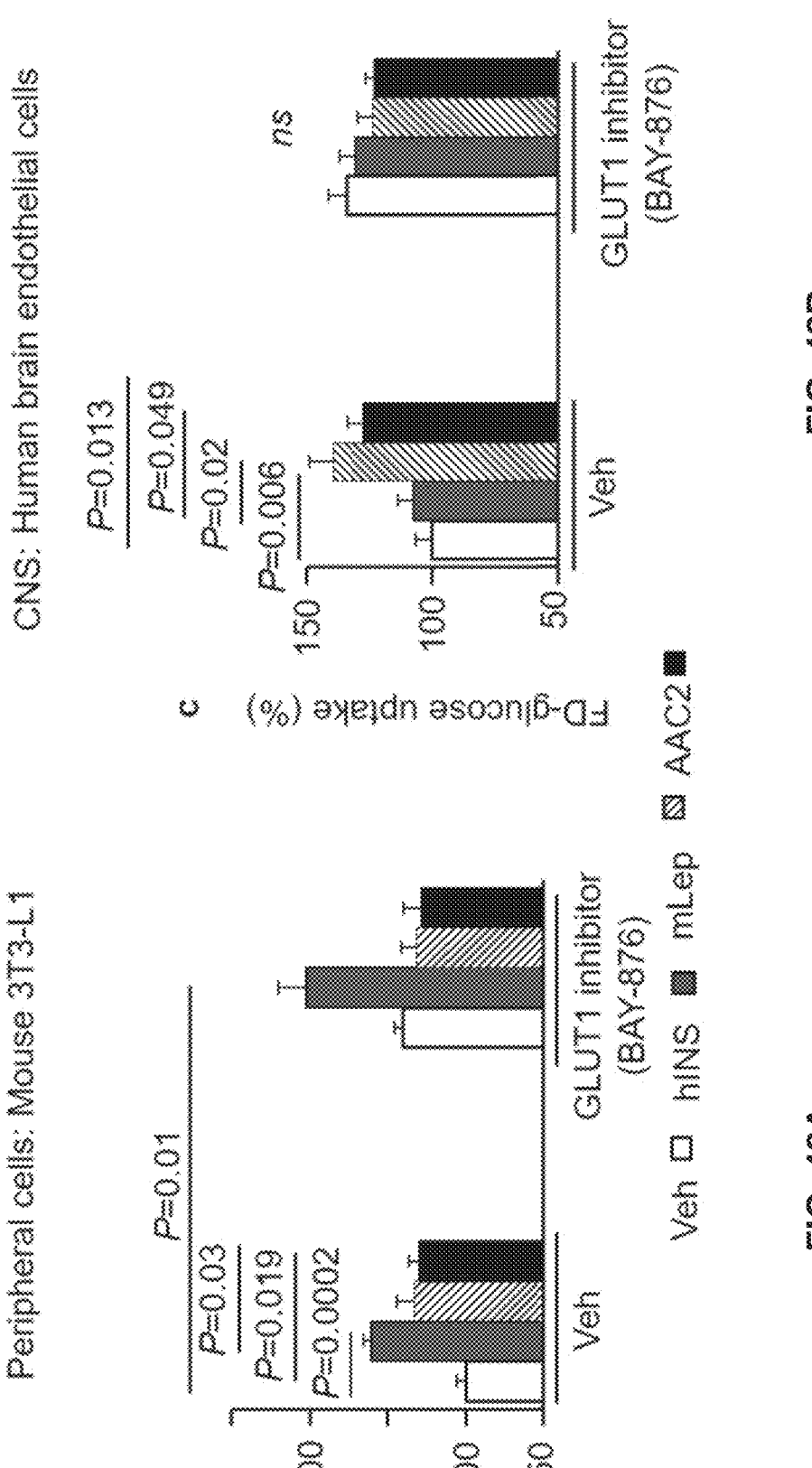
FIGS. 42A and 42B show differences in the mechanism of glucose uptake between AAC2 and insulin in peripheral and central nervous system (CNS) cells.

FIGS. 42A and 42B show differences in the mechanism of glucose uptake between AAC2 and insulin. FIG. 42A shows AAC2 and insulin increase glucose uptake in preadipocytes, but only AAC2 acts via glucose transporter 1 (GLUT1) that is inhibited by BAY-876 inhibitor compared to control. FD-glucose uptake in mouse 3T3-L1 preadipocytes (n=8 per treatment) treated with vehicle (Veh; PBS, open bar) or hINS (1.7 µM), mouse leptin (mLep; 12.5 nM, hatched bar), or AAC2 (0.1 µM black bar) in the presence and absence of GLUT1 inhibitor (BAY-876; 10 nM in DMSO). Cells were pre-treated with or without BAY-876 for 40 min and then FD glucose and treatment reagents were added for additional 80 min of incubation. Data (%) was normalized to FD-glucose uptake in control (Veh) 3T3-L1 cells without inhibitor (100%). Student's independent t-test.

FIG. 42B shows AAC2 but not insulin increase glucose uptake in human blood-brain barrier endothelial cells using glucose transporter 1 (GLUT1). FD-glucose uptake in human brain endothelial cells (hBEC, n=8 per treatment) treated with vehicle (Veh; PBS, open bar) or hINS (1.7 µM), human leptin (hLep; 62.5 nM, hatched bar), or AAC2 (0.1 µM black bar) in the presence and absence of GLUT1 inhibitor (BAY-876; 10 nM in DMSO). Cells were pre-treated with or without BAY-876 for 40 min and then FD glucose and treatment reagents were added for additional 50 min of incubation. Data (%) was normalized to FD-glucose uptake in control (Veh) hBEC without inhibitor (100%). Student's independent t-test. ns, not significant.

Figure 43:
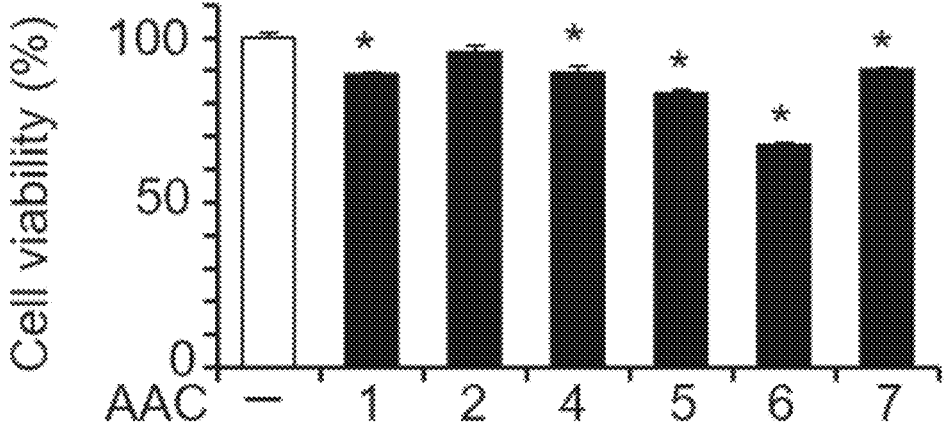
FIG. 43 shows cell toxicity in response to different AAC in mouse 3T3-L1 cells.

FIG. 43 shows cell toxicity in response to different AAC in mouse 3T3-L1 cells. Cytotoxicity was measured in 3T3-L1 preadipocytes treated with AAC compounds (0.1 µM, black bars) or left untreated (white bar) for 24 h (n=4 per treatment condition). Viable cells were quantified using WST-1 assay. Data are shown as % of control. Asterisk, P<0.05 compared to control, Student's independent t-test.

Figure 44:
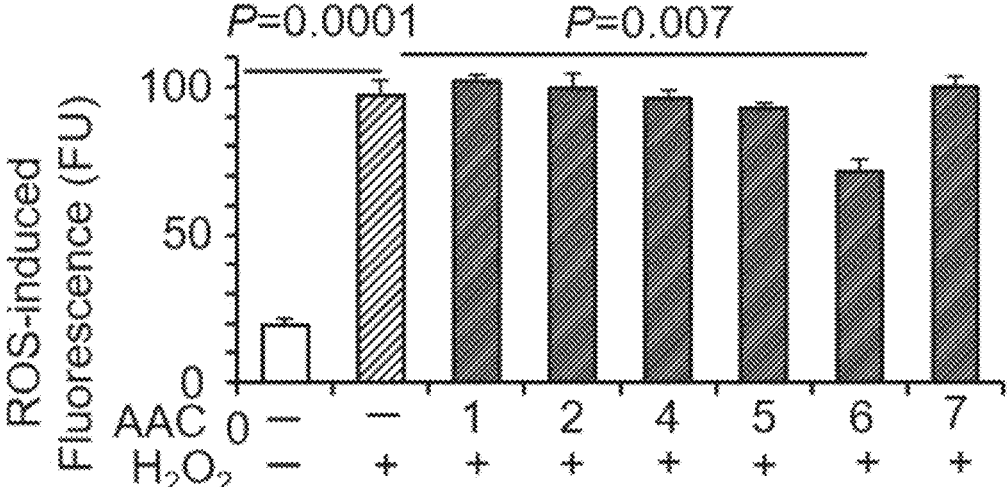
FIG. 44 shows efficacy of different AAC to withstand reactive oxygen species (ROS)-induced stress in mouse 3T3-L1 cells.

FIG. 44 shows efficacy of different AAC to withstand reactive oxygen species (ROS)-induced stress in mouse 3T3-L1 cells. Reactive oxygen species concentration was measured in 3T3-L1 preadipocytes stimulated with $H_2O_2$ for 4 h (200 µM, hatched bars) and treated with and without (open bar) AAC (0.1 µM dark hatched bars) for 24 h. ROS-induced fluorescence was measured using CellROX Green Reagent. Student's independent t-test, n=3/condition.

Example 3: Synergistic Action of IGFBP4 and AAC2

A study was performed in ob/ob mouse model of obesity, insulin resistance, and type 2 diabetes. Treatment groups (n=5) included vehicle (non-treated control), AAC2 nanofiber alone, IGFBP4 peptide alone, and AAC2-IGFBP4 peptide bound to nanofiber.

5-week old male $Lep^{ob}$ mice (ob/ob mice, Jackson #000632-B6.Cg-Lepob/J, Homozygous for Lepob) were randomized into four groups (n=5/group). After 1 week assimilation period, mice were injected (10 µl/g body weight (BW)) into scapular region every 48 h for 4 weeks with:

Group 1: PBS vehicle control,

Group 2: 1 nmol AAC2/g BW,

Group 3: 0.0187 nmol human insulin-like growth factor binding protein 4 (hIGFBP4, Peprotech #350-05B), or Group 4: AAC2/hIGFBP4 combination (1 nmol AAC2 and 0.0187 nmol hIGFBP4/g BW were assembled into complex prior to injection)

Figure 45:
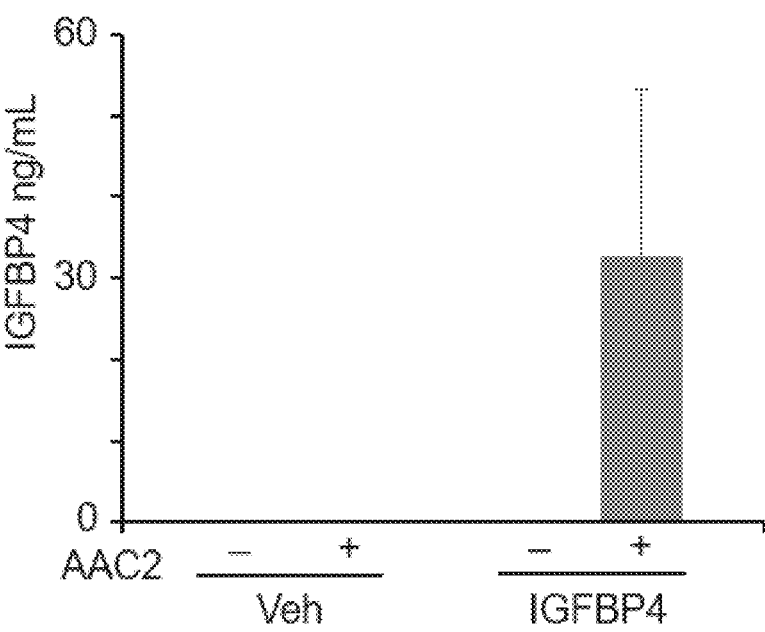
FIG. 45 shows binding to AAC2 protects IGFBP4 from catabolism in the circulation.

FIG. 45 shows binding to AAC2 protects IGFBP4 from catabolism in the circulation. An increase in plasma concentrations of injected IGFBP4 was detected only in a group of mice treated with AAC2-IGFBP4 combination. Free IGFBP4 is a subject of proteolytic degradation.

Figure 46:
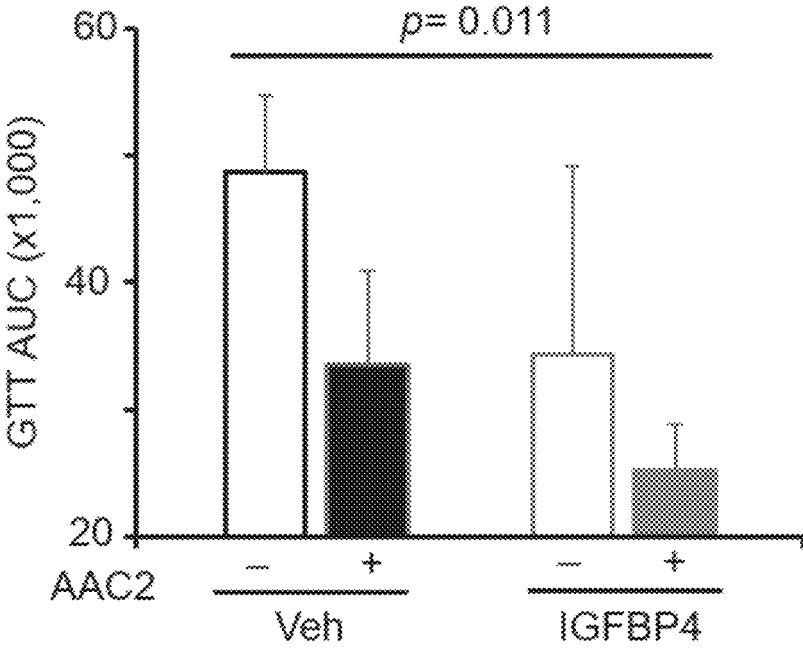
FIG. 46 shows synergistic improvement of glucose tolerance in ob/ob mice treated with AAC2-IGFBP4 combination.

FIG. 46 shows synergistic improvement of glucose tolerance in ob/ob mice treated with AAC2-IGFBP4 combination. Glucose tolerance was measured by glucose tolerance test (GTT). Area under the curve showed the significant change in AAC2-IGFBP4-treated group compared to veh control.

Figure 47:
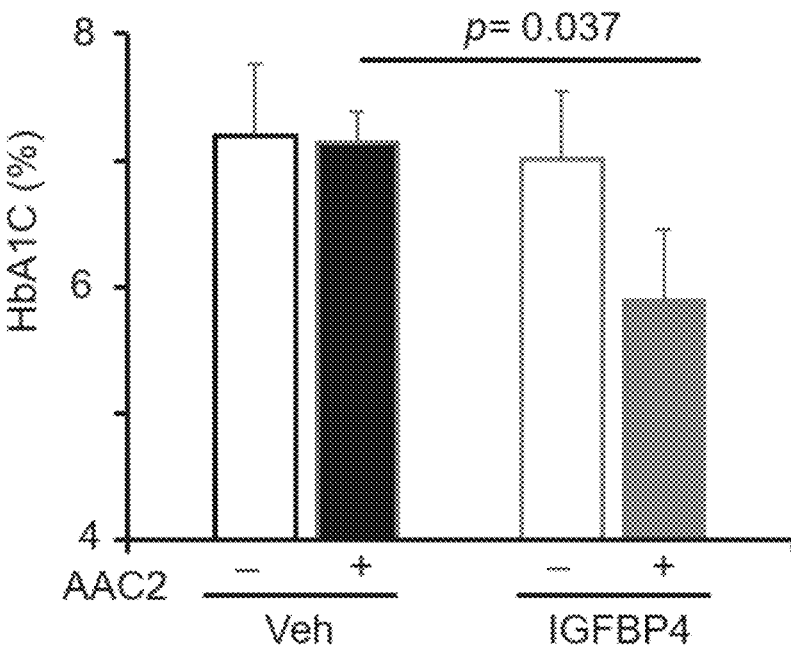
FIG. 47 shows synergistic reduction of HbA1C in ob/ob mice treated with AAC2-IGFBP4 combination.

FIG. 47 shows synergistic reduction of HbA1C in ob/ob mice treated with AAC2-IGFBP4 combination. HbA1C was measured by in blood by ELISA at the end of the study (1 month).

Figure 48:
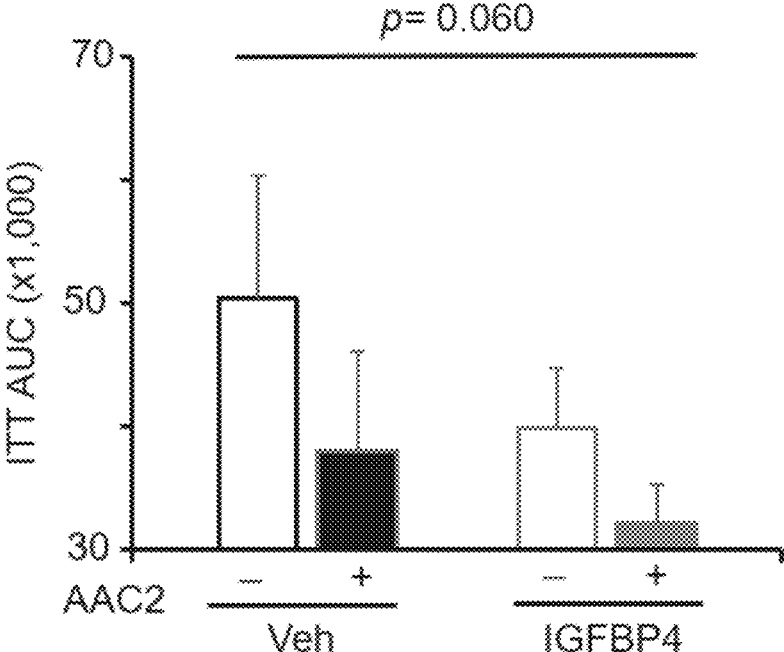
FIG. 48 shows synergistic improvement of insulin resistance in ob/ob mice treated with AAC2-IGFBP4 combination.

FIG. 48 shows synergistic improvement of insulin resistance in ob/ob mice treated with AAC2-IGFBP4 combination. Insulin resistance was measured by insulin tolerance test (ITT). Area under the curve showed the significant change in AAC2-IGFBP4-treated group compared to veh control.

Figures 49A, 49B:
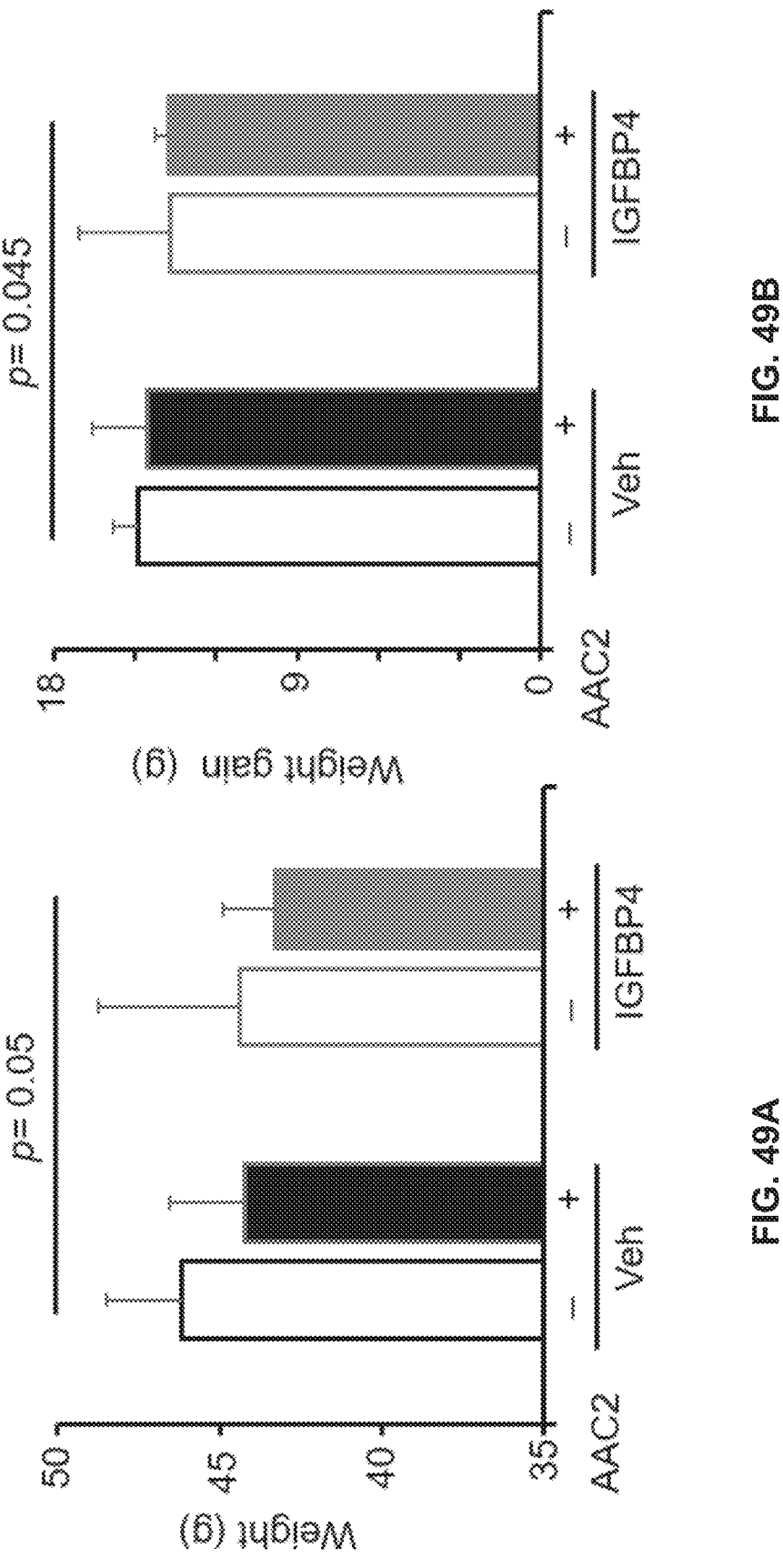
FIGS. 49A and 49B show synergistic improvement of weight and weight gain in ob/ob mice treated with AAC2-IGFBP4 combination.

FIGS. 49A and 49B show synergistic improvement of weight and weight gain in ob/ob mice treated with AAC2-IGFBP4 combination. Weight in all mice was measured prior and at the end of the study (4 weeks). Left panel: weight in all mice groups at the end of the study. Right panel: Weight gain represent initial weight subtracted from the final weight.

Figure 50:
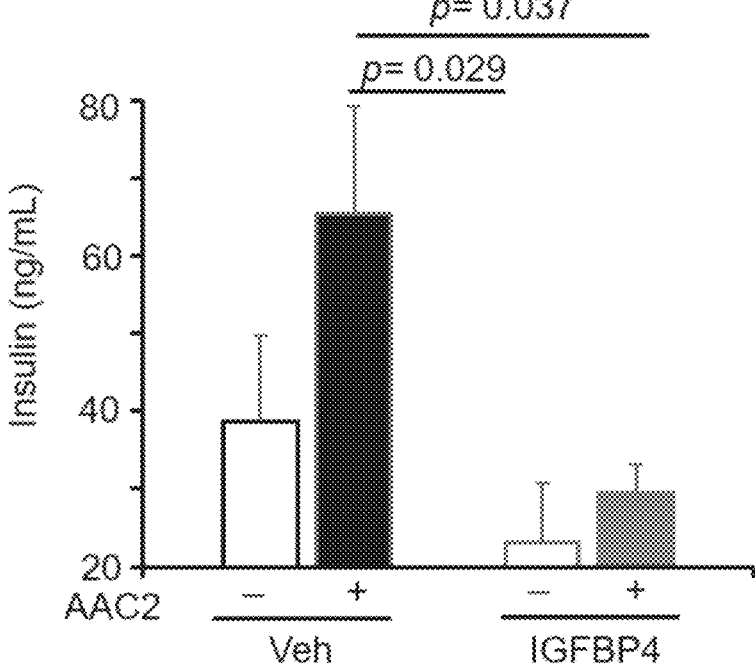
FIG. 50 shows reduction of hyperinsulinemia by free IGFBP4 and bound AAC2-IGFBP4.

FIG. 50 shows reduction of hyperinsulinemia by free IGFBP4 and bound AAC2-IGFBP4. Insulin levels in the blood were measured by ELISA at the end of the study.

Figure 51B:
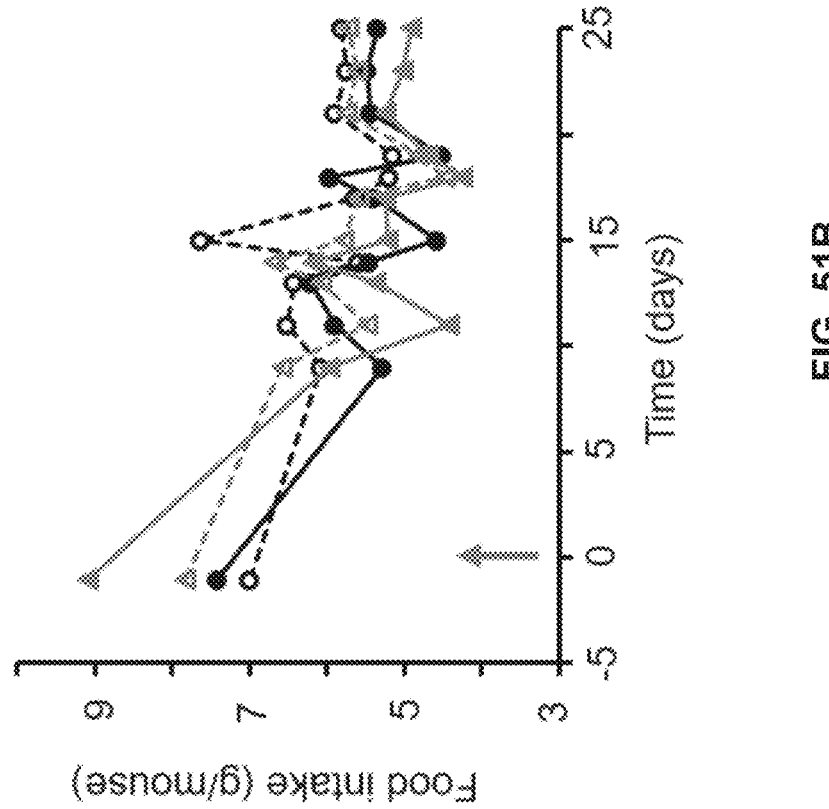
FIGS. 51A and 51B show reduction of food intake by free AAC2 and bound AAC2-IGFBP4.
Figure 51A:
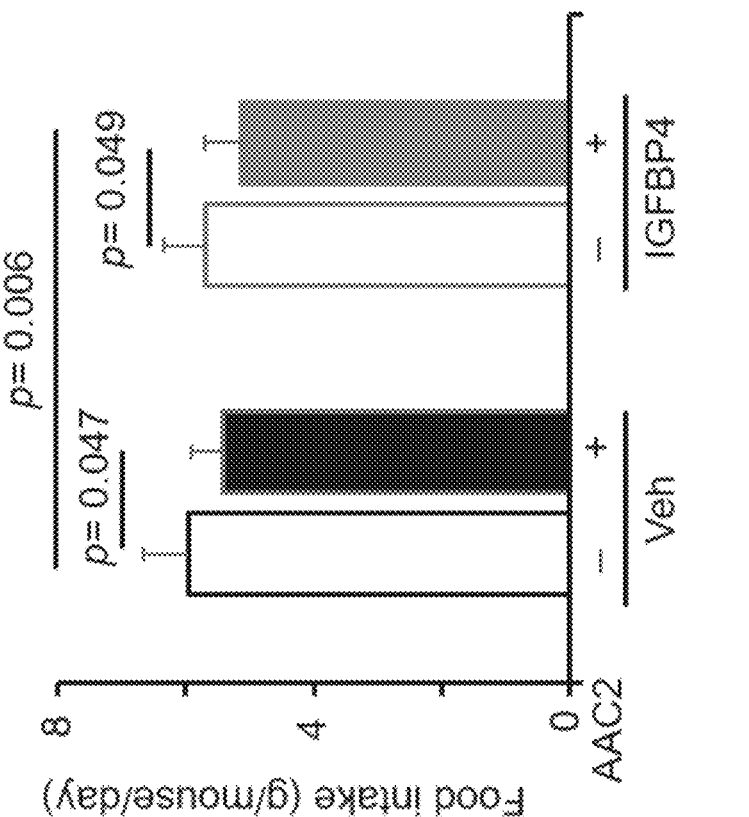

FIGS. 51A and 51B show reduction of food intake by free AAC2 and bound AAC2-IGFBP4. FIG. 51 shows average food intake in all mouse groups. FIG. 51B shows kinetics of daily food intake in each group.

Example 4

Figure 52A:
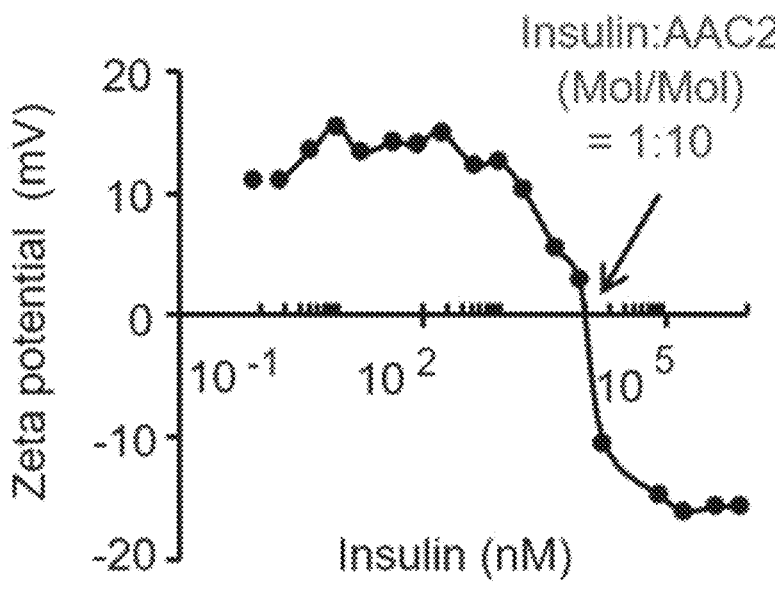
FIG. 52A shows change of zeta potential (mV) in response of binding of negatively charged insulin to positively charged AAC2 nanofibers.
Figure 52B:
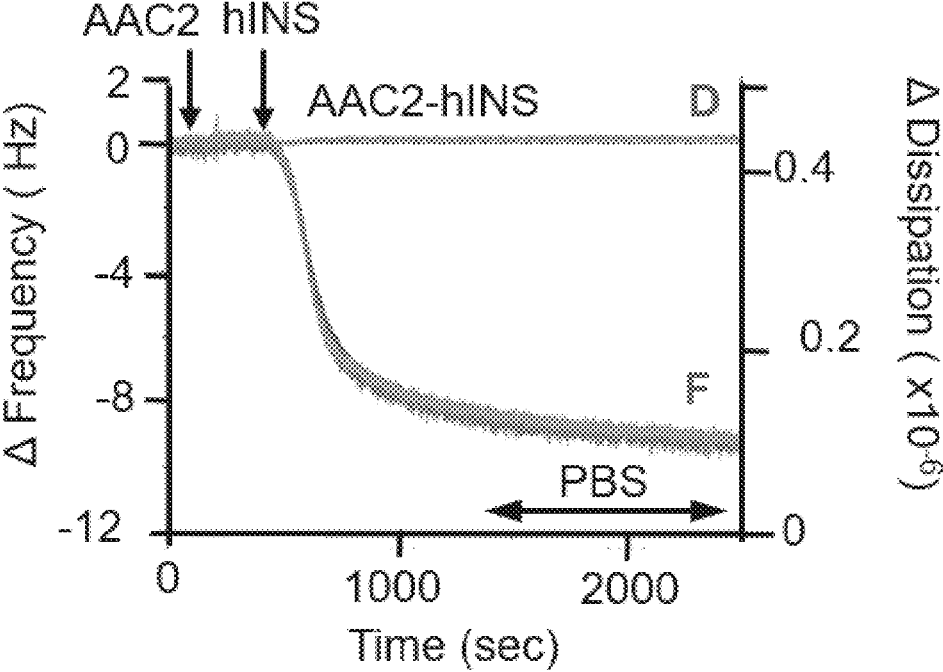
FIG. 52B shows formation of a stable complex between insulin and AAC2 fibers using microbalance measurements of frequency and dissipation upon interaction of molecules.
Figure 52C:
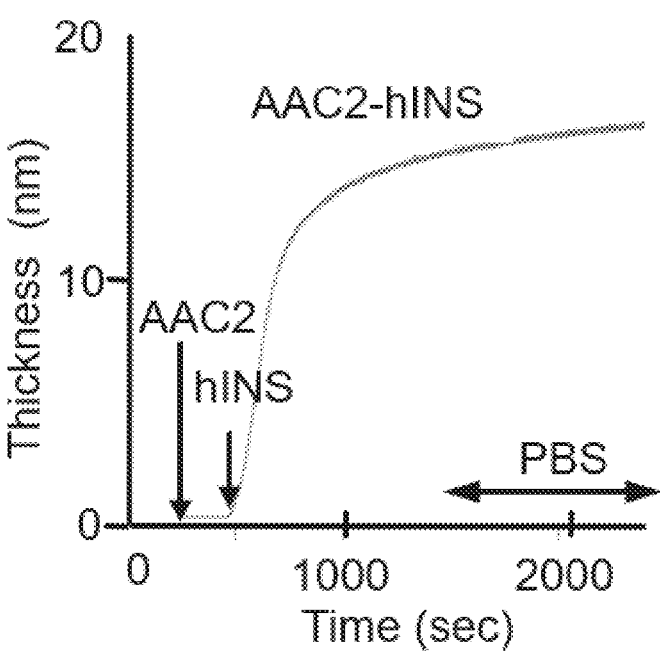
FIG. 52C shows the thickness of the film, formed as a result of the complex between insulin and AAC2.

FIG. 52A shows change of zeta potential (mV) in response of binding of negatively charged insulin to positively charged AAC2 nanofibers. FIG. 52B shows formation of a stable complex between insulin and AAC2 fibers using microbalance measurements of frequency and dissipation upon interaction of molecules. FIG. 52C shows the thickness of the film, formed as a result of the complex between insulin and AAC2.

Figure 53A:
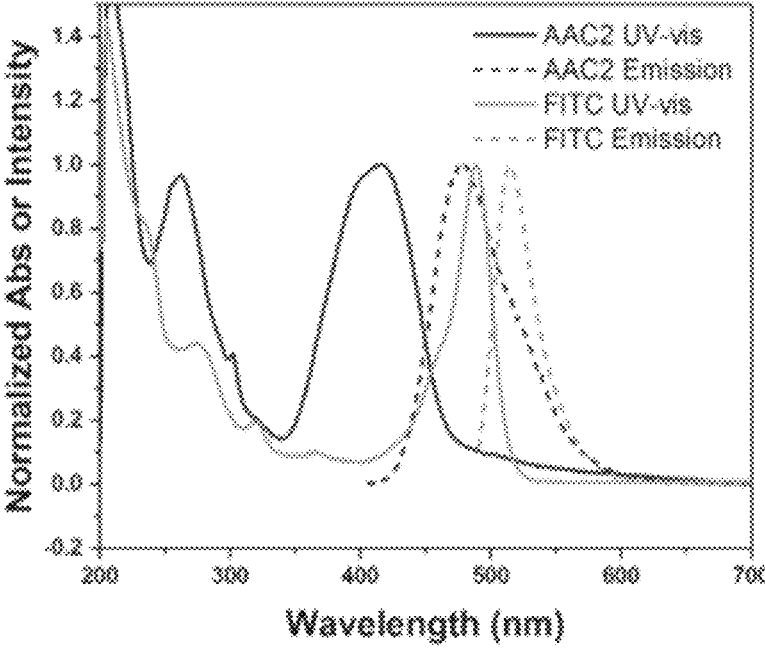
FIG. 53A shows formation of insulin complex with AAC2 by demonstration of Fluorescence Resonance Energy Transfer (FRET) after binding of fluorescent insulin analog (insulin FITC) and an intrinsically-fluorescent AAC2.
Figures 53B, 53C:
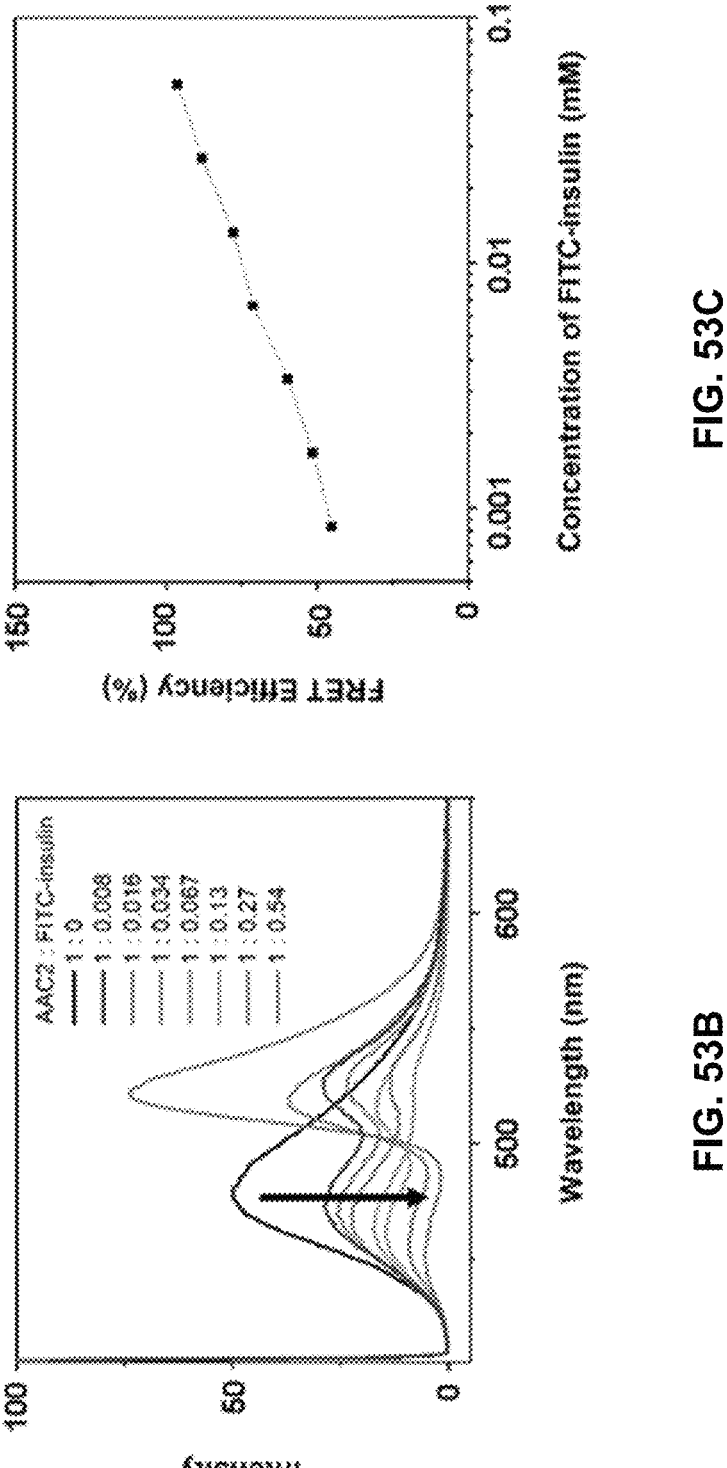
FIG. 53B shows dose-dependent FRET interaction of FITC-insulin with AAC2.
FIG. 53C shows a linear relationship of FRET upon dose-dependent binding of FITC-insulin with AAC2.
Figures 53D, 53E:
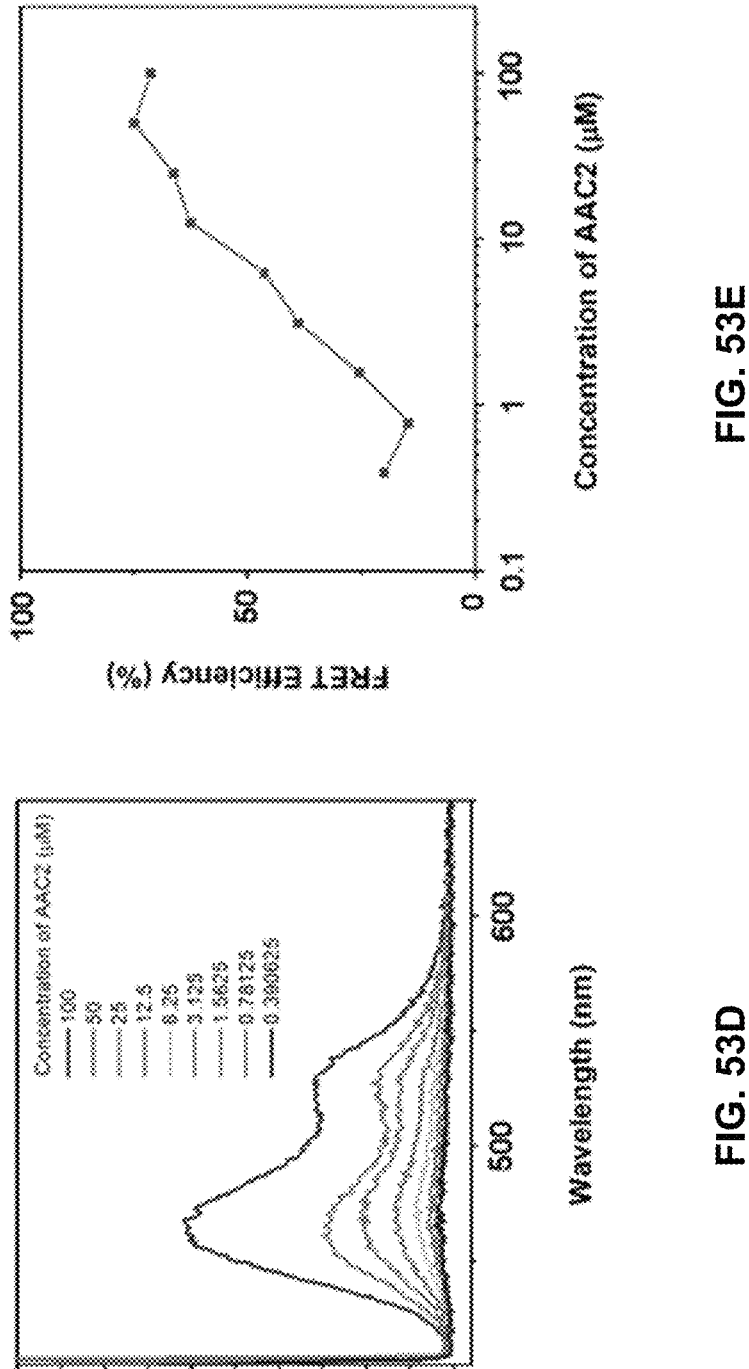
FIG. 53D shows dose-dependent FRET interaction of AAC2 with constant concentrations of FITC-insulin.
FIG. 53E shows stable complex between FITC-insulin and AAC2 forms after a threshold 1 µM concentration of AAC2 is present in the solution.

FIG. 53A shows formation of insulin complex with AAC2 by demonstration of Fluorescence Resonance Energy Transfer (FRET) after binding of fluorescent insulin analog (insulin FITC) and an intrinsically-fluorescent AAC2. FIG. 53B shows dose-dependent FRET interaction of FITC-insulin with AAC2. FIG. 53B shows a linear relationship of FRET upon dose-dependent binding of FITC-insulin with AAC2 FIG. 53D shows dose-dependent FRET interaction of AAC2 with constant concentrations of FITC-insulin. FIG. 53E shows stable complex between FITC-insulin and AAC2 forms after a threshold 1 µM concentration of AAC2 is present in the solution.

Figures 54A, 54B:
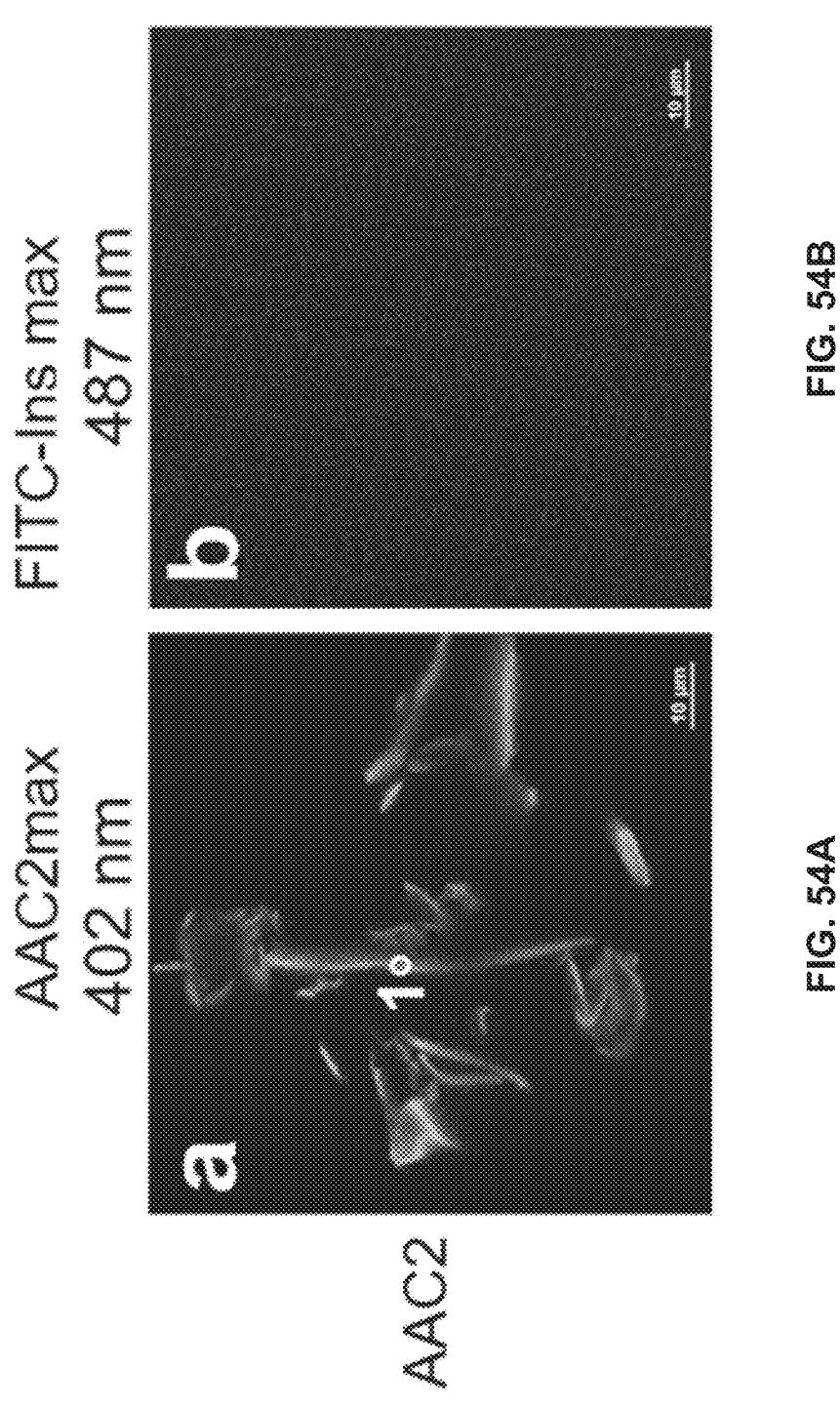
FIGS. 54A and B show fluorescent image of AAC2 fibers at excitation (402 nm) and emission (487 nm) using confocal microscopy.
Figures 54C, 54D:
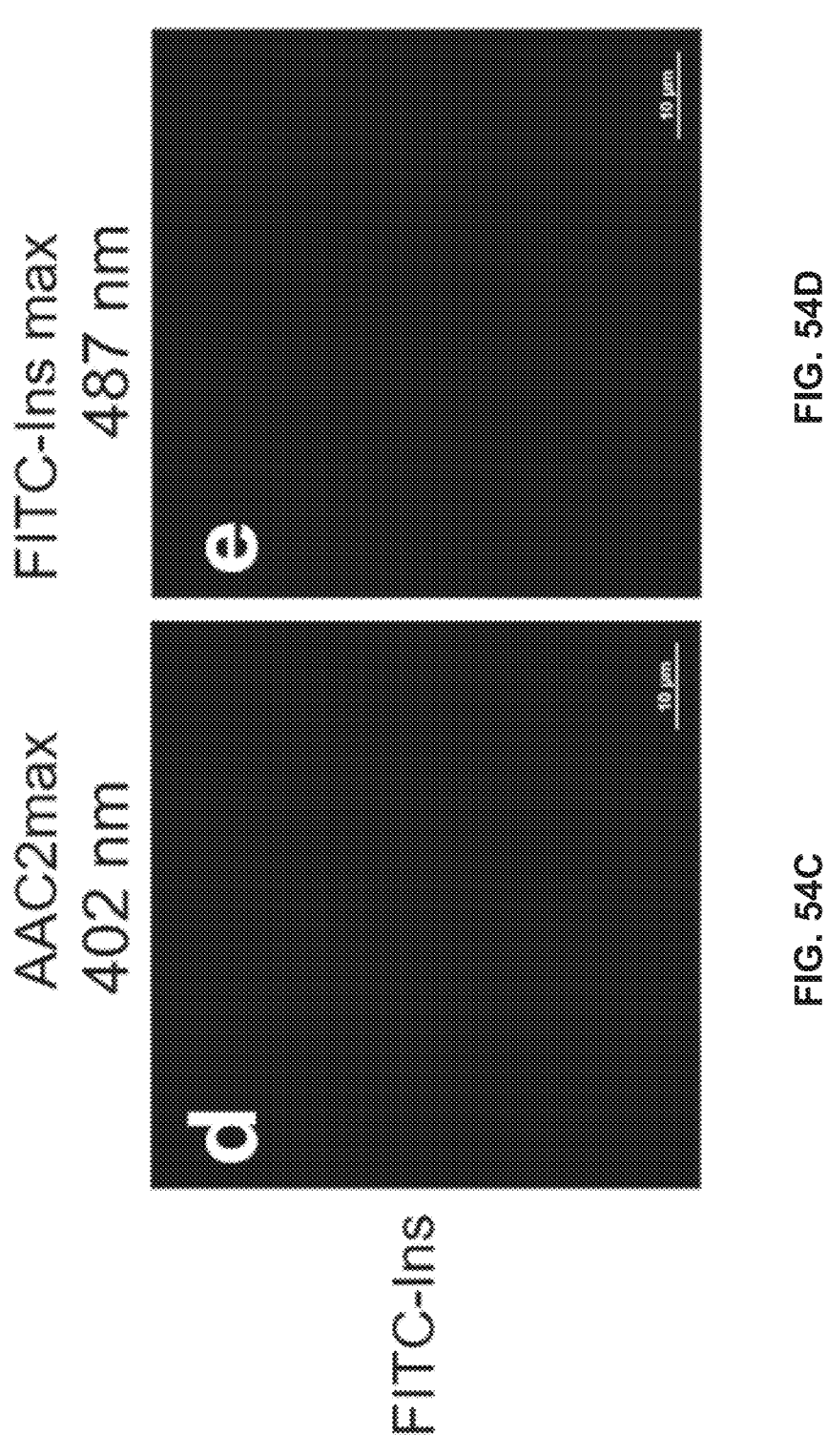
FIGS. 54C and D show the lack of fluorescent image of diffused FITC-insulin in solution at excitation (402 nm) and emission (487 nm) using confocal microscopy.
Figures 54E, 54F:
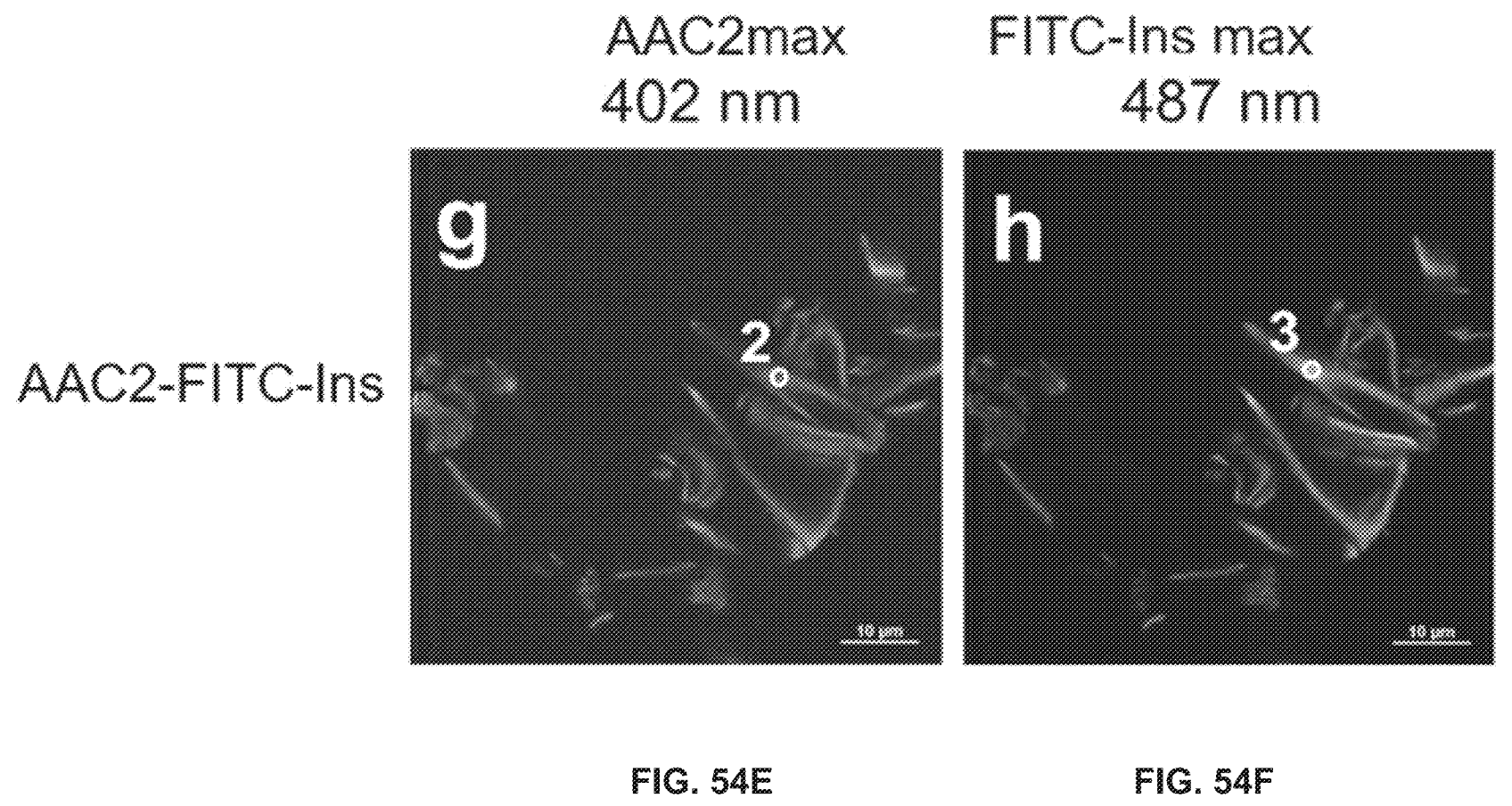

FIGS. 54A and B show fluorescent image of AAC2 fibers at excitation (402 nm) and emission (487 nm) using confocal microscopy. FIGS. 54C and D show the lack of fluorescent image of diffused FITC-insulin in solution at excitation (402 nm) and emission (487 nm) using confocal microscopy. FIGS. 54E and 54F show fluorescent image of FITC insulin bound with AAC2 fibers at excitation (402 nm) and emission (487 nm) using confocal microscopy.

Figure 55A:
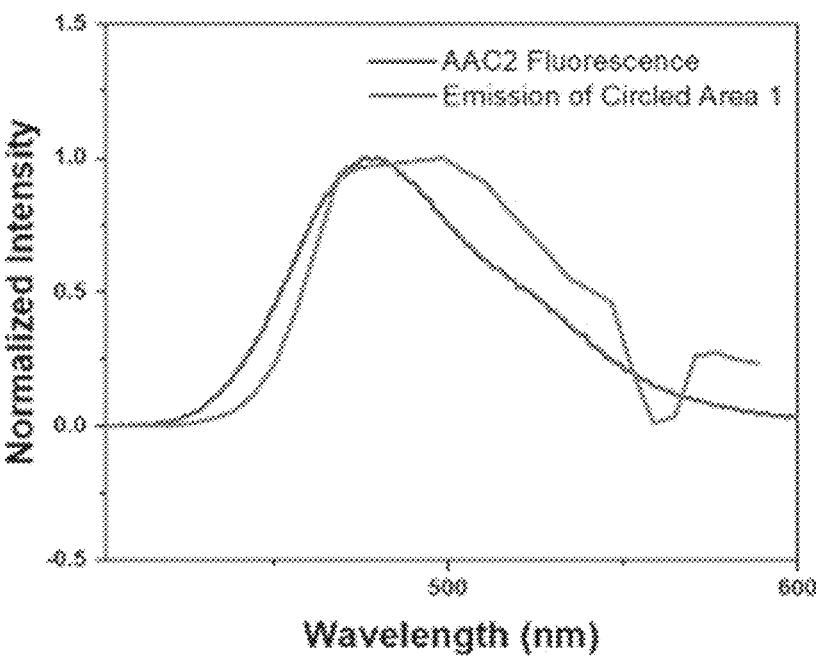
FIG. 55A shows fluorescent spectrum of AAC2 fibers at excitation (402 nm) and emission (487 nm) taken at position 1 in confocal microscopy image 54A.
Figure 55B:
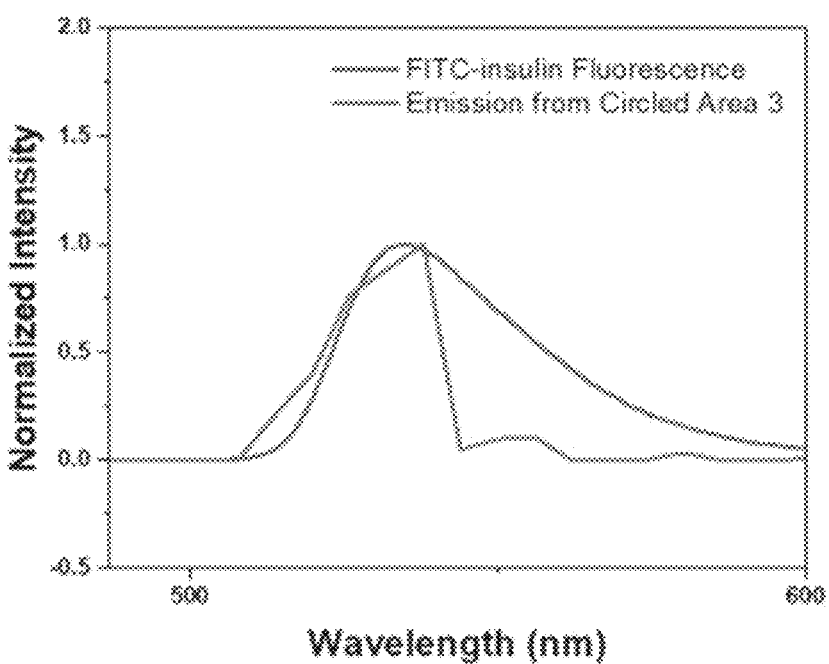
FIG. 55B shows fluorescent spectrum of FITC-insulin bound to AAC2 fibers at excitation (402 nm) and emission (487 nm) taken at position 3 in confocal microscopy image 54F.
Figure 55C:
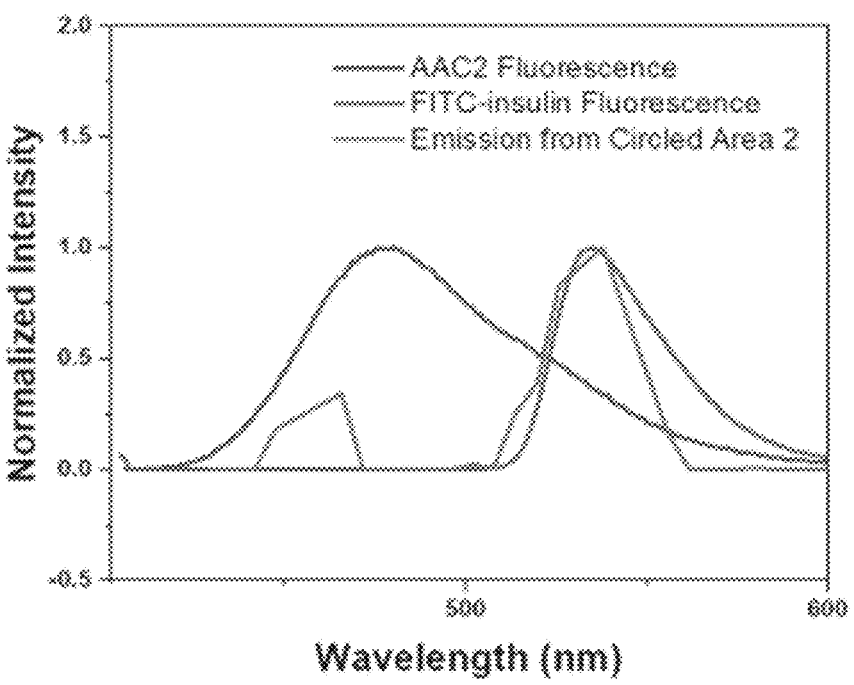
FIG. 55C shows FRET fluorescent spectrum of FITC-insulin bound to AAC2 fibers at excitation (402 nm) and emission (487 nm) taken at position 2 in confocal microscopy image 54E.

FIG. 55A shows fluorescent spectrum of AAC2 fibers at excitation (402 nm) and emission (487 nm) taken at position 1 in confocal microscopy image 54A. FIG. 55B shows fluorescent spectrum of FITC-insulin bound to AAC2 fibers at excitation (402 nm) and emission (487 nm) taken at position 3 in confocal microscopy image 54F. FIG. 55C shows FRET fluorescent spectrum of FITC-insulin bound to AAC2 fibers at excitation (402 nm) and emission (487 nm) taken at position 2 in confocal microscopy image 54E.

Figure 56A:
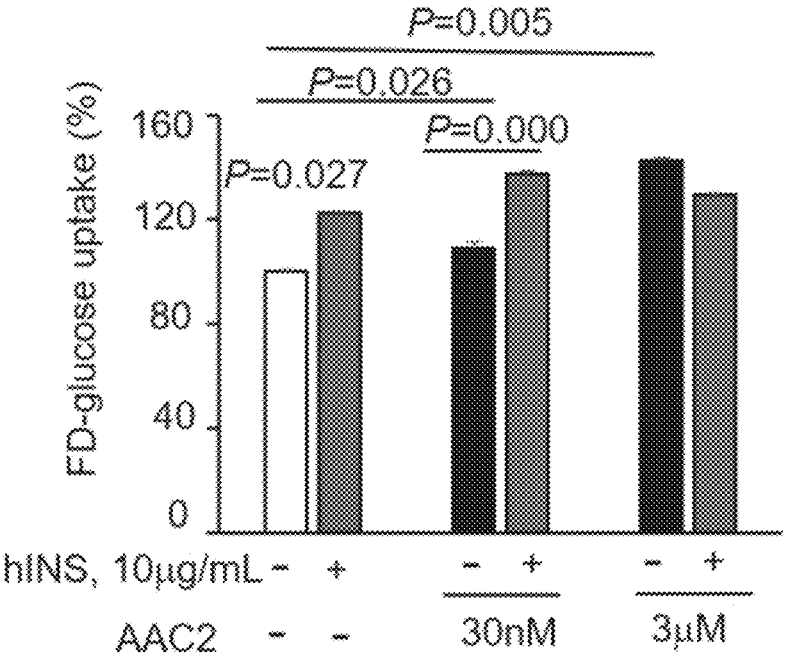
FIG. 56A shows improved efficacy of FD-glucose uptake by insulin (INS) bound with AAC2 (AA2-INS) compared to free INS in peripheral mouse preadipocytes.
Figure 56B:
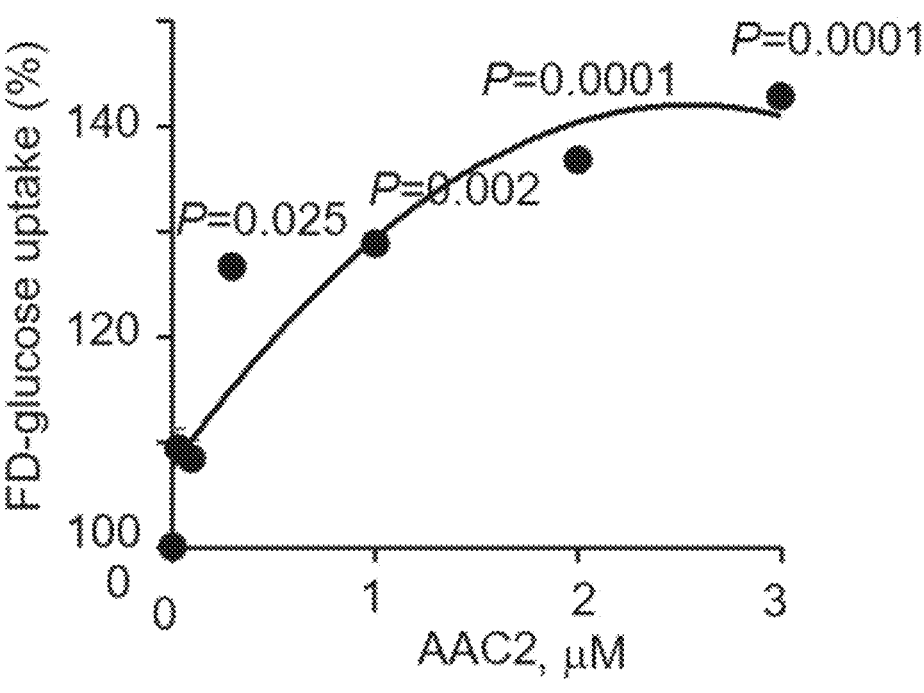
FIG. 56B shows dose-dependent FD-glucose uptake by free AAC2 in peripheral mouse preadipocytes.
Figure 56C:
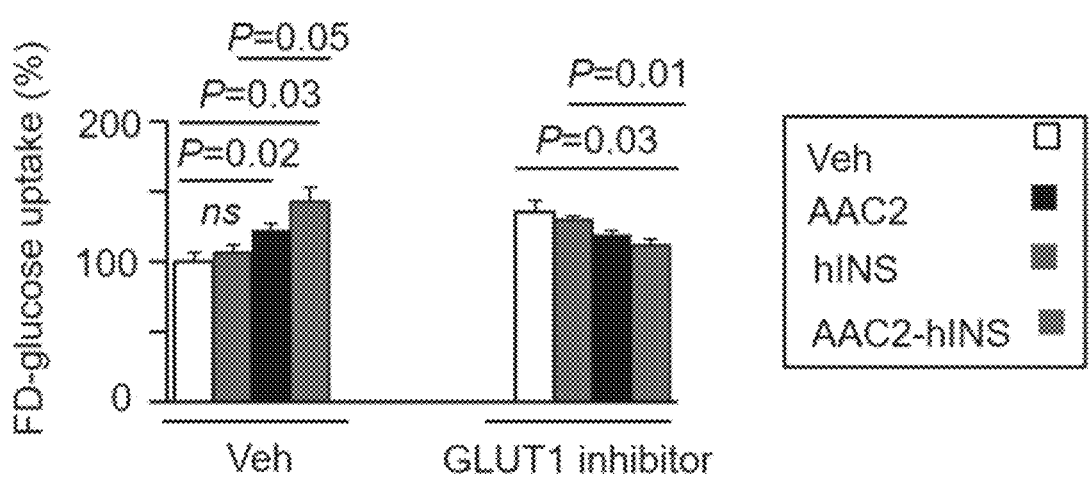
FIG. 56C shows synergistic effect of AA2-INS combination in human blood-brain barrier endothelial cells, representing CNS. The synergistic effect was dependent on glucose transporter 1 (GLUT1), which is the major glucose transporter of CNS.

FIG. 56A shows improved efficacy of FD-glucose uptake by insulin (INS) bound with AAC2 (AA2-INS) compared to free INS in peripheral mouse preadipocytes. FIG. 56B shows dose-dependent FD-glucose uptake by free AAC2 in peripheral mouse preadipocytes. FIG. 56C shows synergistic effect of AA2-INS combination in human blood-brain barrier endothelial cells, representing CNS. The synergistic effect was dependent on glucose transporter 1 (GLUT1), which is the major glucose transporter of CNS.

Figure 57A:
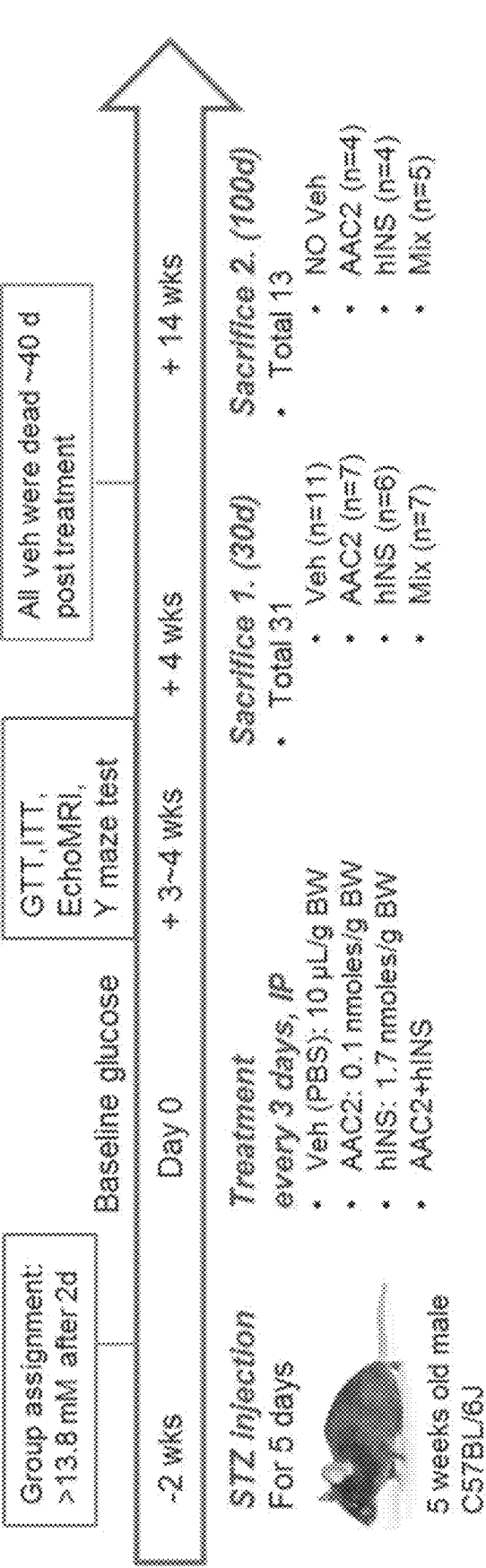
FIG. 57A shows the experimental design of treatment with free AAC2, free INS, and AAC2-INS combination of glycemia-related pathologies (57B-60A) in mice with streptozotocin-induced type 1 diabetes (STZ mice).
Figures 57C, 57D:
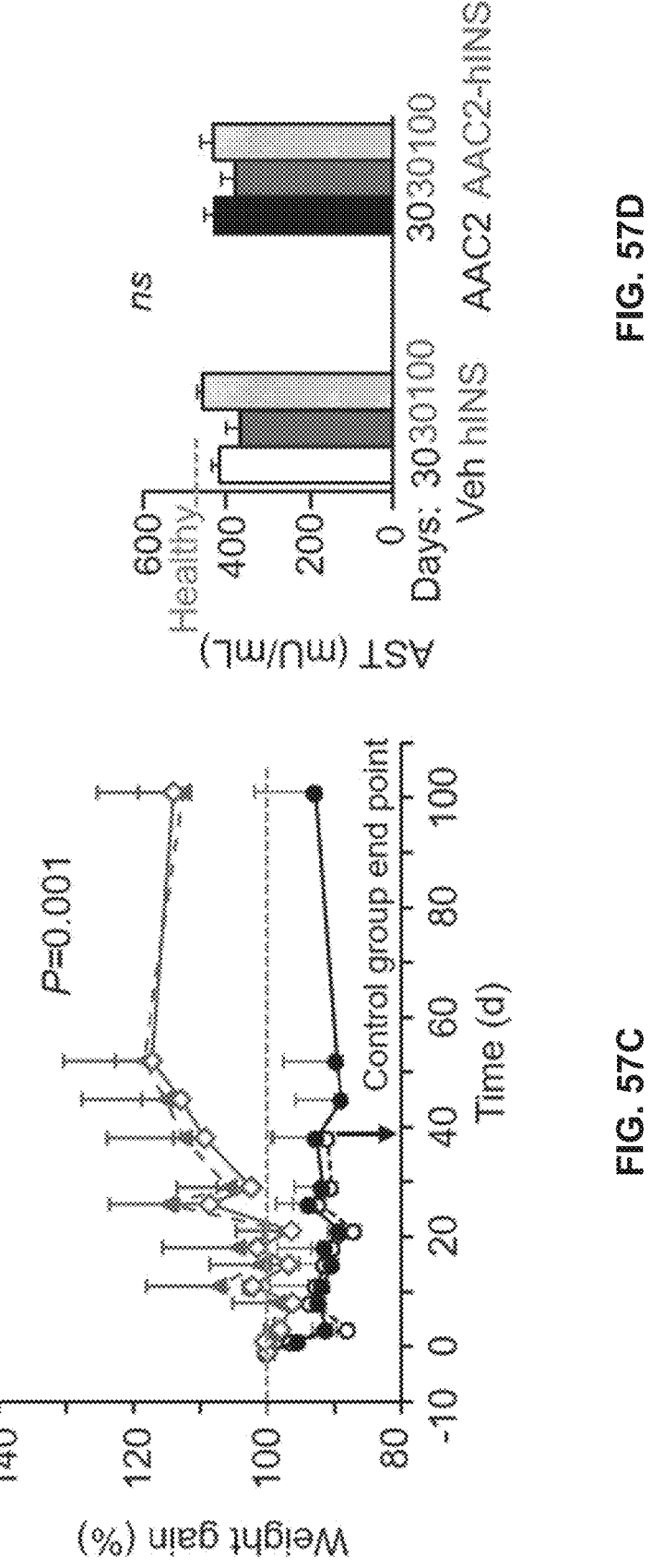
FIG. 57C shows survival of STZ mice upon treatment with free AAC2, free INS, or AAC2-INS combination and growth measured by weight gain in groups treated with INS or AAC2-INS complex. The untreated STZ mice died 32 days after STZ induction of experimental type 1 diabetes.
FIG. 57D shows the lack of liver toxicity in all treated groups of STZ mice that was not significantly different from healthy non-STZ-induced mice. Liver toxicity was measured by plasma levels of liver enzyme aspartate aminotransferase (AST).
Figure 57F:
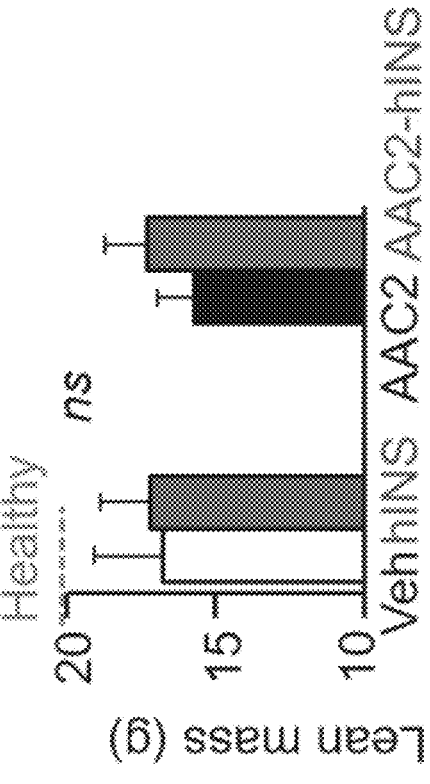
FIG. 57F shows similar lean mass, measured by Echo-MRI, in treated and untreated STZ mice.
Figure 57E:
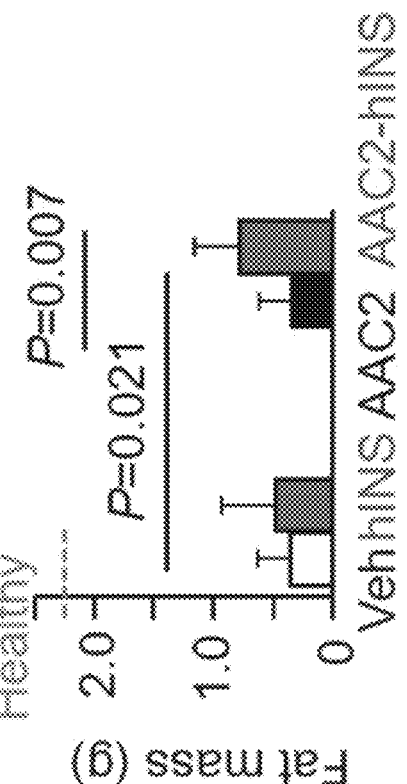
FIG. 57E shows the synergistic retaining of fat mass in STZ mice treated with AAC2-INS combination measured by Echo-MRI.

FIG. 57A shows the experimental design of treatment with free AAC2, free INS, and AAC2-INS combination of glycemia-related pathologies (57B-60A) in mice with streptozotocin-induced type 1 diabetes (STZ mice). FIG. 57B shows onset of hyperglycemia characteristic for type 1 diabetes in STZ mice prior to treatment with free AAC2, free INS, or AAC2-INS combination. FIG. 57C shows survival of STZ mice upon treatment with free AAC2, free INS, or AAC2-INS combination and growth measured by weight gain in groups treated with INS or AAC2-INS complex. The untreated STZ mice died 32 days after STZ induction of experimental type 1 diabetes. FIG. 57D shows the lack of liver toxicity in all treated groups of STZ mice that was not significantly different from healthy non-STZ-induced mice. Liver toxicity was measured by plasma levels of liver enzyme aspartate aminotransferase (AST). FIG. 57E shows the synergistic retaining of fat mass in STZ mice treated with AAC2-INS combination measured by Echo-MRI. FIG. 57F shows similar lean mass, measured by Echo-MRI, in treated and untreated STZ mice.

Figure 58B:
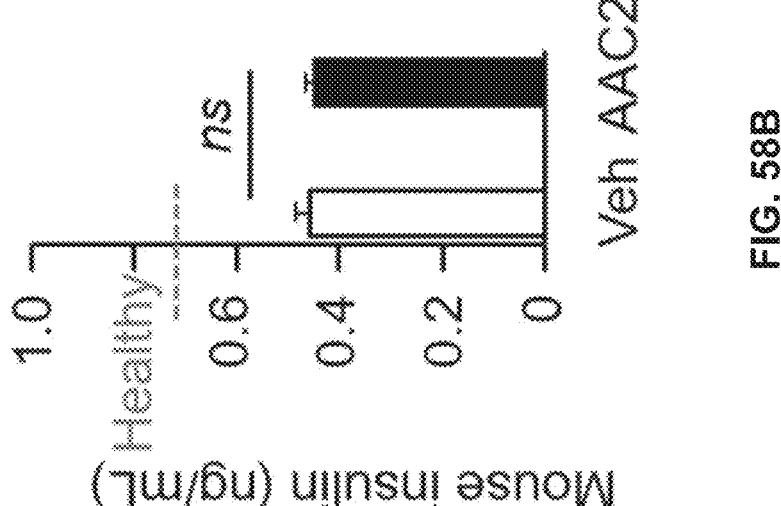
FIG. 58B shows identical levels of endogenous mouse INS in STZ mice treated with AAC2 an untreated control group.
Figure 58A:
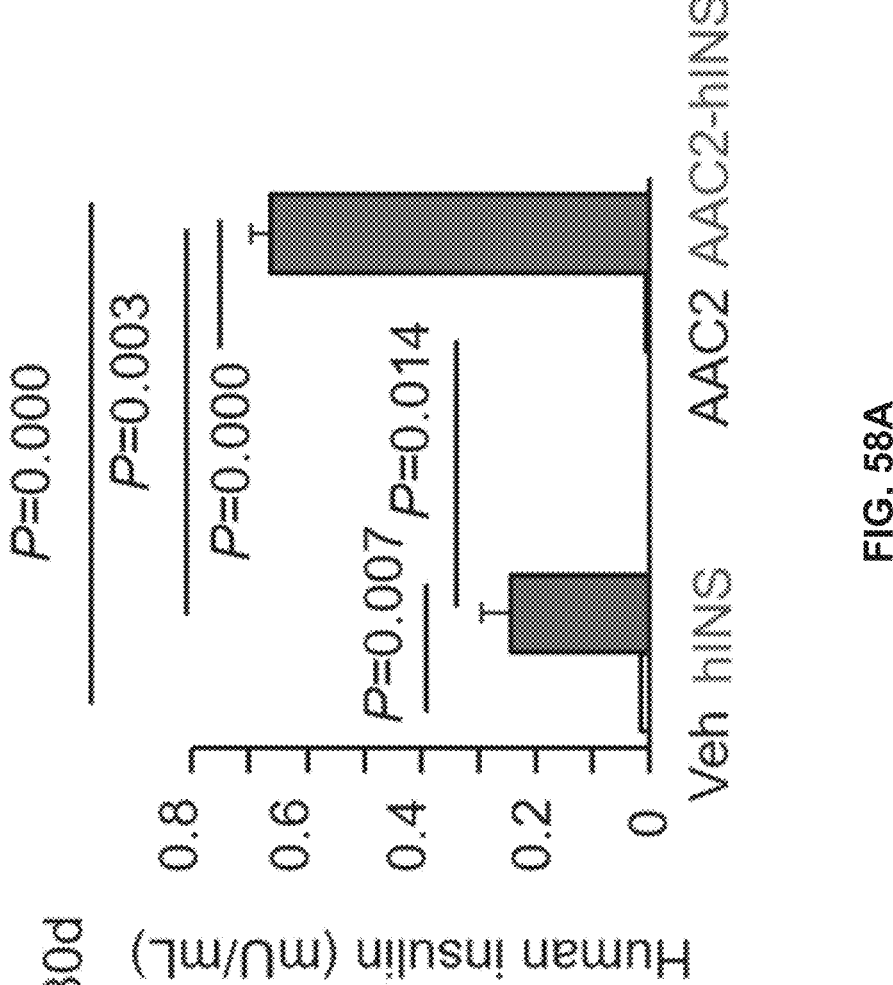
FIG. 58A shows improved stability of AAC2-INS in circulation in STZ mice. Human INS was used for treatment to distinguish from endogenous mouse INS.
Figures 58C, 58D:
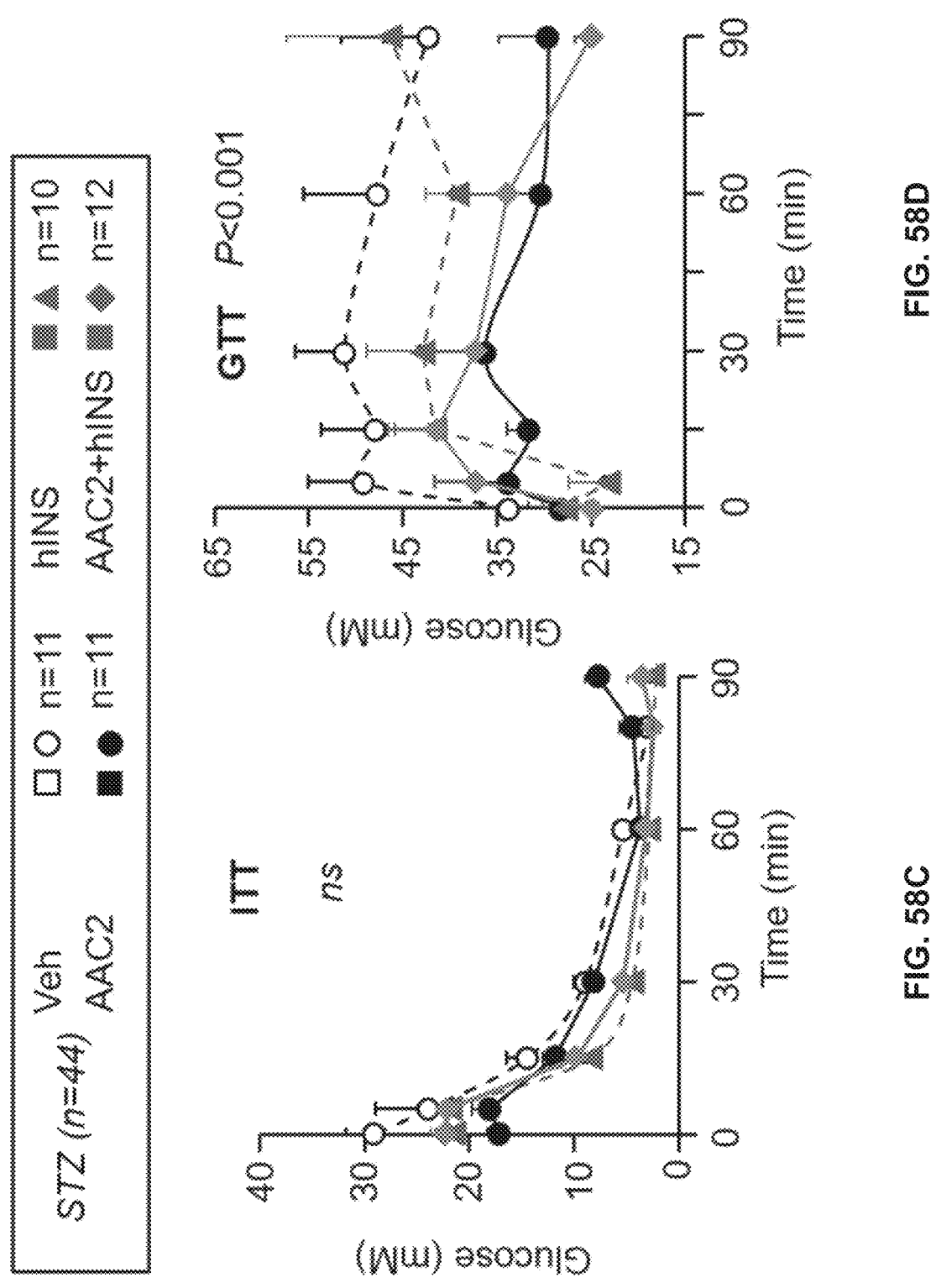
FIG. 58C shows similar insulin sensitivity in all treatment groups without onset of hypoglycemia in AAC2-INS group (58A). Insulin tolerance test (ITT) was used to assess insulin sensitivity.
FIG. 58D shows improved glucose uptake in STZ mice treated with AAC2 or AAC2-INS. Glucose tolerance test (GTT) was used to assess glucose tolerance.
Figures 58E, 58F:
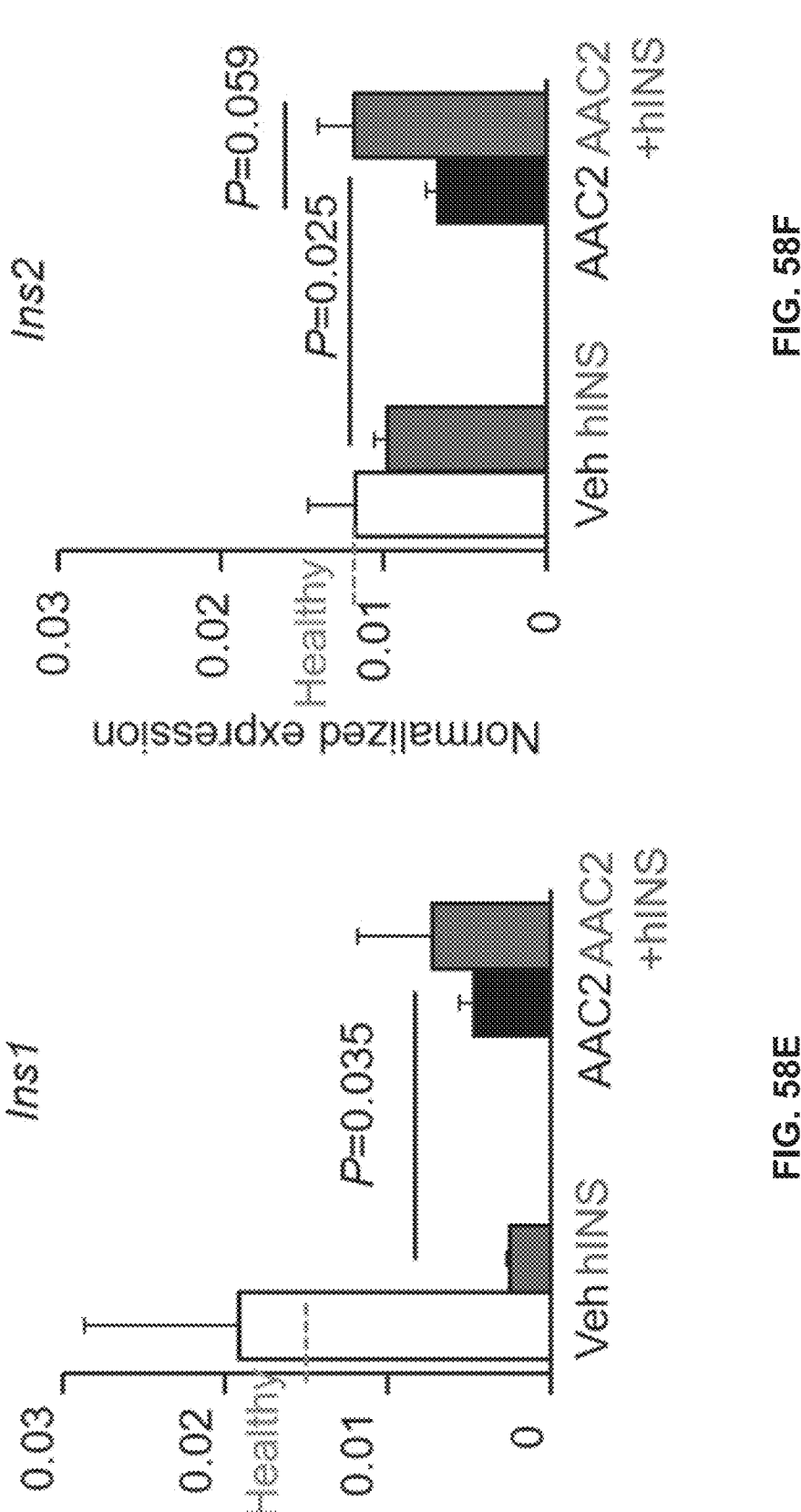
FIG. 58E shows that binding of INS to AAC2 in AAC-INS complex ameliorated detrimental suppression of insulin 1 gene (Ins1) in the brain of STZ mice treated with free INS.
FIG. 58F shows that binding of INS to AAC2 in AAC-INS complex ameliorated detrimental suppression of insulin 2 gene (Ins2) in the brain of STZ mice treated with free AAC2.

FIG. 58A shows improved stability of AAC2-INS in circulation in STZ mice. Human INS was used for treatment to distinguish from endogenous mouse INS. FIG. 58B shows identical levels of endogenous mouse INS in STZ mice treated with AAC2 an untreated control group. FIG. 58C shows similar insulin sensitivity in all treatment groups without onset of hypoglycemia in AAC2-INS group (58A). Insulin tolerance test (ITT) was used to assess insulin sensitivity. FIG. 58D shows improved glucose uptake in STZ mice treated with AAC2 or AAC2-INS. Glucose tolerance test (GTT) was used to assess glucose tolerance. FIG. 58E shows that binding of INS to AAC2 in AAC-INS complex ameliorated detrimental suppression of insulin 1 gene (Ins1) in the brain of STZ mice treated with free INS. FIG. 58F shows that binding of INS to AAC2 in AAC-INS complex ameliorated detrimental suppression of insulin 2 gene (Ins2) in the brain of STZ mice treated with free AAC2.

Figures 59A, 59B:
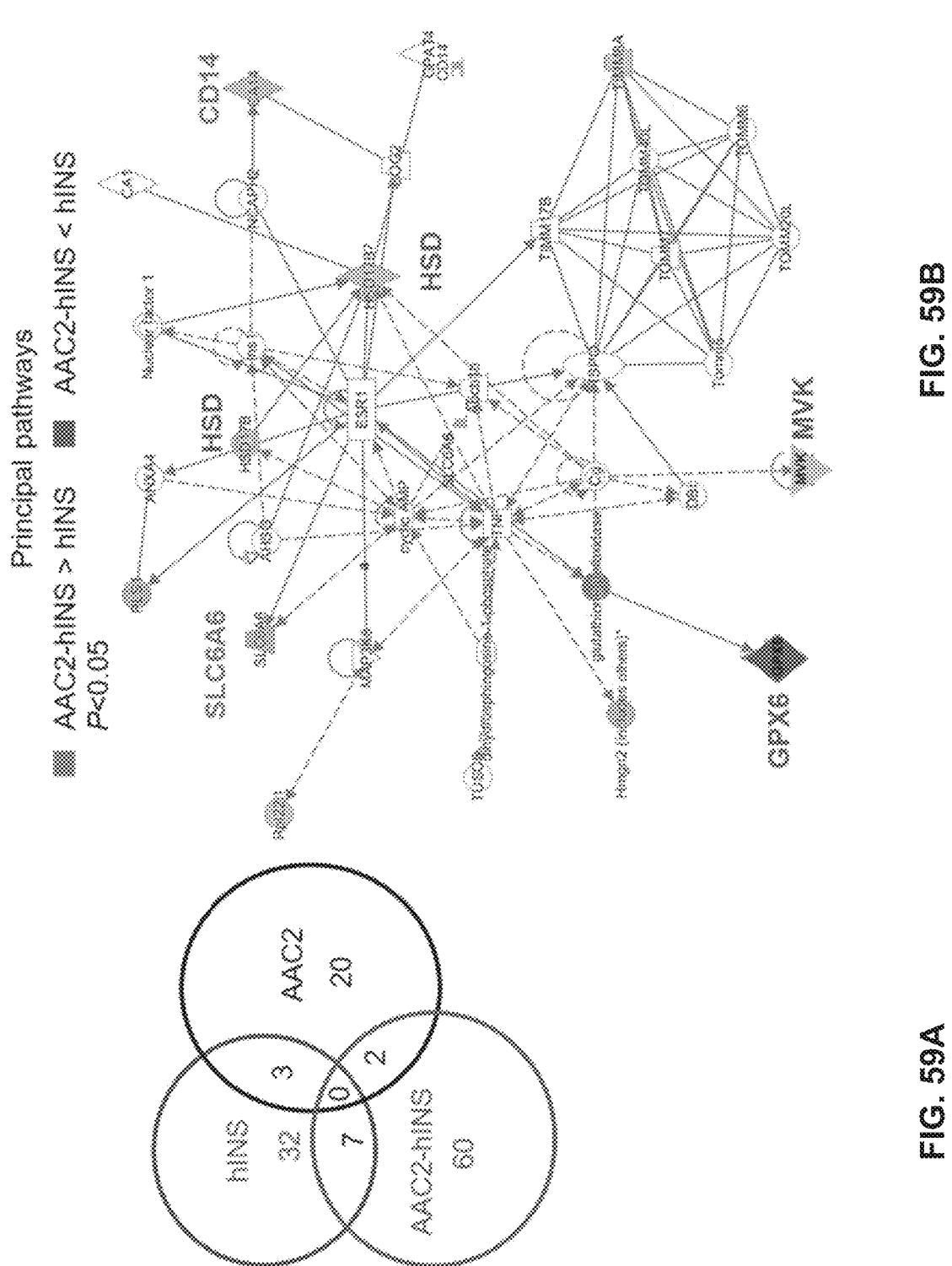
FIG. 59A shows that AAC2-INS and free INS act therapeutically via principally acts different pathways identified based on gene expression in computational Ingenuitu Pathway Analysis (Qiagen, USA). AAC2-INS upregulated taurine pathway (SLC6A6) and carbonic anhydrase pathways (CD14) networks that are relevant for CNS. Free INS acted via cholesterol synthesis pathways (MVK, HSD) and a defense antioxidant pathways (GPX6), that are downregulated by AAC2-INS.
FIG. 59B shows expression of Solute Carrier Family 6 Member 6 (SLC6A6). A principal transporter for neurotransmitter and osmolyte taurine, in all treated STZ mice.
Figures 59C, 59D:
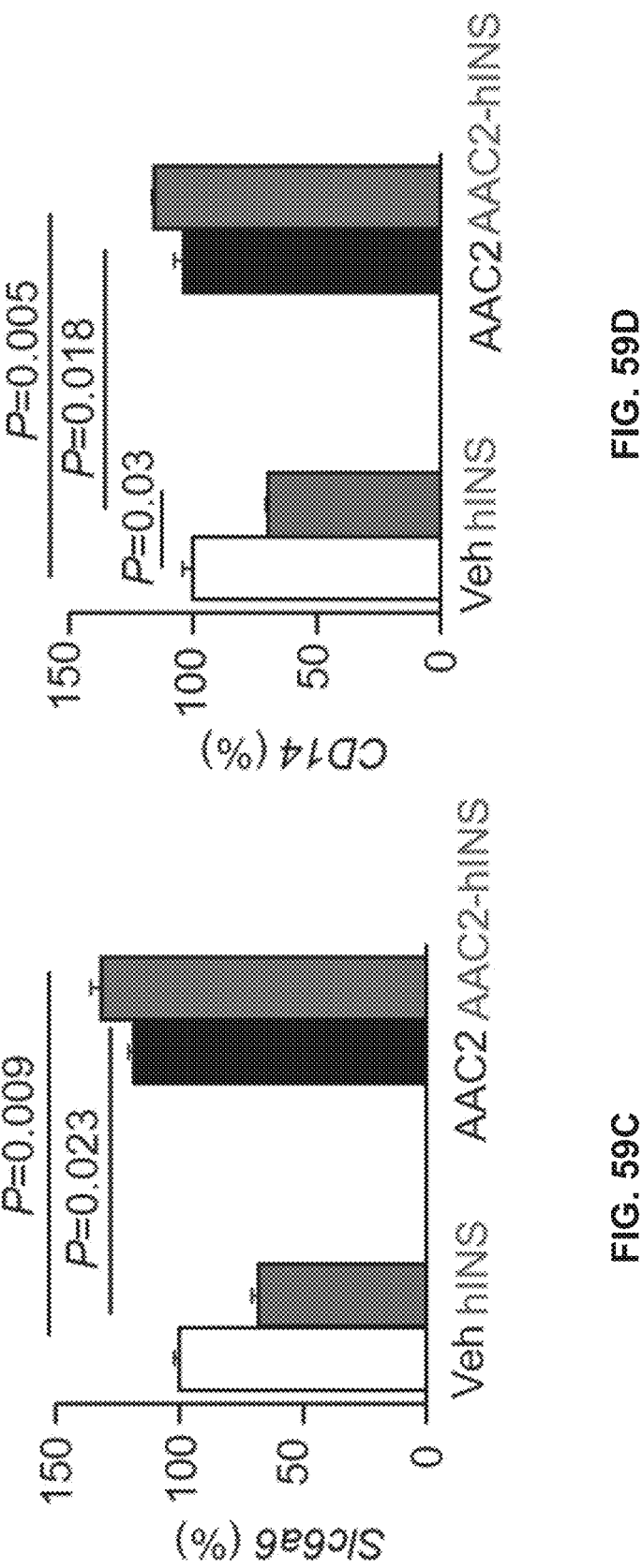
FIG. 59C shows significantly increased expression of Solute Carrier Family 6 Member 6 (SLC6A6) in STZ mice treated with AAC2-INS. SLC6A6 is a principal transporter for neurotransmitter and osmolyte taurine, in all treated STZ mice.
FIG. 59D shows significantly increased expression of Carbonic Anhydrase 14 (CD14) in STZ mice treated with AAC2-INS.CD14 a principal enzyme that is expressed in the brain for maintenance of pH balance the brain.
Figures 59E, 59F:
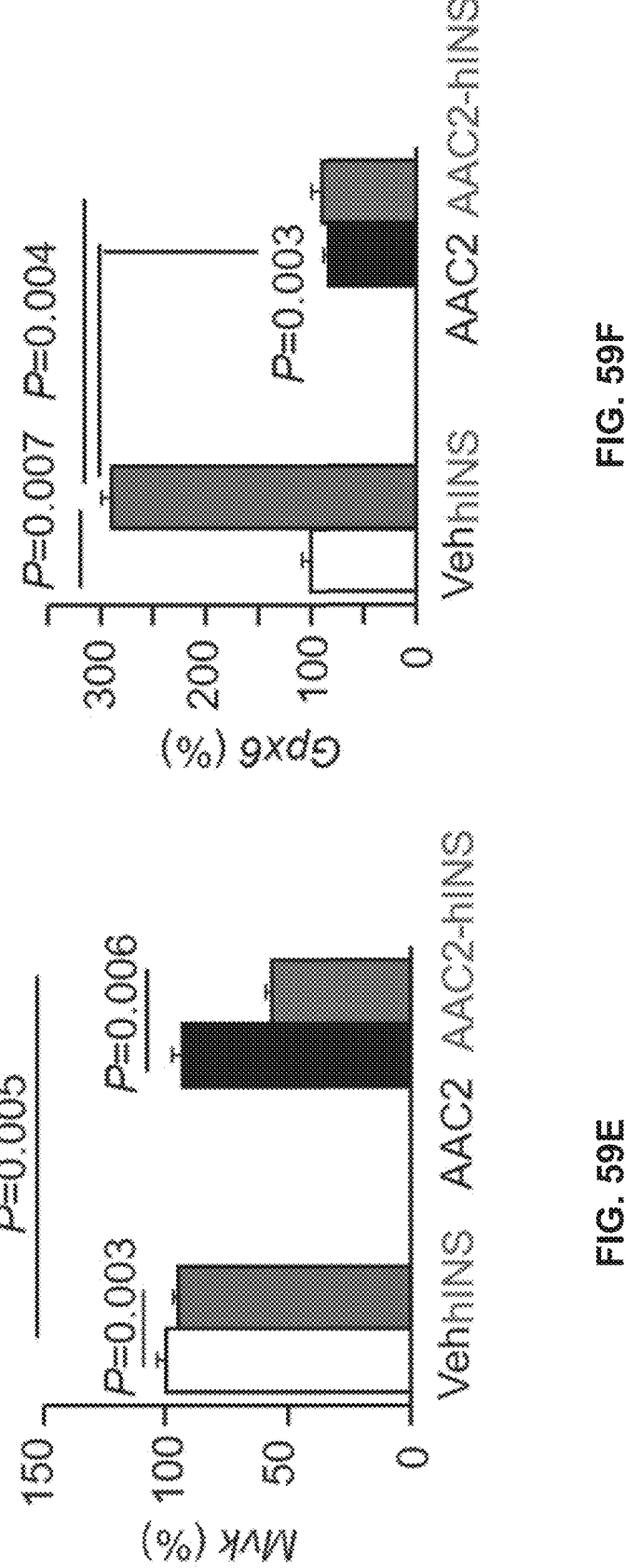
FIG. 59E shows significantly synergistically decreased expression of Mevalonate Kinase (MVK) in STZ mice treated with AAC2-INS. MVK a key kinase in cholesterol synthesis pathway.

FIG. 59A shows that AAC2-INS and free INS act therapeutically via principally acts different pathways identified based on gene expression in computational Ingenuitu Pathway Analysis (Qiagen, USA). AAC2-INS upregulated taurine pathway (SLC6A6) and carbonic anhydrase pathways (CD14) networks that are relevant for CNS. Free INS acted via cholesterol synthesis pathways (MVK, HSD) and a defense antioxidant pathways (GPX6), that are downregulated by AAC2-INS. FIG. 59B shows expression of Solute Carrier Family 6 Member 6 (SLC6A6). A principal transporter for neurotransmitter and osmolyte taurine, in all treated STZ mice. FIG. 59C shows significantly increased expression of Solute Carrier Family 6 Member 6 (SLC6A6) in STZ mice treated with AAC2-INS. SLC6A6 is a principal transporter for neurotransmitter and osmolyte taurine, in all treated STZ mice. FIG. 59D shows significantly increased expression of Carbonic Anhydrase 14 (CD14) in STZ mice treated with AAC2-INS.CD14 a principal enzyme that is expressed in the brain for maintenance of pH balance the brain. FIG. 59E shows significantly synergistically decreased expression of Mevalonate Kinase (MVK) in STZ mice treated with AAC2-INS. MVK a key kinase in cholesterol synthesis pathway. FIG. 60F shows that significantly increased expression of Glutathone peroxidase (GPX6) in STZ mice treated with free INS is abolished in AAC2-INS-treated animals. GPX6 a key antioxidant enzyme induced in the liver in response to oxidative stress.

Figure 60A:
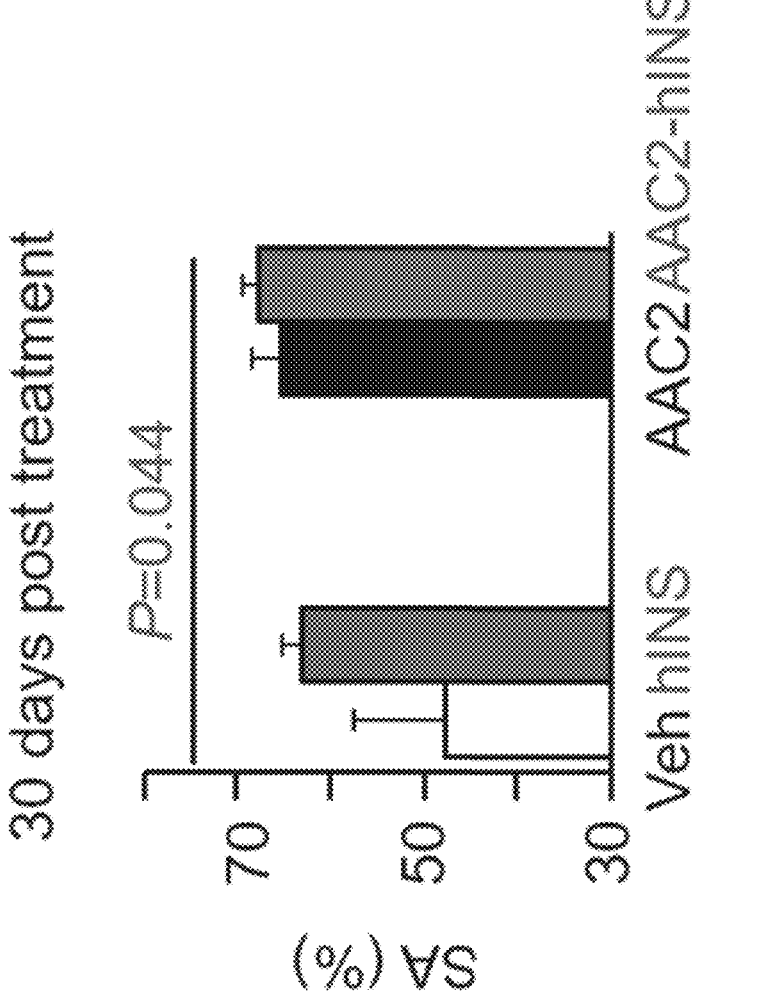
FIG. 60A shows improved cognitive performance in STZ mice treated with AAC2-INS using Y Maze Spontaneous Alternation behavioral test for measuring the willingness of rodents to explore new environments.
Figures 60B, 60C:
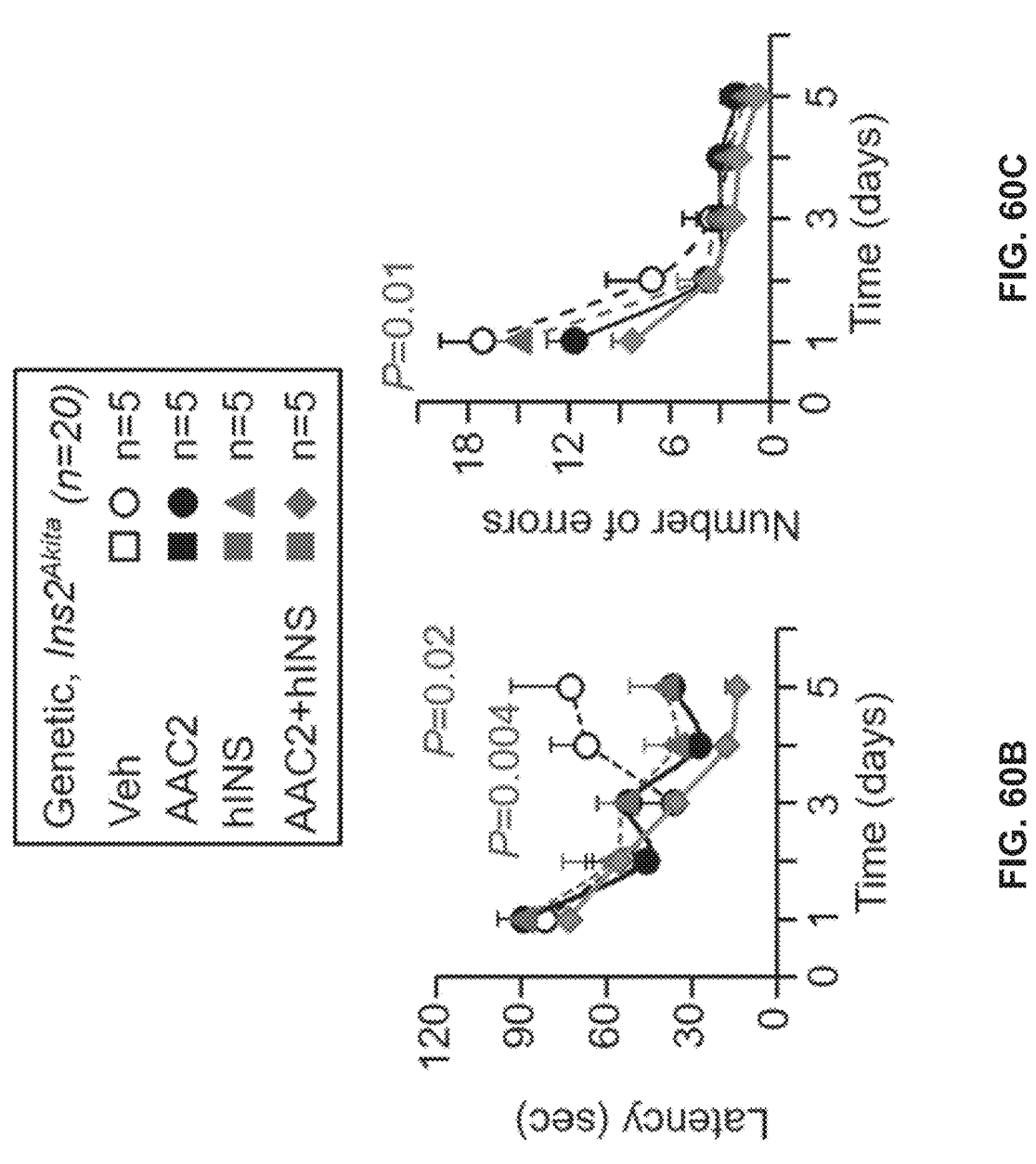
FIGS. 60B to 60D show synergistically improved cognitive performance in Akita mice, a genetic model of type 1 diabetes, which were treated with AAC2-INS. Cognitive performance was measured using Barnes maze behavioral test to measure spatial learning (escape latency (60B) and number of errors (60C)) and memory (60D).
Figure 60D:
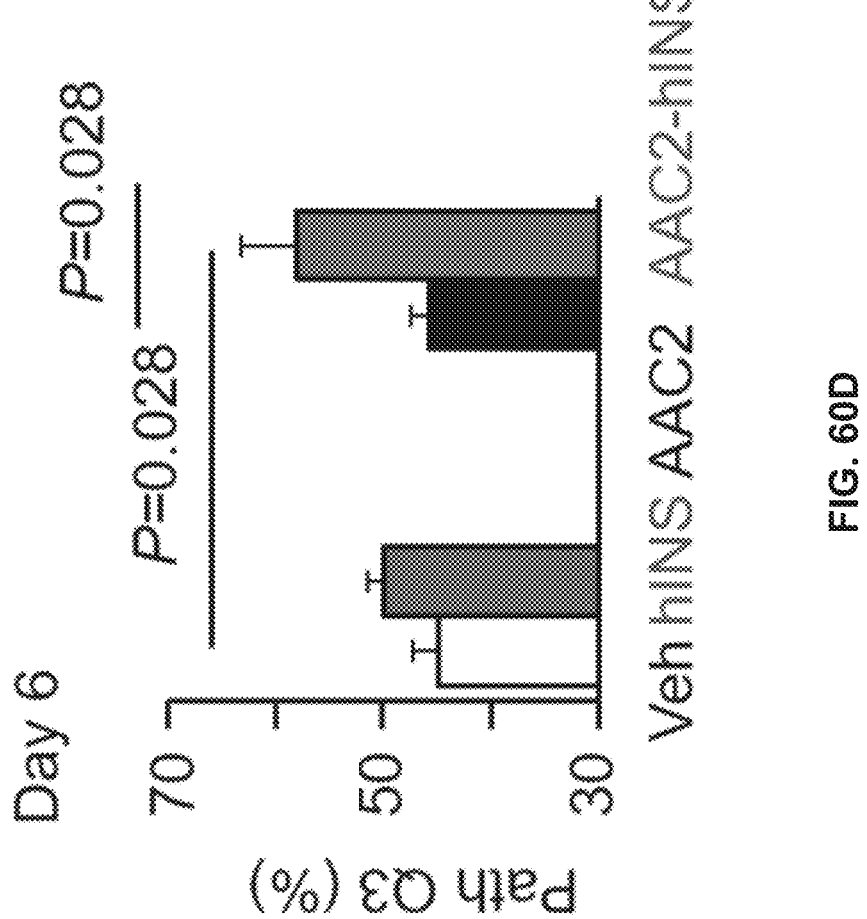

FIG. 60A shows improved cognitive performance in STZ mice treated with AAC2-INS using Y Maze Spontaneous Alternation behavioral test for measuring the willingness of rodents to explore new environments. FIGS. 60B to 60D show synergistically improved cognitive performance in Akita mice, a genetic model of type 1 diabetes, which were treated with AAC2-INS. Cognitive performance was measured using Barnes maze behavioral test to measure spatial learning (escape latency (60B) and number of errors (60C)) and memory (60D).

Example 5: Synergistic Activity of AAC2 and IGFBP4 Combination on Neuromotor Function in Mouse Model of Alzheimer's Disease Study performed in APP/PS1 mice (Jackson laboratory Cat N 005864, B6.Cg-Tg(APPswe,PSEN1dE9)85Dbo/Mmjax).

8-12 weeks old-week old male APP/PS1 mice were randomized into four groups. After 2 weeks acclimation period, we injected (10 µl/g body weight (BW)) into scapular region every 48 h with:

Group 1: PBS vehicle control,
Group 2: 0.2 mM AAC2,
Group 3: 3.74 µM hIGFBP4, or Group 4: AAC2/hIGFBP4 combination of AAC2 and 50 ng of hIGFBP4 per gram body weight.

Human insulin-like growth factor binding protein 4 (hIGFBP4, Peprotech #350-05B) was dissolved with PBS to make 50 μg/mL solution. To make the combination of AAC2/hIGFBP4, we mixed 100 μL of 0.2 mM AAC2 solution with 100 μL of 100 ng/mL hIGFBP4 into 800 μL of PBS to make total 1 mL. Study duration was 4 months.

Figure 61:
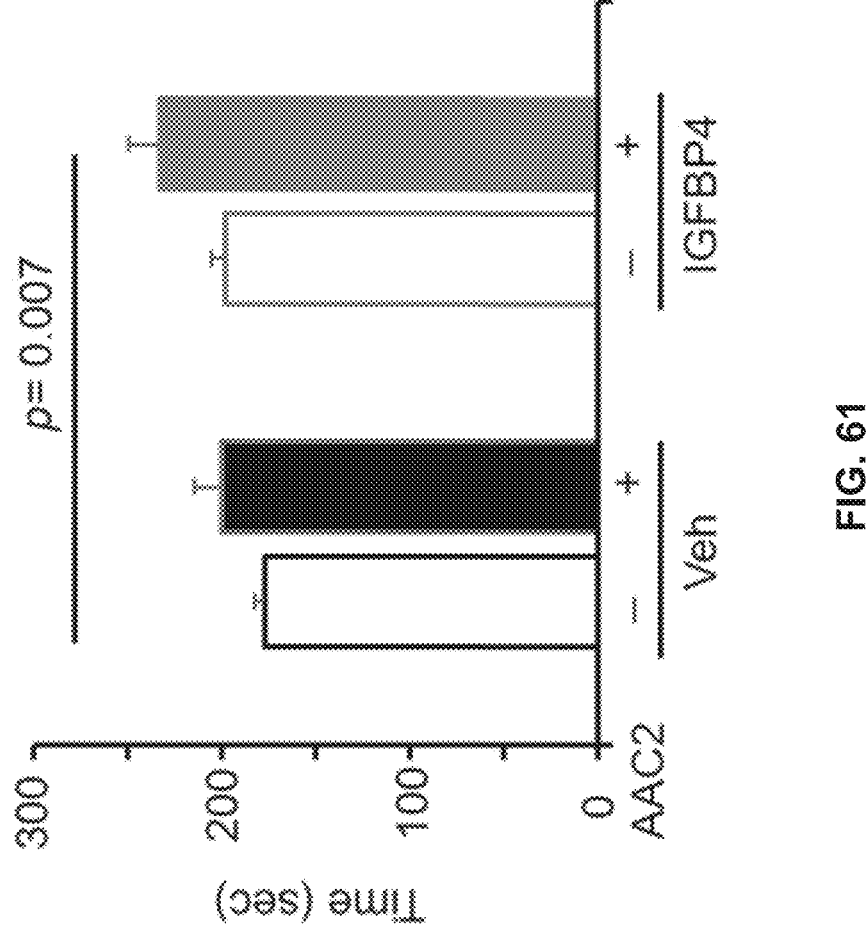
FIG. 61 show synergistic improvement of neuromotor function in APP/PS1 mouse model of Alzheimer's dementia treated with AAC2-IGFBP4 combination using rotarod test.

As shown in FIG. 61, there was synergistic improvement of neuromotor activity in APP/PS1 mice treated with AAC2-IGFBP4 combination. Neuromotor activity was measured by Rotarod test at the end of study duration. This is a canonic test for measurement of neuromotor recovery in patients with traumatic brain injury and aged people.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

---

What is claimed is:

1. A pharmaceutical composition comprising a self-assembled, biocompatible nanostructure non-covalently associated with a thermogenesis-inducing molecule, wherein the thermogenesis-inducing molecule comprises epiregulin, insulin-like growth factor-binding protein 4 (IGFBP4), a disintegrin and metalloproteinase with thrombospondin type 1 motif 9 (ADAMT S9), semaphorin 3E, or a combination thereof, wherein the self-assembled, biocompatible nanostructure comprises compound I wherein the compound I is optionally functionalized at one or more side chains and/or at the C-terminus with a methyl, ethyl, t-butyl, or benzyl ester, and wherein the compound I optionally contains a hydrophobic moiety covalently attached to the C-terminus.

2. A method for treating a condition in a subject selected from the group consisting of visceral fat accumulation, obesity, diabetes, pre-diabetes, hypothermia, and chronic inflammation, comprising administering to the subject an effective amount of the composition of claim 1.

3. The method of claim 2, wherein the composition is administered by injection or infusion.

4. A method for promoting glucose uptake in peripheral tissues of a subject, comprising administering to the subject an effective amount of the composition of claim 1.

5. The method of claim 4, further comprising administering to the subject a therapeutically effective amount of an epidermal growth factor receptor (EGFR) inhibitor, an erythroblastic oncogene B (ErbB) receptor inhibitor, a Mitogen-activated protein kinases (MAPK) inhibitor, or a combination thereof.

6. The method of claim 4, wherein the subject is resistant to insulin.

7. The method of claim 4, wherein the subject has diminished insulin production.

8. The method of claim 4, wherein the subject is obese.

9. A method for enhancing nerve innervation in a subject, comprising administering to the subject an effective amount of the composition of claim 1.

* * * * *

SEQUENCE LISTING

```
<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Synthetic Construct

<400> SEQUENCE: 1

Lys Phe Lys Lys
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is arginyl, histidyl, lysyl, aspartyl,
      glutamyl, seryl, threonyl, cystyl, asparagyl, glutaminyl, prolyl,
      tyrosyl, methionyl, and tryptophanyl
<220> FEATURE:
<221> NAME/KEY: MISC_FEATURE
<222> LOCATION: (3)..(4)
<223> OTHER INFORMATION: Xaa is alanyl, allosoleucyl, arginyl asparagyl,
      aspartyl, cystyl, glutamyl, glutaminyl, glycyl, histidyl,
      isolelucyl, leucyl, lysyl, methionyl, phenylalanyl, prolyl,
      pyroglutamyl, seryl, threonyl, tyrosyl, tryptophanyl, or valyl

<400> SEQUENCE: 2

Xaa Xaa Xaa Xaa
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is arginyl, histidyl, lysyl, aspartyl,
      glutamyl, seryl, threonyl, cystyl, asparagyl, glutaminyl, prolyl,
      tyrosyl, methionyl, or tryptophanyl
<220> FEATURE:
<221> NAME/KEY: MISC_FEATURE
<222> LOCATION: (2)..(2)
<223> OTHER INFORMATION: Xaa is alanyl, allosoleucyl, arginyl asparagyl,
      aspartyl, cystyl, glutamyl, glutaminyl, glycyl, histidyl,
      isolelucyl, leucyl, lysyl, methionyl, phenylalanyl, prolyl,
      pyroglutamyl, seryl, threonyl, tyrosyl, tryptophanyl, or valyl
<220> FEATURE:
```

```
<221> NAME/KEY: MISC_FEATURE
<222> LOCATION: (3)..(3)
<223> OTHER INFORMATION: Xaa is arginyl, histidyl, lysyl, aspartyl,
      glutamyl, seryl, threonyl, cystyl, asparagyl, glutaminyl, prolyl,
      tyrosyl, methionyl, or tryptophanyl
<220> FEATURE:
<221> NAME/KEY: MISC_FEATURE
<222> LOCATION: (4)..(4)
<223> OTHER INFORMATION: Xaa is alanyl, allosoleucyl, arginyl asparagyl,
      aspartyl, cystyl, glutamyl, glutaminyl, glycyl, histidyl,
      isolelucyl, leucyl, lysyl, methionyl, phenylalanyl, prolyl,
      pyroglutamyl, seryl, threonyl, tyrosyl, tryptophanyl, or valyl

<400> SEQUENCE: 3

Xaa Xaa Xaa Xaa
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa isalanyl, allosoleucyl, arginyl asparagyl,
      aspartyl, cystyl, glutamyl, glutaminyl, glycyl, histidyl,
      isolelucyl, leucyl, lysyl, methionyl, phenylalanyl, prolyl,
      pyroglutamyl, seryl, threonyl, tyrosyl, tryptophanyl, or valyl
<220> FEATURE:
<221> NAME/KEY: MISC_FEATURE
<222> LOCATION: (3)..(4)
<223> OTHER INFORMATION: Xaa is arginyl, histidyl, lysyl, aspartyl,
      glutamyl, seryl, threonyl, cystyl, asparagyl, glutaminyl, prolyl,
      tyrosyl, methionyl, or tryptophanyl

<400> SEQUENCE: 4

Xaa Xaa Xaa Xaa
1

<210> SEQ ID NO 5
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is alanyl, allosoleucyl, arginyl asparagyl,
      aspartyl, cystyl, glutamyl, glutaminyl, glycyl, histidyl,
      isolelucyl, leucyl, lysyl, methionyl, phenylalanyl, prolyl,
      pyroglutamyl, seryl, threonyl, tyrosyl, tryptophanyl, or valyl
<220> FEATURE:
<221> NAME/KEY: MISC_FEATURE
<222> LOCATION: (2)..(2)
<223> OTHER INFORMATION: Xaa is arginyl, histidyl, lysyl, aspartyl,
      glutamyl, seryl, threonyl, cystyl, asparagyl, glutaminyl, prolyl,
      tyrosyl, methionyl, or tryptophanyl
<220> FEATURE:
<221> NAME/KEY: MISC_FEATURE
<222> LOCATION: (3)..(3)
<223> OTHER INFORMATION: Xaa is alanyl, allosoleucyl, arginyl asparagyl,
      aspartyl, cystyl, glutamyl, glutaminyl, glycyl, histidyl,
      isolelucyl, leucyl, lysyl, methionyl, phenylalanyl, prolyl,
      pyroglutamyl, seryl, threonyl, tyrosyl, tryptophanyl, or valyl
```

-continued

```
<220> FEATURE:
<221> NAME/KEY: MISC_FEATURE
<222> LOCATION: (4)..(4)
<223> OTHER INFORMATION: Xaa is arginyl, histidyl, lysyl, aspartyl,
      glutamyl, seryl, threonyl, cystyl, asparagyl, glutaminyl, prolyl,
      tyrosyl, methionyl, or tryptophanyl

<400> SEQUENCE: 5

Xaa Xaa Xaa Xaa
1
```